US010982247B2

(12) United States Patent
Behlke et al.

(10) Patent No.: US 10,982,247 B2
(45) Date of Patent: Apr. 20, 2021

(54) DNA POLYMERASE MUTANTS HAVING ENHANCED TEMPLATE DISCRIMINATION ACTIVITY

(71) Applicant: Integrated DNA Technologies, Inc., Coralville, IA (US)

(72) Inventors: Mark Aaron Behlke, Coralville, IA (US); Joseph A. Walder, Chicago, IL (US); Richard Owczarzy, Coralville, IA (US); Scott D. Rose, Coralville, IA (US); Joseph R. Dobosy, Coralville, IA (US); Susan M. Rupp, Marion, IA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 0 days.

(21) Appl. No.: 15/386,631

(22) Filed: Dec. 21, 2016

(65) Prior Publication Data
US 2017/0114379 A1 Apr. 27, 2017

Related U.S. Application Data

(62) Division of application No. 14/542,539, filed on Nov. 14, 2014, now abandoned.

(60) Provisional application No. 61/904,335, filed on Nov. 14, 2013.

(51) Int. Cl.
*C12P 19/34* (2006.01)
*C12N 9/12* (2006.01)

(52) U.S. Cl.
CPC ............ *C12P 19/34* (2013.01); *C12N 9/1252* (2013.01); *C12Y 207/07007* (2013.01)

(58) Field of Classification Search
CPC .............................. C12N 9/1252; C12P 19/34; C12Y 207/07007
See application file for complete search history.

(56) References Cited

U.S. PATENT DOCUMENTS

| | | | |
|---|---|---|---|
| 4,458,066 A | 7/1984 | Caruthers et al. | |
| 4,683,195 A | 7/1987 | Mullis et al. | |
| 4,683,202 A | 7/1987 | Mullis | |
| 4,965,188 A | 10/1990 | Mullis et al. | |
| 5,494,810 A | 2/1996 | Barany et al. | |
| 5,763,181 A | 6/1998 | Han et al. | |
| 6,265,193 B1 | 7/2001 | Brandis et al. | |
| 6,602,695 B2 | 8/2003 | Patel et al. | |
| 7,112,406 B2 | 9/2006 | Behlke et al. | |
| 7,135,291 B2 | 11/2006 | Sagawa et al. | |
| 8,399,197 B2 | 3/2013 | Behlke et al. | |
| 8,759,061 B1 | 6/2014 | Marx et al. | |
| 9,434,988 B2* | 9/2016 | Behlke ................ | C12Q 1/6858 |
| 2009/0068643 A1 | 3/2009 | Behlke et al. | |
| 2010/0075383 A1 | 3/2010 | Behlke et al. | |
| 2010/0167353 A1* | 7/2010 | Walder ................ | C12O 1/6844 |
| | | | 435/91.2 |
| 2010/0203524 A1 | 8/2010 | Efcavitch et al. | |
| 2012/0015405 A1 | 1/2012 | Reichert et al. | |
| 2012/0258455 A1* | 10/2012 | Behlke ................ | C12Q 1/6858 |
| | | | 435/6.11 |
| 2014/0162249 A9* | 6/2014 | Behlke ................ | C12Q 1/6858 |
| | | | 435/6.11 |

FOREIGN PATENT DOCUMENTS

| | | |
|---|---|---|
| DE | 102004005885 A1 | 10/2005 |
| JP | 2011521624 A | 7/2011 |
| JP | 2016530836 A | 9/2016 |
| WO | 9001069 A1 | 2/1990 |
| WO | 9840496 A1 | 3/1998 |
| WO | 0132887 A1 | 5/2001 |
| WO | 2009/135093 A2 | 11/2009 |
| WO | 2011157436 A1 | 6/2011 |
| WO | 2011157437 A1 | 6/2011 |

OTHER PUBLICATIONS

Owczarzy et al., "Stability and Mismatch Discrimination of Locked Nucleic Acid-DNA Duplexes," Biochemistry 47:5336-5353 (2008).
Patel et al., "Insights into DNA Polymerization Mechanisms from Structure and Function Analysis of HIV-1 Reverse Transcriptase," Biochemistry 34:5351-5363 (1995).
Patel et al, "Prokaryotic DNA Polyermase I: Evolution, Structure, and "Base Flipping" Mechanism for Nucleotide Selection," J. Mol. Biol. 308:823-837 (2001).
PCT International Search Report and Written Opinion for International Application No. PCT/US2014/065845 dated Apr. 14, 2015, 14 pages.
Pearson et al., "Improved Tools for biological sequence comparison," Proc. Natl. Acad. Sci. USA 85:2444-2448 (1988).
Shi, "Technologies for Individual Genotyping," Am. J. Pharmacogenomics 2(3):197-205 (2002).
Smith et al., "Comparison of Biosequences," Adv. Appl. Math. 2:482-489 (1970).
Stadtman, "Selenocysteine," Annu. Rev. Biochem. 65:83-100 (1996).
Stenesh et al., "DNA Polymerase from Mesophilic and Thermophilic Bacteria," Biochim, Biophys. Acta 475:32-41 (1977).
Strerath et al., "Directed DNA Polymerase Evolution: Effects of Mutations in Motif C on the Mismatch-Extension Selectivity of Thermus aquaticus DNA Polymerase," ChemBioChem 8:395-401 (2007).
Summerer et al., "Enhanced Fidelity in Mismatch Extension by DNA Polymerase through Directed Combinatorial Enzyme Design," angew. Chem. Int. Ed. 44:4712-4715 (2005).

(Continued)

*Primary Examiner* — Richard G Hutson
(74) *Attorney, Agent, or Firm* — Klintworth & Rozenblat IP LLP

(57) ABSTRACT

This invention relates to mutant DNA polymerases having an enhanced template discrimination activity compared with the corresponding unmodified DNA polymerase counterparts, wherein the amino acid sequence of the mutant DNA polymerase includes at least one substitution at residue positions structurally and functionally homologous or orthologous positions 783 or 784 of an unmodified Taq DNA polymerase.

5 Claims, 22 Drawing Sheets

Specification includes a Sequence Listing.

(56) References Cited

OTHER PUBLICATIONS

Suzuki et al., "Thermus acuaticus DNA Polymerase I Mutants with Altered Fidelity," J. Blol. Chem. 275:32728-32735 (2000).
Tabor et al., "A single residue in DNA polymerases of the *Escherichia coli* DNA polymerase I family is critical for distinguishing between deoxy- and dideoxyribonucleotides," Proc. Nat Acad. Sci. USA 92:6339-6343 (1995).
Takagi et al., "Characterization of DNA Polymerase from *Pyrococcus* sp. Strain KOD1 and Its Application to PCR," Appl. Environ. Microbiol. 63:4504-4510 (1997).
Wang et al., "Crystal Structure of a pol a Family Replication DNA Polymerase from Bacteriophase RB69," Cell 89:1087-1099 (1997).
Weiner et al., "Site-directed mutagenesis of double-stranded DNA by the polymerase chain reaction," Gene 151:119-123 (1994).
Wetmur, "DNA Probes: Applications of the Principles of Nucleic Acid Hybridization," Critical Review in Biochem. and Mol. Biol. 26(3/4):227-259 (1991).
Wiedmann et al., "Ligase Chain Reaction (LCR)-Overview and Applications," PCR Methods and Applications 3:S51-64 (1994).
Wu et al., "The Ligation Amplification Reaction (LAR)-Amplification of Specific DNA Sequences Using Sequential Rounds of Template-Dependent Ligation," Genomics 4:560-569 (1989).
Yang et al., "Mutant Thermotoga neapolitana DNA polymerase I: altered catalytic properties for non-templated nucleotide addition and incorporation of correct nucleotides," Nucleic Acids Res. 30(19):4314-4320 (2002).
Zhang et al., "Selective incorporation of 5-hydroxytryptophan into proteins in mammalian cells," Proc. Natl. Acad. Sci. USA 101(34):8882-8887 (2004).
Sambrook et al., "Molecular Cloning—a Laboratory Manual," Cold Spring Harbor Laboratory, Cold Spring Harbor, N.Y. (1989).
Altschul et al. "Basic Local Alignment Search Tool," J. Mol. Biol. 215:403-410 (1990).
Altschul et al., "Gapped BLAST and PSI-BLAST: a new generation of protein database search programs," Nuc. Acids Res. 25(17):3389-3402 (1977).
Anderson et al., "An expanded genetic code with a functional quadruplet codon," Proc. Natl. Acad. Sci. U.S.A. 101(20):7566-7571 (2004).
Ausubel et al., Current Protocols in Molecular Biology (1995 supplement)—copy to be supplied at a later date.
Ayyadevara, et al., "Discrimination of Primer 3'-Nucleotide Mismatch by Taq DNA Polymerase during Polymerase Chain Reaction," Anal. Biochem. 284(1):11-18 (2000).
Bacher et al., "Selection and Characterization of *Escherichia coli* Variants Capable of Growth on an Otherwise Toxic Tryptophan Analogue," J. Bacteriol. 183(18):5414-5425 (2001).
Barany, F., "Genetic disease detection and DNA amplification using cloned thermostable ligase," Proc. Natl. Acad. Sci. USA 88:189-193 (Jan. 1991).
Barnes, W.M., "The fidelity of Taq polymerase catalyzing PCR is improved by an N-terminal deletion," Gene 112:29-35 (1992).
Beaucage et al., "Deoxynucleoside Phosphoramidites—A New Class of Key Intermediates for Deoxypolynucleotide Synthesis," Tetrahedron Lett. 22(20):1859-1862 (1981).
Beese, et al., "Structure of DNA Polymerase I Klenow Fragment Bound to Duplex DNA," Science 260:352-355 (1993).
Berman, et al., "The Protein Data Bank," Nuc. Acids Res. 28(1):235-242 (2000).
Brown et al. "Chemical Synthesis and Cloning of a Tyrosine tRNA Gene," Meth. Enzymol. 68:109-151 (1979).
Budisa et al., "Proteins with 6-(thienopyrrolyl)alanines as alternative chromophores and pharmaceutically active amino acids," Protein Sci. 10(7):1281-1292 (2001).
Cariello et al., "Fidelity of Thermococcus litoralis DNA polymerase (Vent™) in PCR determined by denaturing gradient gel electrophoresis," Nucleic Acids Res. 19(15):4193-4198 (1991).

Chen, et al., "Single nucleotide polymorphism genotyping: biochemistry, protocol, cost and throughput," Pharmacogenomics J. 3(2):77-96 (2003).
Chen, et al., "Reconstructed evolutionary adaptive paths give polymerases accepting reversible terminators for sequencing and SNP detection," Proc. Nat Acad. Sci. USA 107(5):1948-1953 (2010).
Chien et al., "Deoxyribonucleic Acid Polymerase from the Extreme Thermophile Thermus aquaticus," J. Bacteriol. 127(3):1550-1557 (1976).
Chin, et al., "An Expanded Eukaryotic Genetic Code," Science 301(5635):964-967 (2003).
Diaz et al., "Accuracy of replication in the polymerase chain reaction. Comparison between Thermotoga maritima DNA polymerase and Thermus aquaticus DNA polymerase," Braz. J. Med. Res. 31:1239-1242 (1998).
Dobosy et al., "RNase H-dependent PCR (rhPCR): improved specificity and single nucleotide polymorphism detection using blocked cleavable primers," BMC Biotechnology 11:e80 (2011) 18 pages.
Doublié, et al., "An open and closed case for all polymerases," Structure 7:R31-R35 (1999).
Eom et al., "Structure of Taq polymerse with DNA at the polymerase active site," Nature 382:278-281 (1996).
Fa et al., "Expanding the Substrate Repertoire of a DNA Polymerase by Directed Evolution," J. Am. Chem. Soc. 126:1748-1754 (2004).
Gibson et al., "Enzymatic assembly of DNA molecules up to several hundred kilobases," Nature Methods 6(5):343-345 (2009).
Goodchild, "Conjugates of oligonucleotides and modified oligonucleotides: a review of their synthesis and properties," Bioconjugate Chem. 1(3):165-187 (1990).
Hamano-Takaku et al., "A Mutant *Escherichia coli* Tyrosyl-tRNA Synthetase Utilizes the Unnatural Amino Acid Azatyrosine More Efficiently than Tyrosine," J. Biol. Chem. 275(51):40324-40328 (2000).
Ibba et al., "Genetic code: introducing pyrrolysine," Curr Biol. 12(13):R464-R466 (2002).
Ikeda et al., "Synthesis of a novel histidine analogue and its efficient incorporation into a protein in vivo," Protein Eng. Des. Sel. 16(9):699-706 (2003).
Innis et al., "Optimization of PCRs," PCR Protocols: A Guide to Methods and Applications, pp. 3-12 (1990).
James et al., "Kinetic characterization of ribonuclease S mutants containing photoisomerizable phenylazophenylalanine residues," Protein Eng. Des. Sel. 14(12):983-991 (2001).
Kohrer et al., "Import of amber and ochre suppressor tRNAs into mammalian cells: A general approach to site-specific insertion of amino acid analogues into proteins," Proc. Natl. Acad. Sci. U.S.A. 98(25):14310-14315 (2001).
Kranaster et al., "Engineered DNA Polymerases in Biotechnology," ChemBioChem 11:2077-2084 (2010).
Kwok et al., "Detection of single nucleotide polymorphisms" Curr. Issues Mol. Biol. 5(2):43-60 (2003).
Kwok, "Methods for genotyping single nucleotide polymorphisms" Annu. Rev. Genomics Hum. Genet. 2:235-58 (2001).
Latorra et al., "Enhanced Allele-Specific PCR Discrimination in SNP genotyping using 3' locked nucleic acid (LNA) primers," Human Mut. 22(1):79-85 (2003).
Lawyer et al., "Isolation, Characterization, and Expression in Escherichia coli of the DNA Polymerase Gene from Thermus aquaticus," J. Biol. Chem. 264(11):6427-6437 (1989).
Lecomte et al., "Selective inactivation of the 3' to 5' exonuclease activity of *Escherichia coli* DNA polymerase I by heat," Nucleic Acids Res. 11(21):7505-7515 (1983).
Li et al., "Structure-based design of Taq DNA polymerases with improved properties of dideoxynucleotide incorporation," Proc. Natl. Acad. Sci. USA 96:9491-9496 (1999).
Li et al., "Crystal structures of open and closed forms of binary and ternary complexes of the large fragment of Thermus aquaticus DNA polymerase I: structural basis for nucleotide incorporation," the EMBO Journal 17(24):7514-7525 (1998).
Li et al., "Crystal structures of the Klenow fragment of Thermus aquaticus DNA polymerase I complexed with deoxyribonucleoside triphosphates," Protein Science 7:1116-1123 (1998).

(56) References Cited

OTHER PUBLICATIONS

Lundberg et al., "High-fidelity amplification using a thermostable DNA polymerase isolated from Pyrococcus furiosus," Gene 108:1-6 (1991).
Minnick et al., "Side Chains That Influence Fidelity at the Polymerase Active Site of *Escherichia coli* DNA polymerase I (Klenow Fragment)," J. Biol. Chem. 274(8):3067-3075 (1999).
Morrison et al., "Eukaryotic DNA polymerase amino acid sequence required for 3'→5' exonuclease activity," Proc. Natl. Acad. Sci. USA 88:9473-9744 (1991).
Myers et al., "Reverse Transcription and DNA Amplification by a Thermus thermophilus DNA Polymerase," Biochemistry 30(31):7661-7666 (1991).
Nakamura et al., "Codon usage tabulated from the international DNA sequence databases:status for the year 2000," Nucleic Acids Res. 28(1):292 (2000).
Narang et al., "Improved Phosphotriester Method for the Synthesis of Gene Fragments," Meth. Enzymol. 68:90-99 (1979).
Needleman et al., "A General Method Applicable to the Search for Similarities in the Amino Acid Sequence of Two Proteins," J. Mol. Biol. 48:443-453 (1970).
Newton et al., "Analysis of any point mutation in DNA. The amplification refractory mutation systems (ARMS)" Nucleic Acids Res. 17(7):2503-2515 (1989).
Ngo et al., "Computational Complexity, Protein Structure Prediction, and the Levinthal Paradox," the Protein Folding Jroblem and Terstory Structure Prediction, K. Merz, Jr. and S. Le Grand, Ed. (1994).
Nordstrom et al., "Characterization of Bacteriophage T7 DNA Polymerase Purified to Homogeneity by Antithioredox Immunoadsorbent Chromatography," J. Biol.Chem. 256(6):3112-3117 (1981).
Singapore Search Report and Written Opinion for Singapore Application No. 11201603734Q, dated Dec. 1, 2017, 10 pages.

* cited by examiner (i)

(ii)

(iii)

(i)

(ii)

(iii)

(i)

(ii)

(iii)

(i)

(ii)

(iii)

(i)

(ii)

(iii)

(i)

(ii)

(iii)

(i)

(ii)

(i)

(ii)

(iii)

(i)

(ii)

(iii)

(i)

(ii)

(iii)

SEQUENCE LISTING

```
<160> NUMBER OF SEQ ID NOS: 180

<210> SEQ ID NO 1
<211> LENGTH: 832
<212> TYPE: PRT
<213> ORGANISM: Artificial Sequence
<220> FEATURE:
<223> OTHER INFORMATION: TAQ DNA POLYMERASE PROTEIN SEQUENCE

<400> SEQUENCE: 1

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
                100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
        130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175
```

```
Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
        210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
        370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
        500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
```

```
                595                 600                 605
Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 2
<211> LENGTH: 2626
<212> TYPE: DNA
<213> ORGANISM: Artificial Sequence
<220> FEATURE:
<223> OTHER INFORMATION: TAQ DNA POLYMERASE DNA SEQUENCE

<400> SEQUENCE: 2
aagctcagat ctacctgcct gagggcgtcc ggttccagct ggcccttccc gaggggaga     60 gggaggcgtt tctaaaagcc cttcaggacg ctacccgggg gcgggtggtg aagggtaac   120 atgaggggga tgctgcccct ctttgagccc aagggccggg tcctcctggt ggacggccac   180
cacctggcct accgcacctt ccacgccctg aagggcctca ccaccagccg ggggagccg    240 gtgcaggcgg tctacggctt cgccaagagc ctcctcaagg ccctcaagga ggacggggac   300
gcggtgatcg tggtctttga cgccaaggcc cctccttcc gccacgaggc ctacggggg    360 tacaaggcgg gccggccccc cacgccggag actttcccc ggcaactcgc cctcatcaag    420
gagctggtgg acctcctggg gctggcgcgc tcgaggtcc cggctacga ggcggacgac    480 gtcctggcca gctggccaa gaggcggaa aaggagggct acgaggtccg catcctcacc    540
gccgacaaag acctttacca gctcctttcc gaccgcatcc acgtcctcca ccccgagggg    600
tacctcatca ccccggcctg gctttgggaa aagtacggcc tgaggccccga ccagtgggcc    660 gactaccggg ccctgaccgg ggacgagtcc gacaaccttc ccggggtcaa gggcatcggg    720
gagaagacgg cgaggaagct tctggaggag tgggggagcc tggaagccct cctcaagaac   780
```

```
ctggaccggc tgaagcccgc catccgggag aagatcctgg cccacatgga cgatctgaag      840
ctctcctggg acctggccaa ggtgcgcacc gacctgcccc tggaggtgga cttcgccaaa      900
aggcgggagc ccgaccggga gaggcttagg gcctttctgg agaggcttga gtttggcagc      960
ctcctccacg agttcggcct tctgaaaagc cccaaggccc tggaggaggc ccctggcccc     1020
ccgccggaag gggccttcgt gggctttgtg cttteccgca aggagcccat gtgggccgat     1080
cttctggccc tggccgccgc caggggggc cgggtccacc gggcccccga gccttataaa      1140
gccctcaggg acctgaagga ggcgcggggg cttctcgcca aagacctgag cgttctggcc     1200
ctgagggaag gccttggcct cccgcccggc gacgacccca tgctcctcgc ctacctcctg     1260
gacccttcca acaccacccc cgaggggtg gcccggcgct acggcgggga gtggacggag      1320
gaggcggggg agcgggccgc cctttccgag aggctcttcg ccaacctgtg ggggaggctt     1380 gaggggagg agaggctcct ttggctttac cgggaggtgg agaggcccct ttccgctgtc      1440
ctggcccaca tggaggccac gggggtgcgc ctggacgtgg cctatctcag ggccttgtcc     1500
ctggaggtgg ccgaggagat cgcccgcctc gaggccgagg tcttccgcct ggccggccac     1560
cccttcaacc tcaactcccg ggaccagctg gaaagggtcc tctttgacga gctagggctt     1620
cccgccatcg gcaagacgga gaagaccggc aagcgctcca ccagcgccgc cgtcctggag     1680
gccctccgcg aggcccaccc catcgtggag aagatcctgc agtaccggga gctcaccaag     1740
ctgaagagca cctacattga ccccttgccg gacctcatcc accccaggac gggccgcctc     1800
cacacccgct tcaaccagac ggccacggcc acgggcaggc taagtagctc cgatcccaac     1860
ctccagaaca tccccgtccg cacccccgctt gggcagagga tccgccgggc cttcatcgcc     1920
gaggaggggt ggctattggt ggccctggac tatagccaga tagagctcag ggtgctggcc     1980
cacctctccg gcgacgagaa cctgatccgg gtcttccagg agggggcggga catccacacg     2040 gagaccgcca gctggatgtt cggcgtcccc cgggaggccg tggaccccct gatgcgccgg     2100
gcggccaaga ccatcaactt cggggtcctc tacggcatgt cggcccaccg cctctcccag     2160
gagctagcca tcccttacga ggaggccag gccttcattg agcgctactt tcagagcttc     2220
cccaaggtgc gggcctggat tgagaagacc ctggaggagg caggaggcg ggggtacgtg     2280 gagaccctct tcggccgccg ccgctacgtg ccagacctag aggcccgggt gaagagcgtg     2340
cgggaggcgg ccgagcgcat ggccttcaac atgcccgtcc agggcaccgc cgccgacctc     2400
atgaagctgg ctatggtgaa gctcttcccc aggctggagg aaatggggc caggatgctc     2460 cttcaggtcc acgacgagct ggtcctcgag gccccaaaag agagggcgga ggccgtggcc     2520
cggctggcca aggaggtcat ggagggggtg tatcccctgg ccgtgcccct ggaggtggag     2580
gtggggatag gggaggactg gctctccgcc aaggagtgat accacc                   2626
```

<210> SEQ ID NO 3
<211> LENGTH: 865
<212> TYPE: DNA
<213> ORGANISM: Artificial Sequence
<220> FEATURE:
<223> OTHER INFORMATION: TAQ DNA POLYMERASE CODON-OPTIMIZED SUB-FRAGMENT
      1

<400> SEQUENCE: 3

```
catatgcgtg gtatgctgcc gttgttcgag cctaaaggcc gcgtactgtt agtcgatggt       60
catcacttgg cctatcggac gttccatgca ctcaaaggtc tgacgaccag tcgtggcgaa      120
ccggtccagg ctgtttatgg tttcgctaag tctttgctca aagcactgaa agaagacggg      180
```

```
gacgcggtaa ttgttgtatt tgatgccaaa gcaccgagct tccgccacga agcttatggt    240
ggctacaagg caggacgcgc ccctacccca gaagatttcc cccgtcagct ggcattaatt    300
aaggagttag tagaccttct cggcttagcg cgtctggaag ttccgggtta tgaggcggac    360
gatgtccttg catccttggc taaaaaggcc gaaaaagagg gctacgaagt ccgcatcttg    420
acggcagaca aagatctgta ccagcttctg tctgaccgta ttcatgtttt gcaccctgaa    480
ggctacttaa tcactccggc ctggctctgg aaaagtacg gtctgcgtcc cgatcagtgg    540
gcggattatc gggctttgac gggagatgag agcgacaacc tgccaggagt taagggcatt    600
ggtgaaaaaa ccgcacgtaa gctgcttgaa gagtggggtt ccctggaagc cttgttaaaa    660
aatctggatc gtctcaagcc cgcaattcgt gaaaagatcc tggctcatat ggacgatctt    720
aaattaagtt gggacctggc caaggtgcgc accgatttac gcttgaagt ggattttgca    780 aaacgccgtg agccggaccg ggaacgttta cgcgctttct tagagcgtct ggaattcggt    840
tcactgcttc atgaattcgg tctgt                                          865

<210> SEQ ID NO 4
<211> LENGTH: 880
<212> TYPE: DNA
<213> ORGANISM: Artificial Sequence
<220> FEATURE:
<223> OTHER INFORMATION: TAQ DNA POLYMERASE CODON-OPTIMIZED SUB-FRAGMENT
      2

<400> SEQUENCE: 4
tcggttcact gcttcatgaa ttcggtctgt tagagtctcc taaagcactc gaagaggcac     60
cgtggccgcc cccagaaggt gcttttgttg gcttcgtact ttcccgtaag gagcctatgt    120
gggcagatct tctggcttta gcggctgcac gcggtggccg tgttcaccgg gccctgagc    180 catacaaagc gttacgtgat ctgaaggaag cacgtggctt gctggcaaaa gaccttttctg   240 ttttggccct gcgcgagggt cttggactgc cgccaggcga cgatcccatg ttattggcct    300
atctgttaga ccctagcaat accacacctg aaggggtcgc tcgtcggtat ggcggtgaat    360
ggactgagga agccggagag cgcgccgcat tgtccgaacg gctcttttgca aacttatggg   420 gtcgtctgga aggggaggaa cgtctgttat ggttgtatcg ggaagtcgaa cgtcctcttt    480
cggccgtatt agcgcatatg gaggcaacag gtgtgcgttt agatgtcgcg taccttcggg    540
ccttatcact ggaagttgca gaggaaatcg cccgtctcga ggctgaagtg ttccggttgg    600
ccggtcaccc gtttaacctc aactcccgtg accagctgga acgcgttta ttcgatgagc     660 ttgggcttcc cgcaattggc aaaaccgaaa agactggcaa acgcagtacg agcgctgccg    720
tccttgaggc actccgcgag gctcacccta ttgtagaaaa gatcctgcaa taccgtgagt    780
tgacgaagct taaaagcact tatattgatc ctctcccgga tctgatccat cctcgtaccg    840
gccgcttgca cacgtttc aaccagacgg cgactgcaac                            880

<210> SEQ ID NO 5
<211> LENGTH: 822
<212> TYPE: DNA
<213> ORGANISM: Artificial Sequence
<220> FEATURE:
<223> OTHER INFORMATION: TAQ DNA POLYMERASE CODON-OPTIMIZED SUB-FRAGMENT
      3

<400> SEQUENCE: 5
cacacgtttc aaccagacgg cgactgcaac cggccgtctg tctagctcgg atccaaatct     60
```

| | |
|---|---|
| ccagaacatt ccggtccgta caccettggg ccaacgtatc cgccgggcgt ttatcgctga | 120 |
| ggaaggatgg ttactggtcg cattggacta ctcgcagatt gagctgcgcg tcctcgcaca | 180 |
| tctctctggt gacgaaaatt taatccgcgt gtttcaagag gggcgtgata ttcacacaga | 240 |
| aactgcctca tggatgttcg gtgtcccacg tgaagcagtg gatcctttga tgcgccgtgc | 300 |
| agctaaaaca attaattttg gagtgctgta cggaatgagc gctcatcgct tgagtcagga | 360 |
| actggcaatc ccctacgagg aagcgcaggc attcatcgaa cgttactttc aatcgtttcc | 420 |
| gaaagttcgc gcatggatcg agaagacgct cgaggaaggt cgtcgtcggg gctatgtcga | 480 |
| aactctgttt ggtcgccgtc ggtacgtacc agatcttgaa gcccgcgtca atcggtacg | 540 |
| ggaggctgcg gagcgtatgg catttaatat gcctgtacag ggtactgcag ctgacctcat | 600 |
| gaaactggca atggtcaagc ttttcccgcg cttggaggaa atgggcgcac gtatgcttct | 660 |
| gcaggtccat gacgagctgg tgttagaagc ccctaaggag cgcgccgaag ctgtcgcgcg | 720 |
| cctcgctaaa gaagtgatgg agggcgttta cccattggcc gtaccctcg aagtggaggt | 780 |
| cggtattgga gaagattggt tatctgcaaa ggaagcggcc gc | 822 |

<210> SEQ ID NO 6
<211> LENGTH: 2507
<212> TYPE: DNA
<213> ORGANISM: Artificial Sequence
<220> FEATURE:
<223> OTHER INFORMATION: Complete codon-optimized Taq DNA polymerase DNA Sequence ("OptiTaq")

<400> SEQUENCE: 6

| | |
|---|---|
| catatgcgtg gtatgctgcc gttgttcgag cctaaaggcc gcgtactgtt agtcgatggt | 60 |
| catcacttgg cctatcggac gttccatgca ctcaaaggtc tgacgaccag tcgtggcgaa | 120 |
| ccggtccagg ctgtttatgg tttcgctaag tctttgctca agcactgaa agaagacggg | 180 |
| gacgcggtaa ttgttgtatt tgatgccaaa gcaccgagct ccgccacga agcttatggt | 240 |
| ggctacaagg caggacgcgc ccctacccca gaagatttcc ccgtcagct ggcattaatt | 300 |
| aaggagttag tagaccttct cggcttagcg cgtctggaag ttccgggtta tgaggcggac | 360 |
| gatgtccttg catccttggc taaaaaggcc gaaaagagg gctacgaagt ccgcatcttg | 420 |
| acggcagaca aagatctgta ccagcttctg tctgaccgta ttcatgtttt gcaccctgaa | 480 |
| ggctacttaa tcactccggc ctggctctgg aaaagtacg gtctgcgtcc cgatcagtgg | 540 |
| gcggattatc gggctttgac gggagatgag agcgacaacc tgccaggagt taagggcatt | 600 |
| ggtgaaaaaa ccgcacgtaa gctgcttgaa gagtgggggt tccctggaagc cttgttaaaa | 660 |
| aatctggatc gtctcaagcc cgcaattcgt gaaaagatcc tggctcatat ggacgatctt | 720 |
| aaattaagtt gggacctggc caaggtgcgc accgatttac gcttgaagt ggattttgca | 780 |
| aaacgccgtg agccggaccg ggaacgttta cgcgctttct tagagcgtct ggaattcgt | 840 |
| tcactgcttc atgaattcgg tctgttagag tctcctaaag cactcgaaga ggcaccgtgg | 900 |
| ccgccccag aaggtgcttt tgttggcttc gtactttccc gtaaggagcc tatgtgggca | 960 |
| gatcttctgg ctttagcggc tgcacgcggt ggccgtgttc accgggcccc tgagccatac | 1020 |
| aaagcgttac gtgatctgaa ggaagcacgt ggcttgctgg caaagacct ttctgttttg | 1080 |
| gcctgcgcg agggtcttgg actgccgcca ggcgacgatc ccatgttatt ggcctatctg | 1140 |
| ttagacccta gcaataccac acctgaaggg gtcgctcgtc ggtatggcgg tgaatggact | 1200 |
| gaggaagccg gagagcgcgc cgcattgtcc gaacggctct ttgcaaactt atggggtcgt | 1260 |

```
ctggaagggg aggaacgtct gttatggttg tatcgggaag tcgaacgtcc tctttcggcc    1320
gtattagcgc atatggaggc aacaggtgtg cgtttagatg tcgcgtacct tcgggcctta    1380
tcactggaag ttgcagagga aatcgcccgt ctcgaggctg aagtgttccg gttggccggt    1440
cacccgttta acctcaactc ccgtgaccag ctggaacgcg ttttattcga tgagcttggg    1500
cttcccgcaa ttgcaaaac cgaaaagact ggcaaacgca gtacgagcgc tgccgtcctt    1560
gaggcactcc gcgaggctca ccctattgta gaaaagatcc tgcaataccg tgagttgacg    1620
aagcttaaaa gcacttatat tgatcctctc ccggatctga tccatcctcg taccggccgc    1680
ttgcacacac gtttcaacca gacggcgact gcaaccggcc gtctgtctag ctcggatcca    1740
aatctccaga acattccggt ccgtacaccc ttgggccaac gtatccgccg ggcgtttatc    1800
gctgaggaag gatggttact ggtcgcattg gactactcgc agattgagct gcgcgtcctc    1860
gcacatctct ctggtgacga aaatttaatc cgcgtgtttc aagagggcg tgatattcac    1920 acagaaactg cctcatggat gttcggtgtc ccacgtgaag cagtggatcc tttgatgcgc    1980
cgtgcagcta aaacaattaa ttttggagtg ctgtacggaa tgagcgctca tcgcttgagt    2040
caggaactgg caatccccta cgaggaagcg caggcattca tcgaacgtta ctttcaatcg    2100
tttccgaaag ttcgcgcatg gatcgagaag acgctcgagg aaggtcgtcg tcggggctat    2160
gtcgaaactc tgtttggtcg ccgtcggtac gtaccagatc ttgaagcccg cgtcaaatcg    2220
gtacgggagc tgcggagcg tatggcattt aatatgcctg tacagggtac tgcagctgac    2280
ctcatgaaac tggcaatggt caagcttttc ccgcgcttgg aggaaatggg cgcacgtatg    2340
cttctgcagg tccatgacga gctggtgtta gaagcccta aggagcgcgc cgaagctgtc    2400
gcgcgcctcg ctaaagaagt gatggagggc gtttacccat tggccgtacc cctcgaagtg    2460
gaggtcggta ttggagaaga ttggttatct gcaaaggaag cggccgc                 2507
```

<210> SEQ ID NO 7
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 7

```
aatgggcgca cgtatgcttc tgcagattca tgacgagctg gtgttagaag ccc           53
```

<210> SEQ ID NO 8
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 8

```
gggcttctaa caccagctcg tcatgaatct gcagaagcat acgtgcgccc att           53
```

<210> SEQ ID NO 9
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 9

```
aatgggcgca cgtatgcttc tgcagttcca tgacgagctg gtgttagaag ccc           53
```

<210> SEQ ID NO 10
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 10
gggcttctaa caccagctcg tcatggaact gcagaagcat acgtgcgccc att        53

<210> SEQ ID NO 11
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 11
gggcgcacgt atgcttctgc aggtccagga cgagctggtg ttagaagccc cta        53

<210> SEQ ID NO 12
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 12 tagggggcttc taacaccagc tcgtcctgga cctgcagaag catacgtgcg ccc        53

<210> SEQ ID NO 13
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 13
caaccagacg gcgactgcaa ccggccatct gtctagctcg gatccaaatc tcc        53

<210> SEQ ID NO 14
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 14
ggagatttgg atccgagcta gacagatggc cggttgcagt cgccgtctgg ttg        53

<210> SEQ ID NO 15
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 15
tctgtctagc tcggatccaa atctcaaaaa cattccggtc cgtacaccct tgg        53

<210> SEQ ID NO 16
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 16
ccaagggtgt acggaccgga atgtttttga gatttggatc cgagctagac aga        53

<210> SEQ ID NO 17
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 17
gcgccgtgca gctaaaacaa ttaattgggg agtgctgtac ggaatgagcg ctc        53

<210> SEQ ID NO 18
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 18
gagcgctcat tccgtacagc actccccaat taattgtttt agctgcacgg cgc        53

<210> SEQ ID NO 19
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 19
cgtgtttcaa gagggcgtg atatttggac agaaactgcc tcatggatgt tcg         53

<210> SEQ ID NO 20
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 20
cgaacatcca tgaggcagtt tctgtccaaa tatcacgccc ctcttgaaac acg        53

<210> SEQ ID NO 21
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 21
cgcattggac tactcgcaga ttgagatgcg cgtcctcgca catctctctg gtg        53

<210> SEQ ID NO 22
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 22
caccagagag atgtgcgagg acgcgcatct caatctgcga gtagtccaat gcg        53

<210> SEQ ID NO 23
<211> LENGTH: 56

```
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 23
ggtcgcattg gactactcgc agattctgga gcgcgtcctc gcacatctct ctggtg        56

<210> SEQ ID NO 24
<211> LENGTH: 56
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 24
caccagagag atgtgcgagg acgcgctcca gaatctgcga gtagtccaat gcgacc        56

<210> SEQ ID NO 25
<211> LENGTH: 81
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 25
cgtgaagcag tggatccttt gatgcgccgt gaagctaaaa catggaattt gggagtgctg    60
tacggaatga gcgctcatcg c                                              81

<210> SEQ ID NO 26
<211> LENGTH: 81
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 26
gcgatgagcg ctcattccgt acagcactcc caaattccat gttttagctt cacggcgcat    60
caaaggatcc actgcttcac g                                              81

<210> SEQ ID NO 27
<211> LENGTH: 59
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 27
ggaaatgggc gcacgtatgc ttctgatcgt cttcgacgag ctggtgttag aagccccta     59

<210> SEQ ID NO 28
<211> LENGTH: 59
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 28 tagggggcttc taacaccagc tcgtcgaaga cgatcagaag catacgtgcg cccatttcc    59

<210> SEQ ID NO 29
<211> LENGTH: 59
<212> TYPE: DNA
<213> ORGANISM: Artificial Sequence
<220> FEATURE:
```

<223> OTHER INFORMATION: SYNTHETIC DNA OLIGONUCLEOTIDE

<400> SEQUENCE: 29
ggaaatgggc gcacgtatgc ttctgatttt gctggacgag ctggtgttag aagcccta    59

<210> SEQ ID NO 30
<211> LENGTH: 59
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 30 tagggcttc taacaccagc tcgtccagca aaatcagaag catacgtgcg cccatttcc    59

<210> SEQ ID NO 31
<211> LENGTH: 59
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 31
ggaaatgggc gcacgtatgc ttctgtcctt caacgacgag ctggtgttag aagcccta    59

<210> SEQ ID NO 32
<211> LENGTH: 59
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 32 tagggcttc taacaccagc tcgtcgttga aggacagaag catacgtgcg cccatttcc    59

<210> SEQ ID NO 33
<211> LENGTH: 59
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 33
ggaaatgggc gcacgtatgc ttctgccgtt acaggacgag ctggtgttag aagcccta    59

<210> SEQ ID NO 34
<211> LENGTH: 59
<212> TYPE: DNA
<213> ORGANISM: Artificial Sequence
<220> FEATURE:
<223> OTHER INFORMATION:
      ggaaatgggcgcacgtatgcttctgCCGTTACAGgacgagctggtgttagaagcccta

<400> SEQUENCE: 34 tagggcttc taacaccagc tcgtcctgta acggcagaag catacgtgcg cccatttcc    59

<210> SEQ ID NO 35
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 35
gcgtatggca tttaatatgc ctgtagcggg tactgcagct gacctcatga aac    53

<210> SEQ ID NO 36
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 36
gtttcatgag gtcagctgca gtacccgcta caggcatatt aaatgccata cgc        53

<210> SEQ ID NO 37
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 37
acgtgaagca gtggatcctt tgatgcaccg tgcagctaaa acaattaatt ttg        53

<210> SEQ ID NO 38
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 38
caaaattaat tgttttagct gcacggtgca tcaaaggatc cactgcttca cgt        53

<210> SEQ ID NO 39
<211> LENGTH: 51
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 39
aatgggcgca cgtatgcttc tgcagttcca ggacgagctg gtgttagaag c          51

<210> SEQ ID NO 40
<211> LENGTH: 51
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 40
gcttctaaca ccagctcgtc ctggaactgc agaagcatac gtgcgcccat t          51

<210> SEQ ID NO 41
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 41
aatgggcgca cgtatgcttc tgcagctgca ggacgagctg gtgttagaag ccc        53

<210> SEQ ID NO 42
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

```
<400> SEQUENCE: 42
gggcttctaa caccagctcg tcctgcagct gcagaagcat acgtgcgccc att        53

<210> SEQ ID NO 43
<211> LENGTH: 21
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 43
gactttgctt tccttggtca g                                           21

<210> SEQ ID NO 44
<211> LENGTH: 22
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 44
ggcttatatc caacacttcg tg                                          22

<210> SEQ ID NO 45
<211> LENGTH: 26
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (1)..(1)
<223> OTHER INFORMATION: 5'-FAM (6-carboxyfluorescein)
<220> FEATURE:
<221> NAME/KEY: misc_feature
<222> LOCATION: (9)..(10)
<223> OTHER INFORMATION: ZEN INTERNAL FLUORESCENCE QUENCHER BETWEEN
      RESIDUES 9 AND 10.
<220> FEATURE:
<221> NAME/KEY: misc_feature
<222> LOCATION: (26)..(26)
<223> OTHER INFORMATION: 3'-IBFQ ( Iowa Black FQ (fluorescence
      quencher))

<400> SEQUENCE: 45
atggtcaagg tcgcaagctt gctggt                                      26

<210> SEQ ID NO 46
<211> LENGTH: 96
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 46
gactttgctt tccttggtca ggcagtataa tccaaagatg gtcaaggtcg caagcttgct   60
ggtgaaaagg accccacgaa gtgttggata taagcc                            96

<210> SEQ ID NO 47
<211> LENGTH: 18
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (18)..(18)
```

<223> OTHER INFORMATION: RNA RESIDUE

<400> SEQUENCE: 47
tgtgcagaag gatggagu                                                        18

<210> SEQ ID NO 48
<211> LENGTH: 20
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (20)..(20)
<223> OTHER INFORMATION: RNA RESIDUE

<400> SEQUENCE: 48
ctggtgcttc tctcaggata                                                      20

<210> SEQ ID NO 49
<211> LENGTH: 25
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (1)..(1)
<223> OTHER INFORMATION: 5'-hexachlorofluorescein
<220> FEATURE:
<221> NAME/KEY: misc_feature
<222> LOCATION: (9)..(10)
<223> OTHER INFORMATION: ZEN INTERNAL FLUORESCENCE QUENCHER BETWEEN
      RESIDUES 9 AND 10.
<220> FEATURE:
<221> NAME/KEY: misc_feature
<222> LOCATION: (25)..(25)
<223> OTHER INFORMATION: 3'-IBFQ (Iowa Black FQ (fluorescence quencher))

<400> SEQUENCE: 49
tggaatatgc cctgcgtaaa ctgga                                                25

<210> SEQ ID NO 50
<211> LENGTH: 144
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 50
tgtgcagaag gatggagtgg ggatggtcga gtatctcaga aaagaagaca tggaatatgc          60
cctgcgtaaa ctggatgaca ccaaattccg ctctcatgag ggtgaaactt cctacatccg         120
agtttatcct gagagaagca ccag                                                144

<210> SEQ ID NO 51
<211> LENGTH: 103
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 51
agctctgccc aaagattacc ctgacagcta agtggcagtg gaagttggcc tcagaagtag          60
tggccagctg tgtgtcgggg aacagtaaag gcatgaagct cag                           103

<210> SEQ ID NO 52

```
<211> LENGTH: 103
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 52
agctctgccc aaagattacc ctgacagcta agtggcagtg gaagttggcc tcagaagtag      60
tggccagctg tgtgtcgggg cacagtaaag gcatgaagct cag                       103

<210> SEQ ID NO 53
<211> LENGTH: 103
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 53
agctctgccc aaagattacc ctgacagcta agtggcagtg gaagttggcc tcagaagtag      60
tggccagctg tgtgtcgggg gacagtaaag gcatgaagct cag                       103

<210> SEQ ID NO 54
<211> LENGTH: 103
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 54
agctctgccc aaagattacc ctgacagcta agtggcagtg gaagttggcc tcagaagtag      60
tggccagctg tgtgtcgggg tacagtaaag gcatgaagct cag                       103

<210> SEQ ID NO 55
<211> LENGTH: 23
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 55
ctgagcttca tgcctttact gtt                                              23

<210> SEQ ID NO 56
<211> LENGTH: 23
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 56
ctgagcttca tgcctttact gtc                                              23

<210> SEQ ID NO 57
<211> LENGTH: 23
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 57
ctgagcttca tgcctttact gta                                              23

<210> SEQ ID NO 58
<211> LENGTH: 23
```

```
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 58
ctgagcttca tgcctttact gtg                                              23

<210> SEQ ID NO 59
<211> LENGTH: 22
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 59
ctgagcttca tgcctttact gt                                               22

<210> SEQ ID NO 60
<211> LENGTH: 23
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 60
agctctgccc aaagattacc ctg                                              23

<210> SEQ ID NO 61
<211> LENGTH: 28
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (1)..(1)
<223> OTHER INFORMATION: 5'-FAM (6-carboxyfluorescein)
<220> FEATURE:
<221> NAME/KEY: misc_feature
<222> LOCATION: (9)..(10)
<223> OTHER INFORMATION: ZEN INTERNAL FLUORESCENCE QUENCHER BETWEEN
      RESIDUES 9 AND 10.
<220> FEATURE:
<221> NAME/KEY: misc_feature
<222> LOCATION: (28)..(28)
<223> OTHER INFORMATION: 3'-IBFQ (Iowa Black FQ fluorescence quencher))

<400> SEQUENCE: 61
ttctgaggcc aacttccact gccactta                                         28

<210> SEQ ID NO 62
<211> LENGTH: 23
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE

<400> SEQUENCE: 62
ctgagcttca tgcctttact gtu                                              23

<210> SEQ ID NO 63
<211> LENGTH: 23
<212> TYPE: DNA
<213> ORGANISM: Artificial Sequence
```

<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE

<400> SEQUENCE: 63
ctgagcttca tgcctttact gtc                                           23

<210> SEQ ID NO 64
<211> LENGTH: 23
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE

<400> SEQUENCE: 64
ctgagcttca tgcctttact gta                                           23

<210> SEQ ID NO 65
<211> LENGTH: 23
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE

<400> SEQUENCE: 65
ctgagcttca tgcctttact gtg                                           23

<210> SEQ ID NO 66
<211> LENGTH: 27
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'-C3 SPACER (propanediol)

<400> SEQUENCE: 66
ctgagcttca tgcctttact gtucccc                                       27

<210> SEQ ID NO 67
<211> LENGTH: 27
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'-C3 SPACER (PROPANEDIOL)

```
<400> SEQUENCE: 67
ctgagcttca tgcctttact gtccccc                                              27

<210> SEQ ID NO 68
<211> LENGTH: 27
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'-C3 SPACER (PROPANEDIOL)

<400> SEQUENCE: 68
ctgagcttca tgcctttact gtacccc                                              27

<210> SEQ ID NO 69
<211> LENGTH: 27
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'-C3 SPACER (PROPANEDIOL)

<400> SEQUENCE: 69
ctgagcttca tgcctttact gtgcccc                                              27

<210> SEQ ID NO 70
<211> LENGTH: 25
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (24)..(25)
<223> OTHER INFORMATION: TWO INTERNAL C3 SPACERS (PROPANEDIOL) BETWEEN
      RESIDUES 24 AND 25.

<400> SEQUENCE: 70
ctgagcttca tgcctttact gtucc                                                25

<210> SEQ ID NO 71
<211> LENGTH: 25
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (24)..(25)
```

```
<223> OTHER INFORMATION: TWO INTERNAL C3 SPACERS (PROPANEDIOL) BETWEEN
      RESIDUES 24 AND 25.

<400> SEQUENCE: 71
ctgagcttca tgcctttact gtccc                                              25

<210> SEQ ID NO 72
<211> LENGTH: 25
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (24)..(25)
<223> OTHER INFORMATION: TWO INTERNAL C3 SPACERS (PROPANEDIOL) BETWEEN
      RESIDUES 24 AND 25.

<400> SEQUENCE: 72
ctgagcttca tgcctttact gtacc                                              25

<210> SEQ ID NO 73
<211> LENGTH: 25
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (24)..(25)
<223> OTHER INFORMATION: TWO INTERNAL C3 SPACERS (PROPANEDIOL) BETWEEN
      RESIDUES 24 AND 25.

<400> SEQUENCE: 73
ctgagcttca tgcctttact gtgcc                                              25

<210> SEQ ID NO 74
<211> LENGTH: 21
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 74
ctcactctaa accccagcat t                                                  21

<210> SEQ ID NO 75
<211> LENGTH: 22
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 75
cagcctcatc caaaagagga aa                                                 22

<210> SEQ ID NO 76
<211> LENGTH: 27
<212> TYPE: DNA
<213> ORGANISM: Artificial Sequence
<220> FEATURE:
```

<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'-C3 SPACER (PROPANEDIOL)

<400> SEQUENCE: 76
cagcctcatc caaaagagga aacagga    27

<210> SEQ ID NO 77
<211> LENGTH: 27
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'-C3 SPACER (PROPANEDIOL)

<400> SEQUENCE: 77
cagcctcatc caaaagagga aauagga    27

<210> SEQ ID NO 78
<211> LENGTH: 25
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (24)..(25)
<223> OTHER INFORMATION: TWO INTERNAL C3 SPACERS (PROPANEDIOL) BETWEEN
      RESIDUES 24 AND 25.

<400> SEQUENCE: 78
cagcctcatc caaaagagga aacaa    25

<210> SEQ ID NO 79
<211> LENGTH: 25
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (24)..(25)
<223> OTHER INFORMATION: TWO INTERNAL C3 SPACERS (PROPANEDIOL) BETWEEN
      RESIDUES 24 AND 25.

<400> SEQUENCE: 79
cagcctcatc caaaagagga aauaa    25

<210> SEQ ID NO 80
<211> LENGTH: 22

```
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (1)..(1)
<223> OTHER INFORMATION: 5'-FAM (6-carboxyfluorescein)
<220> FEATURE:
<221> NAME/KEY: misc_feature
<222> LOCATION: (22)..(22)
<223> OTHER INFORMATION: 3'-IBFQ (Iowa Black FQ (fluorescence quencher))

<400> SEQUENCE: 80
cccagagctc cctcagactc ct                                          22

<210> SEQ ID NO 81
<211> LENGTH: 85
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 81
cagcctcatc caaaagagga aataggaccc cagagctccc tcagactcct caggaaacac    60
agacaatgct ggggtttaga gtgag                                        85

<210> SEQ ID NO 82
<211> LENGTH: 2507
<212> TYPE: DNA
<213> ORGANISM: Artificial Sequence
<220> FEATURE:
<223> OTHER INFORMATION: NUCLEOTIDE SEQUENCE OF MUTANT ID 2 (V783F)

<400> SEQUENCE: 82
catatgcgtg gtatgctgcc gttgttcgag cctaaaggcc gcgtactgtt agtcgatggt    60
catcacttgg cctatcggac gttccatgca ctcaaaggtc tgacgaccag tcgtggcgaa   120
ccggtccagg ctgtttatgg tttcgctaag tctttgctca agcactgaa agaagacggg   180 gacgcggtaa ttgttgtatt tgatgccaaa gcaccgagct ccgccacga agcttatggt   240 ggctacaagg caggacgcgc ccctacccca gaagatttcc ccgtcagct ggcattaatt   300 aaggagttag tagaccttct cggcttagcg cgtctggaag ttccgggtta tgaggcggac   360
gatgtccttg catccttggc taaaaaggcc gaaaagagg gctacgaagt ccgcatcttg   420
acggcagaca aagatctgta ccagcttctg tctgaccgta ttcatgtttt gcaccctgaa   480
ggctacttaa tcactccggc ctggctctgg gaaaagtacg gtctgcgtcc cgatcagtgg   540
gcggattatc gggctttgac gggagatgag agcgacaacc tgccaggagt aagggcatt    600 ggtgaaaaaa ccgcacgtaa gctgcttgaa gagtggggtt ccctggaagc cttgttaaaa   660
aatctggatc gtctcaagcc cgcaattcgt gaaaagatcc tggctcatat ggacgatctt   720
aaattaagtt gggacctggc caaggtgcgc accgatttac gcttgaagt ggattttgca    780 aaacgccgtg agccggaccg ggaacgttta cgcgcttct tagagcgtct ggaattcggt   840
tcactgcttc atgaattcgg tctgttagag tctcctaaag cactcgaaga ggcaccgtgg   900 ccgccccag aaggtgcttt tgttggcttc gtactttccc gtaaggagcc tatgtgggca    960
gatcttctgg ctttagcggc tgcacgcggt ggccgtgttc accgggcccc tgagccatac  1020
aaagcgttac gtgatctgaa ggaagcacgt ggcttgctgg caaaagacct ttctgttttg  1080
gccctgcgcg agggtcttgg actgccgcca ggcgacgatc ccatgttatt ggcctatctg  1140
```

```
ttagacccta gcaataccac acctgaaggg gtcgctcgtc ggtatggcgg tgaatggact   1200
gaggaagccg gagagcgcgc cgcattgtcc gaacggctct ttgcaaactt atggggtcgt   1260
ctggaagggg aggaacgtct gttatggttg tatcgggaag tcgaacgtcc tctttcggcc   1320
gtattagcgc atatggaggc aacaggtgtg cgtttagatg tcgcgtacct tcgggcctta   1380
tcactggaag ttgcagagga atcgcccgt ctcgaggctg aagtgttccg gttggccggt   1440
cacccgttta acctcaactc ccgtgaccag ctggaacgcg ttttattcga tgagcttggg   1500
cttcccgcaa ttggcaaaac cgaaaagact ggcaaacgca gtacgagcgc tgccgtcctt   1560
gaggcactcc gcgaggctca ccctattgta gaaaagatcc tgcaataccg tgagttgacg   1620
aagcttaaaa gcacttatat tgatcctctc ccggatctga tccatcctcg taccggccgc   1680
ttgcacacac gtttcaacca gacggcgact gcaaccggcc gtctgtctag ctcggatcca   1740
aatctccaga acattccggt ccgtacaccc ttgggccaac gtatccgccg ggcgtttatc   1800
gctgaggaag gatggttact ggtcgcattg gactactcgc agattgagct gcgcgtcctc   1860
gcacatctct ctggtgacga aaatttaatc cgcgtgtttc aagaggggcg tgatattcac   1920
acagaaactg cctcatggat gttcggtgtc ccacgtgaag cagtggatcc tttgatgcgc   1980
cgtgcagcta aaacaattaa ttttggagtg ctgtacggaa tgagcgctca tcgcttgagt   2040
caggaactgg caatcccctta cgaggaagcg caggcattca tcgaacgtta ctttcaatcg   2100
tttccgaaag ttcgcgcatg gatcgagaag acgctcgagg aaggtcgtcg tcggggctat   2160
gtcgaaactc tgtttggtcg ccgtcggtac gtaccagatc ttgaagcccg cgtcaaatcg   2220
gtacgggagc ctgcggagcg tatggcattt aatatgcctg tacagggtac tgcagctgac   2280
ctcatgaaac tggcaatggt caagcttttc ccgcgcttgg aggaaatggg cgcacgtatg   2340
cttctgcagt tccatgacga gctggtgtta gaagccccta aggagcgcgc cgaagctgtc   2400
gcgcgcctcg ctaaagaagt gatggagggc gtttacccat tggccgtacc cctcgaagtg   2460
gaggtcggta ttggagaaga ttggttatct gcaaaggaag cggccgc                 2507
```

<210> SEQ ID NO 83
<211> LENGTH: 834
<212> TYPE: PRT
<213> ORGANISM: Artificial Sequence
<220> FEATURE:
<223> OTHER INFORMATION: AMINO ACID SEQUENCE OF MUTANT ID 2 (V783F)

<400> SEQUENCE: 83

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125
```

```
Ala Glu Lys Glu Gly Tyr Glu Val Arg Ile Leu Thr Ala Asp Lys Asp
            130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
530                 535                 540
```

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Phe His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Ala Ala

<210> SEQ ID NO 84
<211> LENGTH: 2507
<212> TYPE: DNA
<213> ORGANISM: Artificial Sequence
<220> FEATURE:
<223> OTHER INFORMATION: NUCLEOTIDE SEQUENCE OF MUTANT ID 3 (H784Q)

<400> SEQUENCE: 84
catatgcgtg gtatgctgcc gttgttcgag cctaaaggcc gcgtactgtt agtcgatggt      60
catcacttgg cctatcggac gttccatgca ctcaaaggtc tgacgaccag tcgtggcgaa     120
ccggtccagg ctgtttatgg tttcgctaag tctttgctca aagcactgaa agaagacggg     180
gacgcggtaa ttgttgtatt tgatgccaaa gcaccgagct ccgccacga agcttatggt      240 ggctacaagg caggacgcgc ccctacccca gaagatttcc cccgtcagct ggcattaatt     300
aaggagttag tagaccttct cggcttagcg cgtctggaag ttccgggtta tgaggcggac     360
gatgtccttg catccttggc taaaaaggcc gaaaaagagg gctacgaagt ccgcatcttg     420

-continued

```
acggcagaca aagatctgta ccagcttctg tctgaccgta ttcatgtttt gcaccctgaa    480
ggctacttaa tcactccggc ctggctctgg gaaaagtacg gtctgcgtcc cgatcagtgg    540
gcggattatc gggctttgac gggagatgag agcgacaacc tgccaggagt taagggcatt    600
ggtgaaaaaa ccgcacgtaa gctgcttgaa gagtgggggtt ccctggaagc cttgttaaaa    660
aatctggatc gtctcaagcc cgcaattcgt gaaaagatcc tggctcatat ggacgatctt    720
aaattaagtt gggacctggc caaggtgcgc accgatttac gcttgaagt ggattttgca    780 aaacgccgtg agccggaccg ggaacgttta cgcgctttct tagagcgtct ggaattcggt    840
tcactgcttc atgaattcgg tctgttagag tctcctaaag cactcgaaga ggcaccgtgg    900
ccgcccccag aaggtgcttt tgttggcttc gtactttccc gtaaggagcc tatgtgggca    960
gatcttctgg ctttagcggc tgcacgcggg ggccgtgttc accgggcccc tgagccatac   1020
aaagcgttac gtgatctgaa ggaagcacgt ggcttgctgg caaaagacct ttctgttttg   1080
gccctgcgcg agggtcttgg actgccgcca ggcgacgatc ccatgttatt ggcctatctg   1140 ttagaccta gcaataccac acctgaaggg gtcgctcgtc ggtatggcgg tgaatggact   1200
gaggaagccg gagagcgcgc cgcattgtcc gaacggctct ttgcaaactt atggggtcgt   1260
ctggaagggg aggaacgtct gttatggttg tatcgggaag tcgaacgtcc tctttcggcc   1320
gtattagcgc atatggaggc aacaggtgtg cgtttagatg tcgcgtacct tcgggccta   1380 tcactggaag ttgcagagga atcgcccgt ctcgaggctg aagtgttccg gttggccggt   1440
cacccgttta acctcaactc ccgtgaccag ctggaacgcg ttttattcga tgagcttggg   1500
cttcccgcaa ttggcaaaac cgaaaagact ggcaaacgca gtacgagcgc tgccgtcctt   1560
gaggcactcc gcgaggctca ccctattgta gaaaagatcc tgcaataccg tgagttgacg   1620
aagcttaaaa gcacttatat tgatcctctc ccggatctga tccatcctcg taccggccgc   1680
ttgcacacac gtttcaacca gacggcgact gcaaccggcc gtctgtctag ctcggatcca   1740
aatctccaga acattccggt ccgtacaccc ttgggccaac gtatccgccg ggcgtttatc   1800
gctgaggaag gatggttact ggtcgcattg gactactcgc agattgagct gcgcgtcctc   1860
gcacatctct ctggtgacga aaatttaatc cgcgtgtttc aagaggggcg tgatattcac   1920
acagaaactg cctcatggat gttcggtgtc ccacgtgaag cagtggatcc tttgatgcgc   1980
cgtgcagcta aaacaattaa ttttggagtg ctgtacggaa tgagcgctca tcgcttgagt   2040
caggaactgg caatcccta cgaggaagcg caggcattca tcgaacgtta ctttcaatcg   2100
tttccgaaag ttcgcgcatg gatcgagaag acgctcgagg aaggtcgtcg tcggggctat   2160
gtcgaaactc tgtttggtcg ccgtcggtac gtaccagatc ttgaagcccg cgtcaaatcg   2220
gtacgggagg ctgcggagcg tatggcattt aatatgcctg tacagggtac tgcagctgac   2280
ctcatgaaac tggcaatggt caagcttttc ccgcgcttgg aggaaatggg cgcacgtatg   2340
cttctgcagg tccaggacga gctggtgtta gaagcccta aggagcgcgc cgaagctgtc   2400
gcgcgcctcg ctaaagaagt gatggagggc gtttacccat ggccgtacc cctcgaagtg   2460 gaggtcggta ttggagaaga ttggttatct gcaaaggaag cggccgc              2507
```

<210> SEQ ID NO 85
<211> LENGTH: 834
<212> TYPE: PRT
<213> ORGANISM: Artificial Sequence
<220> FEATURE:
<223> OTHER INFORMATION: AMINO ACID SEQUENCE OF MUTANT ID 3 (H784Q)

<400> SEQUENCE: 85

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415
```

```
Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val Gln
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830
```

Ala Ala

<210> SEQ ID NO 86
<211> LENGTH: 2507
<212> TYPE: DNA
<213> ORGANISM: Artificial Sequence
<220> FEATURE:
<223> OTHER INFORMATION: NUCLEOTIDE SEQUENCE OF MUTANT ID 10 (A661E,
      I665W, F667L)

<400> SEQUENCE: 86

```
catatgcgtg gtatgctgcc gttgttcgag cctaaaggcc gcgtactgtt agtcgatggt      60
catcacttgg cctatcggac gttccatgca ctcaaaggtc tgacgaccag tcgtggcgaa     120
ccggtccagg ctgtttatgg tttcgctaag tctttgctca aagcactgaa agaagacggg     180
gacgcggtaa ttgttgtatt tgatgccaaa gcaccgagct tccgccacga agcttatggt     240
ggctacaagg caggacgcgc ccctacccca gaagatttcc cccgtcagct ggcattaatt     300
aaggagttag tagaccttct cggcttagcg cgtctggaag ttccgggtta tgaggcggac     360
gatgtccttg catccttggc taaaaaggcc gaaaagagg gctacgaagt ccgcatcttg      420
acggcagaca agatctgta ccagcttctg tctgaccgta ttcatgtttt gcaccctgaa      480
ggctacttaa tcactccggc ctggctctgg gaaaagtacg gtctgcgtcc cgatcagtgg     540
gcggattatc gggctttgac gggagatgag agcgacaacc tgccaggagt taagggcatt     600
ggtgaaaaaa ccgcacgtaa gctgcttgaa gagtggggtt ccctggaagc cttgttaaaa     660
aatctggatc gtctcaagcc cgcaattcgt gaaaagatcc tggctcatat ggacgatctt     720
aaattaagtt gggacctggc caaggtgcgc accgatttac cgcttgaagt ggattttgca     780
aaacgccgtg agccggaccg ggaacgttta cgcgctttct tagagcgtct ggaattcggt     840
tcactgcttc atgaattcgg tctgttagag tctcctaaag cactcgaaga ggcaccgtgg     900
ccgcccccag aaggtgcttt tgttggcttc gtactttccc gtaaggagcc tatgtgggca     960
gatcttctgg ctttagcggc tgcacgcggt ggccgtgttc accgggcccc tgagccatac    1020
aaagcgttac gtgatctgaa ggaagcacgt ggcttgctgg caaaagacct ttctgttttg    1080
gccctgcgcg agggtcttgg actgccgcca ggcgacgatc ccatgttatt ggcctatctg    1140
ttagacccta gcaataccac acctgaaggg gtcgctcgtc ggtatggcgg tgaatggact    1200
gaggaagccg gagagcgcgc cgcattgtcc gaacggctct tgcaaactt atggggtcgt     1260
ctggaagggg aggaacgtct gttatggttg tatcgggaag tcgaacgtcc tctttcggcc    1320
gtattagcgc atatggaggc aacaggtgtg cgtttagatg tcgcgtacct tcgggcctta    1380
tcactggaag ttgcagagga atcgcccgt ctcgaggctg aagtgttccg gttggccggt     1440
cacccgttta acctcaactc ccgtgaccag ctggaacgcg ttttattcga tgagcttggg    1500
cttcccgcaa ttggcaaaac cgaaaagact ggcaaacgca gtacgagcgc tgccgtcctt    1560
gaggcactcc gcgaggctca ccctattgta gaaaagatcc tgcaataccg tgagttgacg    1620
aagcttaaaa gcacttatat tgatcctctc ccggatctga tccatcctcg taccggccgc    1680
ttgcacacac gtttcaacca gacggcgact gcaaccggcc gtctgtctag ctcggatcca    1740
aatctccaga acattccggt ccgtacaccc ttgggccaac gtatccgccg ggcgtttatc    1800
gctgaggaag gatggttact ggtcgcattg gactactcgc agattgagct gcgcgtcctc    1860
gcacatctct ctggtgacga aaatttaatc cgcgtgtttc aagagggggcg tgatattcac    1920
acagaaactg cctcatggat gttcggtgtc ccacgtgaag cagtggatcc tttgatgcgc    1980
```

```
cgtgaagcta aacatggaa tttgggagtg ctgtacggaa tgagcgctca tcgcttgagt    2040
caggaactgg caatcccta cgaggaagcg caggcattca tcgaacgtta ctttcaatcg    2100
tttccgaaag ttcgcgcatg gatcgagaag acgctcgagg aaggtcgtcg tcggggctat   2160
gtcgaaactc tgtttggtcg ccgtcggtac gtaccagatc ttgaagcccg cgtcaaatcg   2220
gtacgggagg ctgcggagcg tatggcattt aatatgcctg tacagggtac tgcagctgac   2280
ctcatgaaac tggcaatggt caagcttttc ccgcgcttgg aggaaatggg cgcacgtatg   2340
cttctgcagg tccatgacga gctggtgtta gaagccccta aggagcgcgc cgaagctgtc   2400
gcgcgcctcg ctaaagaagt gatggagggc gtttacccat ggccgtacc cctcgaagtg    2460 gaggtcggta ttggagaaga ttggttatct gcaaaggaag cggccgc                2507
```

<210> SEQ ID NO 87
<211> LENGTH: 834
<212> TYPE: PRT
<213> ORGANISM: Artificial Sequence
<220> FEATURE:
<223> OTHER INFORMATION: AMINO ACID SEQUENCE OF MUTANT ID 10 (A661E, I665W, F667L)

<400> SEQUENCE: 87

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270
```

```
Leu Glu Arg Leu Glu Phe Gly Ser Leu Leu His Glu Phe Gly Leu Leu
            275                 280                 285

Glu Ser Pro Lys Ala Leu Glu Ala Pro Trp Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
                355                 360                 365

Pro Gly Asp Asp Pro Met Leu Leu Ala Tyr Leu Leu Asp Pro Ser Asn
        370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Glu Ala Lys Thr Trp Asn Leu Gly Val Leu Tyr Gly
                660                 665                 670

Met Ser Ala His Arg Leu Ser Gln Glu Leu Ala Ile Pro Tyr Glu Glu
                675                 680                 685
```

```
Ala Gln Ala Phe Ile Glu Arg Tyr Phe Gln Ser Phe Pro Lys Val Arg
        690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
        740                 745                 750
Val Gln Gly Thr Ala Ala Asp Leu Met Lys Leu Ala Met Val Lys Leu
            755                 760                 765
Phe Pro Arg Leu Glu Glu Met Gly Ala Arg Met Leu Leu Gln Val His
770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
            820                 825                 830
Ala Ala

<210> SEQ ID NO 88
<211> LENGTH: 2507
<212> TYPE: DNA
<213> ORGANISM: Artificial Sequence
<220> FEATURE:
<223> OTHER INFORMATION: NUCLEOTIDE SEQUENCE OF  MUTANT ID 18 (V783L,
      H784Q)

<400> SEQUENCE: 88
catatgcgtg gtatgctgcc gttgttcgag cctaaaggcc gcgtactgtt agtcgatggt      60
catcacttgg cctatcggac gttccatgca ctcaaaggtc tgacgaccag tcgtggcgaa     120
ccggtccagg ctgtttatgg tttcgctaag tcttttgctca aagcactgaa agaagacggg     180
gacgcggtaa ttgttgtatt tgatgccaaa gcaccgagct ccgccacga agcttatggt      240 ggctacaagg caggacgcgc ccctacccca gaagatttcc cccgtcagct ggcattaatt     300
aaggagttag tagaccttct cggcttagcg cgtctggaag ttccgggtta tgaggcggac     360
gatgtccttg catccttggc taaaaaggcc gaaaagagg gctacgaagt ccgcatcttg     420
acggcagaca aagatctgta ccagcttctg tctgaccgta ttcatgtttt gcaccctgaa     480
ggctacttaa tcactccggc ctggctctgg gaaaagtacg gtctgcgtcc cgatcagtgg     540
gcggattatc gggctttgac gggagatgag agcgacaacc tgccaggagt taagggcatt     600
ggtgaaaaaa ccgcacgtaa gctgcttgaa gagtggggtt ccctggaagc cttgttaaaa     660
aatctggatc gtctcaagcc cgcaattcgt gaaaagatcc tggctcatat ggacgatctt     720
aaattaagtt gggacctggc caaggtgcgc accgatttac gcttgaagt ggattttgca      780 aaacgccgtg agccggaccg ggaacgttta cgcgctttct tagagcgtct ggaattcggt     840
tcactgcttc atgaattcgg tctgttagag tctcctaaag cactcgaaga ggcaccgtgg     900
ccgcccccag aagtgctttt tgttggcttc gtactttccc gtaaggagcc tatgtgggca     960
gatcttctgg ctttagcggc tgcacgcggt ggccgtgttc accgggcccc tgagccatac    1020
aaagcgttac gtgatctgaa ggaagcacgt ggcttgctgg caaaagacct ttctgttttg    1080
gccctgcgcg agggtcttgg actgccgcca ggcgacgatc ccatgttatt ggcctatctg    1140
ttagacccta gcaataccac acctgaaggg gtcgctcgtc ggtatggcgg tgaatggact    1200
```

```
gaggaagccg agagcgcgc cgcattgtcc gaacggctct ttgcaaactt atggggtcgt    1260
ctggaagggg aggaacgtct gttatggttg tatcggaag tcgaacgtcc tctttcggcc    1320
gtattagcgc atatggaggc aacaggtgtg cgtttagatg tcgcgtacct tcgggcctta    1380
tcactggaag ttgcagagga aatcgcccgt ctcgaggctg aagtgttccg gttggccggt    1440
cacccgttta acctcaactc ccgtgaccag ctggaacgcg ttttattcga tgagcttggg    1500
cttcccgcaa ttggcaaaac cgaaaagact ggcaaacgca gtacgagcgc tgccgtcctt    1560
gaggcactcc gcgaggctca ccctattgta gaaaagatcc tgcaataccg tgagttgacg    1620
aagcttaaaa gcacttatat tgatcctctc ccggatctga tccatcctcg taccggccgc    1680
ttgcacacac gtttcaacca gacggcgact gcaaccggcc gtctgtctag ctcggatcca    1740
aatctccaga acattccggt ccgtacaccc ttgggccaac gtatccgccg ggcgtttatc    1800
gctgaggaag gatggttact ggtcgcattg gactactcgc agattgagct gcgcgtcctc    1860
gcacatctct ctggtgacga aaatttaatc cgcgtgtttc aagaggggcg tgatattcac    1920
acagaaactg cctcatggat gttcggtgtc ccacgtgaag cagtggatcc tttgatgcgc    1980
cgtgcagcta aaacaattaa ttttggagtg ctgtacggaa tgagcgctca tcgcttgagt    2040
caggaactgg caatccccta cgaggaagcg caggcattca tcgaacgtta ctttcaatcg    2100
tttccgaaag ttcgcgcatg gatcgagaag acgctcgagg aaggtcgtcg tcggggctat    2160
gtcgaaactc tgtttggtcg ccgtcggtac gtaccagatc ttgaagcccg cgtcaaatcg    2220
gtacgggagg ctgcggagcg tatggcattt aatatgcctg tacagggtac tgcagctgac    2280
ctcatgaaac tggcaatggt caagcttttc ccgcgcttgg aggaaatggg cgcacgtatg    2340
cttctgcagc tgcaggacga gctggtgtta gaagccccta aggagcgcgc cgaagctgtc    2400
gcgcgcctcg ctaagaagt gatggagggc gtttacccat ggccgtacc cctcgaagtg    2460 gaggtcggta ttggagaaga ttggttatct gcaaaggaag cggccgc               2507
```

<210> SEQ ID NO 89
<211> LENGTH: 834
<212> TYPE: PRT
<213> ORGANISM: Artificial Sequence
<220> FEATURE:
<223> OTHER INFORMATION: AMINO ACID SEQUENCE OF MUTANT ID 18 (V783L, H784Q).

<400> SEQUENCE: 89

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125
```

```
Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
530                 535                 540
```

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Leu Gln
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Ala Ala

<210> SEQ ID NO 90
<211> LENGTH: 58
<212> TYPE: PRT
<213> ORGANISM: Artificial Sequence
<220> FEATURE:
<223> OTHER INFORMATION: AMINO ACID SEQUENCE OF RESIDUES 755-812 OF TAQ
      DNA POLYMERASE

<400> SEQUENCE: 90

Gly Thr Ala Ala Asp Leu Met Lys Leu Ala Met Val Lys Leu Phe Pro
1               5                   10                  15

Arg Leu Glu Glu Met Gly Ala Arg Met Leu Leu Gln Val His Asp Glu
            20                  25                  30

Leu Val Leu Glu Ala Pro Lys Glu Arg Ala Glu Ala Val Ala Arg Leu
        35                  40                  45

Ala Lys Glu Val Met Glu Gly Val Tyr Pro
    50                  55

<210> SEQ ID NO 91
<211> LENGTH: 829
<212> TYPE: PRT
<213> ORGANISM: Artificial Sequence
<220> FEATURE:
<223> OTHER INFORMATION: AMINO ACID SEQUENCE OF DNA polymerase I
    [Thermus igniterrae]

<400> SEQUENCE: 91

```
Met Leu Pro Leu Phe Glu Pro Lys Gly Arg Val Leu Leu Val Asp Gly
1               5                   10                  15

His His Leu Ala Tyr Arg Thr Phe Phe Ala Leu Lys Gly Leu Thr Thr
            20                  25                  30

Ser Arg Gly Glu Pro Val Gln Ala Val Tyr Gly Phe Ala Lys Ser Leu
        35                  40                  45

Leu Lys Ala Leu Lys Glu Asp Gly Asp Val Val Val Val Phe Asp
    50                  55                  60

Ala Lys Ala Pro Ser Phe Arg His Glu Ala Tyr Glu Ala Tyr Lys Ala
65                  70                  75                  80

Gly Arg Ala Pro Thr Pro Glu Asp Phe Pro Arg Gln Leu Ala Leu Ile
                85                  90                  95

Lys Glu Leu Val Asp Leu Leu Gly Leu Val Arg Leu Glu Val Pro Gly
            100                 105                 110

Phe Glu Ala Asp Asp Val Leu Ala Thr Leu Ala Lys Arg Ala Glu Lys
        115                 120                 125

Glu Gly Tyr Glu Val Arg Ile Leu Thr Ala Asp Arg Asp Leu Tyr Gln
    130                 135                 140

Leu Leu Ser Glu Arg Ile Ala Ile Leu His Pro Glu Gly Tyr Leu Ile
145                 150                 155                 160

Thr Pro Ala Trp Leu Tyr Glu Lys Tyr Gly Leu Arg Pro Glu Gln Trp
                165                 170                 175

Val Asp Tyr Arg Ala Leu Ala Gly Asp Pro Ser Asp Asn Ile Pro Gly
            180                 185                 190

Val Lys Gly Ile Gly Glu Lys Thr Ala Gln Arg Leu Ile Arg Glu Trp
        195                 200                 205

Gly Ser Leu Glu Asn Leu Phe Gln His Leu Asp Gln Val Lys Pro Ser
    210                 215                 220

Leu Arg Glu Lys Leu Gln Ala Gly Met Glu Ala Leu Ala Leu Ser Arg
225                 230                 235                 240

Lys Leu Ser Gln Val His Thr Asp Leu Pro Leu Glu Val Asp Phe Gly
                245                 250                 255

Arg Arg Arg Thr Pro Asn Leu Glu Gly Leu Arg Ala Phe Leu Glu Arg
            260                 265                 270

Leu Glu Phe Gly Ser Leu Leu His Glu Phe Gly Leu Leu Glu Gly Pro
        275                 280                 285

Lys Ala Ala Glu Glu Ala Pro Trp Pro Pro Glu Gly Ala Phe Leu
    290                 295                 300

Gly Phe Ser Phe Ser Arg Pro Glu Pro Met Trp Ala Glu Leu Leu Ala
305                 310                 315                 320

Leu Ala Gly Ala Trp Glu Gly Arg Leu His Arg Ala Gln Asp Pro Leu
                325                 330                 335

Arg Gly Leu Arg Asp Leu Lys Gly Val Arg Gly Ile Leu Ala Lys Asp
            340                 345                 350

Leu Ala Val Leu Ala Leu Arg Glu Gly Leu Asp Leu Phe Pro Glu Asp
        355                 360                 365
```

-continued

```
Asp Pro Met Leu Leu Ala Tyr Leu Leu Asp Pro Ser Asn Thr Thr Pro
    370                 375                 380

Glu Gly Val Ala Arg Arg Tyr Gly Gly Glu Trp Thr Glu Asp Ala Gly
385                 390                 395                 400

Glu Arg Ala Leu Leu Ala Glu Arg Leu Phe Gln Thr Leu Lys Glu Arg
                405                 410                 415

Leu Lys Gly Glu Glu Arg Leu Leu Trp Leu Tyr Glu Glu Val Glu Lys
                420                 425                 430

Pro Leu Ser Arg Val Leu Ala Arg Met Glu Ala Thr Gly Val Arg Leu
                435                 440                 445

Asp Val Ala Tyr Leu Gln Ala Leu Ser Leu Glu Val Glu Ala Glu Val
    450                 455                 460

Arg Gln Leu Glu Glu Glu Val Phe Arg Leu Ala Gly His Pro Phe Asn
465                 470                 475                 480

Leu Asn Ser Arg Asp Gln Leu Glu Arg Val Leu Phe Asp Glu Leu Gly
                485                 490                 495

Leu Pro Ala Ile Gly Lys Thr Glu Lys Thr Gly Lys Arg Ser Thr Ser
                500                 505                 510

Ala Ala Val Leu Glu Ala Leu Arg Glu Ala His Pro Ile Val Asp Arg
    515                 520                 525

Ile Leu Gln Tyr Arg Glu Leu Thr Lys Leu Lys Asn Thr Tyr Ile Asp
    530                 535                 540

Pro Leu Pro Ala Leu Val His Pro Lys Thr Gly Arg Leu His Thr Arg
545                 550                 555                 560

Phe Asn Gln Thr Ala Thr Ala Thr Gly Arg Leu Ser Ser Ser Asp Pro
                565                 570                 575

Asn Leu Gln Asn Ile Pro Val Arg Thr Pro Leu Gly Gln Arg Ile Arg
                580                 585                 590

Arg Ala Phe Val Ala Glu Glu Gly Trp Val Leu Val Val Leu Asp Tyr
                595                 600                 605

Ser Gln Ile Glu Leu Arg Val Leu Ala His Leu Ser Gly Asp Glu Asn
    610                 615                 620

Leu Ile Arg Val Phe Gln Glu Gly Arg Asp Ile His Thr Gln Thr Ala
625                 630                 635                 640

Ser Trp Met Phe Gly Val Ser Pro Glu Gly Val Asp Pro Leu Met Arg
                645                 650                 655

Arg Ala Ala Lys Thr Ile Asn Phe Gly Val Leu Tyr Gly Met Ser Ala
                660                 665                 670

His Arg Leu Ser Gly Glu Leu Ser Ile Pro Tyr Glu Glu Ala Val Ala
                675                 680                 685

Phe Ile Glu Arg Tyr Phe Gln Ser Tyr Pro Lys Val Arg Ala Trp Ile
    690                 695                 700

Glu Gly Thr Leu Glu Glu Gly Arg Arg Arg Gly Tyr Val Glu Thr Leu
705                 710                 715                 720

Phe Gly Arg Arg Arg Tyr Val Pro Asp Leu Asn Ala Arg Val Lys Ser
                725                 730                 735

Val Arg Glu Ala Ala Glu Arg Met Ala Phe Asn Met Pro Val Gln Gly
                740                 745                 750

Thr Ala Ala Asp Leu Met Lys Leu Ala Met Val Arg Leu Phe Pro Arg
    755                 760                 765

Leu Gln Glu Leu Gly Ala Arg Met Leu Leu Gln Val His Asp Glu Leu
    770                 775                 780
```

```
Val Leu Glu Ala Pro Lys Asp Arg Ala Glu Arg Val Ala Ala Leu Ala
785                 790                 795                 800

Lys Glu Val Met Glu Gly Val Trp Pro Leu Arg Val Pro Leu Glu Val
                805                 810                 815

Glu Val Gly Leu Gly Glu Asp Trp Leu Ser Ala Lys Glu
                820                 825
```

<210> SEQ ID NO 92
<211> LENGTH: 829
<212> TYPE: PRT
<213> ORGANISM: Artificial Sequence
<220> FEATURE:
<223> OTHER INFORMATION: AMINO ACID SEQUENCE OF DNA polymerase I
      [Thermus islandicus]

<400> SEQUENCE: 92

```
Met Leu Pro Leu Phe Ala Pro Lys Gly Arg Val Leu Leu Val Asp Gly
1               5                   10                  15

His His Leu Ala Tyr Arg Thr Phe Phe Ala Leu Lys Gly Leu Thr Thr
                20                  25                  30

Ser Arg Gly Glu Pro Val Gln Ala Val Tyr Gly Phe Ala Lys Ser Leu
            35                  40                  45

Leu Lys Ala Leu Lys Glu Asp Gly Asp Ala Val Val Val Val Phe Asp
50                  55                  60

Ala Lys Ala Pro Ser Phe Arg His Glu Ala Tyr Glu Gly Tyr Lys Ala
65                  70                  75                  80

Gly Arg Ala Pro Thr Pro Glu Asp Phe Pro Arg Gln Leu Ala Leu Ile
                85                  90                  95

Lys Glu Phe Val Asp Leu Leu Gly Leu Thr Arg Leu Glu Val Pro Gly
            100                 105                 110

Tyr Glu Ala Asp Asp Val Leu Ala Thr Leu Ala Lys Lys Ala Glu Arg
        115                 120                 125

Glu Gly Tyr Glu Val Arg Ile Leu Thr Ala Asp Arg Asp Leu Tyr Gln
    130                 135                 140

Leu Val Ser Asp Arg Ile Ala Ile Leu His Pro Glu Gly Tyr Leu Ile
145                 150                 155                 160

Thr Pro Glu Trp Leu Met Glu Arg Tyr Gly Leu Arg Pro Glu Gln Trp
                165                 170                 175

Val Asp Tyr Arg Ala Leu Ala Gly Asp Pro Ser Asp Asn Ile Pro Gly
            180                 185                 190

Val Lys Gly Ile Gly Glu Lys Arg Ala Ala Gly Leu Ile Arg Glu Trp
        195                 200                 205

Gly Ser Leu Glu Asn Leu Leu Lys His Leu Asp Gln Val Lys Pro Ser
    210                 215                 220

Leu Arg Glu Ala Ile Leu Ala His Met Glu Asp Leu Arg Leu Ser Gln
225                 230                 235                 240

Asp Leu Ser Arg Val Arg Thr Asp Leu Pro Leu Glu Val Asp Phe Ala
                245                 250                 255

Arg Arg Gln Glu Pro Asp Arg Glu Ala Leu Lys Ala Phe Leu Glu Arg
            260                 265                 270

Leu Glu Phe Gly Ser Leu Leu His Glu Phe Gly Leu Leu Glu Gly Pro
        275                 280                 285

Lys Ala Leu Glu Glu Ala Pro Trp Pro Pro Glu Gly Ala Phe Val
    290                 295                 300

Gly Tyr Leu Leu Ser Arg Pro Glu Pro Met Trp Ala Glu Leu Glu Ala
305                 310                 315                 320
```

Leu Ala Ala Ser Lys Glu Gly Arg Val His Arg Ala Leu Asp Pro Leu
            325                 330                 335

Ala Gly Leu Arg Asp Leu Lys Glu Ile Gln Ala Leu Leu Ala Lys Asp
            340                 345                 350

Leu Ala Val Leu Ala Leu Arg Glu Gly Leu Asp Leu Ser Pro Ser His
            355                 360                 365

Asp Pro Met Leu Leu Ala Tyr Leu Leu Asp Pro Ala Asn Thr Thr Pro
            370                 375                 380

Glu Gly Val Ala Arg Arg Tyr Gly Gly Glu Trp Thr Ala Glu Ala Gly
385                 390                 395                 400

Glu Arg Ala Ala Leu Ala Glu Arg Leu Tyr Gly Arg Leu Arg Glu Arg
            405                 410                 415

Leu Glu Gly Glu Glu Lys Leu Leu Trp Leu Tyr Glu Glu Leu Glu Arg
            420                 425                 430

Pro Leu Ser Arg Val Leu Ala His Met Glu Ala Thr Gly Val Arg Leu
            435                 440                 445

Asp Val Pro Tyr Leu Lys Ala Leu Ser Leu Glu Val Glu Ala Glu Val
            450                 455                 460

Arg Arg Val Glu Glu Ala Phe Arg Leu Ala Gly His Pro Phe Asn
465                 470                 475                 480

Leu Asn Ser Arg Asp Gln Leu Glu Arg Val Leu Phe Asp Glu Leu Lys
            485                 490                 495

Leu Pro Ala Ile Gly Lys Thr Glu Lys Thr Gly Lys Arg Ser Thr Ser
            500                 505                 510

Ala Ala Val Leu Glu Ala Leu Arg Glu Ala His Pro Ile Val Gly Lys
            515                 520                 525

Ile Leu Glu Tyr Arg Glu Leu Thr Lys Leu Lys Ser Thr Tyr Ile Asp
            530                 535                 540

Pro Leu Pro Gly Leu Val His Pro Lys Thr Gly Arg Leu His Thr Arg
545                 550                 555                 560

Phe Asn Gln Thr Ala Thr Ala Thr Gly Arg Leu Ser Ser Ser Asp Pro
            565                 570                 575

Asn Leu Gln Asn Ile Pro Val Arg Thr Pro Leu Gly Gln Arg Ile Arg
            580                 585                 590

Arg Ala Phe Val Ala Glu Glu Arg Trp Leu Leu Ala Leu Asp Tyr
            595                 600                 605

Ser Gln Ile Glu Leu Arg Val Leu Ala His Leu Ser Gly Asp Glu Asn
            610                 615                 620

Leu Ile Arg Val Phe Gln Glu Gly Gln Asp Ile His Thr Glu Thr Ala
625                 630                 635                 640

Ser Trp Met Phe Ala Val Pro Lys Glu Ala Val Asp Ser Leu Met Arg
            645                 650                 655

Arg Ala Ala Lys Thr Val Asn Phe Gly Val Leu Tyr Gly Met Ser Ala
            660                 665                 670

His Arg Leu Ser Gln Glu Leu Ser Ile Pro Tyr Glu Glu Ala Ala Ala
            675                 680                 685

Phe Ile Glu Arg Tyr Phe Gln Thr Phe Pro Lys Val Arg Ala Trp Ile
            690                 695                 700

Glu Arg Thr Leu Glu Glu Gly Arg Lys Arg Gly Tyr Val Glu Thr Leu
705                 710                 715                 720

Phe Gly Arg Arg Arg Tyr Val Pro Asp Leu Thr Ala Arg Val Lys Ser
            725                 730                 735

```
Val Arg Glu Ala Ala Glu Arg Met Ala Phe Asn Met Pro Val Gln Gly
            740                 745                 750

Thr Ala Ala Asp Leu Met Lys Leu Ala Met Val Lys Leu Phe Pro Arg
            755                 760                 765

Leu Arg Glu Ala Gly Ala Arg Met Leu Leu Gln Val His Asp Glu Leu
            770                 775                 780

Leu Leu Glu Ala Pro Lys Asp Arg Ala Glu Glu Val Ala Ala Leu Ala
785                 790                 795                 800

Lys Glu Val Met Glu Gly Val Tyr Pro Leu Ala Val Pro Leu Val Val
            805                 810                 815

Glu Val Gly Met Gly Glu Asp Trp Leu Ser Ala Lys Gly
            820                 825

<210> SEQ ID NO 93
<211> LENGTH: 833
<212> TYPE: PRT
<213> ORGANISM: Artificial Sequence
<220> FEATURE:
<223> OTHER INFORMATION: AMINO ACID SEQUENCE OF DNA polymerase I,
      thermostable [Thermus sp. CCB_US3_UF1]

<400> SEQUENCE: 93

Met Leu Pro Leu Phe Ala Pro Lys Gly Arg Ile Leu Leu Val Asp Gly
1               5                   10                  15

His His Leu Ala Tyr Arg Thr Phe Phe Ala Leu Lys Gly Leu Thr Thr
            20                  25                  30

Ser Arg Gly Glu Pro Val Gln Gly Val Tyr Gly Phe Ala Lys Ala Leu
            35                  40                  45

Leu Lys Ala Leu Lys Glu Val Lys Gly Asp Gly Asp Gly Val Ile Val
        50                  55                  60

Val Phe Asp Ala Lys Ala Pro Ser Phe Arg His Gln Ala Tyr Gly Ala
65                  70                  75                  80

Tyr Lys Ala Gly Arg Ala Pro Thr Pro Glu Asp Phe Pro Arg Gln Leu
                85                  90                  95

Ser Leu Ile Lys Glu Leu Val Asp Leu Leu Gly Leu Val Arg Leu Glu
            100                 105                 110

Val Pro Gly Tyr Glu Ala Asp Asp Val Leu Ala Thr Leu Ala Arg Arg
        115                 120                 125

Ala Glu Gly Glu Gly Tyr Glu Val Arg Ile Leu Thr Ala Asp Arg Asp
    130                 135                 140

Leu Tyr Gln Leu Leu Ser Glu Arg Val Ser Ile Leu His Pro Glu Gly
145                 150                 155                 160

His Thr Ile Thr Pro Gln Trp Leu Trp Glu Lys Tyr Gly Leu Arg Pro
                165                 170                 175

Glu Gln Trp Val Asp Tyr Arg Ala Leu Ser Gly Asp Pro Ser Asp Asn
            180                 185                 190

Leu Pro Gly Val Lys Gly Ile Gly Glu Lys Thr Ala Ala Lys Leu Leu
        195                 200                 205

Gln Glu Trp Gly Ser Leu Glu Asn Leu Leu Lys Asn Leu Asp Arg Val
    210                 215                 220

Lys Pro Pro Ser Ile Arg Glu Lys Ile Gln Ala His Leu Glu Asp Leu
225                 230                 235                 240

Arg Leu Ser Gln Asp Leu Ala Arg Val Arg Thr Asp Leu Pro Leu Glu
                245                 250                 255

Val Asp Phe Ala Gly Arg Arg Glu Pro Asp Arg Glu Gly Leu Arg Ala
            260                 265                 270
```

Phe Leu Glu Arg Leu Glu Phe Gly Ser Leu Leu His Glu Phe Gly Leu
        275                 280                 285

Leu Glu Gly Pro Lys Ala Ala Glu Glu Ala Pro Trp Pro Pro Pro Pro
    290                 295                 300

Gly Ala Phe Val Gly Tyr Val Leu Ser Arg Pro Glu Pro Met Trp Ala
305                 310                 315                 320

Asp Leu Ala Leu Ala Ala Gln Glu Gly Arg Val His Arg Ala
            325                 330                 335

Pro Glu Ala Leu Ala Gly Leu Arg Ala Leu Gly Glu Val Arg Gly Leu
            340                 345                 350

Leu Ala Lys Asp Leu Ala Val Leu Ala Leu Arg Glu Gly Leu Glu Ile
            355                 360                 365

Pro Pro Gly Asp Asp Pro Met Leu Leu Ala Tyr Leu Leu Asp Pro Ser
    370                 375                 380

Asn Thr Ser Pro Glu Gly Val Ala Arg Arg Tyr Gly Gly Glu Trp Ala
385                 390                 395                 400

Glu Glu Ala Gly Glu Arg Ala Leu Leu Ala Glu Arg Leu Gln Ala Ala
                405                 410                 415

Leu Trp Ala Arg Leu Glu Gly Glu Glu Arg Leu Arg Trp Leu Tyr Glu
            420                 425                 430

Glu Val Glu Lys Pro Leu Ser Arg Val Leu Ala Arg Met Glu Ala Thr
        435                 440                 445

Gly Val Arg Leu Asp Val Ala Tyr Leu Gln Ala Leu Ala Leu Glu Val
    450                 455                 460

Glu Gly Glu Val Arg Arg Leu Glu Glu Val Phe Arg Leu Ala Gly
465                 470                 475                 480

His Pro Phe Asn Leu Asn Ser Arg Asp Gln Leu Glu Lys Val Leu Phe
            485                 490                 495

Asp Glu Leu Gly Leu Pro Ala Ile Gly Lys Thr Glu Lys Thr Gly Lys
            500                 505                 510

Arg Ser Thr Ser Ala Gln Val Leu Glu Leu Leu Arg Glu Ala His Pro
    515                 520                 525

Ile Val Ala Arg Ile Leu Glu Tyr Arg Glu Leu Thr Lys Leu Lys Ser
    530                 535                 540

Thr Tyr Ile Asp Pro Leu Pro Ala Leu Val His Pro Arg Thr Gly Arg
545                 550                 555                 560

Leu His Thr Arg Phe Asn Gln Thr Ala Thr Ala Thr Gly Arg Leu Ser
            565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Val Leu Val
        595                 600                 605

Ala Leu Asp Tyr Ser Gln Ile Glu Leu Arg Val Leu Ala His Leu Ser
    610                 615                 620

Gly Asp Glu Asn Leu Ile Arg Val Phe Gln Glu Gly Arg Asp Ile His
625                 630                 635                 640

Thr Gln Thr Ala Ser Trp Met Phe Gly Val Pro Pro Glu Ala Val Asp
            645                 650                 655

Pro Leu Met Arg Arg Ala Ala Lys Thr Ile Asn Phe Gly Val Leu Tyr
            660                 665                 670

Gly Met Ser Ala His Arg Leu Ser Gly Glu Leu Ala Ile Pro Tyr Glu
        675                 680                 685

```
Glu Ala Val Ala Phe Ile Glu Arg Tyr Phe Gln Ser Tyr Pro Lys Val
    690                 695                 700

Arg Ala Trp Ile Glu Lys Thr Leu Glu Glu Gly Arg Arg Gly Tyr
705                 710                 715                 720

Val Glu Thr Leu Phe Gly Arg Arg Tyr Val Pro Asp Leu Asn Ala
                725                 730                 735

Arg Val Lys Ser Val Arg Glu Ala Ala Glu Arg Met Ala Phe Asn Met
                740                 745                 750

Pro Val Gln Gly Thr Ala Ala Asp Leu Met Lys Leu Ala Met Val Arg
                755                 760                 765

Leu Phe Pro Leu Leu Pro Gly Val Gly Ala Arg Met Leu Leu Gln Val
    770                 775                 780

His Asp Glu Leu Leu Leu Glu Ala Pro Lys Glu Arg Ala Glu Glu Val
785                 790                 795                 800

Ala Arg Leu Ala Arg Glu Val Met Glu Gly Val Trp Pro Leu Ala Val
                805                 810                 815

Pro Leu Glu Val Glu Val Gly Ile Gly Glu Asp Trp Leu Ala Ala Lys
                820                 825                 830

Gly

<210> SEQ ID NO 94
<211> LENGTH: 830
<212> TYPE: PRT
<213> ORGANISM: Artificial Sequence
<220> FEATURE:
<223> OTHER INFORMATION: AMINO ACID SEQUENCE OF DNA polymerase I
      [Thermus oshimai]

<400> SEQUENCE: 94

Met Leu Pro Leu Phe Glu Pro Lys Gly Arg Val Leu Leu Val Asp Gly
1               5                   10                  15

His His Leu Ala Tyr Arg Thr Phe Phe Ala Leu Lys Gly Leu Thr Thr
                20                  25                  30

Ser Arg Gly Glu Pro Val Gln Ala Val Tyr Gly Phe Ala Lys Ser Leu
            35                  40                  45

Leu Lys Ala Leu Lys Glu Asp Gly Glu Val Ala Ile Val Phe Asp
    50                  55                  60

Ala Lys Ala Pro Ser Phe Arg His Glu Ala Tyr Glu Ala Tyr Lys Ala
65                  70                  75                  80

Gly Arg Ala Pro Thr Pro Glu Asp Phe Pro Arg Gln Leu Ala Leu Ile
                85                  90                  95

Lys Glu Leu Val Asp Leu Leu Gly Leu Val Arg Leu Glu Val Pro Gly
                100                 105                 110

Phe Glu Ala Asp Asp Val Leu Ala Thr Leu Ala Lys Lys Ala Glu Arg
            115                 120                 125

Glu Gly Tyr Glu Val Arg Ile Leu Ser Ala Asp Arg Asp Leu Tyr Gln
130                 135                 140

Leu Leu Ser Asp Arg Ile His Leu Leu His Pro Glu Gly Glu Val Leu
145                 150                 155                 160

Thr Pro Gly Trp Leu Gln Glu Arg Tyr Gly Leu Ser Pro Glu Arg Trp
                165                 170                 175

Val Glu Tyr Arg Ala Leu Val Gly Asp Pro Ser Asp Asn Leu Pro Gly
                180                 185                 190

Val Pro Gly Ile Gly Glu Lys Thr Ala Leu Lys Leu Leu Lys Glu Trp
            195                 200                 205
```

```
Gly Ser Leu Glu Ala Ile Leu Lys Asn Leu Asp Gln Val Lys Pro Glu
    210                 215                 220

Arg Val Arg Glu Ala Ile Arg Asn Asn Leu Asp Lys Leu Gln Met Ser
225                 230                 235                 240

Leu Glu Leu Ser Arg Leu Arg Thr Asp Leu Pro Leu Glu Val Asp Phe
                245                 250                 255

Ala Lys Arg Arg Glu Pro Asp Trp Glu Gly Leu Lys Ala Phe Leu Glu
            260                 265                 270

Arg Leu Glu Phe Gly Ser Leu Leu His Glu Phe Gly Leu Leu Glu Ala
        275                 280                 285

Pro Lys Glu Ala Glu Glu Ala Pro Trp Pro Pro Gly Gly Ala Phe
290                 295                 300

Leu Gly Phe Leu Leu Ser Arg Pro Glu Pro Met Trp Ala Glu Leu Leu
305                 310                 315                 320

Ala Leu Ala Gly Ala Lys Glu Gly Arg Val His Arg Ala Glu Asp Pro
                325                 330                 335

Val Gly Ala Leu Lys Asp Leu Lys Glu Ile Arg Gly Leu Leu Ala Lys
                340                 345                 350

Asp Leu Ser Val Leu Ala Leu Arg Glu Gly Arg Glu Ile Pro Pro Gly
            355                 360                 365

Asp Asp Pro Met Leu Leu Ala Tyr Leu Leu Asp Pro Gly Asn Thr Asn
370                 375                 380

Pro Glu Gly Val Ala Arg Arg Tyr Gly Gly Glu Trp Lys Glu Asp Ala
385                 390                 395                 400

Ala Ala Arg Ala Leu Leu Ser Glu Arg Leu Trp Gln Ala Leu Tyr Pro
                405                 410                 415

Arg Val Ala Glu Glu Arg Leu Leu Trp Leu Tyr Arg Glu Val Glu
                420                 425                 430

Arg Pro Leu Ala Gln Val Leu Ala His Met Glu Ala Thr Gly Val Arg
            435                 440                 445

Leu Asp Val Pro Tyr Leu Glu Ala Leu Ser Gln Glu Val Ala Phe Glu
    450                 455                 460

Leu Glu Arg Leu Glu Ala Glu Val His Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Pro Ile Gly Lys Thr Glu Lys Thr Gly Lys Arg Ser Thr
            500                 505                 510

Ser Ala Ala Val Leu Glu Leu Leu Arg Glu Ala His Pro Ile Val Gly
    515                 520                 525

Arg Ile Leu Glu Tyr Arg Glu Leu Met Lys Leu Lys Ser Thr Tyr Ile
530                 535                 540

Asp Pro Leu Pro Arg Leu Val His Pro Lys Thr Gly Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
            580                 585                 590

Arg Lys Ala Phe Ile Ala Glu Gly His Leu Leu Val Ala Leu Asp
        595                 600                 605

Tyr Ser Gln Ile Glu Leu Arg Val Leu Ala His Leu Ser Gly Asp Glu
    610                 615                 620

Asn Leu Ile Arg Val Phe Arg Glu Gly Lys Asp Ile His Thr Glu Thr
```

Ala Ala Trp Met Phe Gly Val Pro Pro Glu Gly Val Asp Gly Ala Met
            625             630             635             640

Arg Arg Ala Ala Lys Thr Val Asn Phe Gly Val Leu Tyr Gly Met Ser
            645             650             655

Ala His Arg Leu Ser Gln Glu Leu Ser Ile Pro Tyr Glu Glu Ala Ala
            660             665             670

Ala Phe Ile Glu Arg Tyr Phe Gln Ser Phe Pro Lys Val Arg Ala Trp
            675             680             685

Ile Ala Lys Thr Leu Glu Glu Gly Arg Lys Lys Gly Tyr Val Glu Thr
690             695             700

Leu Phe Gly Arg Arg Arg Tyr Val Pro Asp Leu Asn Ala Arg Val Lys
705             710             715             720

Ser Val Arg Glu Ala Ala Glu Arg Met Ala Phe Asn Met Pro Val Gln
            725             730             735

Gly Thr Ala Ala Asp Leu Met Lys Leu Ala Met Val Lys Leu Phe Pro
            740             745             750

Arg Leu Arg Pro Leu Gly Val Arg Ile Leu Leu Gln Val His Asp Glu
            755             760             765

Leu Val Leu Glu Ala Pro Lys Ala Arg Ala Glu Ala Ala Gln Leu
770             775             780

Ala Lys Glu Thr Met Glu Gly Val Tyr Pro Leu Ser Val Pro Leu Glu
785             790             795             800

Val Glu Val Gly Met Gly Glu Asp Trp Leu Ser Ala Lys Ala
            805             810             815

820             825             830

<210> SEQ ID NO 95
<211> LENGTH: 831
<212> TYPE: PRT
<213> ORGANISM: Artificial Sequence
<220> FEATURE:
<223> OTHER INFORMATION: AMINO ACID SEQUENCE OF DNA polymerase I
      [Thermus sp. RL]

<400> SEQUENCE: 95

Met Leu Pro Leu Phe Glu Pro Lys Gly Arg Val Leu Leu Val Asp Gly
1               5                   10                  15

His His Leu Ala Tyr Arg Thr Phe Phe Ala Leu Lys Gly Leu Thr Thr
            20                  25                  30

Ser Arg Gly Glu Pro Val Gln Ala Val Tyr Gly Phe Ala Lys Ser Leu
        35                  40                  45

Leu Lys Ala Leu Lys Glu Asp Gly Tyr Lys Ala Val Phe Val Val Phe
50                  55                  60

Asp Ala Lys Ala Pro Ser Phe Arg His Glu Ala Tyr Glu Ala Tyr Lys
65                  70                  75                  80

Ala Gly Arg Ala Pro Thr Pro Glu Asp Phe Pro Arg Gln Leu Ala Leu
            85                  90                  95

Ile Lys Glu Leu Val Asp Leu Leu Gly Phe Thr Arg Leu Glu Val Gln
            100                 105                 110

Gly Tyr Glu Ala Asp Asp Val Leu Ala Thr Leu Ala Lys Lys Ala Glu
        115                 120                 125

Lys Glu Gly Tyr Glu Val Arg Ile Leu Thr Ala Asp Arg Asp Leu Tyr
    130                 135                 140

Gln Leu Val Ser Asp Arg Val Ala Val Leu His Pro Glu Gly His Leu
145                 150                 155                 160

```
Ile Thr Pro Glu Trp Leu Trp Glu Lys Tyr Gly Leu Arg Pro Glu Gln
                165                 170                 175

Trp Val Asp Phe Arg Ala Leu Val Gly Asp Pro Ser Asp Asn Leu Pro
            180                 185                 190

Gly Val Lys Gly Ile Gly Glu Lys Thr Ala Leu Lys Leu Leu Lys Glu
        195                 200                 205

Trp Gly Ser Leu Glu Asn Ile Leu Lys Asn Leu Asp Arg Val Lys Pro
    210                 215                 220

Glu Ser Val Arg Glu Arg Ile Lys Ala His Leu Glu Asp Leu Lys Leu
225                 230                 235                 240

Ser Leu Glu Leu Ser Arg Val Arg Ala Asp Leu Pro Leu Glu Val Asp
                245                 250                 255

Phe Ala Arg Arg Arg Glu Pro Asp Arg Glu Gly Leu Arg Ala Phe Leu
            260                 265                 270

Glu Arg Leu Glu Phe Gly Ser Leu Leu His Glu Phe Gly Leu Leu Glu
        275                 280                 285

Ala Pro Ala Pro Leu Glu Glu Ala Pro Trp Pro Pro Glu Gly Ala
    290                 295                 300

Phe Val Gly Phe Val Leu Ser Arg Pro Glu Pro Met Trp Ala Glu Leu
305                 310                 315                 320

Lys Ala Leu Ala Ala Cys Lys Glu Gly Arg Val His Arg Ala Lys Asp
                325                 330                 335

Pro Leu Ala Gly Leu Lys Asp Leu Lys Glu Val Arg Gly Leu Leu Ala
            340                 345                 350

Lys Asp Leu Ala Val Leu Ala Leu Arg Glu Gly Leu Asp Leu Ala Pro
        355                 360                 365

Ser Asp Asp Pro Met Leu Leu Ala Tyr Leu Leu Asp Pro Ser Asn Thr
    370                 375                 380

Thr Pro Glu Gly Val Ala Arg Arg Tyr Gly Gly Glu Trp Thr Glu Asp
385                 390                 395                 400

Ala Ala His Arg Ala Leu Leu Ala Glu Arg Leu Gln Gln Asn Leu Leu
                405                 410                 415

Glu Arg Leu Lys Gly Glu Glu Lys Leu Leu Trp Leu Tyr Gln Glu Val
            420                 425                 430

Glu Lys Pro Leu Ser Arg Val Leu Ala His Met Glu Ala Thr Gly Val
        435                 440                 445

Arg Leu Asp Val Ala Tyr Leu Lys Ala Leu Ser Leu Glu Leu Ala Glu
    450                 455                 460

Glu Ile Arg Arg Leu Glu Glu Val Phe Arg Leu Ala Gly His Pro
465                 470                 475                 480

Phe Asn Leu Asn Ser Arg Asp Gln Leu Glu Lys Val Leu Phe Asp Glu
                485                 490                 495

Leu Arg Leu Pro Ala Leu Gly Lys Thr Gln Lys Thr Gly Lys Arg Ser
            500                 505                 510

Thr Ser Ala Ala Val Leu Glu Ala Leu Arg Glu Ala His Pro Ile Val
        515                 520                 525

Glu Lys Ile Leu Gln His Arg Glu Leu Thr Lys Leu Lys Asn Thr Tyr
    530                 535                 540

Val Asp Pro Leu Pro Gly Leu Val His Pro Arg Thr Gly Arg Leu His
545                 550                 555                 560

Thr Arg Phe Asn Gln Thr Ala Thr Ala Thr Gly Arg Leu Ser Ser Ser
                565                 570                 575

Asp Pro Asn Leu Gln Asn Ile Pro Val Arg Thr Pro Leu Gly Gln Arg
```

```
            580                 585                 590
Ile Arg Arg Ala Phe Val Ala Glu Ala Gly Trp Ala Leu Val Ala Leu
            595                 600                 605

Asp Tyr Ser Gln Ile Glu Leu Arg Val Leu Ala His Leu Ser Gly Asp
        610                 615                 620

Glu Asn Leu Ile Arg Val Phe Gln Glu Gly Lys Asp Ile His Thr Gln
625                 630                 635                 640

Thr Ala Ser Trp Met Phe Gly Val Pro Pro Glu Ala Val Asp Pro Leu
                645                 650                 655

Met Arg Arg Ala Ala Lys Thr Val Asn Phe Gly Val Leu Tyr Gly Met
            660                 665                 670

Ser Ala His Arg Leu Ser Gln Glu Leu Ser Ile Pro Tyr Glu Glu Ala
        675                 680                 685

Val Ala Phe Ile Asp Arg Tyr Phe Lys Ser Phe Pro Lys Val Lys Ala
690                 695                 700

Trp Ile Glu Arg Thr Leu Glu Glu Gly Arg Gln Arg Gly Tyr Val Glu
705                 710                 715                 720

Thr Leu Phe Gly Arg Arg Arg Tyr Val Pro Asp Leu Asn Ala Arg Val
                725                 730                 735

Lys Ser Val Arg Glu Ala Ala Glu Arg Met Ala Phe Asn Met Pro Val
            740                 745                 750

Gln Gly Thr Ala Ala Asp Leu Met Lys Leu Ala Met Val Lys Leu Phe
        755                 760                 765

Pro Arg Leu Arg Glu Met Gly Ala Arg Met Leu Leu Gln Val His Asp
770                 775                 780

Glu Leu Leu Glu Ala Pro Gln Ala Arg Ala Glu Glu Val Ala Ala
785                 790                 795                 800

Leu Ala Lys Glu Ala Met Glu Lys Ala Tyr Pro Leu Ala Val Pro Leu
                805                 810                 815

Glu Val Glu Val Gly Ile Gly Glu Asp Trp Leu Ser Ala Lys Gly
            820                 825                 830

<210> SEQ ID NO 96
<211> LENGTH: 831
<212> TYPE: PRT
<213> ORGANISM: Artificial Sequence
<220> FEATURE:
<223> OTHER INFORMATION: AMINO ACID SEQUENCE OF DNA polymerase I
      [Thermus thermophilus SG0.5JP17-16]

<400> SEQUENCE: 96

Met Leu Pro Leu Phe Glu Pro Lys Gly Arg Val Leu Leu Val Asp Gly
1               5                   10                  15

His His Leu Ala Tyr Arg Thr Phe Phe Ala Leu Lys Gly Leu Thr Thr
            20                  25                  30

Ser Arg Gly Glu Pro Val Gln Ala Val Tyr Gly Phe Ala Lys Ser Leu
        35                  40                  45

Leu Lys Ala Leu Lys Glu Asp Gly Tyr Lys Ala Val Phe Val Val Phe
    50                  55                  60

Asp Ala Lys Ala Pro Ser Phe Arg His Glu Ala Tyr Glu Ala Tyr Lys
65                  70                  75                  80

Ala Gly Arg Ala Pro Thr Pro Glu Asp Phe Pro Arg Gln Leu Ala Leu
                85                  90                  95

Ile Lys Glu Leu Val Asp Leu Leu Gly Phe Thr Arg Leu Glu Val Gln
            100                 105                 110
```

```
Gly Tyr Glu Ala Asp Asp Val Leu Ala Thr Leu Ala Lys Lys Ala Glu
            115                 120                 125
Lys Glu Gly Tyr Glu Val Arg Ile Leu Thr Ala Asp Arg Asp Leu Tyr
130                 135                 140
Gln Leu Val Ser Asp Arg Val Ala Val Leu His Pro Glu Gly His Leu
145                 150                 155                 160
Ile Thr Pro Glu Trp Leu Trp Glu Lys Tyr Gly Leu Arg Pro Glu Gln
                165                 170                 175
Trp Val Asp Phe Arg Ala Leu Val Gly Asp Pro Ser Asp Asn Leu Pro
            180                 185                 190
Gly Val Lys Gly Ile Gly Glu Lys Thr Ala Leu Lys Leu Leu Lys Glu
        195                 200                 205
Trp Gly Ser Leu Glu Asn Leu Leu Lys Asn Leu Asp Arg Val Lys Pro
210                 215                 220
Glu Asn Val Arg Glu Lys Ile Lys Ala His Leu Glu Asp Leu Arg Leu
225                 230                 235                 240
Ser Met Glu Leu Ser Arg Val Arg Thr Asp Leu Pro Leu Glu Val Asp
                245                 250                 255
Leu Ala Gln Gly Arg Glu Pro Asp Arg Glu Gly Leu Arg Ala Phe Leu
            260                 265                 270
Glu Arg Leu Glu Phe Gly Ser Leu Leu His Glu Phe Gly Leu Leu Glu
        275                 280                 285
Ala Pro Ala Pro Leu Glu Glu Ala Pro Trp Pro Pro Pro Glu Gly Ala
            290                 295                 300
Phe Val Gly Phe Val Leu Ser Arg Pro Glu Pro Met Trp Ala Glu Leu
305                 310                 315                 320
Lys Ala Leu Ala Ala Cys Arg Asp Gly Arg Val His Arg Ala Ala Asp
                325                 330                 335
Pro Leu Ala Gly Leu Lys Asp Leu Lys Glu Val Arg Gly Leu Leu Ala
            340                 345                 350
Lys Asp Leu Ala Val Leu Ala Ser Arg Glu Gly Leu Asp Leu Val Pro
        355                 360                 365
Gly Asp Asp Pro Met Leu Leu Ala Tyr Leu Leu Asp Pro Ser Asn Thr
370                 375                 380
Thr Pro Glu Gly Val Ala Arg Arg Tyr Gly Gly Glu Trp Thr Glu Asp
385                 390                 395                 400
Ala Ala His Arg Ala Leu Leu Ser Glu Arg Leu His Arg Asn Leu Leu
                405                 410                 415
Lys Arg Leu Glu Gly Glu Glu Lys Leu Leu Trp Leu Tyr His Glu Val
            420                 425                 430
Glu Lys Pro Leu Ser Arg Val Leu Ala His Met Glu Ala Thr Gly Val
        435                 440                 445
Arg Leu Asp Val Ala Tyr Leu Lys Ala Leu Ser Leu Glu Leu Ala Glu
450                 455                 460
Glu Ile Arg Arg Leu Glu Glu Val Phe Arg Leu Ala Gly His Pro
465                 470                 475                 480
Phe Asn Leu Asn Ser Arg Asp Gln Leu Glu Lys Val Leu Phe Asp Glu
                485                 490                 495
Leu Arg Leu Pro Ala Leu Gly Lys Thr Gln Lys Thr Gly Lys Arg Ser
            500                 505                 510
Thr Ser Ala Ala Val Leu Glu Ala Leu Arg Glu Ala His Pro Ile Val
        515                 520                 525
Glu Lys Ile Leu Gln His Arg Glu Leu Thr Lys Leu Lys Asn Thr Tyr
```

```
    Val Asp Pro Leu Pro Gly Leu Val His Pro Arg Thr Gly Arg Leu His
            530                 535                 540
    545                 550                 555                 560

Thr Arg Phe Asn Gln Thr Ala Thr Ala Thr Gly Arg Leu Ser Ser Ser
                        565                 570                 575

Asp Pro Asn Leu Gln Asn Ile Pro Val Arg Thr Pro Leu Gly Gln Arg
                    580                  585                590

Ile Arg Arg Ala Phe Val Ala Glu Ala Gly Trp Ala Leu Val Ala Leu
                595                 600                 605

Asp Tyr Ser Gln Ile Glu Leu Arg Val Leu Ala His Leu Ser Gly Asp
            610                 615                 620

Glu Asn Leu Ile Arg Val Phe Gln Glu Gly Lys Asp Ile His Thr Gln
    625                 630                 635                 640

Thr Ala Ser Trp Met Phe Gly Val Pro Pro Glu Ala Val Asp Pro Leu
                        645                 650                 655

Met Arg Arg Ala Ala Lys Thr Val Asn Phe Gly Val Leu Tyr Gly Met
                    660                 665                 670

Ser Ala His Arg Leu Ser Gln Glu Leu Ala Ile Pro Tyr Glu Glu Ala
                675                 680                 685

Ser Ala Phe Ile Glu Arg Tyr Phe Gln Ser Phe Pro Lys Val Arg Ala
            690                 695                 700

Trp Ile Glu Lys Thr Leu Glu Glu Gly Arg Lys Arg Gly Tyr Val Glu
    705                 710                 715                 720

Thr Leu Phe Gly Arg Arg Arg Tyr Val Pro Asp Leu Asn Ala Arg Val
                        725                 730                 735

Lys Ser Val Arg Glu Ala Ala Glu Arg Met Ala Phe Asn Met Pro Val
                    740                 745                 750

Gln Gly Thr Ala Ala Asp Leu Met Lys Leu Ala Met Val Lys Leu Phe
                755                 760                 765

Pro Arg Leu Arg Glu Met Gly Ala Arg Met Leu Leu Gln Val His Asp
            770                 775                 780

Glu Leu Leu Leu Glu Ala Pro Gln Ala Arg Ala Glu Glu Val Ala Ala
    785                 790                 795                 800

Leu Ala Lys Glu Ala Met Glu Lys Ala Tyr Pro Leu Ala Val Pro Leu
                        805                 810                 815

Glu Val Glu Val Gly Ile Gly Glu Asp Trp Leu Ser Ala Lys Gly
                    820                 825                 830

<210> SEQ ID NO 97
<211> LENGTH: 830
<212> TYPE: PRT
<213> ORGANISM: Artificial Sequence
<220> FEATURE:
<223> OTHER INFORMATION: AMINO ACID SEQUENCE OF DNA polymerase I
      [Thermus scotoductus]

<400> SEQUENCE: 97

Met Leu Pro Leu Phe Glu Pro Lys Gly Arg Val Leu Leu Val Asp Gly
1               5                   10                  15

His His Leu Ala Tyr Arg Thr Phe Phe Ala Leu Lys Gly Leu Thr Thr
                20                  25                  30

Ser Arg Gly Glu Pro Val Gln Ala Val Tyr Gly Phe Ala Lys Ser Leu
            35                  40                  45

Leu Lys Ala Leu Arg Glu Asp Gly Asp Val Val Ile Val Val Phe Asp
        50                  55                  60
```

-continued

Ala Lys Ala Pro Ser Phe Arg His Gln Thr Tyr Glu Ala Tyr Lys Ala
 65                  70                  75                  80

Gly Arg Ala Pro Thr Pro Glu Asp Phe Pro Arg Gln Leu Ala Leu Ile
                 85                  90                  95

Lys Glu Met Val Asp Leu Leu Gly Leu Glu Arg Leu Glu Val Pro Gly
            100                 105                 110

Phe Glu Ala Asp Asp Val Leu Ala Thr Leu Ala Lys Lys Ala Glu Lys
            115                 120                 125

Glu Gly Tyr Glu Val Arg Ile Leu Thr Ala Asp Arg Asp Leu Tyr Gln
        130                 135                 140

Leu Leu Ser Glu Arg Ile Ser Ile Leu His Pro Glu Gly Tyr Leu Ile
145                 150                 155                 160

Thr Pro Glu Trp Leu Trp Glu Lys Tyr Gly Leu Lys Pro Ser Gln Trp
                165                 170                 175

Val Asp Tyr Arg Ala Leu Ala Gly Asp Pro Ser Asp Asn Ile Pro Gly
            180                 185                 190

Val Lys Gly Ile Gly Glu Lys Thr Ala Ala Lys Leu Ile Arg Glu Trp
        195                 200                 205

Gly Ser Leu Glu Asn Leu Leu Lys His Leu Glu Gln Val Lys Pro Ala
    210                 215                 220

Ser Val Arg Glu Lys Ile Leu Ser His Met Glu Asp Leu Lys Leu Ser
225                 230                 235                 240

Leu Glu Leu Ser Arg Val His Thr Asp Leu Leu Gln Val Asp Phe
                245                 250                 255

Ala Arg Arg Arg Glu Pro Asp Arg Glu Gly Leu Lys Ala Phe Leu Glu
            260                 265                 270

Arg Leu Glu Phe Gly Ser Leu Leu His Glu Phe Gly Leu Leu Glu Ser
        275                 280                 285

Pro Val Ala Ala Glu Ala Pro Trp Pro Pro Glu Gly Ala Phe
    290                 295                 300

Val Gly Tyr Val Leu Ser Arg Pro Glu Pro Met Trp Ala Glu Leu Asn
305                 310                 315                 320

Ala Leu Ala Ala Ala Trp Glu Gly Arg Val Tyr Arg Ala Glu Asp Pro
                325                 330                 335

Leu Glu Ala Leu Arg Gly Leu Gly Glu Val Arg Gly Leu Leu Ala Lys
            340                 345                 350

Asp Leu Ala Val Leu Ala Leu Arg Glu Gly Ile Ala Leu Ala Pro Gly
        355                 360                 365

Asp Asp Pro Met Leu Leu Ala Tyr Leu Leu Asp Pro Ser Asn Thr Ala
    370                 375                 380

Pro Glu Gly Val Ala Arg Arg Tyr Gly Gly Glu Trp Thr Glu Glu Ala
385                 390                 395                 400

Gly Glu Arg Ala Leu Leu Ser Glu Arg Leu Tyr Ala Ala Leu Leu Glu
                405                 410                 415

Arg Leu Lys Gly Glu Glu Arg Leu Leu Trp Leu Tyr Glu Glu Val Glu
            420                 425                 430

Lys Pro Leu Ser Arg Val Leu Ala His Met Glu Ala Thr Gly Val Arg
        435                 440                 445

Leu Asp Val Ala Tyr Leu Lys Ala Leu Ser Leu Glu Val Glu Ala Glu
    450                 455                 460

Leu Arg Arg Leu Glu Glu Glu Val His Arg Leu Ala Gly His Pro Phe
465                 470                 475                 480

Asn Leu Asn Ser Arg Asp Gln Leu Glu Arg Val Leu Phe Asp Glu Leu

```
                    485                 490                 495

Gly Leu Pro Ala Ile Gly Lys Thr Glu Lys Thr Gly Lys Arg Ser Thr
                500                 505                 510

Ser Ala Ala Val Leu Glu Ala Leu Arg Glu Ala His Pro Ile Val Asp
            515                 520                 525

Arg Ile Leu Gln Tyr Arg Glu Leu Ser Lys Leu Lys Gly Thr Tyr Ile
        530                 535                 540

Asp Pro Leu Pro Ala Leu Val His Pro Lys Thr Asn Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
            580                 585                 590

Arg Arg Ala Phe Val Ala Glu Glu Gly Trp Arg Leu Val Val Leu Asp
        595                 600                 605

Tyr Ser Gln Ile Glu Leu Arg Val Leu Ala His Leu Ser Gly Asp Glu
    610                 615                 620

Asn Leu Ile Arg Val Phe Gln Glu Gly Gln Asp Ile His Thr Gln Thr
625                 630                 635                 640

Ala Ser Trp Met Phe Gly Val Pro Pro Glu Ala Val Asp Ser Leu Met
                645                 650                 655

Arg Arg Ala Ala Lys Thr Ile Asn Phe Gly Val Leu Tyr Gly Met Ser
            660                 665                 670

Ala His Arg Leu Ser Gly Glu Leu Ala Ile Pro Tyr Glu Glu Ala Val
        675                 680                 685

Ala Phe Ile Glu Arg Tyr Phe Gln Ser Tyr Pro Lys Val Arg Ala Trp
    690                 695                 700

Ile Glu Lys Thr Leu Ala Glu Gly Arg Glu Arg Gly Tyr Val Glu Thr
705                 710                 715                 720

Leu Phe Gly Arg Arg Arg Tyr Val Pro Asp Leu Ala Ser Arg Val Lys
                725                 730                 735

Ser Ile Arg Glu Ala Ala Glu Arg Met Ala Phe Asn Met Pro Val Gln
            740                 745                 750

Gly Thr Ala Ala Asp Leu Met Lys Leu Ala Met Val Lys Leu Phe Pro
        755                 760                 765

Arg Leu Gln Glu Leu Gly Ala Arg Met Leu Leu Gln Val His Asp Glu
    770                 775                 780

Leu Val Leu Glu Ala Pro Lys Glu Gln Ala Glu Val Ala Gln Glu
785                 790                 795                 800

Ala Lys Arg Thr Met Glu Glu Val Trp Pro Leu Lys Val Pro Leu Glu
                805                 810                 815

Val Glu Val Gly Ile Gly Glu Asp Trp Leu Ser Ala Lys Ala
            820                 825                 830

<210> SEQ ID NO 98
<211> LENGTH: 834
<212> TYPE: PRT
<213> ORGANISM: Artificial Sequence
<220> FEATURE:
<223> OTHER INFORMATION: AMINO ACID SEQUENCE OF Thermostable DNA
      Polymerase [Thermus caldophilus]

<400> SEQUENCE: 98

Met Glu Ala Met Leu Pro Leu Phe Glu Pro Lys Gly Arg Val Leu Leu
1               5                   10                  15
```

```
Val Asp Gly His His Leu Ala Tyr Arg Thr Phe Phe Ala Leu Lys Gly
         20                  25                  30

Leu Thr Thr Ser Arg Gly Glu Pro Val Gln Ala Val Tyr Gly Phe Ala
             35                  40                  45

Lys Ser Leu Leu Lys Ala Leu Lys Glu Asp Gly Tyr Lys Ala Val Phe
 50                  55                  60

Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Asn Pro Glu Lys Glu Gly Tyr Glu Val Arg Ile Leu Thr Ala Asp Arg
    130                 135                 140

Asp Leu Asp Gln Leu Val Ser Asp Arg Val Ala Val Leu His Pro Glu
145                 150                 155                 160

Gly His Leu Ile Thr Pro Glu Trp Leu Trp Gln Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Gln Gly Glu Glu Lys Leu Leu Trp Leu Tyr
            420                 425                 430

His Glu Val Glu Lys Pro Leu Ser Arg Val Leu Ala His Met Glu Ala
```

```
                435                 440                 445
Thr Gly Val Arg Leu Asp Val Ala Tyr Leu Gln Ala Leu Ser Leu Glu
    450                 455                 460
Leu Ala Glu Glu Ile Arg Arg Leu Glu Glu Val Phe Arg Leu Ala
465                 470                 475                 480
Gly His Pro Phe Asn Leu Asn Ser Arg Asp Gln Leu Glu Arg Val Leu
                485                 490                 495
Phe Asp Glu Leu Arg Leu Pro Ala Leu Gly Lys Thr Gln Lys Thr Gly
                500                 505                 510
Lys Arg Ser Thr Ser Ala Ala Val Leu Glu Ala Leu Arg Glu Ala His
                515                 520                 525
Pro Ile Val Glu Lys Ile Leu Gln His Arg Glu Leu Thr Lys Leu Lys
            530                 535                 540
Asn Thr Tyr Val Asp Pro Leu Pro Ser Leu Val His Pro Asn Thr Gly
545                 550                 555                 560
Arg Leu His Thr Arg Phe Asn Gln Thr Ala Thr Ala Thr Gly Arg Leu
                565                 570                 575
Ser Ser Ser Asp Pro Asn Leu Gln Asn Ile Pro Val Arg Thr Pro Leu
            580                 585                 590
Gly Gln Arg Ile Arg Arg Ala Phe Val Ala Glu Ala Gly Trp Ala Leu
                595                 600                 605
Val Ala Leu Asp Tyr Ser Gln Ile Glu Leu Arg Val Leu Ala His Leu
        610                 615                 620
Ser Gly Asp Glu Asn Leu Ile Arg Val Phe Gln Glu Gly Lys Asp Ile
625                 630                 635                 640
His Thr Gln Thr Ala Ser Trp Met Phe Gly Val Pro Pro Glu Ala Val
                645                 650                 655
Asp Pro Leu Met Arg Arg Ala Ala Lys Thr Val Asn Phe Gly Val Leu
            660                 665                 670
Tyr Gly Met Ser Ala His Arg Leu Ser Gln Glu Leu Ala Ile Pro Tyr
        675                 680                 685
Glu Glu Ala Val Ala Phe Ile Glu Arg Tyr Phe Gln Ser Phe Pro Lys
    690                 695                 700
Val Arg Ala Trp Ile Glu Lys Thr Leu Glu Glu Gly Arg Lys Arg Gly
705                 710                 715                 720
Tyr Val Glu Thr Leu Phe Gly Arg Arg Arg Tyr Val Pro Asp Leu Asn
                725                 730                 735
Ala Arg Val Lys Ser Val Arg Glu Ala Ala Glu Arg Met Ala Phe Asn
            740                 745                 750
Met Pro Val Gln Gly Thr Ala Ala Asp Leu Met Lys Leu Ala Met Val
        755                 760                 765
Lys Leu Phe Pro Arg Leu Arg Glu Met Gly Ala Arg Met Leu Leu Gln
    770                 775                 780
Val His Asp Glu Leu Leu Leu Glu Ala Pro Gln Ala Gly Ala Glu Glu
785                 790                 795                 800
Val Ala Ala Leu Ala Lys Glu Ala Met Glu Lys Ala Tyr Pro Leu Ala
                805                 810                 815
Val Pro Leu Glu Val Glu Val Gly Met Gly Glu Asp Trp Leu Ser Ala
            820                 825                 830
Lys Gly

<210> SEQ ID NO 99
<211> LENGTH: 834
```

```
<212> TYPE: PRT
<213> ORGANISM: Artificial Sequence
<220> FEATURE:
<223> OTHER INFORMATION: AMINO ACID SEQUENCE OF DNA polymerase I
      [Marinithermus hydrothermalis DSM 14884]

<400> SEQUENCE: 99
```

| | | | | | | | | | | | | | | | |
|---|---|---|---|---|---|---|---|---|---|---|---|---|---|---|---|
| Met | Gln | Gln | Pro | Ser | Leu | Phe | Asp | His | Arg | Pro | Glu | Arg | Ile | Leu | Ile |
| 1 | | | | 5 | | | | | 10 | | | | | 15 | |
| Val | Asp | Gly | His | His | Leu | Ala | Tyr | Arg | Asn | Tyr | Phe | Ala | Leu | Gly | Glu |
| | | | 20 | | | | | 25 | | | | | 30 | | |
| Leu | Thr | Thr | Ser | Arg | Gly | Glu | Pro | Val | Gln | Ala | Val | Tyr | Gly | Phe | Ala |
| | | | 35 | | | | | 40 | | | | | 45 | | |
| Arg | Thr | Leu | Leu | Lys | Leu | Leu | Lys | Glu | Asp | Gly | Asp | Cys | Val | Ile | Val |
| | 50 | | | | | 55 | | | | | 60 | | | | |
| Val | Phe | Asp | Ala | Pro | Gln | Pro | Ser | Phe | Arg | His | Glu | Gln | Phe | Ala | Ala |
| 65 | | | | | 70 | | | | | 75 | | | | | 80 |
| Tyr | Lys | Ala | Gln | Arg | Ala | Pro | Thr | Pro | Glu | Asp | Phe | Lys | Pro | Gln | Leu |
| | | | | 85 | | | | | 90 | | | | | 95 | |
| Glu | Lys | Ile | Lys | Gln | Leu | Val | Asp | Leu | Leu | Gly | Leu | Ala | Arg | Phe | Glu |
| | | | 100 | | | | | 105 | | | | | 110 | | |
| Leu | Ala | Gly | Tyr | Glu | Ala | Asp | Asp | Val | Ile | Gly | Ser | Leu | Ala | Lys | Lys |
| | | | 115 | | | | | 120 | | | | | 125 | | |
| Ala | Glu | Ala | Glu | Gly | Tyr | Glu | Val | Arg | Ile | Val | Thr | Ser | Asp | Arg | Asp |
| | 130 | | | | | 135 | | | | | 140 | | | | |
| Ser | Tyr | Gln | Leu | Leu | Ser | Asp | Lys | Val | Arg | Val | Leu | Lys | Pro | Asp | Gly |
| 145 | | | | | 150 | | | | | 155 | | | | | 160 |
| Glu | Glu | Val | Thr | Pro | Glu | Thr | Val | Arg | Glu | Lys | Tyr | Gly | Val | Thr | Val |
| | | | | 165 | | | | | 170 | | | | | 175 | |
| Ala | Gln | Trp | Val | Asp | Phe | Arg | Ala | Leu | Thr | Gly | Asp | Ala | Ser | Asp | Asn |
| | | | 180 | | | | | 185 | | | | | 190 | | |
| Ile | Pro | Gly | Val | Arg | Gly | Ile | Gly | Ala | Lys | Thr | Ala | Ala | Lys | Leu | Leu |
| | | | 195 | | | | | 200 | | | | | 205 | | |
| Ala | Glu | Trp | Gly | Ser | Leu | Glu | Asn | Leu | Tyr | Ala | His | Leu | Ala | Glu | Val |
| | 210 | | | | | 215 | | | | | 220 | | | | |
| Thr | Pro | Pro | Ser | Val | Arg | Lys | Lys | Leu | Glu | Ala | Gly | Arg | Glu | Lys | Ala |
| 225 | | | | | 230 | | | | | 235 | | | | | 240 |
| Ala | Leu | Ser | Arg | Ala | Leu | Ser | Glu | Ile | His | Thr | Asp | Leu | Ala | Ile | Glu |
| | | | | 245 | | | | | 250 | | | | | 255 | |
| Val | Asp | Phe | Ala | Ala | Cys | His | Arg | Arg | Pro | Val | Asp | Arg | Glu | Ala | Leu |
| | | | 260 | | | | | 265 | | | | | 270 | | |
| Arg | Ala | Phe | Leu | Glu | Ala | Leu | Glu | Phe | Gly | Ser | Ile | Leu | Arg | Glu | Leu |
| | | | 275 | | | | | 280 | | | | | 285 | | |
| Gly | Leu | Ile | Glu | Ala | Arg | Ser | Ala | Glu | Glu | Ala | Pro | Trp | Pro | Pro | Pro |
| | 290 | | | | | 295 | | | | | 300 | | | | |
| Pro | Glu | Ala | Phe | Leu | Gly | Tyr | Val | Leu | Asp | Arg | Pro | Gln | Pro | Met | Trp |
| 305 | | | | | 310 | | | | | 315 | | | | | 320 |
| Ala | Glu | Leu | Lys | Gly | Leu | Ala | Gly | Ala | Trp | Glu | Gly | Arg | Val | Ala | Arg |
| | | | | 325 | | | | | 330 | | | | | 335 | |
| Gly | Pro | Ala | Arg | Ala | Lys | Glu | Leu | Ala | Arg | Phe | Glu | Ala | Val | His | Ala |
| | | | 340 | | | | | 345 | | | | | 350 | | |
| Leu | Gln | Ala | Lys | Asp | Leu | Thr | Val | Trp | Ala | Arg | Arg | Glu | Gly | Val | Arg |
| | | | 355 | | | | | 360 | | | | | 365 | | |
| Val | Gln | Pro | Gly | Glu | Asp | Pro | Leu | Leu | Leu | Ala | Tyr | Leu | Tyr | Asp | Pro |
| | 370 | | | | | 375 | | | | | 380 | | | | |

```
Thr Asn Ser Asp Pro Ala Ala Thr Val Arg Arg Tyr Gly Ala Gly Asp
385                 390                 395                 400

Trp Ser Glu Asp Pro Ala Ala Arg Ala Leu Ala Ala Glu Leu Trp
            405                 410                 415

Arg Ile Leu Gly Glu Arg Leu Ala Gly Glu Ala Leu Trp Trp Leu
                420                 425                 430

Tyr Arg Glu Val Glu Arg Pro Leu Ala Gly Val Leu Ala Glu Met Glu
                435                 440                 445

His Ala Gly Val Arg Val Asp Val Ala Tyr Leu Glu Ala Leu Ser Ala
450                 455                 460

Glu Leu Gly Arg Glu Ile Ala Ala Ile Glu Ala Glu Val His Arg Leu
465                 470                 475                 480

Ala Gly Arg Ala Phe Asn Leu Asn Ser Arg Asp Gln Leu Glu Val Ile
                485                 490                 495

Leu Tyr Asp Glu Leu Gly Leu Thr Pro Thr Arg Arg Thr Gln Lys Thr
                500                 505                 510

Gly Arg Arg Ser Thr Ser Ala Ala Ala Leu Glu Ala Leu Val Gly Ala
                515                 520                 525

His Pro Ile Val Glu Arg Ile Leu Ala Tyr Arg Glu Leu Ser Lys Leu
530                 535                 540

Lys Gly Thr Tyr Leu Asp Pro Leu Pro Arg Leu Val His Pro Ala Thr
545                 550                 555                 560

Gly Arg Ile His Thr Arg Tyr His Gln Thr Gly Thr Ala Thr Gly Arg
                565                 570                 575

Leu Ser Ser Asp Pro Asn Leu Gln Asn Ile Pro Val Arg Thr Glu
                580                 585                 590

Val Gly Arg Arg Ile Arg Arg Ala Phe Val Ala Glu Pro Gly Tyr Val
                595                 600                 605

Leu Val Ala Ala Asp Tyr Ser Gln Ile Glu Leu Arg Val Leu Ala His
                610                 615                 620

Leu Ser Gly Asp Glu Asn Leu Lys Arg Val Phe Gln Glu Arg Arg Asp
625                 630                 635                 640

Ile His Thr Gln Thr Ala Ser Trp Met Phe Gly Val Pro Pro Glu Ala
                645                 650                 655

Val Asp Pro Phe Arg Arg Ala Ala Lys Thr Val Asn Phe Gly Val
            660                 665                 670

Leu Tyr Gly Met Ser Pro His Arg Leu Ser Arg Glu Leu Gly Ile Glu
                675                 680                 685

Tyr Ala Glu Ala Glu Arg Phe Ile Gln Arg Tyr Phe Glu Ser Tyr Pro
                690                 695                 700

Arg Val Gln Ala Tyr Ile Glu Arg Thr Leu Glu Gln Ala Arg Glu Lys
705                 710                 715                 720

Gly Tyr Val Glu Thr Leu Phe Gly Arg Arg Tyr Ile Pro Asp Ile
                725                 730                 735

Arg Ser Arg Asn Arg Asn Val Arg Glu Ala Ala Glu Arg Met Ala Phe
                740                 745                 750

Asn Met Pro Val Gln Gly Thr Ala Ala Asp Leu Met Lys Leu Ala Met
            755                 760                 765

Val Lys Leu Ala Pro Glu Ile Arg Ser Leu Gly Ala Arg Leu Ile Leu
        770                 775                 780

Gln Val His Asp Glu Leu Val Leu Glu Ala Pro Gln Glu Arg Ala Glu
785                 790                 795                 800
```

```
Ala Val Ala Arg Val Val Arg Glu Val Met Glu Gly Ala Trp Ala Leu
                805                 810                 815

Asp Val Pro Leu Glu Val Glu Val Gly Ile Gly Glu Asn Trp Leu Glu
            820                 825                 830

Ala Lys

<210> SEQ ID NO 100
<211> LENGTH: 833
<212> TYPE: PRT
<213> ORGANISM: Artificial Sequence
<220> FEATURE:
<223> OTHER INFORMATION: AMINO ACID SEQUENCE OF DNA polymerase I
      [Thermus filiformis]

<400> SEQUENCE: 100

Met Thr Pro Leu Phe Asp Leu Glu Glu Pro Lys Arg Val Leu Leu
1               5                   10                  15

Val Asp Gly His His Leu Ala Tyr Arg Thr Phe Tyr Ala Leu Ser Leu
                20                  25                  30

Thr Thr Ser Arg Gly Glu Pro Val Gln Met Val Tyr Gly Phe Ala Arg
            35                  40                  45

Ser Leu Leu Lys Ala Leu Lys Glu Asp Gly Gln Ala Val Val Val
    50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
                85                  90                  95

Leu Val Lys Arg Leu Val Asp Leu Gly Leu Val Arg Leu Glu Ala
            100                 105                 110

Pro Gly Tyr Glu Ala Asp Asp Val Leu Gly Thr Leu Ala Lys Lys Ala
            115                 120                 125

Glu Arg Glu Gly Met Glu Val Arg Ile Leu Thr Gly Asp Arg Asp Phe
130                 135                 140

Phe Gln Leu Leu Ser Glu Lys Val Ser Val Leu Leu Pro Asp Gly Thr
145                 150                 155                 160

Leu Val Thr Pro Lys Asp Val Gln Glu Lys Tyr Gly Val Pro Pro Glu
                165                 170                 175

Arg Trp Val Asp Phe Arg Ala Leu Thr Gly Asp Arg Ser Asp Asn Ile
            180                 185                 190

Pro Gly Val Ala Gly Ile Gly Glu Lys Thr Ala Leu Arg Leu Leu Ala
            195                 200                 205

Glu Trp Gly Ser Val Glu Asn Leu Leu Lys Asn Leu Asp Arg Val Lys
210                 215                 220

Pro Asp Ser Val Arg Arg Lys Ile Glu Ala His Leu Glu Asp Leu Arg
225                 230                 235                 240

Leu Ser Leu Asp Leu Ala Arg Ile Arg Thr Asp Leu Pro Leu Glu Val
                245                 250                 255

Asp Phe Lys Ala Leu Arg Arg Arg Thr Pro Asp Leu Glu Gly Leu Arg
            260                 265                 270

Ala Phe Leu Glu Glu Leu Glu Phe Gly Ser Leu Leu His Glu Phe Gly
            275                 280                 285

Leu Leu Gly Gly Glu Lys Pro Arg Glu Ala Pro Trp Pro Pro
290                 295                 300

Glu Gly Ala Phe Val Gly Phe Leu Leu Ser Arg Lys Glu Pro Met Trp
305                 310                 315                 320
```

```
Ala Glu Leu Leu Ala Leu Ala Ala Ala Glu Gly Arg Val His Arg
            325                 330                 335

Ala Thr Ser Pro Val Glu Ala Leu Ala Asp Leu Lys Glu Ala Arg Gly
            340                 345                 350

Phe Leu Ala Lys Asp Leu Ala Val Leu Ala Leu Arg Glu Gly Val Ala
            355                 360                 365

Leu Asp Pro Thr Asp Pro Leu Leu Val Ala Tyr Leu Leu Asp Pro
370                 375                 380

Ala Asn Thr Asn Pro Glu Gly Val Ala Arg Arg Tyr Gly Gly Glu Phe
385                 390                 395                 400

Thr Glu Asp Ala Ala Glu Arg Ala Leu Leu Ser Glu Arg Leu Phe Gln
            405                 410                 415

Asn Leu Phe Pro Arg Leu Ser Glu Lys Leu Leu Trp Leu Tyr Gln Glu
            420                 425                 430

Val Glu Arg Pro Leu Ser Arg Val Leu Ala His Met Glu Ala Arg Gly
            435                 440                 445

Val Arg Leu Asp Val Pro Leu Leu Glu Ala Leu Ser Phe Glu Leu Glu
            450                 455                 460

Lys Glu Met Glu Arg Leu Glu Gly Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Thr Pro Val Gly Arg Thr Glu Lys Thr Gly Lys Arg
            500                 505                 510

Ser Thr Ala Gln Gly Ala Leu Glu Ala Leu Arg Gly Ala His Pro Ile
            515                 520                 525

Val Glu Leu Ile Leu Gln Tyr Arg Glu Leu Ser Lys Leu Lys Ser Thr
            530                 535                 540

Tyr Leu Asp Pro Leu Pro Arg Leu Val His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Lys Ala Phe Val Ala Glu Glu Gly Trp Leu Leu Leu Ala
            595                 600                 605

Ala Asp Tyr Ser Gln Ile Glu Leu Arg Val Leu Ala His Leu Ser Gly
            610                 615                 620

Asp Glu Asn Leu Lys Arg Val Phe Arg Glu Gly Lys Asp Ile His Thr
625                 630                 635                 640

Glu Thr Ala Ala Trp Met Phe Gly Leu Asp Pro Ala Leu Val Asp Pro
            645                 650                 655

Lys Met Arg Arg Ala Ala Lys Thr Val Asn Phe Gly Val Leu Tyr Gly
            660                 665                 670

Met Ser Ala His Arg Leu Ser Gln Glu Leu Gly Ile Asp Tyr Lys Glu
            675                 680                 685

Ala Glu Ala Phe Ile Glu Arg Tyr Phe Gln Ser Phe Pro Lys Val Arg
            690                 695                 700

Ala Trp Ile Glu Arg Thr Leu Glu Glu Gly Arg Thr Arg Gly Tyr Val
705                 710                 715                 720

Glu Thr Leu Phe Gly Arg Arg Arg Tyr Val Pro Asp Leu Ala Ser Arg
            725                 730                 735

Val Arg Ser Val Arg Glu Ala Ala Glu Arg Met Ala Phe Asn Met Pro
```

```
                    740                 745                 750
Val Gln Gly Thr Ala Ala Asp Leu Met Lys Ile Ala Met Val Lys Leu
                755                 760                 765

Phe Pro Arg Leu Lys Pro Leu Gly Ala His Leu Leu Leu Gln Val His
            770                 775                 780

Asp Glu Leu Val Leu Glu Val Pro Glu Asp Arg Ala Glu Glu Ala Lys
785                 790                 795                 800

Ala Leu Val Lys Glu Val Met Glu Asn Thr Tyr Pro Leu Asp Val Pro
                805                 810                 815

Leu Glu Val Glu Val Gly Val Gly Arg Asp Trp Leu Glu Ala Lys Gly
                820                 825                 830

Asp

<210> SEQ ID NO 101
<211> LENGTH: 850
<212> TYPE: PRT
<213> ORGANISM: Artificial Sequence
<220> FEATURE:
<223> OTHER INFORMATION: AMINO ACID SEQUENCE OF DNA polymerase I
      [Meiothermus timidus]

<400> SEQUENCE: 101

Met Gln Gln Arg Ser Leu Phe Asp Pro Glu Pro Glu Thr Gln Pro Lys
1               5                   10                  15

Pro Ala Pro Ala Pro Arg Ala Glu Arg Val Ile Leu Ile Asp Gly His
                20                  25                  30

His Leu Ala Tyr Arg Thr Tyr Phe Ala Phe Glu Lys Leu Thr Thr Ser
            35                  40                  45

Thr Gly Glu Pro Val Gln Ala Ile Phe Gly Phe Leu Arg Thr Leu Leu
        50                  55                  60

Lys Tyr Leu Lys Glu Asn Ser Ser Cys Val Ile Val Val Phe Asp Ala
65              70                  75                  80

Pro Ala Arg Thr Phe Arg His Asp Asn Phe Glu Ala Tyr Lys Ala Gly
                85                  90                  95

Arg Ala Pro Thr Pro Glu Asp Leu Pro Glu Gln Ile Arg Lys Ile Lys
            100                 105                 110

Gln Leu Val Glu Leu Leu Gly Leu Val Cys Leu Glu Val Pro Gly Tyr
        115                 120                 125

Glu Ala Asp Asp Val Ile Gly Thr Leu Ala Lys Lys Ala Glu Ala Glu
    130                 135                 140

Gly Tyr Gln Val Arg Ile Leu Thr Gly Asp Arg Asp Ala Tyr Gln Leu
145                 150                 155                 160

Leu Ser Glu Asn Ile Trp Ile Phe His Pro Asp Gly Ser Ile Ile Gly
                165                 170                 175

Pro Ser Gln Val Arg Glu Lys Tyr Gly Val Ser Val Glu Gln Trp Val
            180                 185                 190

Asp Tyr Arg Ala Leu Thr Gly Asp Ala Ser Asp Asn Ile Pro Gly Ala
        195                 200                 205

Lys Gly Ile Gly Pro Lys Gly Ala Ser Lys Leu Leu Glu Glu Trp Lys
    210                 215                 220

Ser Leu Asp Asn Leu Leu Thr His Leu Glu Glu Val Arg Pro Glu Arg
225                 230                 235                 240

Thr Arg Glu Leu Ile Arg Ala Ser Leu Glu Asp Ile Lys Leu Ser Arg
                245                 250                 255

Glu Leu Ser Gln Ile His Thr Asp Val Pro Leu Glu Pro Glu Leu Cys
```

```
            260                 265                 270
Asp Phe Ser Lys Ala His Arg Arg Glu Pro Lys Thr Ala Glu Leu Arg
            275                 280                 285

Glu Met Leu Glu Arg Leu Glu Phe Gly Ser Ile Leu Arg Asp Leu Gly
        290                 295                 300

Leu Leu Glu Ala His Arg Pro Thr Thr Glu Ala Pro Trp Pro Pro Pro
305                 310                 315                 320

Pro Gly Ala Phe Leu Gly Phe Thr Leu Asp Arg Ala Gln Pro Met Trp
                325                 330                 335

Ala Glu Leu Thr Gly Leu Ala Ala Lys Gly Asp Thr Leu Tyr Arg
            340                 345                 350

Gly Pro Thr Asp Leu Ala Asp Leu Lys Thr Leu Gly Arg Leu Asn Ser
        355                 360                 365

Leu Glu Ala Lys Asp Leu Ser Val Leu Leu Arg Glu Gly Tyr Trp
        370                 375                 380

Val Pro Pro Gly Asp Asp Pro Met Leu Leu Ala Tyr Leu Tyr Asp Pro
385                 390                 395                 400

Ala Asn Ser Glu Pro Ala Gly Thr Val Arg Arg Tyr Gly Ala Gly Asp
                405                 410                 415

Trp Thr Thr Asp Pro Ala Gln Arg Ala Leu Ala Ala Gln Thr Leu Trp
                420                 425                 430

Glu Thr Leu Gly Arg Arg Thr Glu Lys Asp Glu Arg Leu Trp Trp Leu
            435                 440                 445

Tyr Arg Glu Val Glu Gln Pro Leu Ser Gly Ile Leu Ala Arg Met Glu
        450                 455                 460

Val Gln Gly Val Ala Leu Asp Val Pro Tyr Leu Arg Glu Leu Ser Glu
465                 470                 475                 480

Glu Leu Gly Lys Glu Leu Gly Tyr Leu Glu Ala Glu Ile His Arg Leu
                485                 490                 495

Ala Gly Arg Pro Phe Asn Val Asn Ser Arg Asp Gln Leu Glu Ala Ile
            500                 505                 510

Leu Tyr Asp Glu Leu Lys Leu Gln Ala Gly Gly Lys Lys Thr Ala Thr
        515                 520                 525

Gly Lys Arg Ser Thr Ala Ala Ser Val Leu Glu Glu Met Arg Ser Leu
        530                 535                 540

His Pro Ile Val Asp Lys Ile Leu Asp Tyr Arg Glu Leu Ser Lys Leu
545                 550                 555                 560

Lys Ser Thr Tyr Leu Asp Pro Leu Pro Lys Leu Ile His Pro Lys Thr
                565                 570                 575

Gly Arg Leu His Thr Arg Phe Asn Gln Thr Ala Thr Ala Thr Gly Arg
            580                 585                 590

Leu Ser Ser Asp Pro Asn Leu Gln Asn Ile Pro Val Arg Thr Glu
        595                 600                 605

Val Gly Arg Lys Ile Arg Lys Ala Phe Val Ala Arg Pro Gly Tyr Cys
610                 615                 620

Leu Val Ala Ala Asp Tyr Ser Gln Ile Glu Leu Arg Leu Leu Ala His
625                 630                 635                 640

Leu Ser Gly Asp Glu Asn Leu Lys Gln Val Phe Leu Glu Gly Arg Asp
                645                 650                 655

Ile His Thr Gln Thr Ala Ala Trp Met Phe Gly Ile Ala Pro Glu Thr
            660                 665                 670

Val Asp Ser Tyr Arg Arg Arg Ala Ala Lys Thr Val Val Phe Gly Val
                675                 680                 685
```

Leu Tyr Gly Met Ser Ala His Arg Leu Ser Glu Leu Ser Ile Pro
      690                 695                 700

Tyr Ala Glu Ala Glu Gly Phe Ile Glu Arg Tyr Phe Ala Thr Tyr Pro
705                 710                 715                 720

Lys Val Arg Ser Trp Ile Asp Arg Thr Leu Ala Glu Ala Arg Glu Arg
                725                 730                 735

Gly Tyr Val Glu Thr Leu Phe Gly Arg Lys Arg Phe Val Ser Glu Leu
                740                 745                 750

Ser Ala Lys Val Ser Ser Val Arg Gln Ala Ala Glu Arg Met Ala Phe
            755                 760                 765

Asn Met Pro Val Gln Gly Thr Ala Ala Asp Leu Met Lys Leu Ala Met
770                 775                 780

Val Lys Leu Gly Pro Lys Leu Glu Pro Leu Asp Ala His Leu Val Leu
785                 790                 795                 800

Gln Val His Asp Glu Leu Val Ile Glu Ala Pro Arg Glu Arg Ala Glu
                805                 810                 815

Glu Val Ala Glu Leu Ala Arg Glu Thr Met Arg Thr Ala Trp Glu Phe
                820                 825                 830

Glu Val Pro Leu Glu Val Gly Thr Gly Val Gly Glu Asn Trp Leu Glu
            835                 840                 845

Ala Lys
   850

<210> SEQ ID NO 102
<211> LENGTH: 838
<212> TYPE: PRT
<213> ORGANISM: Artificial Sequence
<220> FEATURE:
<223> OTHER INFORMATION: AMINO ACID SEQUENCE OF DNA polymerase I
      [Desulfurobacterium thermolithotrophum]

<400> SEQUENCE: 102

Met Ser Lys Lys Thr Ile Tyr Leu Phe Asp Gly Thr Ser Leu Ala Tyr
1               5                   10                  15

Arg Ala Tyr Tyr Ala Ile Lys Asp Leu Thr Thr Ser Lys Gly Phe Pro
                20                  25                  30

Thr Asn Ala Ile Tyr Gly Phe Ile Arg Met Phe Leu Lys Leu Tyr Lys
            35                  40                  45

Asp Phe Lys Pro Asn Tyr Ile Ala Val Ala Phe Asp Val Gly Lys Lys
        50                  55                  60

Thr Phe Arg Ser Lys Leu Leu Lys Glu Tyr Lys Ala Asn Arg Lys Pro
65                  70                  75                  80

Thr Pro Asp Ser Phe Lys Leu Gln Leu Pro Tyr Ile Lys Lys Phe Leu
                85                  90                  95

Glu Cys Leu Gly Ile Thr Ile Leu Glu Lys Glu Gly Phe Glu Ala Asp
                100                 105                 110

Asp Ile Leu Gly Thr Ala Ala Lys Lys Phe Ala Ser Glu Gly Tyr Arg
            115                 120                 125

Val Phe Val Val Thr Pro Asp Lys Asp Met Arg Gln Leu Ile Asp Gly
        130                 135                 140

Lys Ile Ser Val Ile Ala Ile Asn Lys Thr Gly Gln Lys Glu Ile Tyr
145                 150                 155                 160

Asp Leu Val Ser Phe Lys Glu Lys Tyr Gly Ile Glu Pro Glu Gln Ile
                165                 170                 175

Pro Asp Phe Phe Gly Leu Val Gly Asp Ser Val Asp Asn Ile Pro Gly

-continued

```
                180                 185                 190
Val Pro Ser Ile Gly Glu Lys Thr Ala Gln Lys Leu Ile Ala Glu Phe
            195                 200                 205
Gly Asn Leu Glu Asn Leu Tyr Lys Asn Leu Ser Lys Leu Thr Ser Lys
            210                 215                 220
Arg Arg Glu Val Leu Glu Lys Phe Lys Glu Gln Ala Phe Leu Ser Arg
225                 230                 235                 240
Glu Leu Ala Lys Ile Lys Lys Asn Val Pro Ile Glu Ile Ser Leu Glu
                245                 250                 255
Asn Leu Lys Val Lys Glu Pro Gln Gly Lys Cys Leu Gly Glu Phe Leu
            260                 265                 270
Lys Glu Leu Glu Met Arg Ser Ile Val Ser Glu Leu Lys Lys Leu Phe
            275                 280                 285
Pro Ser Ile Asp Phe Gly Glu Phe Asp Lys Phe Lys Lys Ser Lys Lys
            290                 295                 300
Leu Ser Lys Glu Glu Phe Lys Arg Lys Ile Gln Pro Ala Asp Leu Phe
305                 310                 315                 320
Ser Thr Pro Glu Val Ala Val Ile His Asp Phe Glu Arg Val Ile Ala
                325                 330                 335
Ile Asn Glu Gly Tyr Val Glu Val Asp Phe Lys Glu Ile Glu Glu Phe
            340                 345                 350
Leu Pro Glu Lys Gly Lys Ile Tyr Thr Phe Asp Leu Lys Ser Leu Tyr
            355                 360                 365
His Lys Val Gly Glu Lys Leu Arg Asn Phe Ser Phe Ile Asp Leu Ser
            370                 375                 380
Val Cys Glu Tyr Leu Leu Asn Pro Leu Gln Lys Asp Tyr Ser Ser Lys
385                 390                 395                 400
Asp Ile Leu Lys Lys Arg Leu Gly Val Val Ser Leu Glu Glu Val Lys
                405                 410                 415
Asp Tyr Val His Tyr Thr Leu Asp Ile Gly Lys Glu Ile Leu Asn Glu
            420                 425                 430
Leu Lys Lys Glu Gly Leu Glu Asn Leu Tyr Glu Ser Ile Glu His Pro
            435                 440                 445
Leu Thr Phe Val Leu Tyr Lys Met Glu Lys Arg Gly Val Leu Phe Asp
            450                 455                 460
Lys Glu Tyr Leu Glu Asn Phe Gly Lys Glu Leu Asp Arg Lys Ser Lys
465                 470                 475                 480
Glu Ile Glu Lys Lys Ile Phe Glu Ile Ala Gly Glu Lys Phe Asn Leu
                485                 490                 495
Asn Ser Pro Lys Gln Leu Ser Lys Ile Leu Phe Glu Lys Leu Lys Leu
            500                 505                 510
Lys Pro Leu Lys Lys Thr Lys Ser Gly Tyr Ser Thr Asp Val Glu Thr
            515                 520                 525
Leu Thr Ala Leu Ala Leu Lys Gly His Lys Ile Ala Glu Leu Leu Leu
            530                 535                 540
Glu Tyr Arg Lys Leu Thr Lys Leu Asn Ser Thr Phe Val Lys Gly Ile
545                 550                 555                 560
Leu Lys His Met Asp Glu Asp Gly Arg Val Arg Thr Thr Phe Ile Gln
                565                 570                 575
Thr Gly Thr Ala Thr Gly Arg Leu Ser Ser Ala Glu Pro Asn Leu Gln
            580                 585                 590
Asn Leu Pro Val Ser Asp Glu Ile Ser Lys Lys Ile Arg Tyr Ala Val
            595                 600                 605
```

```
Thr Ala Pro Ala Gly Tyr Asn Leu Val Trp Ala Asp Tyr Ser Gln Ile
    610                 615                 620

Glu Leu Arg Ile Leu Ala His Leu Ser Gln Asp Glu Lys Leu Leu Glu
625                 630                 635                 640

Ala Tyr Arg Lys Gly Arg Asp Ile His Thr Glu Thr Ala Ser Tyr Leu
                645                 650                 655

Phe Gly Ile Ser Ala Glu Glu Val Asp Glu Arg Leu Arg Arg Ile Ala
                660                 665                 670

Lys Thr Val Asn Phe Gly Ile Ile Tyr Gly Met Ser Pro His Gly Leu
            675                 680                 685

Ser Glu Arg Leu Gly Ile Ser Val Glu Glu Ala Glu Lys Tyr Ile Asp
    690                 695                 700

Arg Tyr Phe Glu Lys Phe Pro Lys Val Lys Glu Tyr Ile Glu Asn Thr
705                 710                 715                 720

Leu Arg Glu Ala Tyr Glu Lys Gly Tyr Val Lys Thr Ile Phe Gly Arg
                725                 730                 735

Lys Arg Pro Leu Pro Glu Leu Lys Ser Ser Asn Lys Asn Ile Arg Ser
                740                 745                 750

Phe Gly Glu Arg Ala Ala Val Asn Ala Thr Ile Gln Gly Thr Ala Ala
            755                 760                 765

Asp Ile Met Lys Leu Ala Met Val Lys Leu Tyr Lys Lys Leu Glu Lys
    770                 775                 780

Leu Gly Ala Tyr Met Val Leu Gln Val His Asp Glu Ile Val Ile Glu
785                 790                 795                 800

Ala Leu Glu Glu Lys Thr Glu Glu Ile Met Lys Ile Val Lys Glu Thr
                805                 810                 815

Met Glu Asn Val Val Glu Phe Ser Val Pro Leu Thr Val Asp Val Lys
                820                 825                 830

Val Gly Lys His Trp Ser
            835
```

<210> SEQ ID NO 103
<211> LENGTH: 955
<212> TYPE: PRT
<213> ORGANISM: Artificial Sequence
<220> FEATURE:
<223> OTHER INFORMATION: AMINO ACID SEQUENCE OF DNA polymerase I
      [Caldilinea aerophila DSM 14535 = NBRC 104270]

<400> SEQUENCE: 103

```
Met Pro Gly Arg Val Val Ser Ala Ser Ile Val Ala Pro Arg Asn
1               5                   10                  15

Gly Ala Ser Thr Met Ala Leu Leu Leu Ile Asp Gly His Ser Gln
                20                  25                  30

Ala Tyr Arg Ala Tyr Phe Gly Ile Lys Thr Pro Leu Ser Thr Arg Ala
            35                  40                  45

Gly Glu Pro Thr Ser Ala Val Tyr Gly Phe Thr Arg Lys Leu Leu Ala
    50                  55                  60

Ala Leu Arg Asp Tyr His Pro Asp Cys Ile Ala Val Ala Phe Asp Ala
65                  70                  75                  80

Gly Asp Thr Trp Arg His Ala Glu Phe Pro Asp Tyr Lys Ala Thr Arg
                85                  90                  95

Asp Val Met Pro Asp Asp Met Arg Thr Gln Met Glu Arg Ile Glu Ser
            100                 105                 110

Leu Leu Arg Ala Phe Asn Ile Pro Ile Ile Thr Tyr Pro Asn Phe Glu
```

```
            115                 120                 125
Ala Asp Asp Val Leu Gly Thr Leu Ala Arg Lys Ala Ala Gln Gly
130                 135                 140

His Asp Val Leu Val Met Thr Gly Asp Arg Asp Met Phe Gln Leu Val
145                 150                 155                 160

Asp Glu Arg Val Lys Ile Leu Tyr Thr Ser Gly Gly Pro Asn Pro Val
                    165                 170                 175

Thr Ser Val Tyr Gly Ile Glu Gln Ile Gln Glu Arg Tyr Gly Leu Thr
                180                 185                 190

Pro Gln Gln Phe Ile Asp Phe Lys Ala Leu Thr Gly Asp Ser Ser Asp
            195                 200                 205

Asn Ile Pro Gly Val Pro Gly Val Gly Glu Lys Thr Ala Ile Lys Leu
210                 215                 220

Leu Gln Gln Tyr Gly Ser Ile Glu Gly Ile Tyr Glu His Leu Asp Glu
225                 230                 235                 240

Ile Gly Gly Pro Lys Leu Arg Gln Ala Leu Ser Asp Ala Arg Glu Gln
                245                 250                 255

Val Met Arg Asn Arg Arg Leu Val Thr Ile His Thr Asp Leu Asp Ile
            260                 265                 270

Ser Phe Asp Leu Ala Gln Cys Ala Val His Asp Tyr Asn Pro Asp Ala
            275                 280                 285

Val Leu Glu Leu Phe Asn Glu Leu Glu Phe Arg Ser Leu Leu Lys Glu
290                 295                 300

Leu Pro Ala Ser Thr Arg Asn Ala Ala Glu Ala Leu Ala Thr Glu Pro
305                 310                 315                 320

Gln Gln Ala Gly Gln Met Thr Leu Phe Ser Ala Ala Pro Thr Pro Leu
                325                 330                 335

Thr Ser Leu Thr Ile Asp Gly Glu Arg Thr Val Leu Ile Val Gln Asp
            340                 345                 350

Arg Thr Thr Leu Ala Gln Leu Val Glu Ser Leu Arg Ala Ala Glu Arg
            355                 360                 365

Leu Ser Phe Asp Val Glu Thr Thr Ala Thr Asp Ala Met Gln Ala Ala
370                 375                 380

Leu Val Gly Leu Gly Ile Ala Trp Ala Pro Gly Gln Thr Ala Tyr Ile
385                 390                 395                 400

Pro Val Thr His Thr Ile Gly Glu Gln Leu Asp Trp Ser His Ala Met
                405                 410                 415

Glu Ala Ile Arg Pro Phe Phe Ala Asp Ala Ala Leu Pro Lys Val Ala
                420                 425                 430

His Asn Ala Lys Tyr Asp Leu Ile Val Leu Arg Arg His Gly Leu Asp
            435                 440                 445

Val Met Gly Val Leu Asp Asp Thr Leu Leu Met Ala Trp Leu Leu Asp
            450                 455                 460

Pro Ala Ser Arg Ser Leu Gly Leu Lys Ala Leu Ala Glu Thr Glu Leu
465                 470                 475                 480

Gly Trp Lys Met Thr Glu Leu Ser Glu Leu Ile Gly Ser Gly Arg Lys
                485                 490                 495

Gln Ile Thr Ile Asp Gln Val Pro Leu Glu Gln Ala Ala Tyr Cys
            500                 505                 510

Gly Ala Asp Val Asp Ala Thr Ile Arg Leu Tyr Ala Thr Leu Glu Pro
            515                 520                 525

Arg Leu Arg Glu Ala Gly Leu Glu Glu Leu Tyr Arg Thr Ile Glu Arg
530                 535                 540
```

```
Pro Leu Leu Pro Val Leu Thr Ala Met Glu Met Ala Gly Val Leu Leu
545                 550                 555                 560

Asp Val Glu Phe Leu Lys Gln Met Ser Ala Glu Leu Ser Lys Arg Leu
            565                 570                 575

Tyr Glu Leu Glu Gln Ser Leu Tyr Glu Val Val Gly His Ala Phe Asn
                580                 585                 590

Leu Arg Ser Thr Gln Gln Leu Ser Gln Val Leu Phe Asp Glu Met Gly
        595                 600                 605

Phe Pro Ser Lys Gly Leu Lys Lys Thr Ala Ser Gly His Tyr Ser Thr
    610                 615                 620

Ala Ala Asp Val Leu Glu Thr Leu Ala Ala Tyr Gly Asp Val Leu Ser
625                 630                 635                 640

Pro Thr Gln Gln Arg Leu Ile Glu Leu Ile Leu Glu His Arg Gln Leu
                645                 650                 655

Glu Lys Leu Arg Ser Thr Tyr Val Asp Ala Leu Pro Ala Leu Val Asn
            660                 665                 670

Pro Gln Thr Gly Arg Val His Thr Ser Phe Ser Gln Thr Gly Ala Val
                675                 680                 685

Thr Gly Arg Leu Ser Ser Asn Pro Asn Leu Gln Asn Ile Pro Ile
        690                 695                 700

Arg Thr Glu Ile Gly Arg Glu Ile Arg Ala Ile Val Ala Pro Pro
705                 710                 715                 720

Gly Trp Gln Leu Ile Ser Ala Asp Tyr Ser Gln Val Glu Leu Arg Val
                725                 730                 735

Leu Ala His Met Ala Asn Glu Pro Leu Ile Glu Ala Phe Gln Ala
            740                 745                 750

Asp Gln Asp Ile His Ala Val Thr Ala Ser Lys Leu Phe Gly Val Pro
                755                 760                 765

Val Glu Ala Val Thr Arg Asp Gln Arg Ser Leu Gly Lys Thr Ile Asn
    770                 775                 780

Phe Ala Thr Ile Tyr Gly Val Ser Glu Phe Gly Leu Ser Ser Arg Thr
785                 790                 795                 800

Glu Leu Thr Arg Glu Gln Ala Arg Gln Phe Leu Glu Gln Tyr Phe Gln
                805                 810                 815

Thr Tyr Pro Arg Ile Arg Ala Phe Leu Asp His Ile Leu Glu Glu Ala
            820                 825                 830

Arg Glu Lys Gly Tyr Val Gln Thr Leu Leu Gly Arg Lys Arg Phe Phe
        835                 840                 845

Pro Glu Leu Lys Ser Gly Lys Leu Pro Pro Asn Gln Arg Ala Ala Val
    850                 855                 860

Glu Arg Ala Ala Ile Asn Ala Pro Ile Gln Gly Thr Ala Ala Asp Ile
865                 870                 875                 880

Met Lys Ile Ala Met Ile Arg Leu Tyr Glu Arg Leu Gln Asn Asp Gly
                885                 890                 895

Tyr Arg Thr Arg Leu Leu Ile Gln Val His Asp Glu Leu Val Leu Glu
            900                 905                 910

Ala Pro Pro Glu Glu Leu Glu Ser Ala Thr His Leu Val Arg Glu Thr
        915                 920                 925

Met Ala Asn Ala Tyr Gln Leu Thr Val Pro Leu Lys Val Asp Val Glu
    930                 935                 940

Ile Gly Pro Asn Trp Arg Asp Met Thr Lys Ala
945                 950                 955
```

-continued

<210> SEQ ID NO 104
<211> LENGTH: 829
<212> TYPE: PRT
<213> ORGANISM: Artificial Sequence
<220> FEATURE:
<223> OTHER INFORMATION: AMINO ACID SEQUENCE OF DNA polymerase I
      [[Eubacterium] siraeum]

<400> SEQUENCE: 104

Met Gly Phe Leu Ile Ile Asp Gly Asn Ser Ile Leu Asn Arg Ala Phe
1               5                   10                  15

Tyr Gly Ile Arg Val Leu Thr Asn Ser Arg Gly Val Ala Thr Asn Ala
            20                  25                  30

Val Thr Gly Phe Met Asn Thr Leu Leu Met Leu Glu Lys Asp Val Asp
        35                  40                  45

Pro Asp Met Ile Ala Val Ala Phe Asp Leu Lys Ala Pro Thr Phe Arg
50                  55                  60

His Lys Met Tyr Asp Gly Tyr Lys Ala Asn Arg Lys Gly Met Pro Glu
65                  70                  75                  80

Asp Leu Ala Gln Gln Leu Pro Tyr Met Lys Lys Ile Ile Thr Ala Met
                85                  90                  95

Gly Ile Thr Ile Ile Glu Lys Glu Gly Phe Glu Ala Asp Asp Ile Ile
            100                 105                 110

Gly Thr Val Ser Ala Ala Cys Ala Asp Lys Lys Ile Pro Cys Thr Val
        115                 120                 125

Ser Thr Gly Asp Arg Asp Ser Phe Gln Leu Val Asn Asp Tyr Val Thr
130                 135                 140

Val Arg Leu Ala Lys Thr Lys Gly Asp Ile Tyr Tyr Thr Pro Asp Val
145                 150                 155                 160

Ile Met Glu Glu Tyr Gly Val Thr Pro Lys Gln Met Ile Glu Val Lys
                165                 170                 175

Ala Leu Met Gly Asp Ser Ser Asp Asn Ile Pro Gly Val Pro Gly Ile
            180                 185                 190

Gly Glu Lys Thr Ala Leu Ser Leu Ile Lys Glu Phe Ala Ser Val Asp
        195                 200                 205

Gly Val Tyr Glu Asn Ile Gly Ser Thr Leu Ile Thr Lys Gly Val Arg
210                 215                 220

Thr Lys Leu Glu Asn Gly Lys Glu Ser Cys Tyr Met Ser Arg Gln Leu
225                 230                 235                 240

Ala Glu Ile Cys Leu Thr Ala Pro Ile Asp Thr Glu Leu Ser His Tyr
                245                 250                 255

Val Pro Lys Glu Arg Asp Asp Thr Glu Leu Ala Arg Leu Leu Ser Glu
            260                 265                 270

Leu Glu Met Tyr Lys Met Leu Gln Lys Leu Lys Leu His Pro Thr Ser
        275                 280                 285

Ala Pro Ala Gly Ser Lys Glu Ala Leu Glu Glu Ser Ala Ala Lys Gln
290                 295                 300

Ile Pro Ala Met Pro Ala Gly Asp Ile Val Leu Thr Gln Glu Gly Ser
305                 310                 315                 320

Val Tyr Ala Gly Thr Val Gly Ala Pro Val Glu Leu Ser Asp Gly Glu
                325                 330                 335

Leu Lys Ala Tyr Ala Asp Ser Asp Ser Thr Lys Tyr Thr Phe Asp Ile
            340                 345                 350

Lys Glu Thr Leu Thr Val Thr Gly Cys Glu Arg Leu Lys Asn Asn Arg
        355                 360                 365

```
Phe Asp Thr Thr Leu Ala Ala Tyr Leu Ala Asp Pro Asp Ser Asn Asp
    370                 375                 380

Tyr Ser Leu Ser Arg Leu Cys Ala Gln Tyr Gly Val Pro Glu Gly Asn
385                 390                 395                 400

Ser Ile Gln Glu Lys Ser Ile Thr Val Ala Ala Leu Asn Asp Ile Leu
                405                 410                 415

Asn Cys Lys Ile Ser Glu Thr Gly Ser Ala Ala Val Leu Thr Asp Ile
                420                 425                 430

Glu Ile Pro Leu Ala Thr Val Leu Val Ala Met Glu Arg Glu Gly Val
            435                 440                 445

Ser Ile Asp Ala Asp Gly Ile Lys Ala Phe Gly Lys Glu Val Cys Glu
450                 455                 460

Lys Ala Glu Lys Ile Ser Arg Glu Ile Tyr Glu Tyr Ala Gly Tyr Glu
465                 470                 475                 480

Phe Asn Ile Gly Ser Pro Lys Gln Leu Gly Ser Val Leu Phe Glu Lys
                485                 490                 495

Leu Ala Leu Pro Ser Ala Lys Lys Thr Lys Thr Gly Tyr Ser Thr Asn
            500                 505                 510

Ala Asp Val Leu Glu Ser Leu Met Asp Lys His Pro Ile Val Pro Leu
            515                 520                 525

Ile Thr Glu Tyr Arg Ala Leu Thr Lys Leu Gln Asn Thr Tyr Val Thr
530                 535                 540

Gly Leu Leu Lys Val Val Gly Glu Asp Gly Arg Ile His Ser Thr Phe
545                 550                 555                 560

Lys Gln Thr Glu Thr Arg Thr Gly Arg Ile Ser Ser Ala Glu Pro Asn
                565                 570                 575

Ile Gln Asn Ile Pro Val Arg Thr Pro Leu Gly Arg Glu Met Arg Arg
            580                 585                 590

Phe Phe Thr Ala Lys Asp Gly Tyr Leu Leu Val Asp Ala Asp Tyr Ser
            595                 600                 605

Gln Ile Glu Leu Arg Val Leu Ala His Ile Ser Gly Asp Glu Ile Met
    610                 615                 620

Lys Lys Ala Phe Leu Asp Gly Val Asp Ile His Thr Val Thr Ala Ser
625                 630                 635                 640

Gln Val Phe Asn Gln Pro Ile Glu Trp Val Thr Pro Asp Leu Arg Ser
                645                 650                 655

Lys Ala Lys Ala Val Asn Phe Gly Ile Val Tyr Gly Ile Gly Ala Phe
                660                 665                 670

Ser Leu Ser Lys Asp Ile Gly Val Ser Val Pro Lys Ala Ser Glu Tyr
            675                 680                 685

Ile Arg Ser Tyr Leu Ser Lys Tyr Ser Gly Ile Ala His Tyr Met Glu
    690                 695                 700

Gln Thr Val Ala Lys Ala Lys Arg Asp Gly Tyr Val Glu Thr Met Phe
705                 710                 715                 720

Gly Arg Arg Arg Tyr Ile Lys Glu Leu Ala Ala Lys Asn Lys Asn Leu
                725                 730                 735

Gln Ala Phe Gly Glu Arg Val Ala Lys Asn Thr Pro Ile Gln Gly Thr
            740                 745                 750

Ala Ala Asp Ile Ile Lys Ile Ala Met Ile Lys Val Tyr Asn Arg Leu
            755                 760                 765

Glu Glu Ser Gly Leu Asp Ala Arg Leu Ile Leu Gln Val His Asp Glu
770                 775                 780
```

```
Leu Ile Val Glu Ala Lys Glu Asp Cys Ala Glu Lys Val Ala Leu Leu
785                 790                 795                 800

Leu Lys Glu Glu Met Glu Asn Ala Val Lys Leu Thr Val Pro Met Thr
            805                 810                 815

Val Asp Val Asn Ile Gly Lys Thr Trp Tyr Asp Thr His
        820                 825
```

<210> SEQ ID NO 105
<211> LENGTH: 399
<212> TYPE: PRT
<213> ORGANISM: Artificial Sequence
<220> FEATURE:
<223> OTHER INFORMATION: AMINO ACID SEQUENCE OF DNA polymerase
[Clostridium leptum CAG:27]

<400> SEQUENCE: 105

```
Met Glu Ile Pro Leu Ala Gln Val Leu Ala Arg Met Glu Asn Ile Gly
1               5                   10                  15

Phe Leu Val Asp Gly Glu Ser Ile Arg Val Tyr Gly Glu Arg Leu Glu
            20                  25                  30

Thr Glu Ile Glu Ala Leu Gln Lys Gln Ile Tyr Glu Glu Val Gly Tyr
        35                  40                  45

Glu Phe Asn Ile Asn Ser Pro Lys Gln Leu Gly Asp Ala Leu Phe Val
    50                  55                  60

Lys Leu Gly Leu Pro Ser Gly Lys Lys Thr Lys Thr Gly Tyr Ser Thr
65                  70                  75                  80

Asn Ala Glu Ile Leu Glu Lys Leu Arg Tyr Asp His Pro Ala Val Glu
                85                  90                  95

Leu Val Leu His Tyr Arg Thr Leu Thr Lys Leu Lys Ser Thr Tyr Cys
            100                 105                 110

Glu Gly Met Leu Lys Val Ile Gly Pro Asp Gly Arg Ile His Ser Asn
        115                 120                 125

Phe Asn Gln Thr Glu Thr Arg Thr Gly Arg Ile Ser Ser Thr Glu Pro
    130                 135                 140

Asn Leu Gln Asn Ile Pro Val Arg Thr Glu Leu Gly Arg Glu Leu Arg
145                 150                 155                 160

Lys Phe Phe Leu Ala Lys Glu Gly Trp Val Leu Val Asp Ala Asp Tyr
                165                 170                 175

Ser Gln Ile Glu Leu Arg Val Leu Ala His Ile Ala His Asp Glu Asn
            180                 185                 190

Met Ile Lys Ala Phe Gln Asp Lys Glu Asp Ile His Thr Ile Thr Ala
        195                 200                 205

Ser Gln Val Phe Gly Met Pro Pro Glu Met Val Thr Pro Leu Met Arg
    210                 215                 220

Ser Arg Ala Lys Ala Val Asn Phe Gly Ile Val Tyr Gly Ile Gly Ala
225                 230                 235                 240

Phe Ser Leu Ser Lys Asp Ile Asn Val Ser Arg Lys Glu Ala Gln Arg
                245                 250                 255

Tyr Ile Asp Asp Tyr Leu Thr Leu Tyr Ser Gly Val Asp Arg Tyr Met
            260                 265                 270

Lys Glu Val Val Glu Lys Ala Lys Glu Asp Gly Tyr Val Glu Thr Leu
        275                 280                 285

Phe His Arg Arg Arg Tyr Leu Pro Glu Leu Thr Ala Ser Asn Phe Asn
    290                 295                 300

Leu Arg Ala Phe Gly Glu Arg Val Ala Arg Asn Met Pro Ile Gln Gly
305                 310                 315                 320
```

```
Thr Ala Ala Asp Ile Ile Lys Ile Ala Met Val Arg Val Asp Arg Arg
                325                 330                 335

Leu Lys Arg Glu Asn Met Arg Ala Arg Leu Ile Leu Gln Val His Asp
            340                 345                 350

Glu Leu Ile Val Glu Ala Pro Glu Asp Glu Ala Glu Gln Ala Ala Arg
        355                 360                 365

Ile Leu Thr Glu Glu Met Glu Gly Ala Val Ser Leu Thr Val Pro Met
    370                 375                 380

Val Ala Glu Ala Ser Val Gly Lys Thr Trp Tyr Asp Ala Lys Gly
385                 390                 395

<210> SEQ ID NO 106
<211> LENGTH: 881
<212> TYPE: PRT
<213> ORGANISM: Artificial Sequence
<220> FEATURE:
<223> OTHER INFORMATION: AMINO ACID SEQUENCE OF DNA polymerase I
      [Enterococcus faecium]

<400> SEQUENCE: 106

Met Thr Lys Asn Lys Leu Leu Leu Val Asp Gly Asn Ser Val Ala Phe
1               5                   10                  15

Arg Ala Phe Phe Ala Leu His Asn Ser Leu Glu Arg Phe Lys Asn Arg
            20                  25                  30

Asn Gly Leu His Thr Asn Ala Ile Tyr Ala Phe Asn Thr Met Phe Glu
        35                  40                  45

Asn Val Met Gln Lys Glu Gln Pro Thr His Val Leu Val Ala Phe Asp
    50                  55                  60

Ala Gly Lys Thr Thr Phe Arg Thr Glu Met Tyr Ala Glu Tyr Lys Gly
65                  70                  75                  80

Gly Arg Ser Lys Thr Pro Gly Glu Phe Lys Glu Gln Met Pro Tyr Ile
                85                  90                  95

Arg Asp Leu Leu Thr Gly Leu Gly Val Gln Tyr Tyr Glu Leu Pro Asn
            100                 105                 110

Tyr Glu Ala Asp Asp Ile Ile Gly Thr Leu Ala Glu Lys Val Asp Lys
        115                 120                 125

Asp Gln Phe Asp Val Val Val Leu Ser Gly Asp Arg Asp Leu Thr Gln
    130                 135                 140

Leu Ala Ser Lys Glu Val Lys Val Asp Ile Thr Val Lys Gly Val Ser
145                 150                 155                 160

Asp Ile Glu Ser Tyr Thr Pro Glu His Val Ala Glu Lys Tyr Asp Gly
                165                 170                 175

Leu Thr Pro Lys Gln Ile Ile Asp Met Lys Gly Leu Ala Gly Asp Ala
            180                 185                 190

Ser Asp Asn Ile Pro Gly Val Thr Lys Ile Gly Glu Lys Thr Ala Ile
        195                 200                 205

Lys Leu Leu Lys Gln Tyr Gly Ser Val Glu Gly Ile Tyr Glu His Ile
    210                 215                 220

Asp Glu Met Lys Gln Ser Lys Met Lys Glu Asn Leu Ile Asn Asp Lys
225                 230                 235                 240

Glu Gln Ala Phe Leu Ser Lys Lys Leu Ala Thr Ile Asn Thr Ser Ala
                245                 250                 255

Pro Val Asp Val Ser Ile Asp Ser Leu Lys Tyr Glu Gly Lys Asn Leu
            260                 265                 270

Asp Lys Leu Val Pro Phe Tyr Lys Glu Met Asp Phe Asn Gln Phe Leu
```

```
                    275                 280                 285
Ser Lys Leu Asn Ile Val Glu Glu Val Lys Met Asp Asp Ile Leu
290                 295                 300
Phe Glu Val Val His Glu Phe Lys Glu Glu Met Phe Thr Thr Asp Met
305                 310                 315                 320
Ala Leu Tyr Val Glu Met Met Gly Asp Asn Tyr His Thr Glu Glu Ile
                        325                 330                 335
Val Gly Val Ala Trp Gly Thr Glu Lys Lys Ile Tyr Val Thr Asn Asp
                340                 345                 350
Leu Ser Val Phe Glu Asn Arg Ala Phe His Ser Trp Ile Thr Asp Pro
            355                 360                 365
Thr Arg Leu Lys Lys Val Tyr Asp Ala Lys Arg Thr Tyr Val Ala Leu
370                 375                 380
Asn Arg Tyr Thr Gly Lys Thr Lys Gly Ile Asp Phe Asp Val Leu Leu
385                 390                 395                 400
Gly Ala Tyr Leu Leu Asp Thr Asn Glu Lys Ser Thr Asp Ile Glu Gly
                    405                 410                 415
Ile Ala Ala His Tyr Gly Tyr Asn Asp Ile Gln Ser Asp Glu Ala Val
                    420                 425                 430
Tyr Gly Lys Gly Ala Lys Lys Gly Leu Pro Glu Glu Glu Leu Phe
            435                 440                 445
Phe Ala His Leu Ala Arg Lys Val Ala Ala Ile Asn Ala Leu Thr Pro
450                 455                 460
Lys Leu Ser Gln Glu Leu Ala Asp Lys Asn Gln Glu Asp Leu Phe Arg
465                 470                 475                 480
Lys Met Glu Leu Pro Leu Ser Ile Ile Leu Ala Glu Met Glu Ile Ser
                    485                 490                 495
Gly Ile Lys Val Asp Ala Thr Arg Leu Gln Glu Met Lys Gly Glu Phe
                500                 505                 510
Ser Ala Arg Leu Arg Glu Ile Glu Gln Lys Ile Tyr Glu Glu Ala Gly
            515                 520                 525
Glu Glu Phe Asn Leu Asn Ser Pro Lys Gln Leu Gly Val Ile Leu Phe
530                 535                 540
Glu Lys Met Gly Leu Pro Val Ile Lys Lys Thr Lys Thr Gly Tyr Ser
545                 550                 555                 560
Thr Ala Val Asp Val Leu Glu Gln Leu Arg Glu Gln Ala Pro Ile Val
                    565                 570                 575
Glu Asp Ile Leu Thr Tyr Arg Gln Ile Ala Lys Ile Gln Ser Thr Tyr
                580                 585                 590
Val Glu Gly Leu Leu Lys Val Ile Gln Ser Asp Gly Lys Val His Thr
            595                 600                 605
Arg Tyr Val Gln Thr Leu Thr Gln Thr Gly Arg Leu Ser Ser Val Asp
610                 615                 620
Pro Asn Leu Gln Asn Ile Pro Ile Arg Leu Asp Glu Gly Arg Lys Ile
625                 630                 635                 640
Arg Gln Ala Phe Val Pro Arg Glu Lys Asp Trp Leu Ile Tyr Ser Ser
                    645                 650                 655
Asp Tyr Ser Gln Ile Glu Leu Arg Val Leu Ala His Ile Ser Asn Asp
                660                 665                 670
Glu His Leu Lys Ala Ala Phe Leu Glu Gly Gln Asp Ile His Ala Ser
            675                 680                 685
Thr Ala Met Arg Val Phe Gly Ile Glu Lys Ala Glu Asp Val Thr Pro
690                 695                 700
```

```
Asn Met Arg Arg Gln Ala Lys Ala Val Asn Phe Gly Ile Val Tyr Gly
705                 710                 715                 720

Ile Ser Asp Tyr Gly Leu Ser Gln Asn Leu Gly Ile Ser Arg Lys Ala
                725                 730                 735

Ala Gln Gln Tyr Ile Asp Thr Tyr Phe Glu Lys Tyr Pro Gly Val Lys
            740                 745                 750

Glu Tyr Met Glu Arg Ile Val Arg Glu Ala Lys Asp Gln Gly Tyr Val
        755                 760                 765

Glu Thr Leu Tyr His Arg Arg Tyr Leu Pro Asp Ile Asn Ser Arg
770                 775                 780

Asn Tyr Asn Ile Arg Ser Phe Ala Glu Arg Thr Ala Ile Asn Thr Pro
785                 790                 795                 800

Ile Gln Gly Ser Ala Ala Asp Ile Leu Lys Ile Ala Met Ile Glu Leu
                805                 810                 815

Asp Lys Arg Leu Lys Glu Thr Gly Leu Gln Ala Thr Met Leu Leu Gln
            820                 825                 830

Val His Asp Glu Leu Val Phe Glu Val Pro Lys Lys Glu Leu Glu Ser
        835                 840                 845

Leu Asp Lys Leu Val Lys Glu Val Met Glu Gln Ala Val Ser Leu His
    850                 855                 860

Val Pro Leu Ile Thr Asp Ser Ser Trp Gly Lys Thr Trp Tyr Glu Ala
865                 870                 875                 880

Lys

<210> SEQ ID NO 107
<211> LENGTH: 881
<212> TYPE: PRT
<213> ORGANISM: Artificial Sequence
<220> FEATURE:
<223> OTHER INFORMATION: AMINO ACID SEQUENCE OF DNA polymerase I
      [Facklamia hominis]

<400> SEQUENCE: 107

Met Leu Ile Asp Gly Ser Ser Leu Ala Phe Arg Ala Phe Tyr Ser Ile
1               5                   10                  15

Leu Asp Ile Asp Arg Phe Thr Asn Arg Gln Gly Leu His Thr Asn Ala
                20                  25                  30

Ile Tyr Ser Phe Lys Arg Met Leu Asp Asn Val Leu Ala Glu Phe Glu
            35                  40                  45

Pro Ser His Val Leu Val Phe Asp Lys Ser Pro Asn Thr Ile Arg
        50                  55                  60

Lys Glu Lys Phe Asp Gln Tyr Lys Gly Gly Arg Ser Lys Thr Pro Ala
65                  70                  75                  80

Glu Phe Thr Glu Gln Met Pro Tyr Phe Ala Pro Leu Leu Glu Gly Tyr
                85                  90                  95

Gly Ile Arg His Tyr Ala Met Asp Tyr Tyr Glu Ala Asp Asp Ile Ile
            100                 105                 110

Gly Thr Leu Ser Arg Leu Ala Asp Pro Lys Asp Gln Val Val Val Leu
        115                 120                 125

Ser Gly Asp Lys Asp Leu Thr Gln Leu Ala Ser Asp Gln Val Thr Val
    130                 135                 140

Tyr Ile Thr Arg Lys Gly Val Ser Asp Leu Val Val Tyr Ser Pro Thr
145                 150                 155                 160

Thr Ile Gln Glu Lys Trp Gly Ile Arg Pro Glu Gln Ile Ile Asp Met
                165                 170                 175
```

```
Lys Gly Leu Met Gly Asp Ser Ser Asp Asn Tyr Pro Gly Ile Thr Arg
            180                 185                 190

Val Gly Glu Lys Thr Ala Leu Lys Leu Leu His Gln Phe Gly Ser Val
        195                 200                 205

Glu Gly Leu Tyr Gln Ser Leu Asp Gln Leu Lys Ala Ser Lys Leu Lys
    210                 215                 220

Glu Asn Ile Ile Lys Asp Lys Asp Gln Ala Phe Leu Ser Lys Asp Leu
225                 230                 235                 240

Ala Arg Ile Leu Leu Asp Val Pro Leu Glu Ile Asp Leu Ala Asp Ile
                245                 250                 255

Glu Arg Gly Glu Met Asp Thr Gln Ala Leu Asn Asp Leu Tyr Arg Gln
            260                 265                 270

Leu Asp Phe Gln Ser Phe Leu Gln Glu Leu Asp Ala Lys Ser Val Leu
        275                 280                 285

Asp Asp Pro Ser Ala Ser Leu Ala Asp Phe Asp Leu Leu Val Leu Glu
    290                 295                 300

Asp Gln Ala Asp Phe Asp Gly Leu Ala Trp Pro Asp Arg Gly Ile Tyr
305                 310                 315                 320

His Thr Glu Gln Leu Asp Glu Asn Tyr His Phe Ala Lys Val Glu Ala
                325                 330                 335

Val Cys Trp Ala Asp Pro Glu Thr Lys Lys Ala Tyr Val Thr Ser Ala
            340                 345                 350

Asp Leu Ala Phe Thr Asn Pro Ala Phe Lys Ala Trp Leu Glu Asp Ser
        355                 360                 365

Ser Lys Leu Lys Asp Cys Leu Asp Phe Lys Lys Glu Ala Val Ile Ala
    370                 375                 380

Ala Arg Tyr Gly Leu Asp Leu Ala Gly Met Gly Glu Asp Val Ser Ile
385                 390                 395                 400

Met Ala Tyr Leu Val Asp Thr Leu Gln Thr His Glu Leu Ala Asp Leu
                405                 410                 415

Ser Gln Ser Phe Gly Leu Gly Gln Val Ile Pro Tyr Asp Val Glu Val
            420                 425                 430

Tyr Gly Lys Gly Val Lys Gly Val Pro Glu Asp Glu Ala Val Phe
        435                 440                 445

Gln Gly His Leu Val Leu Lys Leu Gln Cys Leu His Ala Leu Met Glu
    450                 455                 460

Pro Leu Leu Ala Lys Leu Glu Glu Leu Asp Met Val Gly Leu Tyr Arg
465                 470                 475                 480

Glu Met Glu Gln Pro Leu Ala Arg Cys Leu Ala Lys Met Glu Ile Thr
                485                 490                 495

Gly Ile Lys Val Asn Gln Glu Val Leu Glu Ala Lys Asn Gln Glu Val
            500                 505                 510

Leu Ala Arg Leu Ala Gln Met Glu Lys Ser Ile Tyr Asp Leu Ala Gly
        515                 520                 525

His Ser Phe Asn Val Asn Ser Pro Lys Gln Leu Gly Gln Val Leu Phe
    530                 535                 540

Glu Glu Leu Lys Leu Pro Val Ile Lys Lys Thr Lys Thr Gly Tyr Ser
545                 550                 555                 560

Thr Ala Ala Asp Val Leu Asp Lys Leu Val Gln Val His Pro Ile Ile
                565                 570                 575

Gln Ala Ile Leu Asp Tyr Arg Gln Ile Ala Lys Leu Gln Ser Thr Tyr
            580                 585                 590
```

```
Leu Ala Gly Leu Gln Pro Phe Ile Lys Glu Asp Gly Lys Ile His Thr
            595                 600                 605

Arg Tyr Thr Gln Thr Leu Thr Gln Thr Gly Arg Leu Ser Ser Thr Asp
610                 615                 620

Pro Asn Leu Gln Asn Ile Pro Ile Arg Ile Glu Glu Gly Arg Leu Val
625                 630                 635                 640

Arg Ala Ala Phe Val Pro Ser Gln Pro Gly Trp Gln Met Leu Gly Ala
                645                 650                 655

Asp Tyr Ser Gln Ile Glu Leu Arg Val Leu Ala His Ile Ser Gly Asp
            660                 665                 670

Glu His Met Lys Arg Ala Phe Gln Asn Gly Glu Asp Ile His Ser Ala
        675                 680                 685

Thr Ala Arg Arg Val Phe Gln Leu Asp Glu Asp Gln Glu Val Asp Ala
690                 695                 700

Asp His Arg Arg Gln Ala Lys Ala Val Asn Phe Gly Ile Val Tyr Gly
705                 710                 715                 720

Ile Ser Asp Tyr Gly Leu Ser Gln Asn Leu Asn Ile Ser Arg Gln Ala
                725                 730                 735

Ala Lys Thr Phe Ile Asp Arg Tyr Phe Glu Glu Phe Pro Lys Ile Arg
            740                 745                 750

Gln Tyr Met Asp Glu Ile Val Glu Gln Ala Lys Ser Asp Gly Tyr Val
        755                 760                 765

Ser Thr Leu Phe His Arg Arg Arg Tyr Leu Pro Asp Ile His Ala Lys
770                 775                 780

Asn Phe Asn Leu Arg Ser Phe Ala Glu Arg Thr Ala Met Asn Ser Pro
785                 790                 795                 800

Ile Gln Gly Thr Ala Ala Asp Ile Ile Lys Leu Ala Met Val Arg Leu
                805                 810                 815

Gln Ala Arg Leu Glu Glu Ala Gly Leu Ser Ser Arg Leu Leu Leu Gln
            820                 825                 830

Ile His Asp Glu Leu Ile Leu Glu Gly Pro Lys Glu Glu Met Pro Gln
        835                 840                 845

Leu Gln Lys Leu Val Val Glu Val Met Glu Ser Ala Ala Asp Leu Ser
850                 855                 860

Val Pro Leu Lys Val Asp Asp His Ile Gly Asp Asn Trp Tyr Asp Leu
865                 870                 875                 880

Lys

<210> SEQ ID NO 108
<211> LENGTH: 877
<212> TYPE: PRT
<213> ORGANISM: Artificial Sequence
<220> FEATURE:
<223> OTHER INFORMATION: AMINO ACID SEQUENCE OF DNA polymerase I
      [Bacillus anthracis]

<400> SEQUENCE: 108

Met Glu Lys Lys Val Val Leu Val Asp Gly Asn Asn Ile Ala Tyr Arg
1               5                   10                  15

Ala Phe Phe Ala Leu Pro Leu Leu Asn Asn Asp Lys Gly Ile His Thr
                20                  25                  30

Asn Ala

-continued

```
Phe Arg His Lys Ala Tyr Ser Glu Tyr Lys Gly Arg Gln Lys Thr
 65                  70                  75                  80

Pro Pro Glu Leu Ser Glu Gln Phe Pro Phe Ile Arg Glu Met Leu Asp
                 85                  90                  95

Ala Phe Asn Val Pro Arg Tyr Glu Leu Glu Asn Tyr Glu Ala Asp Asp
                100                 105                 110

Ile Met Gly Thr Leu Ala Lys Glu Ala Ser Glu Gln Gly Ala Ser Val
                115                 120                 125

Lys Val Ile Ser Gly Asp Lys Asp Leu Leu Gln Leu Val Ser Asp Asn
130                 135                 140

Thr Leu Val Cys Ile Pro Arg Lys Gly Ile Thr Glu Val Asp Glu Tyr
145                 150                 155                 160

Thr Lys Glu Ala Leu Phe Glu Lys Tyr Ser Leu Ser Pro Lys Gln Ile
                165                 170                 175

Ile Asp Met Lys Gly Leu Met Gly Asp Gln Ser Asp Asn Ile Pro Gly
                180                 185                 190

Val Pro Gly Val Gly Glu Lys Thr Ala Ile Lys Leu Leu Thr Gln Phe
                195                 200                 205

Gly Thr Val Glu Glu Val Tyr Glu Asn Ile Asp Gln Val Ser Gly Lys
210                 215                 220

Lys Leu Lys Glu Lys Leu Glu Ala Asn Lys Asp Gln Ala Leu Met Ser
225                 230                 235                 240

Lys Asp Leu Ala Thr Ile Ile Thr Asp Ala Pro Ile Thr Val Asn Val
                245                 250                 255

Asp Asp Met Glu Tyr Lys Gly Tyr Glu Ala Ser Asp Val Ile Pro Met
                260                 265                 270

Phe Glu Asn Leu Gly Phe Thr Ser Leu Leu Asn Lys Leu Gly Val Thr
                275                 280                 285

Pro Glu Glu Thr Ala Pro Ala Glu Leu Asp Asp Ile Thr Phe Asp Ile
                290                 295                 300

Val Glu Glu Val Thr Glu Glu Met Leu Gln Gln Asp Ser Ala Leu Ile
305                 310                 315                 320

Val Glu Val Gln Glu Asp Asn Tyr His Lys Ala Asp Ile Gln Gly Phe
                325                 330                 335

Gly Ile Gln Asn Glu Asn Gly Cys Tyr Phe Ile Gln Thr Asp Ile Ala
                340                 345                 350

Leu Lys Ser Asp Ala Phe Lys Glu Trp Leu Ala Asp Gly Glu Met Arg
                355                 360                 365

Lys Tyr Thr Phe Asp Ala Lys Arg Ala Ile Val Ala Leu Lys Trp Asn
                370                 375                 380

Gly Ile Asp Met Gln Gly Ile Asp Phe Asp Leu Leu Ile Ala Ala Tyr
385                 390                 395                 400

Leu Leu Asp Pro Ala Asp Thr Asp Lys Asp Phe Arg Thr Val Ala Lys
                405                 410                 415

Met Lys Glu Thr His Ala Val Lys Ser Asp Glu Val Tyr Gly Lys
                420                 425                 430

Gly Ala Lys Arg Ala Val Pro Glu Leu Glu Ile Val Ala Glu His Val
                435                 440                 445

Ala Arg Lys Val His Val Leu Tyr Asp Val Lys Gln Thr Phe Val Glu
                450                 455                 460

Glu Leu Glu Lys Asn Glu Gln Tyr Glu Leu Phe Thr Glu Leu Glu Leu
465                 470                 475                 480

Pro Leu Ala Arg Val Leu Ala Asp Met Glu Val Lys Gly Val Lys Val
```

```
                    485                 490                 495
Asp Thr Glu Arg Leu Arg Asn Met Gly Glu Glu Leu Ala Gly Arg Leu
                500                 505                 510

Lys Glu Met Glu Gln Glu Ile Tyr Lys Leu Ala Gly Thr Glu Phe Asn
            515                 520                 525

Ile Asn Ser Pro Lys Gln Leu Gly Val Ile Leu Phe Glu Asn Leu Asn
        530                 535                 540

Leu Pro Val Ile Lys Lys Thr Lys Thr Gly Tyr Ser Thr Ser Ala Asp
545                 550                 555                 560

Val Leu Asp Lys Leu Met Asp His His Glu Ile Ile Pro Asn Ile Leu
                565                 570                 575

His Tyr Arg Gln Leu Gly Lys Leu Asn Ser Thr Tyr Ile Glu Gly Leu
            580                 585                 590

Leu Lys Val Val His Glu Asp Ser Ser Lys Ile His Thr Arg Phe Asn
        595                 600                 605

Gln Val Leu Thr Gln Thr Gly Arg Leu Ser Ser Thr Asp Pro Asn Leu
        610                 615                 620

Gln Asn Ile Pro Ile Arg Leu Glu Glu Gly Arg Lys Ile Arg Gln Ala
625                 630                 635                 640

Phe Val Pro Ser Glu Glu Gly Trp Ile Met Tyr Ala Ala Asp Tyr Ser
                645                 650                 655

Gln Ile Glu Leu Arg Val Leu Ala His Ile Ala Asn Asp Lys Gly Leu
            660                 665                 670

Val Glu Ala Phe Gln His Asp Met Asp Ile His Thr Lys Thr Ala Met
        675                 680                 685

Asp Val Phe Gly Val Glu Lys Asp Glu Val Thr Ser Asn Met Arg Arg
        690                 695                 700

Gln Ala Lys Ala Val Asn Phe Gly Ile Val Tyr Gly Ile Ser Asp Tyr
705                 710                 715                 720

Gly Leu Ser Gln Asn Leu Gly Ile Thr Arg Lys Ala Ala Ala Glu Phe
                725                 730                 735

Ile Glu Lys Tyr Leu Glu Ser Phe Pro Gly Val Gln Glu Tyr Met Asp
            740                 745                 750

Asp Ile Val Lys Asp Ala Lys Gln Lys Gly Tyr Val Ala Thr Leu Leu
        755                 760                 765

Asn Arg Arg Arg Tyr Ile Pro Glu Ile Thr Ser Arg Asn Phe Asn Leu
        770                 775                 780

Arg Ser Phe Ala Glu Arg Thr Ala Met Asn Thr Pro Ile Gln Gly Thr
785                 790                 795                 800

Ala Ala Asp Ile Ile Lys Lys Ala Met Ile Ile Met Ala Asp Arg Leu
                805                 810                 815

Glu Glu Glu Gly Leu Gln Ala Arg Leu Leu Leu Gln Val His Asp Glu
            820                 825                 830

Leu Ile Phe Glu Ala Pro Lys Glu Glu Val Glu Lys Leu Glu Lys Leu
        835                 840                 845

Val Pro Glu Val Met Glu His Ala Ile Glu Leu Ala Val Pro Leu Lys
        850                 855                 860

Val Asp Tyr Ser Tyr Gly Pro Thr Trp Tyr Asp Ala Lys
865                 870                 875

<210> SEQ ID NO 109
<211> LENGTH: 877
<212> TYPE: PRT
<213> ORGANISM: Artificial Sequence
```

<220> FEATURE:
<223> OTHER INFORMATION: AMINO ACID SEQUENCE OF DNA polymerase I
     [Bacillus cereus ATCC 10987]

<400> SEQUENCE: 109

```
Met Glu Lys Lys Val Val Leu Val Asp Gly Asn Asn Ile Ala Tyr Arg
1               5                   10                  15

Ala Phe Phe Ala Leu Pro Leu Leu Asn Asn Asp Lys Gly Ile His Thr
            20                  25                  30

Asn Ala Ile Tyr Gly Phe Thr Met Met Leu Met Arg Ile Leu Glu Glu
        35                  40                  45

Glu Lys Pro Thr His Met Leu Val Ala Phe Asp Ala Gly Lys Thr Thr
    50                  55                  60

Phe Arg His Lys Thr Tyr Ser Glu Tyr Lys Gly Gly Arg Gln Lys Thr
65                  70                  75                  80

Pro Pro Glu Leu Ser Glu Gln Phe Pro Phe Ile Arg Glu Met Leu Asp
                85                  90                  95

Ala Phe Asn Val Pro Arg Tyr Glu Leu Glu Asn Tyr Glu Ala Asp Asp
            100                 105                 110

Ile Met Gly Thr Leu Ala Lys Glu Ala

-continued

```
            385                 390                 395                 400
Leu Leu Asp Pro Ala Asp Thr Asp Lys Asp Phe Arg Thr Val Ala Lys
                    405                 410                 415
Met Lys Glu Thr His Ala Val Lys Ser Asp Glu Val Tyr Gly Lys
                420                 425                 430
Gly Ala Lys Arg Ala Val Pro Glu Leu Glu Ile Val Ala Glu His Val
            435                 440                 445
Ala Arg Lys Val His Val Leu Tyr Asp Val Lys Gln Thr Phe Val Glu
450                 455                 460
Glu Leu Glu Lys Asn Glu Gln Tyr Glu Leu Phe Thr Glu Leu Glu Leu
465                 470                 475                 480
Pro Leu Ala Arg Val Leu Ala Asp Met Glu Val Lys Gly Val Lys Val
                485                 490                 495
Asp Thr Glu Arg Leu Arg Asn Met Gly Glu Glu Leu Ala Gly Arg Leu
                500                 505                 510
Lys Glu Met Glu Gln Glu Ile Tyr Lys Leu Ala Gly Arg Glu Phe Asn
            515                 520                 525
Ile Asn Ser Pro Lys Gln Leu Gly Val Ile Leu Phe Glu Asn Leu Asn
530                 535                 540
Leu Pro Val Ile Lys Lys Thr Lys Thr Gly Tyr Ser Thr Ser Ala Asp
545                 550                 555                 560
Val Leu Asp Lys Leu Met Asp His His Glu Ile Ile Pro Asn Ile Leu
                565                 570                 575
His Tyr Arg Gln Leu Gly Lys Leu Asn Ser Thr Tyr Ile Glu Gly Leu
                580                 585                 590
Leu Lys Val Val His Glu Asp Ser Ser Lys Ile His Thr Arg Phe Asn
            595                 600                 605
Gln Val Leu Thr Gln Thr Gly Arg Leu Ser Ser Thr Asp Pro Asn Leu
            610                 615                 620
Gln Asn Ile Pro Ile Arg Leu Glu Glu Gly Arg Lys Ile Arg Gln Ala
625                 630                 635                 640
Phe Val Pro Ser Glu Glu Gly Trp Ile Met Tyr Ala Ala Asp Tyr Ser
                645                 650                 655
Gln Ile Glu Leu Arg Val Leu Ala His Ile Ala Asn Asp Lys Gly Leu
                660                 665                 670
Val Glu Ala Phe Gln His Asp Met Asp Ile His Thr Lys Thr Ala Met
            675                 680                 685
Asp Val Phe Gly Val Glu Lys Asp Glu Val Thr Ser Asn Met Arg Arg
            690                 695                 700
Gln Ala Lys Ala Val Asn Phe Gly Ile Val Tyr Gly Ile Ser Asp Tyr
705                 710                 715                 720
Gly Leu Ser Gln Asn Leu Gly Ile Thr Arg Lys Ala Ala Ala Glu Phe
                725                 730                 735
Ile Glu Lys Tyr Leu Glu Ser Phe Pro Gly Val Gln Glu Tyr Met Asp
                740                 745                 750
Asp Ile Val Lys Asp Ala Lys Gln Lys Gly Tyr Val Ala Thr Leu Leu
            755                 760                 765
Asn Arg Arg Arg Tyr Ile Pro Glu Ile Thr Ser Arg Asn Phe Asn Leu
            770                 775                 780
Arg Ser Phe Ala Glu Arg Thr Ala Met Asn Thr Pro Ile Gln Gly Thr
785                 790                 795                 800
Ala Ala Asp Ile Ile Lys Lys Ala Met Ile Ile Met Ala Asp Arg Leu
                805                 810                 815
```

```
Glu Glu Glu Gly Leu Gln Ala Arg Leu Leu Gln Val His Asp Glu
            820                 825                 830

Leu Ile Phe Glu Ala Pro Lys Glu Glu Ile Glu Lys Leu Glu Lys Leu
            835                 840                 845

Val Pro Glu Val Met Glu His Ala Ile Glu Leu Ala Val Pro Leu Lys
850                 855                 860

Val Asp Tyr Ser Tyr Gly Pro Thr Trp Tyr Asp Ala Lys
865                 870                 875

<210> SEQ ID NO 110
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 110
gggcgcacgt atgcttctgc aggtcggtga cgagctggtg ttagaagccc cta          53

<210> SEQ ID NO 111
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 111 tagggggcttc taacaccagc tcgtcaccga cctgcagaag catacgtgcg ccc          53

<210> SEQ ID NO 112
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 112
gggcgcacgt atgcttctgc aggtcgcgga cgagctggtg ttagaagccc cta          53

<210> SEQ ID NO 113
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 113 tagggggcttc taacaccagc tcgtccgcga cctgcagaag catacgtgcg ccc          53

<210> SEQ ID NO 114
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 114
gggcgcacgt atgcttctgc aggtcagcga cgagctggtg ttagaagccc cta          53

<210> SEQ ID NO 115
<211> LENGTH: 53
<212> TYPE: DNA
<213> ORGANISM: Artificial Sequence
<220> FEATURE:
```

```
<223> OTHER INFORMATION: SYNTHETIC DNA OLIGONUCLEOTIDE

<400> SEQUENCE: 115
tagggctttc taacaccagc tcgtcgctga cctgcagaag catacgtgcg ccc        53

<210> SEQ ID NO 116
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 116
gggcgcacgt atgcttctgc aggtcacgga cgagctggtg ttagaagccc cta        53

<210> SEQ ID NO 117
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 117
tagggctttc taacaccagc tcgtccgtga cctgcagaag catacgtgcg ccc        53

<210> SEQ ID NO 118
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 118
gggcgcacgt atgcttctgc aggtctgcga cgagctggtg ttagaagccc cta        53

<210> SEQ ID NO 119
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 119
tagggctttc taacaccagc tcgtcgcaga cctgcagaag catacgtgcg ccc        53

<210> SEQ ID NO 120
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 120
gggcgcacgt atgcttctgc aggtcgtaga cgagctggtg ttagaagccc cta        53

<210> SEQ ID NO 121
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 121
tagggctttc taacaccagc tcgtctacga cctgcagaag catacgtgcg ccc        53
```

```
<210> SEQ ID NO 122
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 122
gggcgcacgt atgcttctgc aggtcttgga cgagctggtg ttagaagccc cta          53

<210> SEQ ID NO 123
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 123 tagggcttc taacaccagc tcgtccaaga cctgcagaag catacgtgcg ccc           53

<210> SEQ ID NO 124
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 124
gggcgcacgt atgcttctgc aggtcattga cgagctggtg ttagaagccc cta          53

<210> SEQ ID NO 125
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 125 tagggcttc taacaccagc tcgtcaatga cctgcagaag catacgtgcg ccc           53

<210> SEQ ID NO 126
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 126
gggcgcacgt atgcttctgc aggtcatgga cgagctggtg ttagaagccc cta          53

<210> SEQ ID NO 127
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 127 tagggcttc taacaccagc tcgtccatga cctgcagaag catacgtgcg ccc           53

<210> SEQ ID NO 128
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE
```

<400> SEQUENCE: 128
gggcgcacgt atgcttctgc aggtcccaga cgagctggtg ttagaagccc cta            53

<210> SEQ ID NO 129
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 129 tagggggcttc taacaccagc tcgtctggga cctgcagaag catacgtgcg ccc            53

<210> SEQ ID NO 130
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 130
gggcgcacgt atgcttctgc aggtctttga cgagctggtg ttagaagccc cta            53

<210> SEQ ID NO 131
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 131 tagggggcttc taacaccagc tcgtcaaaga cctgcagaag catacgtgcg ccc            53

<210> SEQ ID NO 132
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 132
gggcgcacgt atgcttctgc aggtctatga cgagctggtg ttagaagccc cta            53

<210> SEQ ID NO 133
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 133 tagggggcttc taacaccagc tcgtcataga cctgcagaag catacgtgcg ccc            53

<210> SEQ ID NO 134
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 134
gggcgcacgt atgcttctgc aggtctggga cgagctggtg ttagaagccc cta            53

<210> SEQ ID NO 135
<211> LENGTH: 53

```
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 135 tagggcttc taacaccagc tcgtcccaga cctgcagaag catacgtgcg ccc          53

<210> SEQ ID NO 136
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 136
gggcgcacgt atgcttctgc aggtcgatga cgagctggtg ttagaagccc cta          53

<210> SEQ ID NO 137
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 137 tagggcttc taacaccagc tcgtcatcga cctgcagaag catacgtgcg ccc          53

<210> SEQ ID NO 138
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 138
gggcgcacgt atgcttctgc aggtcgaaga cgagctggtg ttagaagccc cta          53

<210> SEQ ID NO 139
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 139 tagggcttc taacaccagc tcgtcttcga cctgcagaag catacgtgcg ccc          53

<210> SEQ ID NO 140
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 140
gggcgcacgt atgcttctgc aggtcaacga cgagctggtg ttagaagccc cta          53

<210> SEQ ID NO 141
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 141
```

-continued tagggcttc taacaccagc tcgtcgttga cctgcagaag catacgtgcg ccc    53

<210> SEQ ID NO 142
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 142
gggcgcacgt atgcttctgc aggtcaaaga cgagctggtg ttagaagccc cta    53

<210> SEQ ID NO 143
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 143 tagggcttc taacaccagc tcgtctttga cctgcagaag catacgtgcg ccc    53

<210> SEQ ID NO 144
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 144
gggcgcacgt atgcttctgc aggtccggga cgagctggtg ttagaagccc cta    53

<210> SEQ ID NO 145
<211> LENGTH: 53
<212> TYPE: DNA
<213> ORGANISM: Artificial Sequence
<220> FEATURE:
<223> OTHER INFORMATION: SYNTHETIC DNA OLIGONUCLEOTIDE

<400> SEQUENCE: 145 tagggcttc taacaccagc tcgtcccgga cctgcagaag catacgtgcg ccc    53

<210> SEQ ID NO 146
<211> LENGTH: 2507
<212> TYPE: DNA
<213> ORGANISM: Artificial Sequence
<220> FEATURE:
<223> OTHER INFORMATION: NUCLEOTIDE SEQUENCE OF MUTANT ID 20 (H784A)

<400> SEQUENCE: 146
catatgcgtg gtatgctgcc gttgttcgag cctaaaggcc gcgtactgtt agtcgatggt    60
catcacttgg cctatcggac gttccatgca ctcaaaggtc tgacgaccag tcgtggcgaa    120
ccggtccagg ctgtttatgg tttcgctaag tctttgctca agcactgaa agaagacggg    180 gacgcggtaa ttgttgtatt tgatgccaaa gcaccgagct ccgccacga agcttatggt    240 ggctacaagg caggacgcgc ccctacccca gaagatttcc ccgtcagct ggcattaatt    300 aaggagttag tagaccttct cggcttagcg cgtctggaag ttccggggtta tgaggcggac    360 gatgtccttg catccttggc taaaaaggcc gaaaagagg gctacgaagt ccgcatcttg    420
acggcagaca aagatctgta ccagcttctg tctgaccgta ttcatgtttt gcaccctgaa    480
ggctacttaa tcactccggc ctggctctgg gaaaagtacg gtctgcgtcc cgatcagtgg    540
gcggattatc gggctttgac gggagatgag agcgacaacc tgccaggagt aagggcatt    600

```
ggtgaaaaaa ccgcacgtaa gctgcttgaa gagtggggtt ccctggaagc cttgttaaaa      660
aatctggatc gtctcaagcc cgcaattcgt gaaaagatcc tggctcatat ggacgatctt      720
aaattaagtt gggacctggc caaggtgcgc accgatttac cgcttgaagt ggattttgca      780
aaacgccgtg agccggaccg gaacgtttta cgcgctttct tagagcgtct ggaattcggt      840
tcactgcttc atgaattcgg tctgttagag tctcctaaag cactcgaaga ggcaccgtgg      900
ccgcccccag aaggtgcttt tgttggcttc gtactttccc gtaaggagcc tatgtgggca      960
gatcttctgg ctttagcggc tgcacgcggt ggccgtgttc accgggcccc tgagccatac     1020
aaagcgttac gtgatctgaa ggaagcacgt ggcttgctgg caaaagacct ttctgttttg     1080
gccctgcgcg agggtcttgg actgccgcca ggcgacgatc ccatgttatt ggcctatctg     1140
ttagacccta gcaataccac acctgaaggg gtcgctcgtc ggtatggcgg tgaatggact     1200
gaggaagccg agagcgcgc cgcattgtcc gaacggctct tgcaaactt atggggtcgt       1260 ctggaagggg aggaacgtct gttatggttg tatcgggaag tcgaacgtcc tctttcggcc     1320
gtattagcgc atatggaggc aacaggtgtg cgtttagatg tcgcgtacct tcgggcctta     1380 tcactgaag ttgcagagga atcgcccgt ctcgaggctg aagtgttccg gttggccggt        1440
cacccgttta acctcaactc ccgtgaccag ctggaacgcg tttattcga tgagcttggg      1500 cttcccgcaa ttggcaaaac cgaaaagact ggcaaacgca gtacgagcgc tgccgtcctt     1560
gaggcactcc gcgaggctca ccctattgta gaaaagatcc tgcaataccg tgagttgacg     1620
aagcttaaaa gcacttatat tgatcctctc ccggatctga tccatcctcg taccggccgc     1680
ttgcacacac gtttcaacca gacggcgact gcaaccggcc gtctgtctag ctcggatcca     1740
aatctccaga acattccggt ccgtacaccc ttgggccaac gtatccgccg ggcgtttatc     1800
gctgaggaag gatggttact ggtcgcattg gactactcgc agattgagct gcgcgtcctc     1860
gcacatctct ctggtgacga aaatttaatc cgcgtgtttc aagaggggcg tgatattcac     1920
acagaaactg cctcatggat gttcggtgtc ccacgtgaag cagtggatcc tttgatgcgc     1980
cgtgcagcta aaacaattaa ttttggagtg ctgtacggaa tgagcgctca tcgcttgagt     2040
caggaactgg caatcccta cgaggaagcg caggcattca tcgaacgtta ctttcaatcg     2100
tttccgaaag ttcgcgcatg gatcgagaag acgctcgagg aaggtcgtcg tcggggctat     2160
gtcgaaactc tgtttggtcg ccgtcggtac gtaccgatcc ttgaagcccg cgtcaaatcg     2220
gtacgggagg ctgcggagcg tatggcattt aatatgcctg tacagggtac tgcagctgac     2280
ctcatgaaac tggcaatggt caagcttttc ccgcgcttgg aggaaatggg cgcacgtatg     2340
cttctgcagg tcgcggacga gctggtgtta gaagccccta aggagcgcgc gaagctgtc     2400 gcgcgcctcg ctaaagaagt gatggagggc gtttacccat tggccgtacc cctcgaagtg     2460
gaggtcggta ttggagaaga ttggttatct gcaaaggaag cggccgc                   2507
```

<210> SEQ ID NO 147
<211> LENGTH: 834
<212> TYPE: PRT
<213> ORGANISM: Artificial Sequence
<220> FEATURE:
<223> OTHER INFORMATION: AMINO ACID SEQUENCE OF MUTANT ID 20 (H784A)

<400> SEQUENCE: 147

```
Met Arg Gly Met Leu Pro Leu Phe Glu Pro Lys Gly Arg Val Leu Leu
1               5                  10                  15

Val Asp Gly His His Leu Ala Tyr Arg Thr Phe His Ala Leu Lys Gly
```

```
                    20                  25                  30
Leu Thr Thr Ser Arg Gly Glu Pro Val Gln Ala Val Tyr Gly Phe Ala
                35                  40                  45
Lys Ser Leu Leu Lys Ala Leu Lys Glu Asp Gly Asp Ala Val Ile Val
            50                  55                  60
Val Phe Asp Ala Lys Ala Pro Ser Phe Arg His Glu Ala Tyr Gly Gly
65                  70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Gly Leu Ala Arg Leu Glu
            100                 105                 110
Val Pro Gly Tyr Glu Ala Asp Asp Val Leu Ala Ser Leu Ala Lys Lys
            115                 120                 125
Ala Glu Lys Glu Gly Tyr Glu Val Arg Ile Leu Thr Ala Asp Lys Asp
            130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
                180                 185                 190
Leu Pro Gly Val Lys Gly Ile Gly Glu Lys Thr Ala Arg Lys Leu Leu
                195                 200                 205
Glu Glu Trp Gly Ser Leu Glu Ala Leu Leu Lys Asn Leu Asp Arg Leu
            210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
                260                 265                 270
Leu Glu Arg Leu Glu Phe Gly Ser Leu Leu His Glu Phe Gly Leu Leu
            275                 280                 285
Glu Ser Pro Lys Ala Leu Glu Glu Ala Pro Trp Pro Pro Pro Glu Gly
            290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
            355                 360                 365
Pro Gly Asp Asp Pro Met Leu Leu Ala Tyr Leu Leu Asp Pro Ser Asn
            370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
            435                 440                 445
```

```
Val Arg Leu Asp Val Ala Tyr Leu Arg Ala Leu Ser Leu Glu Val Ala
    450                 455                 460

Glu Glu Ile Ala Arg Leu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val Ala
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Ala Ala

<210> SEQ ID NO 148
<211> LENGTH: 2507
<212> TYPE: DNA
```

<213> ORGANISM: Artificial Sequence
<220> FEATURE:
<223> OTHER INFORMATION: NUCLEOTIDE SEQUENCE OF MUTANT ID 21 (H784S)

<400> SEQUENCE: 148

```
catatgcgtg gtatgctgcc gttgttcgag cctaaaggcc gcgtactgtt agtcgatggt      60
catcacttgg cctatcggac gttccatgca ctcaaaggtc tgacgaccag tcgtggcgaa     120
ccggtccagg ctgtttatgg tttcgctaag tctttgctca aagcactgaa agaagacggg     180
gacgcggtaa ttgttgtatt tgatgccaaa gcaccgagct ccgccacga agcttatggt      240
ggctacaagg caggacgcgc ccctacccca gaagatttcc ccgtcagct ggcattaatt      300
aaggagttag tagaccttct cggcttagcg cgtctggaag ttccgggtta tgaggcggac     360
gatgtccttg catccttggc taaaaaggcc gaaaagagg gctacgaagt ccgcatcttg      420
acggcagaca aagatctgta ccagcttctg tctgaccgta ttcatgtttt gcaccctgaa     480
ggctacttaa tcactccggc ctggctctgg gaaaagtacg gtctgcgtcc cgatcagtgg     540
gcggattatc gggctttgac gggagatgag agcgacaacc tgccaggagt taagggcatt     600
ggtgaaaaaa ccgcacgtaa gctgcttgaa gagtggggtt ccctggaagc cttgttaaaa     660
aatctggatc gtctcaagcc cgcaattcgt gaaaagatcc tggctcatat ggacgatctt     720
aaattaagtt gggacctggc caaggtgcgc accgatttac cgcttgaagt ggattttgca     780
aaacgccgtg agccggaccg ggaacgttta cgcgctttct tagagcgtct ggaattcggt     840
tcactgcttc atgaattcgg tctgttagag tctcctaaag cactcgaaga ggcaccgtgg     900
ccgcccccag aaggtgcttt tgttggcttc gtactttccc gtaaggagcc tatgtgggca     960
gatcttctgg ctttagcggc tgcacgcggt ggccgtgttc accgggcccc tgagccatac    1020
aaagcgttac gtgatctgaa ggaagcacgt ggcttgctgg caaaagacct ttctgttttg    1080
gccctgcgcg agggtcttgg actgccgcca ggcgacgatc ccatgttatt ggcctatctg    1140
ttagacccta gcaataccac acctgaaggg gtcgctcgtc ggtatggcgg tgaatggact    1200
gaggaagccg gagagcgcgc cgcattgtcc gaacggctct ttgcaaactt atgggggtcgt   1260
ctggaagggg aggaacgtct gttatggttg tatcgggaag tcgaacgtcc tctttcggcc    1320
gtattagcgc atatggaggc aacaggtgtg cgtttagatg tcgcgtacct tcgggcctta    1380
tcactggaag ttgcagagga aatcgcccgt ctcgaggctg aagtgttccg gttgccggt     1440
cacccgttta acctcaactc ccgtgaccag ctggaacgcg ttttattcga tgagcttggg    1500
cttcccgcaa ttggcaaaac cgaaaagact ggcaaacgca gtacgagcgc tgccgtcctt    1560
gaggcactcc gcgaggctca ccctattgta gaaaagatcc tgcaataccg tgagttgacg    1620
aagcttaaaa gcacttatat tgatcctctc ccggatctga tccatcctcg taccggccgc    1680
ttgcacacac gtttcaacca gacggcgact gcaaccggcc gtctgtctag ctcggatcca    1740
aatctccaga acattccggt ccgtacaccc ttgggccaac gtatccgccg ggcgtttatc    1800
gctgaggaag gatggttact ggtcgcattg gactactcgc agattgagct gcgcgtcctc    1860
gcacatctct ctggtgacga aaatttaatc cgcgtgtttc aagagggggcg tgatattcac    1920
acagaaactg cctcatggat gttcggtgtc ccacgtgaag cagtggatcc tttgatgcgc    1980
cgtgcagcta aaacaattaa tttggagtg ctgtacggaa tgagcgctca tcgcttgagt     2040
caggaactgg caatccccta cgaggaagcg caggcattca tcgaacgtta ctttcaatcg    2100
tttccgaaag ttcgcgcatg gatcgagaag acgctcgagg aaggtcgtcg tcggggctat    2160
gtcgaaactc tgtttggtcg ccgtcggtac gtaccagatc ttgaagcccg cgtcaaatcg    2220
```

```
gtacgggagg ctgcggagcg tatggcattt aatatgcctg tacagggtac tgcagctgac    2280
ctcatgaaac tggcaatggt caagctttc ccgcgcttgg aggaaatggg cgcacgtatg    2340
cttctgcagg tcagcgacga gctggtgtta gaagccccta aggagcgcgc cgaagctgtc    2400
gcgcgcctcg ctaaagaagt gatggagggc gtttacccat tggccgtacc cctcgaagtg    2460
gaggtcggta ttggagaaga ttggttatct gcaaaggaag cggccgc                  2507
```

<210> SEQ ID NO 149
<211> LENGTH: 834
<212> TYPE: PRT
<213> ORGANISM: Artificial Sequence
<220> FEATURE:
<223> OTHER INFORMATION: AMINO ACID SEQUENCE OF MUTANT ID 21 (H784S)

<400> SEQUENCE: 149

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
```

```
            305                 310                 315                 320
        Leu Leu Ala Leu Ala Ala Arg Gly Gly Arg Val His Arg Ala Pro
                        325                 330                 335
        Glu Pro Tyr Lys Ala Leu Arg Asp Leu Lys Glu Ala Arg Gly Leu Leu
                        340                 345                 350
        Ala Lys Asp Leu Ser Val Leu Ala Leu Arg Glu Gly Leu Gly Leu Pro
                        355                 360                 365
        Pro Gly Asp Asp Pro Met Leu Leu Ala Tyr Leu Leu Asp Pro Ser Asn
                        370                 375                 380
        Thr Thr Pro Glu Gly Val Ala Arg Arg Tyr Gly Gly Glu Trp Thr Glu
        385                 390                 395                 400
        Glu Ala Gly Glu Arg Ala Ala Leu Ser Glu Arg Leu Phe Ala Asn Leu
                        405                 410                 415
        Trp Gly Arg Leu Glu Gly Glu Glu Arg Leu Leu Trp Leu Tyr Arg Glu
                        420                 425                 430
        Val Glu Arg Pro Leu Ser Ala Val Leu Ala His Met Glu Ala Thr Gly
                        435                 440                 445
        Val Arg Leu Asp Val Ala Tyr Leu Arg Ala Leu Ser Leu Glu Val Ala
                        450                 455                 460
        Glu Glu Ile Ala Arg Leu Glu Ala Glu Val Phe Arg Leu Ala Gly His
        465                 470                 475                 480
        Pro Phe Asn Leu Asn Ser Arg Asp Gln Leu Glu Arg Val Leu Phe Asp
                        485                 490                 495
        Glu Leu Gly Leu Pro Ala Ile Gly Lys Thr Glu Lys Thr Gly Lys Arg
                        500                 505                 510
        Ser Thr Ser Ala Ala Val Leu Glu Ala Leu Arg Glu Ala His Pro Ile
                        515                 520                 525
        Val Glu Lys Ile Leu Gln Tyr Arg Glu Leu Thr Lys Leu Lys Ser Thr
                        530                 535                 540
        Tyr Ile Asp Pro Leu Pro Asp Leu Ile His Pro Arg Thr Gly Arg Leu
        545                 550                 555                 560
        His Thr Arg Phe Asn Gln Thr Ala Thr Ala Thr Gly Arg Leu Ser Ser
                        565                 570                 575
        Ser Asp Pro Asn Leu Gln Asn Ile Pro Val Arg Thr Pro Leu Gly Gln
                        580                 585                 590
        Arg Ile Arg Arg Ala Phe Ile Ala Glu Glu Gly Trp Leu Leu Val Ala
                        595                 600                 605
        Leu Asp Tyr Ser Gln Ile Glu Leu Arg Val Leu Ala His Leu Ser Gly
                        610                 615                 620
        Asp Glu Asn Leu Ile Arg Val Phe Gln Glu Gly Arg Asp Ile His Thr
        625                 630                 635                 640
        Glu Thr Ala Ser Trp Met Phe Gly Val Pro Arg Glu Ala Val Asp Pro
                        645                 650                 655
        Leu Met Arg Arg Ala Ala Lys Thr Ile Asn Phe Gly Val Leu Tyr Gly
                        660                 665                 670
        Met Ser Ala His Arg Leu Ser Gln Glu Leu Ala Ile Pro Tyr Glu Glu
                        675                 680                 685
        Ala Gln Ala Phe Ile Glu Arg Tyr Phe Gln Ser Phe Pro Lys Val Arg
                        690                 695                 700
        Ala Trp Ile Glu Lys Thr Leu Glu Glu Gly Arg Arg Gly Tyr Val
        705                 710                 715                 720
        Glu Thr Leu Phe Gly Arg Arg Arg Tyr Val Pro Asp Leu Glu Ala Arg
                        725                 730                 735
```

```
Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val Ser
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Ala Ala

<210> SEQ ID NO 150
<211> LENGTH: 2507
<212> TYPE: DNA
<213> ORGANISM: Artificial Sequence
<220> FEATURE:
<223> OTHER INFORMATION: NUCLEOTIDE SEQUENCE OF MUTANT ID 22 (H784T)

<400> SEQUENCE: 150
```

| | | | | | |
|---|---|---|---|---|---|
| catatgcgtg | gtatgctgcc | gttgttcgag | cctaaaggcc | gcgtactgtt | agtcgatggt | 60 |
| catcacttgg | cctatcggac | gttccatgca | ctcaaaggtc | tgacgaccag | tcgtggcgaa | 120 |
| ccggtccagg | ctgtttatgg | tttcgctaag | tcttttgctca | aagcactgaa | agaagacggg | 180 |
| gacgcggtaa | ttgttgtatt | tgatgccaaa | gcaccgagct | tccgccacga | agcttatggt | 240 |
| ggctacaagg | caggacgcgc | ccctacccca | gaagatttcc | ccgtcagct | ggcattaatt | 300 |
| aaggagttag | tagaccttct | cggcttagcg | cgtctggaag | ttccgggtta | tgaggcggac | 360 |
| gatgtccttg | catccttggc | taaaaaggcc | gaaaagagg | gctacgaagt | ccgcatcttg | 420 |
| acggcagaca | aagatctgta | ccagcttctg | tctgaccgta | ttcatgtttt | gcaccctgaa | 480 |
| ggctacttaa | tcactccggc | ctggctctgg | gaaaagtacg | gtctgcgtcc | cgatcagtgg | 540 |
| gcggattatc | gggctttgac | gggagatgag | agcgacaacc | tgccaggagt | taagggcatt | 600 |
| ggtgaaaaaa | ccgcacgtaa | gctgcttgaa | gagtggggtt | ccctggaagc | cttgttaaaa | 660 |
| aatctggatc | gtctcaagcc | cgcaattcgt | gaaaagatcc | tggctcatat | ggacgatctt | 720 |
| aaattaagtt | gggacctggc | caaggtgcgc | accgatttac | gcttgaagt | ggattttgca | 780 |
| aaacgccgtg | agccggaccg | ggaacgttta | cgcgctttct | tagagcgtct | ggaattcggt | 840 |
| tcactgcttc | atgaattcgg | tctgttagag | tctcctaaag | cactcgaaga | ggcaccgtgg | 900 |
| ccgcccccag | aaggtgcttt | tgttggcttc | gtactttccc | gtaaggagcc | tatgtgggca | 960 |
| gatcttctgg | ctttagcggc | tgcacgcggt | ggccgtgttc | accgggcccc | tgagccatac | 1020 |
| aaagcgttac | gtgatctgaa | ggaagcacgt | ggcttgctgg | caaaagacct | ttctgttttg | 1080 |
| gccctgcgcg | agggtcttgg | actgccgcca | ggcgacgatc | ccatgttatt | ggcctatctg | 1140 |
| ttagacccta | gcaataccac | acctgaaggg | gtcgctcgtc | ggtatggcgg | tgaatggact | 1200 |
| gaggaagccg | gagagcgcgc | cgcattgtcc | gaacggctct | ttgcaaactt | atggggtcgt | 1260 |
| ctggaagggg | aggaacgtct | gttatggttg | tatcgggaag | tcgaacgtcc | tctttcggcc | 1320 |
| gtattagcgc | atatggaggc | aacaggtgtg | cgtttagatg | tcgcgtacct | tcgggcctta | 1380 |
| tcactggaag | ttgcagagga | aatcgcccgt | ctcgaggctg | aagtgttccg | gttggccggt | 1440 |

-continued

```
cacccgttta acctcaactc ccgtgaccag ctggaacgcg ttttattcga tgagcttggg    1500
cttcccgcaa ttggcaaaac cgaaaagact ggcaaacgca gtacgagcgc tgccgtcctt    1560
gaggcactcc gcgaggctca ccctattgta gaaaagatcc tgcaataccg tgagttgacg    1620
aagcttaaaa gcacttatat tgatcctctc ccggatctga tccatcctcg taccggccgc    1680
ttgcacacac gtttcaacca gacggcgact gcaaccggcc gtctgtctag ctcggatcca    1740
aatctccaga acattccggt ccgtacaccc ttgggccaac gtatccgccg ggcgtttatc    1800
gctgaggaag gatggttact ggtcgcattg gactactcgc agattgagct gcgcgtcctc    1860
gcacatctct ctggtgacga aaatttaatc cgcgtgtttc aagaggggcg tgatattcac    1920
acagaaactg cctcatggat gttcggtgtc ccacgtgaag cagtggatcc tttgatgcgc    1980
cgtgcagcta aaacaattaa ttttggagtg ctgtacggaa tgagcgctca tcgcttgagt    2040
caggaactgg caatccccta cgaggaagcg caggcattca tcgaacgtta ctttcaatcg    2100
tttccgaaag ttcgcgcatg gatcgagaag acgctcgagg aaggtcgtcg tcggggctat    2160
gtcgaaactc tgtttggtcg ccgtcggtac gtaccagatc ttgaagcccg cgtcaaatcg    2220
gtacgggagg ctgcggagcg tatggcattt aatatgcctg tacagggtac tgcagctgac    2280
ctcatgaaac tggcaatggt caagcttttc ccgcgcttgg aggaaatggg cgcacgtatg    2340
cttctgcagg tcacggacga gctggtgtta gaagccccta aggagcgcgc cgaagctgtc    2400
gcgcgcctcg ctaaagaagt gatggagggc gtttacccat tggccgtacc cctcgaagtg    2460
gaggtcggta ttggagaaga ttggttatct gcaaaggaag cggccgc                  2507
```

<210> SEQ ID NO 151
<211> LENGTH: 834
<212> TYPE: PRT
<213> ORGANISM: Artificial Sequence
<220> FEATURE:
<223> OTHER INFORMATION: AMINO ACID SEQUENCE OF MUTANT ID 22 (H784T)

<400> SEQUENCE: 151

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175
```

```
Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
        260                 265                 270

Leu Glu Arg Leu Glu Phe Gly Ser Leu Leu His Glu Phe Gly Leu Leu
    275                 280                 285

Glu Ser Pro Lys Ala Leu Glu Glu Ala Pro Trp Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
        340                 345                 350

Ala Lys Asp Leu Ser Val Leu Ala Leu Arg Glu Gly Leu Gly Leu Pro
    355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
        420                 425                 430

Val Glu Arg Pro Leu Ser Ala Val Leu Ala His Met Glu Ala Thr Gly
    435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
        500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
        580                 585                 590

Arg Ile Arg Arg Ala Phe Ile Ala Glu Glu Gly Trp Leu Leu Val Ala
```

```
            595                 600                 605
Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                    645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val Thr
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Ala Ala

<210> SEQ ID NO 152
<211> LENGTH: 1964
<212> TYPE: DNA
<213> ORGANISM: Artificial Sequence
<220> FEATURE:
<223> OTHER INFORMATION: NUCLEOTIDE SEQUENCE OF MUTANT ID 24 (H784V).

<400> SEQUENCE: 152
gattatcggg ctttgacggg agatgagagc gacaacctgc caggagttaa gggcattggt      60
gaaaaaaccg cacgtaagct gcttgaagag tggggttccc tggaagcctt gttaaaaaat     120
ctggatcgtc tcaagcccgc aattcgtgaa aagatcctgg ctcatatgga cgatcttaaa     180
ttaagttggg acctggccaa ggtgcgcacc gatttaccgc ttgaagtgga ttttgcaaaa     240
cgccgtgagc cggaccggga acgtttacgc gcttttctta gcgtctggga attcggttca     300
ctgcttcatg aattcggtct gttagagtct cctaaagcac tcgaagaggc accgtggccg     360
cccccagaag gtgcttttgt tggcttcgta ctttcccgta aggagcctat gtgggcagat     420
cttctggctt tagcggctgc acgcggtggc cgtgttcacc gggcccctga gccatacaaa     480
gcgttacgtg atctgaagga agcacgtggc ttgctggcaa agacctttc tgttttggcc     540 ctgcgcgagg tcttggact gccgccaggc gacgatccca tgttattggc ctatctgtta     600 gacccctagca ataccacacc tgaaggggtc gctcgtcggt atggcggtga atggactgag     660
gaagccggag agcgcgccgc attgtccgaa cggctctttg caaacttatg gggtcgtctg     720
```

```
gaaggggagg aacgtctgtt atggttgtat cgggaagtcg aacgtcctct ttcggccgta      780
ttagcgcata tggaggcaac aggtgtgcgt ttagatgtcg cgtaccttcg ggccttatca      840
ctggaagttg cagaggaaat cgcccgtctc gaggctgaag tgttccggtt ggccggtcac      900
ccgtttaacc tcaactcccg tgaccagctg aacgcgttt tattcgatga gcttgggctt       960
cccgcaattg gcaaaaccga aaagactggc aaacgcagta cgagcgctgc cgtccttgag     1020
gcactccgcg aggctcaccc tattgtagaa aagatcctgc aataccgtga gttgacgaag     1080
cttaaaagca cttatattga tcctctcccg gatctgatcc atcctcgtac cggccgcttg     1140
cacacacgtt tcaaccagac ggcgactgca accggccgtc tgtctagctc ggatccaaat     1200
ctccagaaca ttccggtccg tacacccttg ggccaacgta tccgccgggc gtttatcgct     1260
gaggaaggat ggttactggt cgcattggac tactcgcaga ttgagctgcg cgtcctcgca     1320
catctctctg gtgacgaaaa tttaatccgc gtgtttcaag aggggcgtga tattcacaca     1380
gaaactgcct catggatgtt cggtgtccca cgtgaagcag tggatccttt gatgcgccgt     1440
gcagctaaaa caattaattt tggagtgctg tacggaatga gcgctcatcg cttgagtcag     1500
gaactggcaa tccctacga ggaagcgcag gcattcatcg aacgttactt tcaatcgttt      1560
ccgaaagttc gcgcatggat cgagaagacg ctcgaggaag gtcgtcgtcg gggctatgtc     1620
gaaactctgt ttggtcgccg tcggtacgta ccagatcttg aagcccgcgt caaatcggta     1680
cgggaggctg cggagcgtat ggcatttaat atgcctgtac agggtactgc agctgaccctc    1740 atgaaactgg caatggtcaa gcttttcccg cgcttggagg aaatgggcgc acgtatgctt     1800
ctgcaggtcg tagacgagct ggtgttagaa gcccctaagg agcgcgccga agctgtcgcg     1860
cgcctcgcta aagaagtgat ggagggcgtt tacccattgg ccgtacccct cgaagtggag     1920
gtcggtattg gagaagattg gttatctgca aaggaagcgg ccgc                      1964
```

<210> SEQ ID NO 153
<211> LENGTH: 834
<212> TYPE: PRT
<213> ORGANISM: Artificial Sequence
<220> FEATURE:
<223> OTHER INFORMATION: AMINO ACID SEQUENCE OF MUTANT ID 24 (H784V).

<400> SEQUENCE: 153

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140
```

```
Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
            165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
            325                 330                 335

Glu Pro Tyr Lys Ala Leu Arg Asp Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560
```

-continued

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
        580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val Val
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Ala Ala

<210> SEQ ID NO 154
<211> LENGTH: 2507
<212> TYPE: DNA
<213> ORGANISM: Artificial Sequence
<220> FEATURE:
<223> OTHER INFORMATION: NUCLEOTIDE SEQUENCE OF MUTANT ID 26 (H784I)

<400> SEQUENCE: 154
catatgcgtg gtatgctgcc gttgttcgag cctaaaggcc gcgtactgtt agtcgatggt    60
catcacttgg cctatcggac gttccatgca ctcaaaggtc tgacgaccag tcgtggcgaa   120
ccggtccagg ctgtttatgg tttcgctaag tctttgctca agcactgaa agaagacggg   180 gacgcggtaa ttgttgtatt tgatgccaaa gcaccgagct ccgccacga agcttatggt   240 ggctacaagg caggacgcgc ccctacccca gaagatttcc ccgtcagct ggcattaatt   300 aaggagttag tagaccttct cggcttagcg cgtctggaag ttccgggtta tgaggcggac   360
gatgtccttg catccttggc taaaaaggcc gaaaagagg gctacgaagt ccgcatcttg   420
acggcagaca aagatctgta ccagcttctg tctgaccgta ttcatgtttt gcaccctgaa   480

-continued

| | |
|---|---|
| ggctacttaa tcactccggc ctggctctgg gaaaagtacg gtctgcgtcc cgatcagtgg | 540 |
| gcggattatc gggctttgac gggagatgag agcgacaacc tgccaggagt taagggcatt | 600 |
| ggtgaaaaaa ccgcacgtaa gctgcttgaa gagtgggggtt ccctggaagc cttgttaaaa | 660 |
| aatctggatc gtctcaagcc cgcaattcgt gaaaagatcc tggctcatat ggacgatctt | 720 |
| aaattaagtt gggacctggc caaggtgcgc accgatttac cgcttgaagt ggattttgca | 780 |
| aaacgccgtg agccggaccg ggaacgttta cgcgctttct tagagcgtct ggaattcggt | 840 |
| tcactgcttc atgaattcgg tctgttagag tctcctaaag cactcgaaga ggcaccgtgg | 900 |
| ccgcccccag aaggtgcttt tgttggcttc gtactttccc gtaaggagcc tatgtgggca | 960 |
| gatcttctgg ctttagcggc tgcacgcggt ggccgtgttc accgggcccc tgagccatac | 1020 |
| aaagcgttac gtgatctgaa ggaagcacgt ggcttgctgg caaaagacct ttctgttttg | 1080 |
| gccctgcgcg agggtcttgg actgccgcca ggcgacgatc ccatgttatt ggcctatctg | 1140 |
| ttagacccta gcaataccac acctgaaggg gtcgctcgtc ggtatggcgg tgaatggact | 1200 |
| gaggaagccg gagagcgcgc cgcattgtcc gaacggctct ttgcaaactt atggggtcgt | 1260 |
| ctggaagggg aggaacgtct gttatggttg tatcgggaag tcgaacgtcc tctttcggcc | 1320 |
| gtattagcgc atatggaggc aacaggtgtg cgtttagatg tcgcgtacct tcgggcctta | 1380 |
| tcactggaag ttgcagagga aatcgcccgt ctcgaggctg aagtgttccg gttggccggt | 1440 |
| cacccgttta acctcaactc ccgtgaccag ctggaacgcg ttttattcga tgagcttggg | 1500 |
| cttcccgcaa ttggcaaaac cgaaaagact ggcaaacgca gtacgagcgc tgccgtcctt | 1560 |
| gaggcactcc gcgaggctca ccctattgta gaaaagatcc tgcaataccg tgagttgacg | 1620 |
| aagcttaaaa gcacttatat tgatcctctc ccggatctga tccatcctcg taccggccgc | 1680 |
| ttgcacacac gtttcaacca gacggcgact gcaaccggcc gtctgtctag ctcggatcca | 1740 |
| aatctccaga acattccggt ccgtacaccc ttgggccaac gtatccgccg ggcgtttatc | 1800 |
| gctgaggaag gatggttact ggtcgcattg gactactcgc agattgagct gcgcgtcctc | 1860 |
| gcacatctct ctggtgacga aaatttaatc cgcgtgtttc aagaggggcg tgatattcac | 1920 |
| acagaaactg cctcatggat gttcggtgtc ccacgtgaag cagtggatcc tttgatgcgc | 1980 |
| cgtgcagcta aaacaattaa ttttggagtg ctgtacggaa tgagcgctca tcgcttgagt | 2040 |
| caggaactgg caatcccta cgaggaagcg caggcattca tcgaacgtta ctttcaatcg | 2100 |
| tttccgaaag ttcgcgcatg gatcgagaag acgctcgagg aaggtcgtcg tcggggctat | 2160 |
| gtcgaaactc tgtttggtcg ccgtcggtac gtaccagatc ttgaagcccg cgtcaaatcg | 2220 |
| gtacgggagg ctgcggagcg tatggcattt aatatgcctg tacagggtac tgcagctgac | 2280 |
| ctcatgaaac tggcaatggt caagcttttc ccgcgcttgg aggaaatggg cgcacgtatg | 2340 |
| cttctgcagg tcattgacga gctggtgtta gaagcccta aggagcgcgc cgaagctgtc | 2400 |
| gcgcgcctcg ctaaagaagt gatggagggc gtttacccat tggccgtacc cctcgaagtg | 2460 |
| gaggtcggta ttgagaagaga ttggttatct gcaaaggaag cggccgc | 2507 |

<210> SEQ ID NO 155
<211> LENGTH: 834
<212> TYPE: PRT
<213> ORGANISM: Artificial Sequence
<220> FEATURE:
<223> OTHER INFORMATION: AMINO ACID SEQUENCE OF MUTANT ID 26 (H784I)

<400> SEQUENCE: 155

Met Arg Gly Met Leu Pro Leu Phe Glu Pro Lys Gly Arg Val Leu Leu

-continued

```
1               5                   10                  15
Val Asp Gly His His Leu Ala Tyr Arg Thr Phe His Ala Leu Lys Gly
                20                  25                  30
Leu Thr Thr Ser Arg Gly Glu Pro Val Gln Ala Val Tyr Gly Phe Ala
                35                  40                  45
Lys Ser Leu Leu Lys Ala Leu Lys Glu Asp Gly Asp Ala Val Ile Val
                50                  55                  60
Val Phe Asp Ala Lys Ala Pro Ser Phe Arg His Glu Ala Tyr Gly Gly
65                      70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Leu Gly Leu Ala Arg Leu Glu
                100                 105                 110
Val Pro Gly Tyr Glu Ala Asp Asp Val Leu Ala Ser Leu Ala Lys Lys
                115                 120                 125
Ala Glu Lys Glu Gly Tyr Glu Val Arg Ile Leu Thr Ala Asp Lys Asp
                130                 135                 140
Leu Tyr Gln Leu Leu Ser Asp Arg Ile His Val Leu His Pro Glu Gly
145                     150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
                180                 185                 190
Leu Pro Gly Val Lys Gly Ile Gly Glu Lys Thr Ala Arg Lys Leu Leu
                195                 200                 205
Glu Glu Trp Gly Ser Leu Glu Ala Leu Leu Lys Asn Leu Asp Arg Leu
                210                 215                 220
Lys Pro Ala Ile Arg Glu Lys Ile Leu Ala His Met Asp Asp Leu Lys
225                     230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
                260                 265                 270
Leu Glu Arg Leu Glu Phe Gly Ser Leu Leu His Glu Phe Gly Leu Leu
                275                 280                 285
Glu Ser Pro Lys Ala Leu Glu Glu Ala Pro Trp Pro Pro Pro Glu Gly
                290                 295                 300
Ala Phe Val Gly Phe Val Leu Ser Arg Lys Glu Pro Met Trp Ala Asp
305                     310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
370                     375                 380
Thr Thr Pro Glu Gly Val Ala Arg Arg Tyr Gly Gly Glu Trp Thr Glu
385                     390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
```

```
Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val Val
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

Ala Ala
```

<210> SEQ ID NO 156
<211> LENGTH: 2507
<212> TYPE: DNA
<213> ORGANISM: Artificial Sequence
<220> FEATURE:
<223> OTHER INFORMATION: NUCLEOTIDE SEQUENCE OF MUTANT ID 27 (H784M)

<400> SEQUENCE: 156

```
catatgcgtg gtatgctgcc gttgttcgag cctaaaggcc gcgtactgtt agtcgatggt      60
catcacttgg cctatcggac gttccatgca ctcaaaggtc tgacgaccag tcgtggcgaa     120
ccggtccagg ctgtttatgg tttcgctaag tctttgctca agcactgaa agaagacggg      180
gacgcggtaa ttgttgtatt tgatgccaaa gcaccgagct tccgccacga agcttatggt     240
ggctacaagg caggacgcgc ccctacccca gaagatttcc cccgtcagct ggcattaatt     300
aaggagttag tagaccttct cggcttagcg cgtctggaag ttccgggtta tgaggcggac     360
gatgtccttg catccttggc taaaaaggcc gaaaagagg gctacgaagt ccgcatcttg      420
acggcagaca agatctgta ccagcttctg tctgaccgta ttcatgtttt gcaccctgaa      480
ggctacttaa tcactccggc ctggctctgg aaaagtacg gtctgcgtcc gatcagtgg      540
gcggattatc gggctttgac gggagatgag agcgacaacc tgccaggagt taagggcatt     600
ggtgaaaaaa ccgcacgtaa gctgcttgaa gagtggggtt ccctggaagc cttgttaaaa     660
aatctggatc gtctcaagcc cgcaattcgt gaaaagatcc tggctcatat ggacgatctt     720
aaattaagtt gggacctggc caaggtgcgc accgatttac cgcttgaagt ggattttgca     780
aaacgccgtg agccggaccg ggaacgttta cgcgctttct tagagcgtct ggaattcggt     840
tcactgcttc atgaattcgg tctgttagag tctcctaaag cactcgaaga ggcaccgtgg     900
ccgcccccag aaggtgcttt tgttggcttc gtactttccc gtaaggagcc tatgtgggca     960
gatcttctgg ctttagcggc tgcacgcggt ggccgtgttc accgggcccc tgagccatac    1020
aaagcgttac gtgatctgaa ggaagcacgt ggcttgctgg caaaagacct ttctgttttg    1080
gccctgcgcg agggtcttgg actgccgcca ggcgacgatc ccatgttatt ggcctatctg    1140
ttagacccta gcaataccac acctgaaggg gtcgctcgtc ggtatggcgg tgaatggact    1200
gaggaagccg gagagcgcgc cgcattgtcc gaacggctct ttgcaaactt atggggtcgt    1260
ctggaagggg aggaacgtct gttatggttg tatcgggaag tcgaacgtcc tctttcggcc    1320
gtattagcgc atatggaggc aacagttgtg cgtttagatg tcgcgtacct tcgggcctta    1380
tcactggaag ttgcagagga atcgcccgt ctcgaggctg aagtgttccg gttggccggt     1440
cacccgttta acctcaactc ccgtgaccag ctggaacgcg ttttattcga tgagcttggg    1500
cttcccgcaa ttggcaaaac cgaaaagact ggcaaacgca gtacgagcgc tgccgtcctt    1560
gaggcactcc gcgaggctca ccctattgta gaaaagatcc tgcaataccg tgagttgacg    1620
aagcttaaaa gcacttatat tgatcctctc ccggatctga tccatcctcg taccggccgc    1680
ttgcacacac gtttcaacca gacggcgact gcaaccggcc gtctgtctag ctcggatcca    1740
aatctccaga acattccggt ccgtacaccc ttgggccaac gtatccgccg ggcgtttatc    1800
gctgaggaag gatggttact ggtcgcattg gactactcgc agattgagct gcgcgtcctc    1860
gcacatctct ctggtgacga aaatttaatc gcgtgtttc aagaggggcg tgatattcac    1920
acagaaactg cctcatggat gttcggtgtc ccacgtgaag cagtggatcc tttgatgcgc    1980
cgtgcagcta aaacaattaa ttttggagtg ctgtacggaa tgagcgctca tcgcttgagt    2040
caggaactgg caatccccta cgaggaagcg caggcattca tcgaacgtta ctttcaatcg    2100
```

```
tttccgaaag ttcgcgcatg gatcgagaag acgctcgagg aaggtcgtcg tcggggctat    2160
gtcgaaactc tgtttggtcg ccgtcggtac gtaccagatc ttgaagcccg cgtcaaatcg    2220
gtacgggagg ctgcggagcg tatggcattt aatatgcctg tacagggtac tgcagctgac    2280
ctcatgaaac tggcaatggt caagcttttc ccgcgcttgg aggaaatggg cgcacgtatg    2340
cttctgcagg tcatggacga gctggtgtta gaagccccta aggagcgcgc cgaagctgtc    2400
gcgcgcctcg ctaaagaagt gatggagggc gtttacccat ggccgtacc cctcgaagtg    2460 gaggtcggta ttggagaaga ttggttatct gcaaaggaag cggccgc                  2507
```

<210> SEQ ID NO 157
<211> LENGTH: 834
<212> TYPE: PRT
<213> ORGANISM: Artificial Sequence
<220> FEATURE:
<223> OTHER INFORMATION: AMINO ACID SEQUENCE OF MUTANT ID 27 (H784M)

<400> SEQUENCE: 157

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
```

```
            290                 295                 300
Ala Phe Val Gly Phe Val Leu Ser Arg Lys Glu Pro Met Trp Ala Asp
305                 310                 315                 320
Leu Leu Ala Leu Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
                450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
                515                 520                 525
Val Glu Lys Ile Leu Gln Tyr Arg Glu Leu Thr Lys Leu Lys Ser Thr
                530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
                580                 585                 590
Arg Ile Arg Arg Ala Phe Ile Ala Glu Glu Gly Trp Leu Leu Val Ala
                595                 600                 605
Leu Asp Tyr Ser Gln Ile Glu Leu Arg Val Leu Ala His Leu Ser Gly
                610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
                675                 680                 685
Ala Gln Ala Phe Ile Glu Arg Tyr Phe Gln Ser Phe Pro Lys Val Arg
                690                 695                 700
Ala Trp Ile Glu Lys Thr Leu Glu Glu Gly Arg Arg Gly Tyr Val
705                 710                 715                 720
```

Glu Thr Leu Phe Gly Arg Arg Tyr Val Pro Asp Leu Glu Ala Arg
              725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val Met
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Ala Ala

<210> SEQ ID NO 158
<211> LENGTH: 2507
<212> TYPE: DNA
<213> ORGANISM: Artificial Sequence
<220> FEATURE:
<223> OTHER INFORMATION: NUCLEOTIDE SEQUENCE OF MUTANT ID 29 (H784F)

<400> SEQUENCE: 158

| | | | | | | |
|---|---|---|---|---|---|---|
| catatgcgtg | gtatgctgcc | gttgttcgag | cctaaaggcc | gcgtactgtt | agtcgatggt | 60 |
| catcacttgg | cctatcggac | gttccatgca | ctcaaaggtc | tgacgaccag | tcgtggcgaa | 120 |
| ccggtccagg | ctgtttatgg | tttcgctaag | tctttgctca | agcactgaa | agaagacggg | 180 |
| gacgcggtaa | ttgttgtatt | tgatgccaaa | gcaccgagct | tccgccacga | agcttatggt | 240 |
| ggctacaagg | caggacgcgc | ccctacccca | gaagatttcc | cccgtcagct | ggcattaatt | 300 |
| aaggagttag | tagaccttct | cggcttagcg | cgtctggaag | ttccgggtta | tgaggcggac | 360 |
| gatgtccttg | catccttggc | taaaaaggcc | gaaaagagg | gctacgaagt | ccgcatcttg | 420 |
| acggcagaca | agatctgta | ccagcttctg | tctgaccgta | ttcatgtttt | gcaccctgaa | 480 |
| ggctacttaa | tcactccggc | ctggctctgg | aaaagtacg | gtctgcgtcc | cgatcagtgg | 540 |
| gcggattatc | gggctttgac | gggagatgag | agcgacaacc | tgccaggagt | taagggcatt | 600 |
| ggtgaaaaaa | ccgcacgtaa | gctgcttgaa | gagtggggtt | ccctggaagc | cttgttaaaa | 660 |
| aatctggatc | gtctcaagcc | cgcaattcgt | gaaaagatcc | tggctcatat | ggacgatctt | 720 |
| aaattaagtt | gggacctggc | caaggtgcgc | accgatttac | gcttgaagt | ggattttgca | 780 |
| aaacgccgtg | agccggaccg | ggaacgttta | cgcgctttct | tagagcgtct | ggaattcggt | 840 |
| tcactgcttc | atgaattcgg | tctgttagag | tctcctaaag | cactcgaaga | ggcaccgtgg | 900 |
| ccgcccccag | aaggtgcttt | tgttggcttc | gtactttccc | gtaaggagcc | tatgtgggca | 960 |
| gatcttctgg | ctttagcggc | tgcacgcggt | ggccgtgttc | accgggcccc | tgagccatac | 1020 |
| aaagcgttac | gtgatctgaa | ggaagcacgt | ggcttgctgg | caaaagacct | ttctgttttg | 1080 |
| gccctgcgcg | agggtcttgg | actgccgcca | ggcgacgatc | ccatgttatt | ggcctatctg | 1140 |
| ttagacccta | gcaataccac | acctgaaggg | gtcgctcgtc | ggtatggcgg | tgaatggact | 1200 |
| gaggaagccg | gagagcgcgc | cgcattgtcc | gaacggctct | ttgcaaactt | atggggtcgt | 1260 |
| ctggaagggg | aggaacgtct | gttatggttg | tatcggaag | tcgaacgtcc | tctttcggcc | 1320 |
| gtattagcgc | atatggaggc | aacaggtgtg | cgtttagatg | tcgcgtacct | tcgggcctta | 1380 |

```
tcactggaag ttgcagagga aatcgcccgt ctcgaggctg aagtgttccg gttggccggt    1440
cacccgttta acctcaactc ccgtgaccag ctggaacgcg ttttattcga tgagcttggg    1500
cttcccgcaa ttggcaaaac cgaaaagact ggcaaacgca gtacgagcgc tgccgtcctt    1560
gaggcactcc gcgaggctca ccctattgta gaaaagatcc tgcaataccg tgagttgacg    1620
aagcttaaaa gcacttatat tgatcctctc ccggatctga tccatcctcg taccggccgc    1680
ttgcacacac gtttcaacca gacggcgact gcaaccggcc gtctgtctag ctcggatcca    1740
aatctccaga acattccggt ccgtacaccc ttgggccaac gtatccgccg ggcgtttatc    1800
gctgaggaag gatggttact ggtcgcattg gactactcgc agattgagct gcgcgtcctc    1860
gcacatctct ctggtgacga aaatttaatc cgcgtgtttc aagaggggcg tgatattcac    1920
acagaaactg cctcatggat gttcggtgtc ccacgtgaag cagtggatcc tttgatgcgc    1980
cgtgcagcta aaacaattaa ttttggagtg ctgtacggaa tgagcgctca tcgcttgagt    2040
caggaactgg caatcccta cgaggaagcg caggcattca tcgaacgtta ctttcaatcg    2100
tttccgaaag ttcgcgcatg gatcgagaag acgctcgagg aaggtcgtcg tcggggctat    2160
gtcgaaactc tgtttggtcg ccgtcggtac gtaccagatc ttgaagcccg cgtcaaatcg    2220
gtacgggagg ctgcggagcg tatggcattt aatatgcctg tacagggtac tgcagctgac    2280
ctcatgaaac tggcaatggt caagcttttc ccgcgcttgg aggaaatggg cgcacgtatg    2340
cttctgcagg tctttgacga gctggtgtta gaagcccta aggagcgcgc cgaagctgtc    2400
gcgcgcctcg ctaaagaagt gatggagggc gtttacccat tggccgtacc cctcgaagtg    2460
gaggtcggta ttggagaaga ttggttatct gcaaaggaag cggccgc          2507
```

<210> SEQ ID NO 159
<211> LENGTH: 834
<212> TYPE: PRT
<213> ORGANISM: Artificial Sequence
<220> FEATURE:
<223> OTHER INFORMATION: AMINO ACID SEQUENCE OF MUTANT ID 29 (H784F)

<400> SEQUENCE: 159

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160
```

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
            210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln

```
                        580                 585                 590
Arg Ile Arg Arg Ala Phe Ile Ala Glu Glu Gly Trp Leu Leu Val Ala
            595                 600                 605
Leu Asp Tyr Ser Gln Ile Glu Leu Arg Val Leu Ala His Leu Ser Gly
        610                 615                 620
Asp Glu Asn Leu Ile Arg Val Phe Gln Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
        675                 680                 685
Ala Gln Ala Phe Ile Glu Arg Tyr Phe Gln Ser Phe Pro Lys Val Arg
    690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
Val Gln Gly Thr Ala Ala Asp Leu Met Lys Leu Ala Met Val Lys Leu
        755                 760                 765
Phe Pro Arg Leu Glu Glu Met Gly Ala Arg Met Leu Leu Gln Val Phe
    770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
            820                 825                 830
Ala Ala

<210> SEQ ID NO 160
<211> LENGTH: 2507
<212> TYPE: DNA
<213> ORGANISM: Artificial Sequence
<220> FEATURE:
<223> OTHER INFORMATION: NUCLEOTIDE SEQUENCE OF MUTANT ID 30 (H784Y)

<400> SEQUENCE: 160
catatgcgtg gtatgctgcc gttgttcgag cctaaaggcc gcgtactgtt agtcgatggt      60
catcacttgg cctatcggac gttccatgca ctcaaaggtc tgacgaccag tcgtggcgaa     120
ccggtccagg ctgtttatgg tttcgctaag tctttgctca aagcactgaa agaagacggg     180
gacgcggtaa ttgttgtatt tgatgccaaa gcaccgagct ccgccacga agcttatggt      240 ggctacaagg caggacgcgc ccctacccca gaagatttcc cccgtcagct ggcattaatt     300
aaggagttag tagaccttct cggcttagcg cgtctggaag ttccgggtta tgaggcggac     360
gatgtccttg catccttggc taaaaaggcc gaaaagagg ctacgaagt ccgcatcttg      420 acggcagaca agatctgta ccagcttctg tctgaccgta ttcatgtttt gcaccctgaa      480
ggctacttaa tcactccggc ctggctctgg gaaaagtacg gtctgcgtcc cgatcagtgg     540
gcggattatc gggctttgac gggagatgag agcgacaacc tgccaggagt taagggcatt     600
```

-continued

```
ggtgaaaaaa ccgcacgtaa gctgcttgaa gagtgggggtt ccctggaagc cttgttaaaa      660
aatctggatc gtctcaagcc cgcaattcgt gaaaagatcc tggctcatat ggacgatctt      720
aaattaagtt gggacctggc caaggtgcgc accgatttac cgcttgaagt ggattttgca      780
aaacgccgtg agccggaccg ggaacgttta cgcgctttct tagagcgtct ggaattcggt      840
tcactgcttc atgaattcgg tctgttagag tctcctaaag cactcgaaga ggcaccgtgg      900
ccgcccccag aaggtgcttt tgttggcttc gtactttccc gtaaggagcc tatgtgggca      960
gatcttctgg ctttagcggc tgcacgcggt ggccgtgttc accgggcccc tgagccatac     1020
aaagcgttac gtgatctgaa ggaagcacgt ggcttgctgg caaaagacct ttctgttttg     1080
gccctgcgcg agggtcttgg actgccgcca ggcgacgatc ccatgttatt ggcctatctg     1140 ttagaccota gcaataccac acctgaaggg gtcgctcgtc ggtatggcgg tgaatggact     1200
gaggaagccg gagagcgcgc cgcattgtcc gaacggctct ttgcaaactt atgggtcgt     1260 ctggaagggg aggaacgtct gttatggttg tatcggaag tcgaacgtcc tctttcggcc     1320
gtattagcgc atatggaggc aacaggtgtg cgtttagatg tcgcgtacct tcgggccta    1380 tcactggaag ttgcagagga atcgcccgt ctcgaggctg aagtgttccg gttggccggt     1440
cacccgttta acctcaactc ccgtgaccag ctggaacgcg ttttattcga tgagcttggg     1500
cttcccgcaa ttggcaaaac cgaaaagact ggcaaacgca gtacgagcgc tgccgtcctt     1560
gaggcactcc gcgaggctca ccctattgta gaaaagatcc tgcaataccg tgagttgacg     1620
aagcttaaaa gcacttatat tgatcctctc ccggatctga tccatcctcg taccggccgc     1680
ttgcacacac gtttcaacca gacggcgact gcaaccggcc gtctgtctag ctcggatcca     1740
aatctccaga acattccggt ccgtacaccc ttgggccaac gtatccgccg ggcgtttatc     1800
gctgaggaag gatggttact ggtcgcattg gactactcgc agattgagct gcgcgtcctc     1860
gcacatctct ctggtgacga aaatttaatc cgcgtgtttc aagaggggcg tgatattcac     1920
acagaaactg cctcatggat gttcggtgtc ccacgtgaag cagtggatcc tttgatgcgc     1980
cgtgcagcta aaacaattaa ttttggagtg ctgtacggaa tgagcgctca tcgcttgagt     2040
caggaactgg caatcccta cgaggaagcg caggcattca tcgaacgtta ctttcaatcg     2100
tttccgaaag ttcgcgcatg gatcgagaag acgctcgagg aaggtcgtcg tcggggctat     2160
gtcgaaactc tgtttggtcg ccgtcggtac gtaccagatc ttgaagcccg cgtcaaatcg     2220
gtacgggagg ctgcggagcg tatggcattt aatatgcctg tacagggtac tgcagctgac     2280
ctcatgaaac tggcaatggt caagcttttc ccgcgcttgg aggaaatggg cgcacgtatg     2340
cttctgcagg tctatgacga gctggtgtta aagcccta aggagcgcgc cgaagctgtc     2400
gcgcgcctcg ctaaagaagt gatggagggc gtttacccat tggccgtacc cctcgaagtg     2460
gaggtcggta ttggagaaga ttggttatct gcaaaggaag cggccgc                  2507
```

<210> SEQ ID NO 161
<211> LENGTH: 834
<212> TYPE: PRT
<213> ORGANISM: Artificial Sequence
<220> FEATURE:
<223> OTHER INFORMATION: AMINO ACID SEQUENCE OF MUTANT ID 30 (H784Y)

<400> SEQUENCE: 161

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

```
Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
 50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
                100                 105                 110

Val Pro Gly Tyr Glu Ala Asp Val Leu Ala Ser Leu Ala Lys Lys
                115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
                195                 200                 205

Glu Glu Trp Gly Ser Leu Glu Ala Leu Leu Lys Asn Leu Asp Arg Leu
                210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
                275                 280                 285

Glu Ser Pro Lys Ala Leu Glu Glu Ala Pro Trp Pro Pro Pro Glu Gly
                290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
                355                 360                 365

Pro Gly Asp Asp Pro Met Leu Leu Ala Tyr Leu Leu Asp Pro Ser Asn
                370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445
```

```
Val Arg Leu Asp Val Ala Tyr Leu Arg Ala Leu Ser Leu Glu Val Ala
    450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
            595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
            690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
                740                 745                 750
Val Gln Gly Thr Ala Ala Asp Leu Met Lys Leu Ala Met Val Lys Leu
            755                 760                 765
Phe Pro Arg Leu Glu Glu Met Gly Ala Arg Met Leu Leu Gln Val Tyr
770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
                820                 825                 830
Ala Ala

<210> SEQ ID NO 162
<211> LENGTH: 25
<212> TYPE: DNA
<213> ORGANISM: Artificial Sequence
```

```
<220> FEATURE:
<223> OTHER INFORMATION: SYNTHETIC DNA OLIGONUCLEOTIDE
<220> FEATURE:
<221> NAME/KEY: misc_feature
<222> LOCATION: (1)..(1)
<223> OTHER INFORMATION: 5'-PHOSPHATE

<400> SEQUENCE: 162
ggttcactgc ttcatgaatt cggtc                                                25

<210> SEQ ID NO 163
<211> LENGTH: 32
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (1)..(1)
<223> OTHER INFORMATION: 5'-PHOSPHATE

<400> SEQUENCE: 163
catatgtatt ctccttctta aagttaaaca aa                                        32

<210> SEQ ID NO 164
<211> LENGTH: 26
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (1)..(1)
<223> OTHER INFORMATION: 5'-FAM (6-carboxyfluorescein)
<220> FEATURE:
<221> NAME/KEY: misc_feature
<222> LOCATION: (26)..(26)
<223> OTHER INFORMATION: 3'-IBFQ (Iowa Black FQ (fluorescence quencher))

<400> SEQUENCE: 164
atggtcaagg tcgcaagctt gctggt                                               26

<210> SEQ ID NO 165
<211> LENGTH: 27
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
<221> NAME/KEY: misc_feature
<222> LOCATION: (1)..(1)
<223> OTHER INFORMATION: 5'-FAM (6-carboxyfluorescein)
<220> FEATURE:
<221> NAME/KEY: misc_feature
<222> LOCATION: (14)..(14)
<223> OTHER INFORMATION: RNA RESIDUE
<220> FEATURE:
<221> NAME/KEY: misc_feature
<222> LOCATION: (27)..(27)
<223> OTHER INFORMATION: 3'-IBFQ (Iowa BlacK FQ (fluorescence quencher)

<400> SEQUENCE: 165
ttctgaggcc aacuccactg ccactta                                              27

<210> SEQ ID NO 166
<211> LENGTH: 22
<212> TYPE: DNA
<213> ORGANISM: Artificial Sequence
<220> FEATURE:
<223> OTHER INFORMATION: SYNTHETIC DNA OLIGONUCLEOTIDE
<220> FEATURE:
```

```
<221> NAME/KEY: misc_feature
<222> LOCATION: (1)..(1)
<223> OTHER INFORMATION: 5'-FAM (6-carboxyfluorescein)
<220> FEATURE:
<221> NAME/KEY: misc_feature
<222> LOCATION: (11)..(11)
<223> OTHER INFORMATION: RNA RESIDUE
<220> FEATURE:
<221> NAME/KEY: misc_feature
<222> LOCATION: (22)..(22)
<223> OTHER INFORMATION: 3'-IBFQ (Iowa Black FQ (fluorescence quencher))

<400> SEQUENCE: 166
cccagagctc cctcagactc ct                                              22

<210> SEQ ID NO 167
<211> LENGTH: 1676
<212> TYPE: DNA
<213> ORGANISM: Artificial Sequence
<220> FEATURE:
<223> OTHER INFORMATION: NUCLEOTIDE SEQUENCE OF MUTANT ID 37 (OptiTaq
      KlenTaq)

<400> SEQUENCE: 167
catatgggtt cactgcttca tgaattcggt ctgttagagt ctcctaaagc actcgaagag     60
gcaccgtggc cgcccccaga aggtgctttt gttggcttcg tactttcccg taaggagcct    120
atgtgggcag atcttctggc tttagcggct gcacgcggtg gccgtgttca ccgggcccct    180
gagccataca aagcgttacg tgatctgaag gaagcacgtg gcttgctggc aaaagacctt    240
tctgttttgg ccctgcgcga gggtcttgga ctgccgccag cgacgatcc catgttattg     300 gcctatctgt tagaccctag caataccaca cctgaagggg tcgctcgtcg gtatggcggt    360
gaatggactg aggaagccgg agagcgcgcc gcattgtccg aacggctctt tgcaaactta    420
tggggtcgtc tggaagggga ggaacgtctg ttatggttgt atcgggaagt cgaacgtcct    480
ctttcggccg tattagcgca tatggaggca acaggtgtgc gtttagatgt cgcgtacctt    540
cgggccttat cactggaagt tgcagaggaa atcgcccgtc tcgaggctga agtgttccgg    600
ttggccggtc acccgtttaa cctcaactcc cgtgaccagc tggaacgcgt tttattcgat    660
gagcttgggc ttcccgcaat tggcaaaacc gaaaagactg gcaaacgcag tacgagcgct    720
gccgtccttg aggcactccg cgaggctcac cctattgtag aaaagatcct gcaataccgt    780
gagttgacga agcttaaaag cacttatatt gatcctctcc cggatctgat ccatcctcgt    840
accggccgct gcacacacg tttcaaccag acggcgactg caaccggccg tctgtctagc    900
tcggatccaa atctccagaa cattccggtc cgtacaccct gggccaacg tatccgccgg    960 gcgtttatcg ctgaggaagg atggttactg gtcgcattgg actactcgca gattgagctg   1020
cgcgtcctcg cacatctctc tggtgacgaa aatttaatcc gcgtgtttca agaggggcgt   1080
gatattcaca cagaaactgc ctcatggatg ttcggtgtcc cacgtgaagc agtggatcct   1140
ttgatgcgcc gtgcagctaa acaattaat tttggagtgc tgtacggaat gagcgctcat    1200
cgcttgagtc aggaactggc aatcccctac gaggaagcgc aggcattcat cgaacgttac   1260
tttcaatcgt ttccgaaagt tcgcgcatgg atcgagaaga cgctcgagga aggtcgtcgt   1320
cggggctatg tcgaaactct gtttggtcgc cgtcggtacg taccagatct tgaagcccgc   1380
gtcaaatcgg tacgggaggc tgcggagcgt atggcattta atatgcctgt acagggtact   1440
gcagctgacc tcatgaaact ggcaatggtc aagcttttcc cgcgcttgga ggaaatgggc   1500
gcacgtatgc ttctgcaggt ccatgacgag ctggtgttag aagcccctaa ggagcgcgcc   1560
```

```
gaagctgtcg cgcgcctcgc taaagaagtg atggagggcg tttacccatt ggccgtaccc    1620
ctcgaagtgg aggtcggtat tggagaagat tggttatctg caaaggaagc ggccgc        1676
```

<210> SEQ ID NO 168
<211> LENGTH: 557
<212> TYPE: PRT
<213> ORGANISM: Artificial Sequence
<220> FEATURE:
<223> OTHER INFORMATION: AMINO ACID SEQUENCE OF MUTANT ID 37 (OptiTaq KlenTaq)

<400> SEQUENCE: 168

```
Met Gly Ser Leu Leu His Glu Phe Gly Leu Leu Glu Ser Pro Lys Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu Ala
        35                  40                  45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
        115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
        195                 200                 205

Ser Arg Asp Gln Leu Glu Arg Val Leu Phe Asp Glu Leu Gly Leu Pro
    210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270

Pro Asp Leu Ile His Pro Arg Thr Gly Arg Leu His Thr Arg Phe Asn
        275                 280                 285

Gln Thr Ala Thr Ala Thr Gly Arg Leu Ser Ser Ser Asp Pro Asn Leu
    290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
```

```
                340             345             350
Arg Val Phe Gln Glu Gly Arg Asp Ile His Thr Glu Thr Ala Ser Trp
            355                 360                 365

Met Phe Gly Val Pro Arg Glu Ala Val Asp Pro Leu Met Arg Arg Ala
        370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
        435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Arg Ala Glu Ala Val Ala Arg Leu Ala Lys Glu
        515                 520                 525

Val Met Glu Gly Val Tyr Pro Leu Ala Val Pro Leu Glu Val Glu Val
    530                 535                 540

Gly Ile Gly Glu Asp Trp Leu Ser Ala Lys Glu Ala Ala
545                 550                 555

<210> SEQ ID NO 169
<211> LENGTH: 1676
<212> TYPE: DNA
<213> ORGANISM: Artificial Sequence
<220> FEATURE:
<223> OTHER INFORMATION: NUCLEOTIDE SEQUENCE OF MUTANT ID 38 (A661E,
      I665W, F667L KlenTaq)

<400> SEQUENCE: 169
catatgggtt cactgcttca tgaattcggt ctgttagagt ctcctaaagc actcgaagag    60
gcaccgtggc cgcccccaga aggtgctttt gttggcttcg tactttcccg taaggagcct   120
atgtgggcag atcttctggc tttagcggct gcacgcggtg ccgtgttca ccgggcccct    180 gagccataca aagcgttacg tgatctgaag gaagcacgtg gcttgctggc aaaagacctt   240
tctgttttgg ccctgcgcga gggtcttgga ctgccgccag cgacgatcc catgttattg    300 gcctatctgt tagaccctag caataccaca cctgaagggg tcgctcgtcg gtatggcggt   360
gaatggactg aggaagccgg agagcgcgcc gcattgtccg aacggctctt tgcaaactta   420
tggggtcgtc tggaagggga ggaacgtctg ttatggttgt atcgggaagt cgaacgtcct   480
ctttcggccg tattagcgca tatggaggca acaggtgtgc gtttagatgt cgcgtacctt   540
cgggccttat cactggaagt tgcagaggaa atcgcccgtc tcgaggctga agtgttccgg   600
ttggccggtc acccgtttaa cctcaactcc cgtgaccagc tggaacgcgt tttattcgat   660
gagcttgggc ttcccgcaat tggcaaaacc gaaaagactg caaacgcag tacgagcgct   720 gccgtccttg aggcactccg cgaggctcac cctattgtag aaaagatcct gcaataccgt   780
gagttgacga agcttaaaag cacttatatt gatcctctcc cggatctgat ccatcctcgt   840
```

```
accggccgct tgcacacacg tttcaaccag acggcgactg caaccggccg tctgtctagc    900
tcggatccaa atctccagaa cattccggtc cgtacaccct tgggccaacg tatccgccgg    960
gcgtttatcg ctgaggaagg atggttactg gtcgcattgg actactcgca gattgagctg   1020
cgcgtcctcg cacatctctc tggtgacgaa aatttaatcc gcgtgtttca agaggggcgt   1080
gatattcaca cagaaactgc ctcatggatg ttcggtgtcc cacgtgaagc agtggatcct   1140
ttgatgcgcc gtgaagctaa acatggaatt tgggagtgc tgtacggaat gagcgctcat    1200
cgcttgagtc aggaactggc aatccctac gaggaagcgc aggcattcat cgaacgttac    1260
tttcaatcgt ttccgaaagt tcgcgcatgg atcgagaaga cgctcgagga aggtcgtcgt   1320
cggggctatg tcgaaactct gtttggtcgc cgtcggtacg taccagatct tgaagcccgc   1380
gtcaaatcgg tacgggaggc tgcggagcgt atggcattta atatgcctgt acagggtact   1440
gcagctgacc tcatgaaact ggcaatggtc aagcttttcc cgcgcttgga ggaaatgggc   1500
gcacgtatgc ttctgcaggt ccatgacgag ctggtgttag aagccctaa ggagcgcgcc    1560 gaagctgtcg cgcgcctcgc taaagaagtg atggagggcg tttacccatt ggccgtaccc   1620
ctcgaagtgg aggtcggtat tggagaagat tggttatctg caaaggaagc ggccgc       1676
```

<210> SEQ ID NO 170
<211> LENGTH: 557
<212> TYPE: PRT
<213> ORGANISM: Artificial Sequence
<220> FEATURE:
<223> OTHER INFORMATION: AMINO ACID SEQUENCE OF MUTANT ID 38 (A661E, I665W, F667L KlenTaq)

<400> SEQUENCE: 170

```
Met Gly Ser Leu Leu His Glu Phe Gly Leu Leu Glu Ser Pro Lys Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu Ala
        35                  40                  45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
        115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
        195                 200                 205
```

```
Ser Arg Asp Gln Leu Glu Arg Val Leu Phe Asp Glu Leu Gly Leu Pro
    210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
                260                 265                 270

Pro Asp Leu Ile His Pro Arg Thr Gly Arg Leu His Thr Arg Phe Asn
            275                 280                 285

Gln Thr Ala Thr Ala Thr Gly Arg Leu Ser Ser Ser Asp Pro Asn Leu
290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
                340                 345                 350

Arg Val Phe Gln Glu Gly Arg Asp Ile His Thr Glu Thr Ala Ser Trp
                355                 360                 365

Met Phe Gly Val Pro Arg Glu Ala Val Asp Pro Leu Met Arg Arg Glu
370                 375                 380

Ala Lys Thr Trp Asn Leu Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
                420                 425                 430

Thr Leu Glu Glu Gly Arg Arg Arg Gly Tyr Val Glu Thr Leu Phe Gly
                435                 440                 445

Arg Arg Arg Tyr Val Pro Asp Leu Glu Ala Arg Val Lys Ser Val Arg
            450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
                500                 505                 510

Glu Ala Pro Lys Glu Arg Ala Glu Ala Val Ala Arg Leu Ala Lys Glu
            515                 520                 525

Val Met Glu Gly Val Tyr Pro Leu Ala Val Pro Leu Glu Val Glu Val
530                 535                 540

Gly Ile Gly Glu Asp Trp Leu Ser Ala Lys Glu Ala Ala
545                 550                 555
```

<210> SEQ ID NO 171
<211> LENGTH: 1676
<212> TYPE: DNA
<213> ORGANISM: Artificial Sequence
<220> FEATURE:
<223> OTHER INFORMATION: NUCLEOTIDE SEQUENCE OF MUTANT ID 39 (V783F KlenTaq).

<400> SEQUENCE: 171

```
catatgggtt cactgcttca tgaattcggt ctgttagagt ctcctaaagc actcgaagag    60
```

-continued

```
gcaccgtggc cgcccccaga aggtgctttt gttggcttcg tactttcccg taaggagcct    120
atgtgggcag atcttctggc tttagcggct gcacgcggtg ccgtgttca ccgggcccct    180
gagccataca aagcgttacg tgatctgaag gaagcacgtg gcttgctggc aaaagacctt    240
tctgttttgg ccctgcgcga gggtcttgga ctgccgccag cgacgatcc catgttattg    300
gcctatctgt tagaccctag caataccaca cctgaagggg tcgctcgtcg gtatggcggt    360
gaatggactg aggaagccgg agagcgcgcc gcattgtccg aacggctctt tgcaaactta    420
tggggtcgtc tggaagggga ggaacgtctg ttatggttgt atcgggaagt cgaacgtcct    480
cttcggccg tattagcgca tatggaggca acaggtgtgc gtttagatgt cgcgtacctt    540
cgggccttat cactggaagt tgcagaggaa atcgcccgtc tcgaggctga agtgttccgg    600
ttggccggtc acccgtttaa cctcaactcc cgtgaccagc tggaacgcgt tttattcgat    660
gagcttgggc ttcccgcaat tggcaaaacc gaaaagactg gcaaacgcag tacgagcgct    720
gccgtccttg aggcactccg cgaggctcac cctattgtag aaaagatcct gcaataccgt    780
gagttgacga agcttaaaag cacttatatt gatcctctcc cggatctgat ccatcctcgt    840
accggccgct tgcacacacg tttcaaccag acggcgactg caaccggccg tctgtctagc    900
tcggatccaa atcccagaa cattccggtc cgtacaccct gggccaacg tatccgccgg    960
gcgtttatcg ctgaggaagg atggttactg tcgcattgg actactcgca gattgagctg   1020
cgcgtcctcg cacatctctc tggtgacgaa aatttaatcc gcgtgtttca agaggggcgt   1080
gatattcaca cagaaactgc ctcatggatg ttcggtgtcc cacgtgaagc agtggatcct   1140
ttgatgcgcc gtgcagctaa acaattaat tttggagtgc tgtacggaat gagcgctcat   1200
cgcttgagtc aggaactggc aatcccctac gaggaagcgc aggcattcat cgaacgttac   1260
tttcaatcgt ttccgaaagt tcgcgcatgg atcgagaaga cgctcgagga aggtcgtcgt   1320
cggggctatg tcgaaactct gtttggtcgc cgtcggtacg taccagatct tgaagcccgc   1380
gtcaaatcgg tacgggaggc tgcggagcgt atggcattta atatgcctgt acagggtact   1440
gcagctgacc tcatgaaact ggcaatggtc aagctttcc cgcgcttgga ggaaatgggc   1500
gcacgtatgc ttctgcagtt ccatgacgag ctggtgttag aagcccctaa ggagcgcgcc   1560
gaagctgtcg cgcgcctcgc taaagaagtg atggagggcg tttacccatt ggccgtaccc   1620
ctcgaagtgg aggtcggtat tggagaagat tggttatctg caaaggaagc ggccgc       1676
```

<210> SEQ ID NO 172
<211> LENGTH: 557
<212> TYPE: PRT
<213> ORGANISM: Artificial Sequence
<220> FEATURE:
<223> OTHER INFORMATION: AMINO ACID SEQUENCE OF MUTANT ID 39 (V783F KlenTaq).

<400> SEQUENCE: 172

```
Met Gly Ser Leu Leu His Glu Phe Gly Leu Leu Glu Ser Pro Lys Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu Ala
        35                  40                  45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65                  70                  75                  80
```

```
Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
                115                 120                 125

Ala Ala Leu Ser Glu Arg Leu Phe Ala Asn Leu Trp Gly Arg Leu Glu
                130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
                180                 185                 190

Leu Glu Ala Glu Val Phe Arg Leu Ala Gly His Pro Phe Asn Leu Asn
                195                 200                 205

Ser Arg Asp Gln Leu Glu Arg Val Leu Phe Asp Glu Leu Gly Leu Pro
                210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
                260                 265                 270

Pro Asp Leu Ile His Pro Arg Thr Gly Arg Leu His Thr Arg Phe Asn
                275                 280                 285

Gln Thr Ala Thr Ala Thr Gly Arg Leu Ser Ser Ser Asp Pro Asn Leu
                290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
                340                 345                 350

Arg Val Phe Gln Glu Gly Arg Asp Ile His Thr Glu Thr Ala Ser Trp
                355                 360                 365

Met Phe Gly Val Pro Arg Glu Ala Val Asp Pro Leu Met Arg Arg Ala
                370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
                420                 425                 430

Thr Leu Glu Glu Gly Arg Arg Arg Gly Tyr Val Glu Thr Leu Phe Gly
                435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495
```

```
Glu Met Gly Ala Arg Met Leu Leu Gln Leu His Asp Glu Leu Val Leu
            500                 505                 510

Glu Ala Pro Lys Glu Arg Ala Glu Ala Val Ala Arg Leu Ala Lys Glu
        515                 520                 525

Val Met Glu Gly Val Tyr Pro Leu Ala Val Pro Leu Glu Val Glu Val
    530                 535                 540

Gly Ile Gly Glu Asp Trp Leu Ser Ala Lys Glu Ala Ala
545                 550                 555

<210> SEQ ID NO 173
<211> LENGTH: 1676
<212> TYPE: DNA
<213> ORGANISM: Artificial Sequence
<220> FEATURE:
<223> OTHER INFORMATION: NUCLEOTIDE SEQUENCE OF MUTANT ID 40 (H784Q
      KlenTaq)

<400> SEQUENCE: 173
catatgggtt cactgcttca tgaattcggt ctgttagagt ctcctaaagc actcgaagag      60
gcaccgtggc cgcccccaga aggtgctttt gttggcttcg tactttcccg taaggagcct    120
atgtgggcag atcttctggc tttagcggct gcacgcggtg ccgtgttca ccgggccccct    180
gagccataca aagcgttacg tgatctgaag gaagcacgtg gcttgctggc aaaagacctt    240
tctgttttgg ccctgcgcga gggtcttgga ctgccgccag cgacgatcc catgttattg    300
gcctatctgt tagaccctag caataccaca cctgaagggg tcgctcgtcg gtatggcggt    360
aatggactg aggaagccgg agagcgcgcc gcattgtccg aacggctctt tgcaaactta    420
tggggtcgtc tggaagggga ggaacgtctg ttatggttgt atcgggaagt cgaacgtcct    480
cttcggccg tattagcgca tatgaggca caggtgtgc gtttagatgt cgcgtacctt    540
cgggccttat cactggaagt tgcagaggaa atcgcccgtc tcgaggctga agtgttccgg    600
ttggccggtc acccgttaa cctcaactcc cgtgaccagc tggaacgcgt tttattcgat    660
gagcttgggc ttcccgcaat tggcaaaacc gaaaagactg gcaaacgcag tacgagcgct    720
gccgtccttg aggcactccg cgaggctcac cctattgtag aaaagatcct gcaataccgt    780
gagttgacga agcttaaaag cacttatatt gatcctctcc cggatctgat ccatcctcgt    840
accggccgct tgcacacacg tttcaaccag acggcgactg caaccggccg tctgtctagc    900
tcggatccaa atcccagaa cattccggtc cgtacaccct gggccaacg tatccgccgg    960
gcgtttatcg ctgaggaagg atggttactg gtcgcattgg actactcgca gattgagctg   1020
cgcgtcctcg cacatctctc tggtgacgaa aatttaatcc gcgtgtttca agaggggcgt   1080
gatattcaca cagaaactgc ctcatggatg ttcggtgtcc cacgtgaagc agtggatcct   1140
ttgatgcgcc gtcagctaa acaattaat tttggagtgc tgtacggaat gagcgctcat   1200
cgcttgagtc aggaactggc aatccctac gaggaagcgc aggcattcat cgaacgttac   1260
tttcaatcgt ttccgaaagt cgcgcatgg atcgagaaga cgctcgagga aggtcgtcgt   1320
cggggctatg tcgaaactct gtttggtcgc cgtcggtacg taccagatct tgaagcccgc   1380
gtcaaatcgg tacgggaggc tgcggagcgt atggcattta atatgcctgt acagggtact   1440
gcagctgacc tcatgaaact ggcaatggtc aagcttttcc cgcgcttgga ggaaatgggc   1500
gcacgtatgc ttctgcaggt ccaggacgag ctggtgttag aagcccctaa ggagcgcgcc   1560
gaagctgtcg cgcgcctcgc taaagaagtg atggagggcg tttacccatt ggccgtaccc   1620
ctcgaagtgg aggtcggtat tggagaagat tggttatctg caaaggaagc ggccgc       1676
```

<210> SEQ ID NO 174
<211> LENGTH: 557
<212> TYPE: PRT
<213> ORGANISM: Artificial Sequence
<220> FEATURE:
<223> OTHER INFORMATION: AMINO ACID SEQUENCE OF MUTANT ID 40 (H784Q KlenTaq)

<400> SEQUENCE: 174

```
Met Gly Ser Leu Leu His Glu Phe Gly Leu Leu Glu Ser Pro Lys Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu Ala
            35                  40                  45

Ala Ala Arg Gly Gly Arg Val His Arg Ala Pro Glu Pro Tyr Lys Ala
        50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
        130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
                180                 185                 190

Leu Glu Ala Glu Val Phe Arg Leu Ala Gly His Pro Phe Asn Leu Asn
            195                 200                 205

Ser Arg Asp Gln Leu Glu Arg Val Leu Phe Asp Glu Leu Gly Leu Pro
        210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270

Pro Asp Leu Ile His Pro Arg Thr Gly Arg Leu His Thr Arg Phe Asn
        275                 280                 285

Gln Thr Ala Thr Ala Thr Gly Arg Leu Ser Ser Ser Asp Pro Asn Leu
    290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
        355                 360                 365
```

```
Met Phe Gly Val Pro Arg Glu Ala Val Asp Pro Leu Met Arg Arg Ala
    370                 375                 380
Ala Lys Thr Ile Asn Phe Gly Val Leu Tyr Gly Met Ser Ala His Arg
385                 390                 395                 400
Leu Ser Gln Glu Leu Ala Ile Pro Tyr Glu Glu Ala Gln Ala Phe Ile
                405                 410                 415
Glu Arg Tyr Phe Gln Ser Phe Pro Lys Val Arg Ala Trp Ile Glu Lys
            420                 425                 430
Thr Leu Glu Glu Gly Arg Arg Arg Gly Tyr Val Glu Thr Leu Phe Gly
        435                 440                 445
Arg Arg Arg Tyr Val Pro Asp Leu Glu Ala Arg Val Lys Ser Val Arg
    450                 455                 460
Glu Ala Ala Glu Arg Met Ala Phe Asn Met Pro Val Gln Gly Thr Ala
465                 470                 475                 480
Ala Asp Leu Met Lys Leu Ala Met Val Lys Leu Phe Pro Arg Leu Glu
                485                 490                 495
Glu Met Gly Ala Arg Met Leu Leu Gln Val Gln Asp Glu Leu Val Leu
            500                 505                 510
Glu Ala Pro Lys Glu Arg Ala Glu Ala Val Ala Arg Leu Ala Lys Glu
        515                 520                 525
Val Met Glu Gly Val Tyr Pro Leu Ala Val Pro Leu Glu Val Glu Val
    530                 535                 540
Gly Ile Gly Glu Asp Trp Leu Ser Ala Lys Glu Ala Ala
545                 550                 555
```

<210> SEQ ID NO 175
<211> LENGTH: 1676
<212> TYPE: DNA
<213> ORGANISM: Artificial Sequence
<220> FEATURE:
<223> OTHER INFORMATION: NUCLEOTIDE SEQUENCE OF MUTANT ID 41 (V783L
      H784Q KlenTaq)

<400> SEQUENCE: 175

```
catatgggtt cactgcttca tgaattcggt ctgttagagt ctcctaaagc actcgaagag    60
gcaccgtggc cgcccccaga aggtgctttt gttggcttcg tactttcccg taaggagcct   120
atgtgggcag atcttctggc tttagcggct gcacgcggtg ccgtgttca ccggccccct   180
gagccataca aagcgttacg tgatctgaag gaagcacgtg gcttgctggc aaaagacctt   240
tctgttttgg ccctgcgcga gggtcttgga ctgccgccag cgacgatcc catgttattg   300
gcctatctgt tagaccctag caataccaca cctgaagggg tcgctcgtcg gtatggcggt   360
gaatggactg aggaagccgg agagcgcgcc gcattgtccg aacggctctt tgcaaactta   420
tggggtcgtc tggaagggga ggaacgtctg ttatggttgt atcgggaagt cgaacgtcct   480
ctttcggccg tattagcgca tatggaggca acaggtgtgc gtttagatgt cgcgtacctt   540
cgggccttat cactggaagt tgcagaggaa atcgcccgtc tcgaggctga agtgttccgg   600
ttggccggtc acccgtttaa cctcaactcc cgtgaccagc tggaacgcgt tttattcgat   660
gagcttgggc ttcccgcaat tggcaaaacc gaaaagactg gcaaacgcag tacgagcgct   720
gccgtccttg aggcactccg cgaggctcac cctattgtag aaaagatcct gcaataccgt   780
gagttgacga agcttaaaag cacttatatt gatcctctcc cggatctgat ccatcctcgt   840
accggccgct tgcacacacg tttcaaccag acggcgactg caaccggccg tctgtctagc   900
tcggatccaa atctccagaa cattccggtc cgtacaccct gggccaacg tatccgccgg   960
```

-continued

```
gcgtttatcg ctgaggaagg atggttactg gtcgcattgg actactcgca gattgagctg    1020
cgcgtcctcg cacatctctc tggtgacgaa aatttaatcc gcgtgtttca agaggggcgt    1080
gatattcaca cagaaactgc ctcatggatg ttcggtgtcc cacgtgaagc agtggatcct    1140
ttgatgcgcc gtgcagctaa aacaattaat tttggagtgc tgtacggaat gagcgctcat    1200
cgcttgagtc aggaactggc aatcccctac gaggaagcgc aggcattcat cgaacgttac    1260
tttcaatcgt ttccgaaagt tcgcgcatgg atcgagaaga cgctcgagga aggtcgtcgt    1320
cggggctatg tcgaaactct gtttggtcgc cgtcggtacg taccagatct tgaagcccgc    1380
gtcaaatcgg tacgggaggc tgcggagcgt atggcattta atatgcctgt acagggtact    1440
gcagctgacc tcatgaaact ggcaatggtc aagcttttcc cgcgcttgga ggaaatgggc    1500
gcacgtatgc ttctgcagct gcaggacgag ctggtgttag aagcccctaa ggagcgcgcc    1560
gaagctgtcg cgcgcctcgc taaagaagtg atggagggcg tttacccatt ggccgtaccc    1620
ctcgaagtgg aggtcggtat tggagaagat tggttatctg caaaggaagc ggccgc       1676
```

<210> SEQ ID NO 176
<211> LENGTH: 557
<212> TYPE: PRT
<213> ORGANISM: Artificial Sequence
<220> FEATURE:
<223> OTHER INFORMATION: AMINO ACID SEQUENCE OF MUTANT ID 41 (V783L H784Q KlenTaq)

<400> SEQUENCE: 176

```
Met Gly Ser Leu Leu His Glu Phe Gly Leu Leu Glu Ser Pro Lys Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu Ala
        35                  40                  45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
                180                 185                 190

Leu Glu Ala Glu Val Phe Arg Leu Ala Gly His Pro Phe Asn Leu Asn
            195                 200                 205

Ser Arg Asp Gln Leu Glu Arg Val Leu Phe Asp Glu Leu Gly Leu Pro
    210                 215                 220

Ala Ile Gly Lys Thr Glu Lys Thr Gly Lys Arg Ser Thr Ser Ala Ala
```

```
                225                 230                 235                 240
Val Leu Glu Ala Leu Arg Glu Ala His Pro Ile Val Glu Lys Ile Leu
                245                 250                 255
Gln Tyr Arg Glu Leu Thr Lys Leu Lys Ser Thr Tyr Ile Asp Pro Leu
                260                 265                 270
Pro Asp Leu Ile His Pro Arg Thr Gly Arg Leu His Thr Arg Phe Asn
                275                 280                 285
Gln Thr Ala Thr Ala Thr Gly Arg Leu Ser Ser Ser Asp Pro Asn Leu
                290                 295                 300
Gln Asn Ile Pro Val Arg Thr Pro Leu Gly Gln Arg Ile Arg Arg Ala
305                 310                 315                 320
Phe Ile Ala Glu Glu Gly Trp Leu Leu Val Ala Leu Asp Tyr Ser Gln
                325                 330                 335
Ile Glu Leu Arg Val Leu Ala His Leu Ser Gly Asp Glu Asn Leu Ile
                340                 345                 350
Arg Val Phe Gln Glu Gly Arg Asp Ile His Thr Glu Thr Ala Ser Trp
                355                 360                 365
Met Phe Gly Val Pro Arg Glu Ala Val Asp Pro Leu Met Arg Arg Ala
                370                 375                 380
Ala Lys Thr Ile Asn Phe Gly Val Leu Tyr Gly Met Ser Ala His Arg
385                 390                 395                 400
Leu Ser Gln Glu Leu Ala Ile Pro Tyr Glu Glu Ala Gln Ala Phe Ile
                405                 410                 415
Glu Arg Tyr Phe Gln Ser Phe Pro Lys Val Arg Ala Trp Ile Glu Lys
                420                 425                 430
Thr Leu Glu Glu Gly Arg Arg Arg Gly Tyr Val Glu Thr Leu Phe Gly
                435                 440                 445
Arg Arg Arg Tyr Val Pro Asp Leu Glu Ala Arg Val Lys Ser Val Arg
                450                 455                 460
Glu Ala Ala Glu Arg Met Ala Phe Asn Met Pro Val Gln Gly Thr Ala
465                 470                 475                 480
Ala Asp Leu Met Lys Leu Ala Met Val Lys Leu Phe Pro Arg Leu Glu
                485                 490                 495
Glu Met Gly Ala Arg Met Leu Leu Gln Leu His Asp Glu Leu Val Leu
                500                 505                 510
Glu Ala Pro Lys Glu Arg Ala Glu Ala Val Ala Arg Leu Ala Lys Glu
                515                 520                 525
Val Met Glu Gly Val Tyr Pro Leu Ala Val Pro Leu Glu Val Glu Val
                530                 535                 540
Gly Ile Gly Glu Asp Trp Leu Ser Ala Lys Glu Ala Ala
545                 550                 555

<210> SEQ ID NO 177
<211> LENGTH: 1676
<212> TYPE: DNA
<213> ORGANISM: Artificial Sequence
<220> FEATURE:
<223> OTHER INFORMATION: NUCLEOTIDE SEQUENCE OF MUTANT ID 42 (H784S
      KlenTaq)

<400> SEQUENCE: 177
catatgggtt cactgcttca tgaattcggt ctgttagagt ctcctaaagc actcgaagag    60
gcaccgtggc cgcccccaga aggtgctttt gttggcttcg tactttcccg taaggagcct   120
atgtgggcag atcttctggc tttagcggct gcacgcggtg gccgtgttca ccgggcccct   180
```

```
gagccataca aagcgttacg tgatctgaag gaagcacgtg gcttgctggc aaaagacctt    240
tctgttttgg ccctgcgcga gggtcttgga ctgccgccag cgacgatcc catgttattg     300 gcctatctgt tagaccctag caataccaca cctgaagggg tcgctcgtcg gtatggcggt    360
gaatggactg aggaagccgg agagcgcgcc gcattgtccg aacggctctt tgcaaactta    420
tggggtcgtc tggaagggga ggaacgtctg ttatggttgt atcgggaagt cgaacgtcct    480
ctttcggccg tattagcgca tatgga ggca acaggtgtgc gtttagatgt cgcgtacctt    540
cgggccttat cactggaagt tgcagaggaa atcgcccgtc tcgaggctga agtgttccgg    600
ttggccggtc acccgtttaa cctcaactcc cgtgaccagc tggaacgcgt tttattcgat    660
gagcttgggc ttcccgcaat tggcaaaacc gaaaagactg gcaaacgcag tacgagcgct    720
gccgtccttg aggcactccg cgaggctcac cctattgtag aaaagatcct gcaataccgt    780
gagttgacga agcttaaaag cacttatatt gatcctctcc cggatctgat ccatcctcgt    840
accggccgct tgcacacacg tttcaaccag acggcgactg caaccggccg tctgtctagc    900
tcggatccaa atctccagaa cattccggtc cgtacaccct gggccaacg tatccgccgg    960 gcgtttatcg ctgaggaagg atggttactg gtcgcattgg actactcgca gattgagctg   1020
cgcgtcctcg cacatctctc tggtgacgaa aatttaatcc gcgtgtttca agaggggcgt   1080
gatattcaca cagaaactgc ctcatggatg ttcggtgtcc cacgtgaagc agtggatcct   1140 tgatgcgcc gtgcagctaa acaattaat tttggagtgc tgtacggaat gagcgctcat     1200
cgcttgagtc aggaactggc aatcccctac gaggaagcgc aggcattcat cgaacgttac   1260
tttcaatcgt ttccgaaagt tcgcgcatgg atcgagaaga cgctcgagga aggtcgtcgt   1320
cggggctatg tcgaaactct gtttggtcgc cgtcggtacg taccagatct tgaagcccgc   1380
gtcaaatcgg tacgggaggc tgcggagcgt atggcattta atatgcctgt acagggtact   1440
gcagctgacc tcatgaaact ggcaatggtc aagcttttcc cgcgcttgga ggaaatgggc   1500
gcacgtatgc ttctgcaggt cagcgacgag ctggtgttag aagcccctaa ggagcgcgcc   1560
gaagctgtcg cgcgcctcgc taaagaagtg atggagggcg tttacccatt ggccgtaccc   1620
ctcgaagtgg aggtcggtat tggagaagat tggttatctg caaaggaagc ggccgc        1676
```

<210> SEQ ID NO 178
<211> LENGTH: 557
<212> TYPE: PRT
<213> ORGANISM: Artificial Sequence
<220> FEATURE:
<223> OTHER INFORMATION: AMINO ACID SEQUENCE OF MUTANT ID 42 (H784S KlenTaq)

<400> SEQUENCE: 178

```
Met Gly Ser Leu Leu His Glu Phe Gly Leu Leu Glu Ser Pro Lys Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Ala Leu Ala
        35                  40                  45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95
```

```
Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
        130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
            195                 200                 205

Ser Arg Asp Gln Leu Glu Arg Val Leu Phe Asp Glu Leu Gly Leu Pro
        210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270

Pro Asp Leu Ile His Pro Arg Thr Gly Arg Leu His Thr Arg Phe Asn
            275                 280                 285

Gln Thr Ala Thr Ala Thr Gly Arg Leu Ser Ser Ser Asp Pro Asn Leu
        290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
            355                 360                 365

Met Phe Gly Val Pro Arg Glu Ala Val Asp Pro Leu Met Arg Arg Ala
    370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
        435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val Ser Asp Glu Leu Val Leu
            500                 505                 510

Glu Ala Pro Lys Glu Arg Ala Glu Ala Val Ala Arg Leu Ala Lys Glu
```

515                 520                 525
Val Met Glu Gly Val Tyr Pro Leu Ala Val Pro Leu Glu Val Glu Val
              530                 535                 540

Gly Ile Gly Glu Asp Trp Leu Ser Ala Lys Glu Ala Ala
545                 550                 555

<210> SEQ ID NO 179
<211> LENGTH: 1676
<212> TYPE: DNA
<213> ORGANISM: Artificial Sequence
<220> FEATURE:
<223> OTHER INFORMATION: NUCLEOTIDE SEQUENCE OF MUTANT ID 43 (H784Y KlenTaq)

<400> SEQUENCE: 179

| | | | | | |
|---|---|---|---|---|---|
| catatgggtt | cactgcttca | tgaattcggt | ctgttagagt | ctcctaaagc | actcgaagag | 60 |
| gcaccgtggc | cgccccccaga | aggtgctttt | gttggcttcg | tactttcccg | taaggagcct | 120 |
| atgtgggcag | atcttctggc | tttagcggct | gcacgcggtg | gccgtgttca | ccgggcccct | 180 |
| gagccataca | aagcgttacg | tgatctgaag | gaagcacgtg | gcttgctggc | aaaagacctt | 240 |
| tctgttttgg | ccctgcgcga | gggtcttgga | ctgccgccag | cgacgatcc | catgttattg | 300 |
| gcctatctgt | tagaccctag | caataccaca | cctgaagggg | tcgctcgtcg | gtatggcggt | 360 |
| gaatggactg | aggaagccgg | agagcgcgcc | gcattgtccg | aacggctctt | tgcaaactta | 420 |
| tggggtcgtc | tggaagggga | ggaacgtctg | ttatggttgt | atcgggaagt | cgaacgtcct | 480 |
| ctttcggccg | tattagcgca | tatggaggca | acaggtgtgc | gtttagatgt | cgcgtacctt | 540 |
| cgggccttat | cactggaagt | tgcagaggaa | atcgcccgtc | tcgaggctga | agtgttccgg | 600 |
| ttggccggtc | acccgtttaa | cctcaactcc | cgtgaccagc | tggaacgcgt | tttattcgat | 660 |
| gagcttgggc | ttcccgcaat | tggcaaaacc | gaaaagactg | gcaaacgcag | tacgagcgct | 720 |
| gccgtccttg | aggcactccg | cgaggctcac | cctattgtag | aaaagatcct | gcaataccgt | 780 |
| gagttgacga | agcttaaaag | cacttatatt | gatcctctcc | cggatctgat | ccatcctcgt | 840 |
| accggccgct | tgcacacacg | tttcaaccag | acggcgactg | caaccggccg | tctgtctagc | 900 |
| tcggatccaa | atctccagaa | cattccggtc | cgtacaccct | gggccaacg | tatccgccgg | 960 |
| gcgtttatcg | ctgaggaagg | atggttactg | gtcgcattgg | actactcgca | gattgagctg | 1020 |
| cgcgtcctcg | cacatctctc | tggtgacgaa | aatttaatcc | gcgtgtttca | agaggggcgt | 1080 |
| gatattcaca | cagaaactgc | ctcatggatg | ttcggtgtcc | cacgtgaagc | agtggatcct | 1140 |
| ttgatgcgcc | gtgcagctaa | aacaattaat | tttggagtgc | tgtacggaat | gagcgctcat | 1200 |
| cgcttgagtc | aggaactggc | aatcccctac | gaggaagcgc | aggcattcat | cgaacgttac | 1260 |
| tttcaatcgt | ttccgaaagt | tcgcgcatgg | atcgagaaga | cgctcgagga | aggtcgtcgt | 1320 |
| cggggctatg | tcgaaactct | gtttggtcgc | cgtcggtacg | taccagatct | tgaagcccgc | 1380 |
| gtcaaatcgg | tacgggaggc | tgcggagcgt | atggcattta | atatgcctgt | acagggtact | 1440 |
| gcagctgacc | tcatgaaact | ggcaatggtc | aagcttttcc | cgcgcttgga | ggaaatgggc | 1500 |
| gcacgtatgc | ttctgcaggt | ctatgacgag | ctggtgttag | aagcccctaa | ggagcgcgcc | 1560 |
| gaagctgtcg | cgcgcctcgc | taagaagtg | atggagggcg | tttacccatt | ggccgtaccc | 1620 |
| ctcgaagtgg | aggtcggtat | tggagaagat | tggttatctg | caaaggaagc | ggccgc | 1676 |

<210> SEQ ID NO 180
<211> LENGTH: 557
<212> TYPE: PRT

<213> ORGANISM: Artificial Sequence
<220> FEATURE:
<223> OTHER INFORMATION: AMINO ACID SEQUENCE OF MUTANT ID 43 (H784Y KlenTaq)

<400> SEQUENCE: 180

| | | | | | | | | | | | | | | |
|---|---|---|---|---|---|---|---|---|---|---|---|---|---|---|
| Met | Gly | Ser | Leu | Leu | His | Glu | Phe | Gly | Leu | Leu | Glu | Ser | Pro | Lys | Ala |
| 1 | | | | 5 | | | | | 10 | | | | | 15 | |
| Leu | Glu | Glu | Ala | Pro | Trp | Pro | Pro | Glu | Gly | Ala | Phe | Val | Gly | Phe | |
| | | | 20 | | | | | 25 | | | | | 30 | | |
| Val | Leu | Ser | Arg | Lys | Glu | Pro | Met | Trp | Ala | Asp | Leu | Leu | Ala | Leu | Ala |
| | | | 35 | | | | | 40 | | | | | 45 | | |
| Ala | Ala | Arg | Gly | Gly | Arg | Val | His | Arg | Ala | Pro | Glu | Pro | Tyr | Lys | Ala |
| | 50 | | | | | 55 | | | | | 60 | | | | |
| Leu | Arg | Asp | Leu | Lys | Glu | Ala | Arg | Gly | Leu | Leu | Ala | Lys | Asp | Leu | Ser |
| 65 | | | | | 70 | | | | | 75 | | | | | 80 |
| Val | Leu | Ala | Leu | Arg | Glu | Gly | Leu | Gly | Leu | Pro | Pro | Gly | Asp | Asp | Pro |
| | | | | 85 | | | | | 90 | | | | | 95 | |
| Met | Leu | Leu | Ala | Tyr | Leu | Leu | Asp | Pro | Ser | Asn | Thr | Thr | Pro | Glu | Gly |
| | | | | 100 | | | | | 105 | | | | | 110 | |
| Val | Ala | Arg | Arg | Tyr | Gly | Gly | Glu | Trp | Thr | Glu | Glu | Ala | Gly | Glu | Arg |
| | | | | 115 | | | | | 120 | | | | | 125 | |
| Ala | Ala | Leu | Ser | Glu | Arg | Leu | Phe | Ala | Asn | Leu | Trp | Gly | Arg | Leu | Glu |
| | 130 | | | | | 135 | | | | | 140 | | | | |
| Gly | Glu | Glu | Arg | Leu | Leu | Trp | Leu | Tyr | Arg | Glu | Val | Glu | Arg | Pro | Leu |
| 145 | | | | | 150 | | | | | 155 | | | | | 160 |
| Ser | Ala | Val | Leu | Ala | His | Met | Glu | Ala | Thr | Gly | Val | Arg | Leu | Asp | Val |
| | | | | 165 | | | | | 170 | | | | | 175 | |
| Ala | Tyr | Leu | Arg | Ala | Leu | Ser | Leu | Glu | Val | Ala | Glu | Glu | Ile | Ala | Arg |
| | | | 180 | | | | | 185 | | | | | 190 | | |
| Leu | Glu | Ala | Glu | Val | Phe | Arg | Leu | Ala | Gly | His | Pro | Phe | Asn | Leu | Asn |
| | | | | 195 | | | | | 200 | | | | | 205 | |
| Ser | Arg | Asp | Gln | Leu | Glu | Arg | Val | Leu | Phe | Asp | Glu | Leu | Gly | Leu | Pro |
| | 210 | | | | | 215 | | | | | 220 | | | | |
| Ala | Ile | Gly | Lys | Thr | Glu | Lys | Thr | Gly | Lys | Arg | Ser | Thr | Ser | Ala | Ala |
| 225 | | | | | 230 | | | | | 235 | | | | | 240 |
| Val | Leu | Glu | Ala | Leu | Arg | Glu | Ala | His | Pro | Ile | Val | Glu | Lys | Ile | Leu |
| | | | | 245 | | | | | 250 | | | | | 255 | |
| Gln | Tyr | Arg | Glu | Leu | Thr | Lys | Leu | Lys | Ser | Thr | Tyr | Ile | Asp | Pro | Leu |
| | | | 260 | | | | | 265 | | | | | 270 | | |
| Pro | Asp | Leu | Ile | His | Pro | Arg | Thr | Gly | Arg | Leu | His | Thr | Arg | Phe | Asn |
| | | | 275 | | | | | 280 | | | | | 285 | | |
| Gln | Thr | Ala | Thr | Ala | Thr | Gly | Arg | Leu | Ser | Ser | Ser | Asp | Pro | Asn | Leu |
| | 290 | | | | | 295 | | | | | 300 | | | | |
| Gln | Asn | Ile | Pro | Val | Arg | Thr | Pro | Leu | Gly | Gln | Arg | Ile | Arg | Arg | Ala |
| 305 | | | | | 310 | | | | | 315 | | | | | 320 |
| Phe | Ile | Ala | Glu | Glu | Gly | Trp | Leu | Leu | Val | Ala | Leu | Asp | Tyr | Ser | Gln |
| | | | | 325 | | | | | 330 | | | | | 335 | |
| Ile | Glu | Leu | Arg | Val | Leu | Ala | His | Leu | Ser | Gly | Asp | Glu | Asn | Leu | Ile |
| | | | 340 | | | | | 345 | | | | | 350 | | |
| Arg | Val | Phe | Gln | Glu | Gly | Arg | Asp | Ile | His | Thr | Glu | Thr | Ala | Ser | Trp |
| | | 355 | | | | | 360 | | | | | 365 | | | |
| Met | Phe | Gly | Val | Pro | Arg | Glu | Ala | Val | Asp | Pro | Leu | Met | Arg | Arg | Ala |
| | 370 | | | | | 375 | | | | | 380 | | | | |

-continued

```
Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
        435                 440                 445

Arg Arg Arg Tyr Val Pro Asp Leu Glu Ala Arg Val Lys Ser Val Arg
    450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val Tyr Asp Glu Leu Val Leu
            500                 505                 510

Glu Ala Pro Lys Glu Arg Ala Glu Ala Val Ala Arg Leu Ala Lys Glu
        515                 520                 525

Val Met Glu Gly Val Tyr Pro Leu Ala Val Pro Leu Glu Val Glu Val
    530                 535                 540

Gly Ile Gly Glu Asp Trp Leu Ser Ala Lys Glu Ala Ala
545                 550                 555
```

DNA POLYMERASE MUTANTS HAVING ENHANCED TEMPLATE DISCRIMINATION ACTIVITY

CROSS-REFERENCE TO RELATED APPLICATIONS

This application is a divisional of U.S. patent application Ser. No. 14/542,539, filed Nov. 14, 2014, which claims benefit of priority under 35 U.S.C. 119 to U.S. provisional patent application Ser. No. 61/904,335, filed Nov. 14, 2013, and entitled "DNA POLYMERASE MUTANTS HAVING ENHANCED TEMPLATE DISCRIMINATION ACTIVITY," the contents of which are herein incorporated by reference in its entirety.

SEQUENCE LISTING

The instant application contains a Sequence Listing that has been submitted in ASCII format via EFS-Web and is hereby incorporated by reference in its entirety. Said ASCII copy, created on Jan. 8, 2015, is named IDT01-003-US-DIV ST25.txt, and is 362,479 bytes in size.

FIELD

This invention relates to mutant DNA polymerases having enhanced primer and/or template discrimination activities and uses of the same for polymerase-based assays for genetic diagnostic analysis.

BACKGROUND

The ability to accurately diagnose a given genetic condition and to predictably treat a genetically-based disorder requires reliable methods for accurately determining genetic sequence information. Many genetically-based disorders are associated with single nucleotide polymorphisms (SNP's) in protein coding genes. The presence of SNP's associated with a genetically-based disorder, such as a cancer, can be difficult to detect owing to the small numbers of genetically altered cells in the population that encode the allele(s) ("rare alleles").

Polymerase-based assays, such as the polymerase chain reaction (PCR), have important impact and widespread use in genetic diagnostics and molecular medicine. Polymerases synthesize DNA sequences by the addition of nucleotides to the 3' end of a short oligonucleotide (abbreviated to "primer" in the following). The primer is hybridized to the single stranded sequence that is going to be amplified ("template"). DNA polymerases catalyze formation of a phosphodiester bond between the 3'-oxygen at the 3'-terminus of the primer and the incoming deoxynucleoside triphosphate ("dNTP"). This chemical reaction ("primer extension") adds a nucleotide to the primer (e.g., to the nascent growing DNA chain). Primer extension is base specific, in that the deoxynucleoside triphosphate that is complementary to the base in the template is added to the primer. The fidelity of DNA polymerase enzymes is very high and the rate of mutations introduced into the replicated DNA strand is low; however, the precise error rate varies between different DNA polymerase enzymes and these rates have been well characterized. The extension reaction can be repeated until the end of the template is reached.

The majority of polymerase-based assays for detecting SNP's rely upon having the polymerase enzyme discriminate between at least two different substrates. The first substrate contains the desired SNP that is to be detected; the second substrate contains the normal nucleotide that is not to be detected. Polymerase-based discrimination can be achieved by providing the first substrate as the preferred polymerase-competent substrate for assay. This discrimination can be maximized to the extent that the first substrate is the only polymerase-competent substrate present for assay.

Many strategies are known in the art for establishing conditions that favor polymerase-based discrimination among substrates having minimal nucleotide differences, such as those containing only single nucleotide differences. One strategy relies on a polymerase's inability to efficiently initiate synthesis on substrates lacking a 3'-paired nucleotide on the primer. An allele-specific primer design is a primer in which the 3'-nucleotide forms a perfect match with the complementary base at the location containing the SNP-containing allele and forms a mismatched pairing when annealed to an allele lacking the SNP. The primer:template for the SNP-containing allele serves as the preferred polymerase-competent substrate since the polymerase can efficiently initiate primed synthesis from such substrates. Examples of these strategies are described in Chen et al., "Single nucleotide polymorphism genotyping: biochemistry, protocol, cost and throughput" Pharmacogenomics J. 3(2): 77-96 (2003); Kwok et al., "Detection of single nucleotide polymorphisms" Curr. Issues Mol. Biol. 5(2):43-60 (April 2003); Shi, "Technologies for individual genotyping: detection of genetic polymorphisms in drug targets and disease genes" Am. J. Pharmacogenomics 2(3):197-205 (2002); and Kwok, "Methods for genotyping single nucleotide polymorphisms" Annu. Rev. Genomics Hum. Genet. 2:235-58 (2001). A strategy to improve selectivity for this class of allele-specific PCR primers is to introduce a second mutation at the penultimate base, next to the 3'-terminal nucleotide of the primer (i.e., next to the SNP site). As before, the 3'-terminal residue will either be a match or mismatch to the base under interrogation in the sample nucleic acid (SNP), but now the primer will either have two adjacent mismatches to the target (both 3'-terminal and penultimate base) or a single mismatch to the target (at only the penultimate base, with the 3'-terminal base being a match). See, for example, Newton et al., "Analysis of any point mutation in DNA. The amplification refractory mutation systems (ARMS)" Nucleic Acids Res. 17(7):2503-15 (1989). Yet another strategy to improve selectivity for this class of allele-specific PCR primers is to employ a chemically modified nucleic acid residue at the 3'-end of the primer, such as a locked nucleic acid (LNA), which reduces the ability of DNA polymerase to initiate DNA synthesis from a 3'-terminal mismatch. See, for example, Latorra et al., "SNP genotyping using 3' locked nucleic acid (LNA) primers" Human Mut. 22(1):79-85 (2003).

Template substrate discrimination can be enhanced in polymerase-based assays by requiring a second nucleic acid enzyme catalyze formation of one or more primers for use in the polymerase-based assay. In one such assay, the ligase chain reaction assay, a DNA ligase is used with a polymerase to detect a template containing a SNP. Since polymerase-based assays require primers having a minimum length to hybridize to the template substrate, a DNA ligase can be used to generate polymerase primers from sub-optimal length oligonucleotides. The assay relies upon hybridizing two probes directly over the SNP polymorphic site, whereby ligation can occur if the probes are identical to the target DNA. Two probes are designed; an allele-specific probe which hybridizes to the target DNA so that its 3' base is situated directly over the SNP nucleotide and a second probe that hybridizes the template downstream in the complementary strand of the SNP polymorphic site providing a 5' end for the ligation reaction. If the allele-specific probe matches the target DNA, it will fully hybridize to the target DNA and ligation can occur. Ligation does not generally occur in the presence of a mismatched 3'-base. Once the oligonucleotide product is formed, it can serve as a primer or as a template for polymerase-based assays. Examples of this strategy are described in Barany F. "Genetic disease detection and DNA amplification using cloned thermostable ligase." *Proc Natl Acad Sci USA*. 1991 January 1; 88(1):189-93 and Wiedmann M., Wilson W. J., Czajka J., Luo J., Barany F., Batt C. A. "Ligase chain reaction (LCR)—overview and applications." *PCR Methods and Applications* 1994 February; 3(4): S51-64.

Since a polymerase-competent substrate requires a primer:template having an available 3'-hydroxyl group on the primer, another strategy known in the art, RNase H-based PCR (rhPCR), can be used for improving polymerase-based discrimination. The rhPCR method makes use of RNase H enzymes to convert a primer lacking a 3'-hydroxyl group ("blocked primer") or a primer that is otherwise disabled and cannot support PCR to a primer containing a 3'-hydroxyl group ("unblocked primer") that can support PCR. A blocked primer in rhPCR includes an oligonucleotide having a blocked 3'-end or other modification which prevents either priming or template function of the oligonucleotide and an internal RNA residue, which serves as a cleavage site. Type II RNase H recognizes annealed primer:template duplexes containing these blocked primers and cleaves the primer strand 5' of the RNA residue to generate a 3'-hydroxyl group at the adjacent DNA residue. Since RNase H enzymes do not cleave substrates containing an unpaired RNA reside at a mismatched site, allele-specific template discrimination can be achieved by placement of the RNA residue at the location complementary to the SNP on the selected allele template. The resultant Type II RNase H cleavage product can serve as a polymerase competent substrate. Examples of this enzyme cleaving strategy, similar RNase H strategies, and methods of blocking primer extension or inhibiting template function and thereby disabling PCR are described in U.S. Pat. No. 7,112,406 to Behlke et al., entitled POLYNOMIAL AMPLIFICATION OF NUCLEIC ACIDS, U.S. Pat. No. 5,763,181 to Han et al., entitled CONTINOUS FLUOROMETRIC ASSAY FOR DETECTING NUCLEIC ACID CLEAVAGE, U.S. Pat. No. 7,135,291 to Sagawa et al., entitled METHOD OF DETECTING NUCLEOTIDE POLYMORPHISM; U.S. Pat. App. No. 20090068643 to Behlke and Walder, entitled DUAL FUNCTION PRIMERS FOR AMPLIFYING DNA AND METHODS OF USE; and U.S. Pat. App. No. 20100167353 to Walder et al., entitled RNASE H-BASED ASSAYS UTILIZING MODIFIED RNA MONOMERS.

The field has focused on substrate-based approaches, such as those exemplified above, for improving detection of genetic differences and rare alleles. Yet the sensitivity of polymerase-based assays remains limited by the formation of non-specific amplification products that arise from ectopic or aberrant primer-related extension products independent of the desired templates. The inherent reactivity of the polymerase appears largely responsible for producing such artifacts during amplification.

Any further improvements in mismatch discrimination may therefore require a modified polymerase enzyme endowed with inherently better 3'-nucleotide discrimination when used with one or more of the described strategies. A modified polymerase enzyme having activity differing from the unmodified form can be prepared by chemical or enzymatic modification of the protein or mutagenesis of corresponding gene that encodes the protein. The latter approach is generally preferred owing to the fact that genetically altered genes encoding a given mutant protein can be stably maintained, expressed and purified to yield enzyme preparations having well-characterized properties.

While an unbiased mutagenesis strategy can be used to generate a library of mutant polymerase genes, this approach has certain disadvantages. Many millions of mutant enzymes must be screened for activity and success is often dependent upon the chance that effective mutations are present in the limited pool generated by random mutagenesis. Direct genetic selection methods are not sufficiently sensitive for identifying mutations that pertain to secondary functions falling outside of an essential polymerase activity. The vast majority of mutant polymerase genes in a positive selection assay will likely encode protein that retains the functional attributes of the normal polymerase enzyme. Thus, secondary screening procedures that use biochemical assays must be done to identify whether any mutant polymerases have the desired activity. Notwithstanding the technical difficulties of setting up the initial selection process, the attendant costs associated with performing the secondary screens using biochemical assays is prohibitive if more than one hundred clones need to be purified and assayed.

An alternative approach is to apply a biased mutagenesis strategy that is specifically targeted to a preselected region of a gene implicated in function. In this approach, one first identifies genetic regions by a selection method. One such selection method is a comparative phylogenetic analysis of a particular gene that is required for organisms of diverse origins. The principle of comparative phylogenetic analysis is premised on the hypothesis that diverse organisms will not share protein coding sequences in essential genes unless those sequences are evolutionary constrained for reasons related to essential protein function.

A phylogenetic comparative analysis of genes encoding DNA polymerases can provide insights about possible amino acid residues important to polymerase functions. The overall folding pattern of DNA polymerases resembles the human right hand and contains three distinct subdomains of palm, fingers, and thumb. (See, for example. Beese et al., Science 260:352-355, 1993; Patel et al., Biochemistry 34:5351-5363, 1995). While the structure of the fingers and thumb subdomains vary greatly between polymerases that differ in size and in cellular functions, the catalytic palm subdomains are all superimposable. For example, motif A, which interacts with the incoming dNTP and stabilizes the transition state during chemical catalysis, is superimposable with a root mean deviation of about one Angstrom among mammalian pol a and prokaryotic pol I family DNA polymerases (Wang et al., Cell 89:1087-1099, 1997). Motif A begins structurally at an antiparallel β-strand containing predominantly hydrophobic residues and continues to an α-helix. The primary amino acid sequence of DNA polymerase active sites is exceptionally conserved.

In addition to being well-conserved, the active site of DNA polymerases has also been shown to be relatively mutable, capable of accommodating certain amino acid substitutions without reducing DNA polymerase activity significantly. (See, e.g., U.S. Pat. No. 6,602,695). Such mutant DNA polymerases can offer various selective advantages in, e.g., diagnostic and research applications comprising nucleic acid synthesis reactions. We identify mutations in protein sequence using the single-letter amino acid codes and an integer number that indicates location of the mutation from the beginning of the protein sequence. The single-letter amino acids codes are well known in the art, e.g., Stryer et al., Biochemistry, 5.sup.th ed., Freeman and Company (2002). As an example, aspartic acid ("D") is changed to glycine ("G") in D580G mutant and the change is located 580 amino acids from the beginning of the protein sequence.

Reichert et al. conducted a comparative phylogenetic analysis of thermoactive DNA polymerases from thermophilic bacteria, wherein the protein coding sequences of DNA Polymerase I enzymes were aligned for thirteen phylogenetically distinct species. The analysis revealed that eight amino acid positions within a 15-amino acid long motif located at amino acid positions 645-685 (in reference to Thermus sp. Z05 DNA polymerase ("Z05 DNA Polymerase") might tolerate alterations without compromising core enzyme function.

Comparative phylogenetic analysis does not provide specific functional information pertaining non-conserved amino acids, other than to suggest that non-conserved amino acids are not likely critical to core enzyme functions. For that reason, specific mutations were introduced into a recombinant gene encoding a variant of the Z05 DNA Polymerase ("Z05 D580G polymerase") and the resultant Z05 D580G polymerase mutants were screened for their ability to provide a reduced ability to extend an oligonucleotide primer with a 3'-mismatch to a template. Reichert et al. found that one such mutant, Z05 D580G V667E polymerase, displayed better discrimination (~2-fold) than the parental Z05 D580G polymerase. See U.S. Pat. App. No. 2012/0015405 to Reichert et al., entitled DNA POLYMERASES WITH INCREASED 3'-MISMATCH DISCRIMINATION.

The comparative phylogenetic analysis has limitations with respect to identifying DNA polymerase activities that display improved 3'-nucleotide discrimination. This is due to the fact that all DNA polymerases of a given enzyme class are confronted with similar template substrates and nucleotide pools across the spectrum of phylogenetically diverse organisms. Given the fact that all DNA polymerases must display 3'-nucleotide mismatch discrimination to preserve high fidelity replication of daughter template strands, it is not surprising that one can apply comparative phylogenetic analysis to identify possible amino acid positions that might affect mismatch discrimination. For template substrates having different 3'-end modifications that are presented to a polymerase only in a biochemical assay, such as those used in several PCR-based assays for rare allele detection, there is a need for identifying DNA polymerases having improved 3'-nucleotide discrimination.

Taq DNA Polymerase is an enzyme that was discovered in Thermus aquaticus bacterium (Chien, A., et al., J Bacteriol. 1976, 127: 1550-1557). The enzyme is classified as deoxyribonucleic acid polymerase, class I (enzyme code, EC 2.7.7.7). Its catalytic activity is to amplify DNA sequences. The peptide and gene sequences of Taq DNA polymerase enzyme isolated from nature are well known in prior art and are listed in Table 1 (Lawyer, F. C., et al., J. Biol. Chem. 1989, 264: 6427-6437; Genbank database ID J04639.1).

TABLE 1

DNA and amino acid sequence of native Taq DNA polymerase.

| Type | Sequence |
|---|---|
| Protein sequence (N to C terminus) [SEQ ID NO: 1] | MRGMLPLFEPKGRVLLVDGHHLAYRTFHALKGLTTSRGEPVQAVYGFAKSLLKALKED GDAVIVVFDAKAPSFRHEAYGGYKAGRAPTPEDFPRQLALIKELVDLLGLARLEVPGY EADDVLASLAKKAEKEGYEVRILTADKDLYQLLSDRIHVLHPEGYLITPAWLWEKYGL RPDQWADYRALTGDESDNLPGVKGIGEKTARKLLEEWGSLEALLKNLDRLKPAIREKI LAHMDDLKLSWDLAKVRTDLPLEVDFAKRREPDRERLRAFLERLEFGSLLHEFGLLES PKALEEAPWPPPEGAFVGFVLSRKEPMWADLLALAAARGGRVHRAPEPYKALRDLKEA RGLLAKDLSVLALREGLGLPPGDDPMLLAYLLDPSNTTPEGVARRYGGEWTEEAGERA ALSERLFANLWGRLEGEERLLWLYREVERPLSAVLAHMEATGVRLDVAYLRALSLEVA EEIARLEAEVFRLAGHPFNLNSRDQLERVLFDELGLPAIGKTEKTGKRSTSAAVLEAL REAHPIVEKILQYRELTKLKSTYIDPLPDLIHPRTGRLHTRFNQTATATGRLSSSDPN LQNIPVRTPLGQRIRRAFIAEEGWLLVALDYSQIELRVLAHLSGDENLIRVFQEGRDI HTETASWMFGVPREAVDPLMRRAAKTINFGVLYGMSAHRLSQELAIPYEEAQAFIERY FQSFPKVRAWIEKTLEEGRRRGYVETLFGRRRYVPDLEARVKSVREAAERMAFNMPVQ GTAADLMKLAMVKLFPRLEEMGARMLLQVHDELVLEAPKERAEAVARLAKEVMEGVYP LAVPLEVEVGIGEDWLSAKE |
| DNA sequence (5' to 3') [SEQ ID NO: 2] | aagctcagat ctacctgcct gagggcgtcc ggttccagct ggcccttccc gaggggggaga gggaggcgtt tctaaaagcc cttcaggacg ctacccgggg gcgggtggtg gaagggtaac atgaggggga tgctgcccct ctttgagccc aagggccggg tcctcctggt ggacggccac cacctggcct accgcacctt ccacgccctg aagggcctca ccaccagccg gggggagccg gtgcaggcgg tctacggctt cgccaagagc ctcctcaagg ccctcaagga ggacggggac gcggtgatcg tggtctttga cgccaaggcc ccctccttcc gccacgaggc ctacgggggg tacaaggcgg gccgggcccc cacgccggag gactttcccc ggcaactcgc cctcatcaag gagctggtgg acctcctggg gctggcgcgc ctcgaggtcc cgggctacga ggcggacgac gtcctggcca gcctggccaa gaaggcggaa aaggagggct acgaggtccg catcctcacc gccgacaaag acctttacca gctccttttcc gaccgcatcc acgtcctcca ccccgagggg tacctcatca ccccggcctg gctttgggaa aagtacggcc tgaggcccga ccagtgggcc gactaccggg ccctgaccgg ggacgagtcc gacaaccttc ccggggtcaa gggcatcggg gagaagacgg cgaggaagct tctggaggag tggggagcc tggaagccct cctcaagaac ctggaccggc tgaagcccgc catccgggag aagatcctgg cccacatgga cgatctgaag ctctcctggg acctggccaa ggtgcgcacc gacctgcccc tggaggtgga cttcgccaaa aggcgggagc ccgaccggga gaggcttagg gcctttctgg agaggcttga gtttggcagc ctcctccacg agttcggcct tctgaaaagc cccaaggccc tggaggaggc ccctggccc ccgccggaag gggcttcgt gggctttgtg cttcccgca aggagcccat gtgggccgat cttctggccc tggccgccgc caggggggc cgggtccacc gggcccccga gccttataaa gccctcaggg |

TABLE 1-continued

DNA and amino acid sequence of native Taq DNA polymerase.

| Type | Sequence |
|------|----------|
|  | acctgaagga ggcgcggggg cttctcgcca aagacctgag cgttctggcc |
|  | ctgagggaag gccttggcct cccgcccggc gacgacccca tgctcctcgc |
|  | ctacctcctg gacccttcca acaccacccc cgaggggtg gcccggcgct |
|  | acggcgggga gtggacggag gaggcggggg agcgggccgc cctttccgag |
|  | aggctcttcg ccaacctgtg ggggaggctt gaggggagg agaggctcct |
|  | ttggctttac cgggaggtgg agaggcccct ttccgctgtc ctggcccaca |
|  | tggaggccac gggggtgcgc ctggacgtgg cctatctcag ggccttgtcc |
|  | ctggaggtgg ccgaggagat cgcccgcctc gaggccgagg tcttccgcct |
|  | ggccggccac cccttcaacc tcaactcccg ggaccagctg gaaagggtcc |
|  | tctttgacga gctagggctt cccgccatcg gcaagacgga gaagaccggc |
|  | aagcgctcca ccagcgccgc cgtcctggag gccctccgcg aggcccaccc |
|  | catcgtggag aagatcctgc agtaccggga gctcaccaag ctgaagagca |
|  | cctacattga cccttgccg gacctcatcc acccaggac gggccgcctc |
|  | cacacccgct tcaaccagac ggccacggcc acgggcaggc taagtagctc |
|  | cgatcccaac ctccagaaca tccccgtccg caccccgctt gggcagagga |
|  | tccgccgggc cttcatcgcc gaggaggggt ggctattggt ggcctggac |
|  | tatagccaga tagagctcag ggtgctggcc cacctctccg gcgacgagaa |
|  | cctgatccgg gtcttccagg aggggcggga catccacacg gagaccgcca |
|  | gctggatgtt cggcgtcccc cgggaggccg tggacccct gatgcgccgg |
|  | gcggccaaga ccatcaactt cggggtcctc tacggcatgt cggcccaccg |
|  | cctctcccag gagctagcca tccccttacga ggaggcccag gccttcattg |
|  | agcgctactt tcagagcttc cccaaggtgc gggcctggat tgagaagacc |
|  | ctggaggagg gcaggaggcg ggggtacgtg gagaccctct tcggccgccg |
|  | ccgctacgtg ccagacctag aggcccgggt gaagagcgtg cgggaggcgg |
|  | ccgagcgcat ggccttcaac atgcccgtcc agggcaccgc cgccgacctc |
|  | atgaagctgg ctatggtgaa gctcttcccc aggctggagg aaatgggggc |
|  | caggatgctc cttcaggtcc acgacgagct ggtcctcgag gccccaaaag |
|  | agagggcgga ggccgtggcc cggctggcca aggaggtcat ggaggggtg |
|  | tatcccctgg ccgtgcccct ggaggtggag gtggggatag gggaggactg |
|  | gctctccgcc aaggagtgat accacc |

Taq DNA polymerase extends primers composed from deoxyribonucleotides, however, some chemical modifications of the primer are tolerated and do not decrease much the efficiency of primer extension reactions. For example, when the nucleotide at 3' primer terminus is ribonucleotide instead of deoxyribonucleotide, Taq DNA polymerase can extend such primer with significant efficiency and speed.

BRIEF SUMMARY OF THE INVENTION

In one aspect, a mutant Taq DNA polymerase having an enhanced template discrimination activity compared with an unmodified Taq DNA polymerase is provided. The amino acid sequence of the mutant Taq DNA polymerase includes at least one substitution at residue positions 783 or 784 of the unmodified Taq DNA polymerase.

In another aspect, a mutant thermostable DNA polymerase having an enhanced template discrimination activity compared with an unmodified thermostable DNA polymerase is provided. The amino acid sequence of the mutant thermostable DNA polymerase includes at least one substitution at residue positions orthologous to positions 783 or 784 of the unmodified Taq DNA polymerase.

In another aspect, a mutant DNA polymerase having an enhanced template discrimination activity compared with the corresponding unmodified DNA polymerase is provided, wherein the mutant DNA polymerase includes a thermostable polymerase. The amino acid sequence of the mutant DNA polymerase peptide includes at least one substitution at residue positions orthologous to positions 783 or 784 of the unmodified Taq DNA polymerase, wherein the mutant DNA polymerase is selected from the group of species consisting of E. coli, Eubacterium siraeum, Clostridium leptum, Enterococcus, Facklamia hominis, Bacillus anthracis and Bacillus cereus ATCC 10987.

In another aspect, a mutant non-VH-related DNA polymerase having an enhanced template discrimination activity compared with its unmodified non-VH-related DNA polymerase counterpart is provided, wherein the mutant non-VH-related DNA polymerase includes a thermostable polymerase. The amino acid sequence of the mutant non-VH-related DNA polymerase includes at least one substitution at residue positions orthologous to reside positions 783 and/or 784 of the unmodified Taq DNA polymerase.

In another aspect, recombinant nucleic acid encoding any of the mutant DNA polymerases of described above is provided.

In another aspect, a method for conducting primer extension is provided. The method includes the step of contacting a mutant DNA polymerase as described above with a primer, a polynucleotide template, and nucleoside triphosphates under conditions suitable for a primer extension method, thereby producing an extended primer.

In another aspect, a kit for producing an extended primer, comprising: at least one container providing a mutant DNA polymerase as described above.

In another aspect, a reaction mixture is provided that includes a mutant DNA polymerase as described above, at least one primer, a polynucleotide template, and nucleoside triphosphates.

In another aspect, a method for performing rhPCR is provided that includes the step of performing primer extension with a mutant DNA polymerase as described above.

In another aspect, a mutant Taq DNA polymerase having an enhanced template discrimination activity compared with an unmodified Taq DNA polymerase is provided. The amino acid sequence of the mutant Taq DNA polymerase comprises one of following selected substitutions: (1) A661E; I665W; F667L [SEQ ID NO:87]; (2) V783F [SEQ ID NO:83]; (3) H784Q [SEQ ID NO:85]; (4) V783L; H784Q [SEQ ID NO:89]; (5) H784A [SEQ ID NO: 147]; (6) H784S [SEQ ID NO: 149]; (7) H784I [SEQ ID NO:155]; (8) H784T [SEQ ID NO:151], (9) H784V [SEQ ID NO: 153]; (10) H784M [SEQ ID NO: 157]; (11) H784F [SEQ ID NO: 159]; or (12) H784Y [SEQ ID NO:161].

In another aspect, a mutant Taq DNA polymerase having a deleted 5' exonuclease domain (KlenTaq) and containing additional mutations, having an enhanced template discrimination activity compared with an unmodified Taq DNA polymerase is provided. The amino acid sequence of the mutant Taq DNA polymerase comprises one of following selected substitutions: (1) A661E; I665W; F667L [SEQ ID NO: 170]; (2) V783F [SEQ ID NO: 172]; (3) H784Q [SEQ ID NO: 174]; (4) V783L; H784Q [SEQ ID NO: 176]; (5) H784S [SEQ ID NO: 178]; or (6) H784Y [SEQ ID NO: 180].

DETAILED DESCRIPTION

Figure 1:
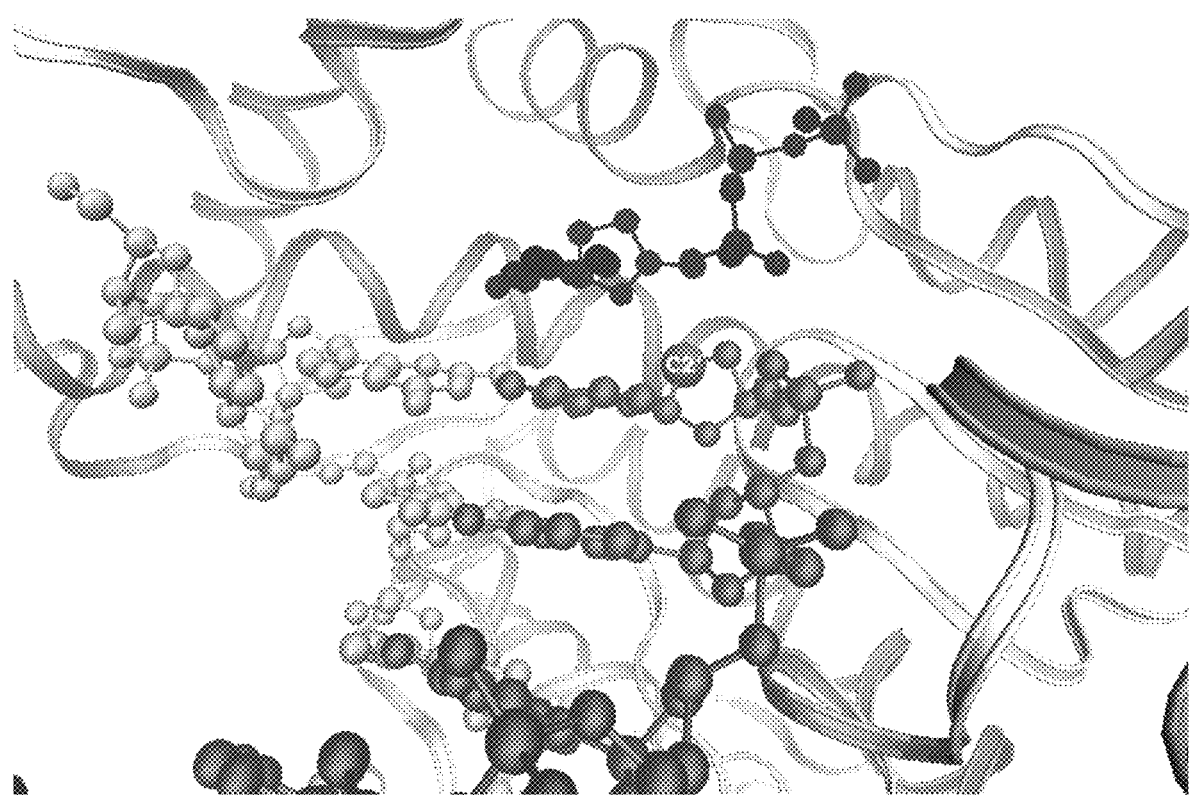
FIG. 1 depicts a model of the active site constructed from the known Taq DNA polymerase PDB ID 2KTQ crystal structure. The polymerase backbone is displayed using ribbons. The "C2'" label indicates the 2' carbon atom at the primer terminal nucleotide. The dNTP is binding in the pocket above the primer.
Figure 2A:
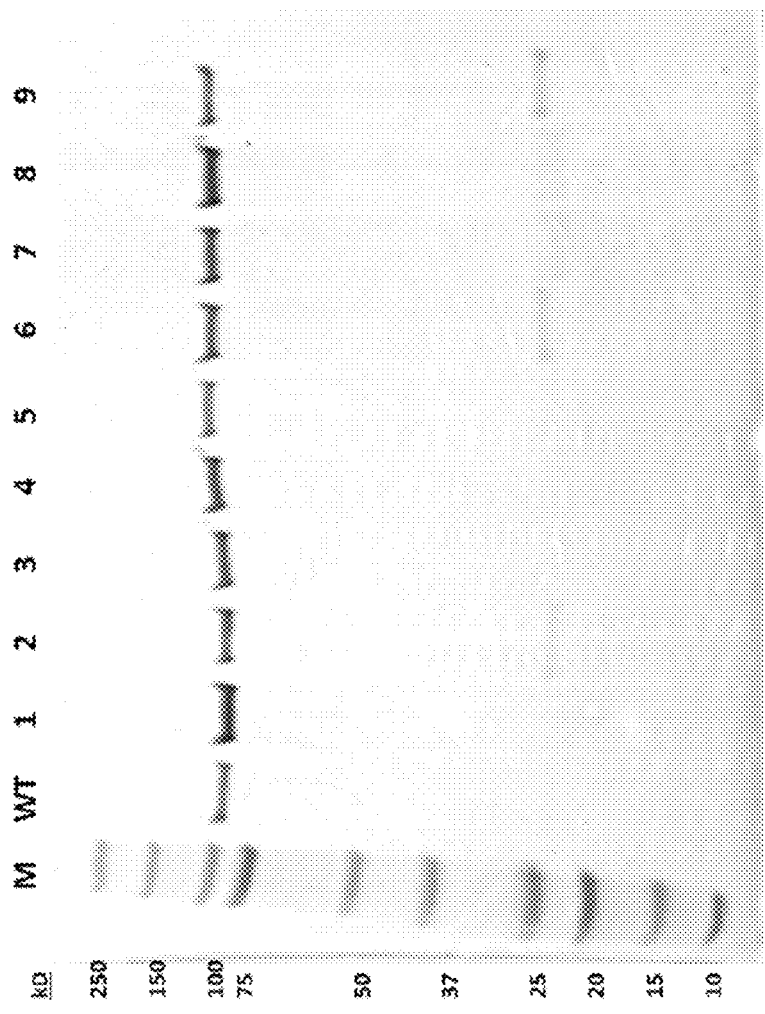
FIG. 2A shows gel images depicting purified protein for the Taq DNA polymerase mutants and wild type Taq DNA polymerase. Legend: Aliquots of purified recombinant proteins were separated by polyacrylamide gel electrophoresis (PAGE) and stained with Coomassie Brilliant Blue. The Marker lane (M) is indicated, showing protein size markers identified in kilodaltons (kDa).
Figure 2B:
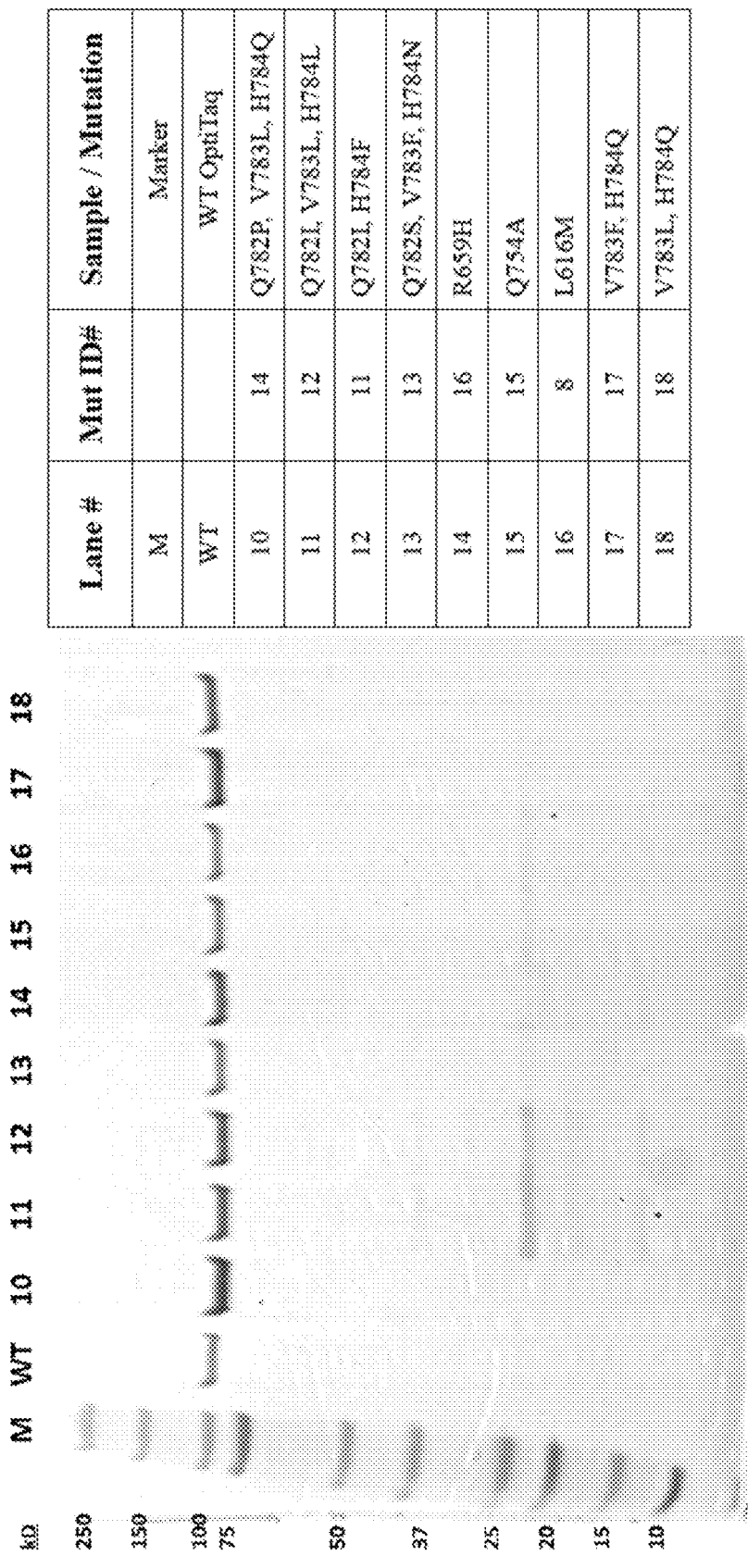
FIG. 2B shows gel images depicting purified protein for the Taq DNA polymerase mutants and wild type Taq DNA polymerase. Legend as in FIG. 2A.
Figure 2C:
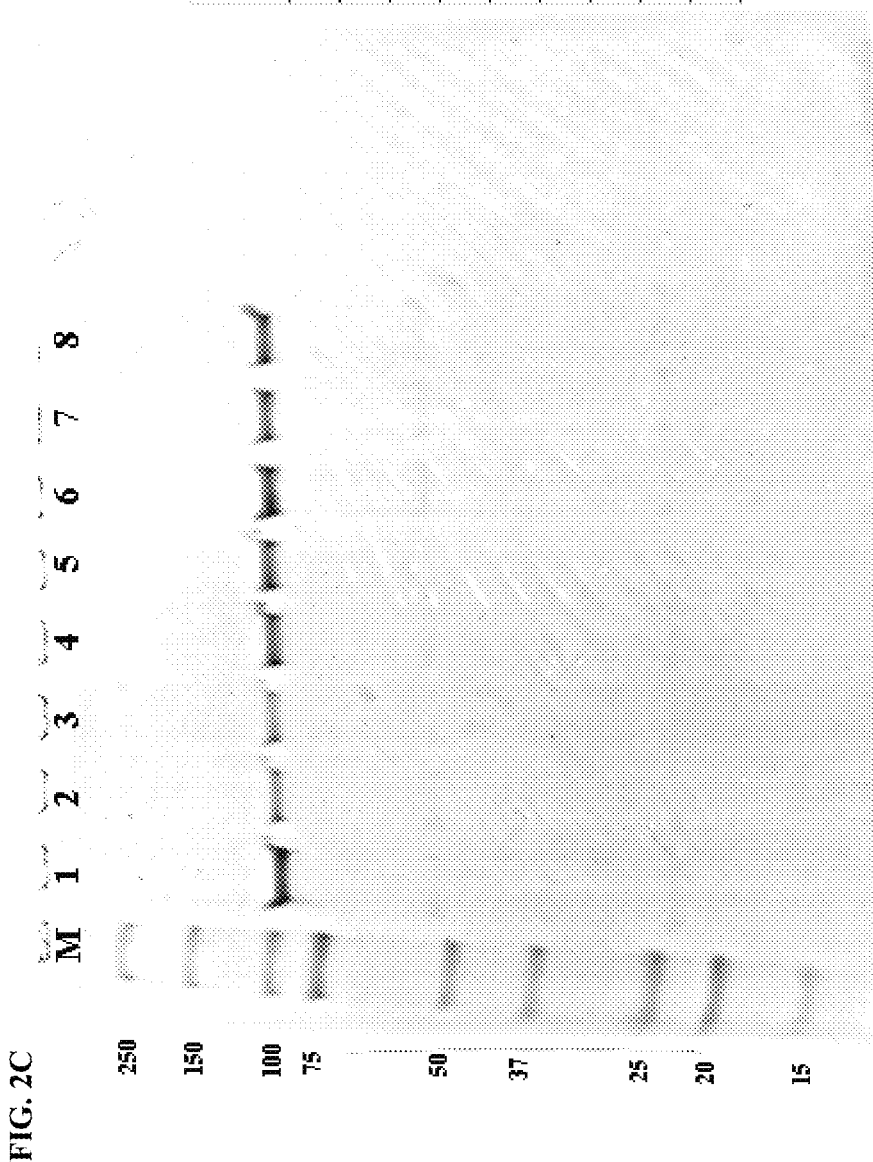
FIG. 2C shows gel images depicting purified protein for the Taq DNA polymerase mutants and wild type Taq DNA polymerase. Legend as in FIG. 2A.
Figure 2D:
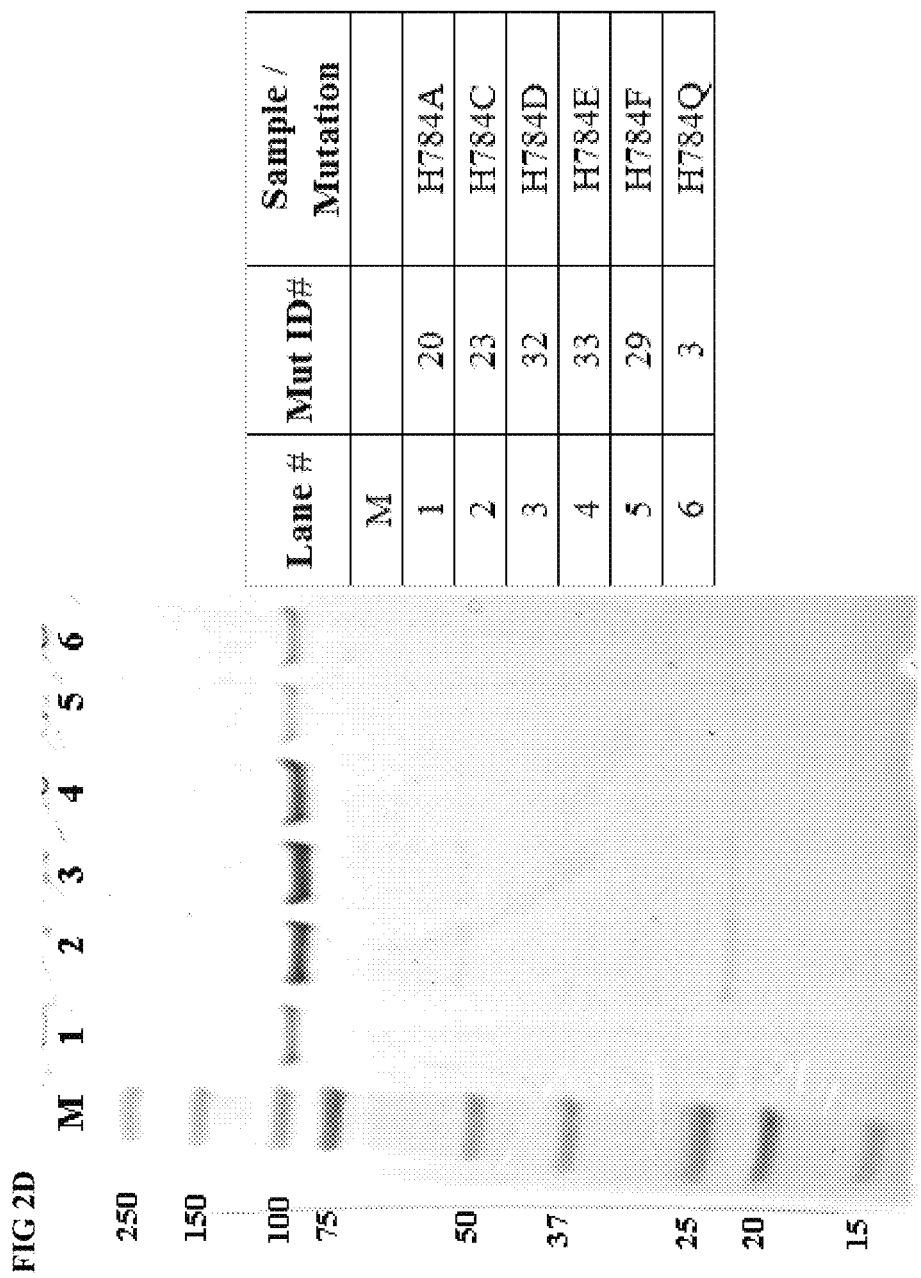
FIG. 2D shows gel images depicting purified protein for the Taq DNA polymerase mutants and wild type Taq DNA polymerase. Legend as in FIG. 2A.

The current invention provides novel thermostable DNA polymerases, including specific examples derived from *Thermus aquaticus* (Taq) DNA polymerase. These polymerases offer improvements to existing methods for nucleic acid amplification, genotyping, and detection of rare alleles. New assay formats comprising the use of these novel thermostable DNA polymerases are also provided.

Definitions

To aid in understanding the invention, several terms are defined below.

Terms used herein are intended as "open" terms (for example, the term "including" should be interpreted as "including but not limited to," the term "having" should be interpreted as "having at least," the term "includes" should be interpreted as "includes but is not limited to," etc.).

The articles "a" and "an" refer to one or to more than one (for example, to at least one) of the grammatical object of the article.

The terms "about" and "approximately" shall generally mean an acceptable degree of error for the quantity measured given the nature or precision of the measurements. Exemplary degrees of error are within 20-25 percent (%), typically, within 10%, and more typically, within 5% of a given value or range of values.

Furthermore, in those instances where a convention analogous to "at least one of A,B and C, etc." is used, in general such a construction is intended in the sense of one having ordinary skill in the art would understand the convention (for example, "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or "B" or "A and B."

All language such as "from," "to," "up to," "at least," "greater than," "less than," and the like, include the number recited and refer to ranges which can subsequently be broken down into sub-ranges.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

The term "conventional" or "natural" when referring to nucleic acid bases, nucleoside triphosphates, or nucleotides refers to those which occur naturally in the polynucleotide being described (i.e., for DNA these are dATP, dGTP, dCTP and dTTP). Additionally, dITP, and 7-deaza-dGTP are frequently utilized in place of dGTP and 7-deaza-dATP can be utilized in place of dATP in in vitro DNA synthesis reactions, such as sequencing. Collectively, these may be referred to as dNTPs.

The term "unconventional" or "modified" when referring to a nucleic acid base, nucleoside, or nucleotide includes modification, derivations, or analogues of conventional bases, nucleosides, or nucleotides that naturally occur in a particular polynucleotide. Certain unconventional nucleotides are modified at the 2' position of the ribose sugar in comparison to conventional dNTPs. Thus, although for RNA the naturally occurring nucleotides are ribonucleotides (i.e., ATP, GTP, CTP, UTP, collectively rNTPs), because these nucleotides have a hydroxyl group at the 2' position of the sugar, which, by comparison is absent in dNTPs, as used herein, ribonucleotides are unconventional nucleotides as substrates for DNA polymerases. As used herein, unconventional nucleotides include, but are not limited to, compounds used as terminators for nucleic acid sequencing. Exemplary terminator compounds include but are not limited to those compounds that have a 2',3' dideoxy structure and are referred to as dideoxynucleoside triphosphates. The dideoxynucleoside triphosphates ddATP, ddTTP, ddCTP and ddGTP are referred to collectively as ddNTPs.

The term "nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

The terms "nucleic acid" and "oligonucleotide," as used herein, refer to polydeoxyribonucleotides (containing 2-deoxy-D-ribose), polyribonucleotides (containing D-ribose), and to any other type of polynucleotide which is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Lett. 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (e.g., a DNA polymerase or reverse transcriptase) in an appropriate buffer and at a suitable temperature. Primer extension can also be carried out in the absence of one or more of the nucleoside triphosphates in which case an extension product of limited length is produced. As used herein, the term "primer" is intended to encompass the oligonucleotides used in ligation-mediated reactions, in which one oligonucleotide is "extended" by ligation to a second oligonucleotide which hybridizes at an adjacent position. Thus, the term "primer extension", as used herein, refers to both the polymerization of individual nucleoside triphosphates using the primer as a point of initiation of DNA synthesis and to the ligation of two oligonucleotides to form an extended product.

A primer is preferably a single-stranded DNA. The appropriate length of a primer depends on the intended use of the primer but typically ranges from 6 to 50 nucleotides, preferably from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product. The region of the primer which is sufficiently complementary to the template to hybridize is referred to herein as the hybridizing region. Primers may incorporate modified residues other than DNA, so long as these alternations do not impede priming or template functionality.

The phrase "3'-nucleotide discrimination" refers to a property of a DNA polymerase to catalyze a primer extension reaction with greater specificity for deoxyribonucleotides and less efficiently when the nucleotide at the primer 3' terminus was chemically modified. For example, a mutated Taq DNA polymerase that displays 3'-nucleotide discrimination exhibits selectivity for deoxyribonucleotide primer and suppressed catalytic activity when the primer is for example modified with ribonucleotides.

The term "3'-mismatch discrimination" refers to a property of a DNA polymerase to distinguish a fully complementary sequence from a mismatch-containing (nearly complementary) sequence where the nucleic acid to be extended (for example, a primer or other oligonucleotide) has a mismatch at the 3' terminus of the nucleic acid compared to the template to which the nucleic acid hybridizes. In some embodiments, the nucleic acid to be extended comprises a mismatch at the 3' end relative to the fully complementary sequence.

The term "rare allele discrimination" refers to a property of a DNA polymerase to preferentially replicate a first nucleic acid in a population of nucleic acids that includes a plurality of a second nucleic acid, wherein the first nucleic acid is under-represented in the population of nucleic acids relative to the plurality of a second nucleic acid. Typically, the first nucleic acid may be under-represented in the population of nucleic acids that contain a plurality of a second nucleic acids by a ratio of the first nucleic acid to the second nucleic acid in the range from about 1:10 to about 1:1,000,000, including 1:100, 1:1,000; 1:10,000 and 1:100,000, among other ratios. Typically, though not exclusively, a polymerase having rare allele discrimination can be used to detect a SNP difference between a first nucleic acid and a second nucleic acid, as further elaborated herein.

The phrase "template discrimination activity" refers to a DNA polymerase having at least one of 3'-nucleotide discrimination, 3'-mismatch discrimination, rare allele discrimination and combinations thereof.

The phrase "enhanced template discrimination activity" refers to a DNA polymerase having at least one of 3'-nucleotide discrimination, 3'-mismatch discrimination and rare allele discrimination, or combinations thereof, wherein the DNA polymerase displays greater activity than a reference DNA polymerase. For example, a DNA polymerase mutant having "enhanced template discrimination activity" displays at least one of 3'-nucleotide discrimination, 3'-mismatch discrimination, rare allele discrimination and combinations thereof that is greater than the corresponding activity of the naturally-occurring, wild-type DNA polymerase from which the DNA polymerase mutant was derived.

A "template discrimination activity assay" refers to an assay for assessing the ability of a polymerase to discriminate between two templates that differ in one or more variables. Assays designed to reveal 3'-nucleotide discrimination, 3'-mismatch discrimination or rare allele discrimination are examples of template discrimination activity assays.

The term "quantification cycle value," denoted as Cq, refers to the amplification cycle number at which positive signal is first detected.

The term "discrimination quantification cycle value," denoted as ΔCq, refers to a calculated difference between a first reference state and a second reference state, wherein both the first and second reference states differ in terms of only one variable. For examples, a first and second reference states can refer to identical polymerase reactions that differ in polymerases, such as a wild-type polymerase and a polymerase mutant, that differ in primer template nucleotide sequence, such as a mismatched primer template and a matched primer template, or that differ in primer template 3'-nucleotide ribose structure, such as a primer template containing a 3'-deoxyribose moiety and a primer template containing a 3'-ribose moiety.

The term "differential discrimination quantification cycle value," denoted as ΔΔCq, refers to a calculated difference between a first discrimination quantification cycle value and a second discrimination quantification cycle value for polymerase reactions that differ in two variables. In the context of the present disclosure, the ΔΔCq value is a measure of the improvement that a given polymerase mutant displays relative to the wild-type polymerase in a template discrimination activity assay. A preferred ΔΔCq value depends upon the nature of the assay, but generally a preferred ΔΔCq value is at least 1.0 and is typically greater than 1.0.

The terms "target", "target sequence", "target region", and "target nucleic acid," as used herein, are synonymous and refer to a region or sequence of a nucleic acid which is to be amplified, sequenced or detected.

The term "template" refers to a nucleic acid that includes at least one single stranded region. The term "template" as it modifies "substrate" refers to a nucleic acid that is used in a hybridization reaction to anneal with a primer and/or an extension reaction with a polymerase.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, Biochemistry, 47: 5336-5353, which are incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two step cycles have a high temperature denaturation step followed by a hybridization/elongation (or ligation) step. Three step cycles comprise a denaturation step followed by a hybridization step followed by a separate elongation or ligation step.

An "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., Biochemistry, 5.sup.th ed., Freeman and Company (2002), which is incorporated by reference. Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13): R464-R466, which are both incorporated by reference). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," Proc. Natl. Acad. Sci. U.S.A. 101(24):8882-8887, Anderson et al. (2004) "An expanded genetic code with a functional quadruplet codon" Proc. Natl. Acad. Sci. U.S.A. 101(20):7566-7571, Ikeda et al. (2003) "Synthesis of a novel histidine analogue and its efficient incorporation into a protein in vivo," Protein Eng. Des. Sel. 16(9):699-706, Chin et al. (2003) "An Expanded Eukaryotic Genetic Code," Science 301(5635):964-967, James et al. (2001) "Kinetic characterization of ribonuclease S mutants containing photoisomerizable phenylazophenylalanine residues," Protein Eng. Des. Sel. 14(12):983-991, Kohrer et al. (2001) "Import of amber and ochre suppressor tRNAs into mammalian cells: A general approach to site-specific insertion of amino acid analogues into proteins," Proc. Natl. Acad. Sci. U.S.A. 98(25):14310-14315, Bacher et al. (2001) "Selection and Characterization of *Escherichia coli* Variants Capable of Growth on an Otherwise Toxic Tryptophan Analogue," J. Bacteriol. 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," J. Biol. Chem. 275(51):40324-40328, and Budisa et al. (2001) "Proteins with {beta}-(thienopyrrolyl)alanines as alternative chromophores and pharmaceutically active amino acids," Protein Sci. 10(7):1281-1292, which are each incorporated by reference.

The term "residue" is synonymous and interchangeable with "amino acid" or "nucleotide" depending upon context.

As used herein, a "polymerase" refers to an enzyme that catalyzes the polymerization of nucleotides. Generally, the enzyme will initiate synthesis at the 3'-end of the primer annealed to a nucleic acid template sequence. "DNA polymerase" catalyzes the polymerization of deoxyribonucleotides. Known DNA polymerases include, for example, *Pyrococcus furiosus* (Pfu) DNA polymerase (Lundberg et al., 1991, Gene, 108:1), *E. coli* DNA polymerase I (Lecomte and Doubleday, 1983, Nucleic Acids Res. 11:7505), T7 DNA polymerase (Nordstrom et al., 1981, J. Biol. Chem. 256:3112), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent DNA polymerase, Cariello et al., 1991, Nucleic Acids Res, 19: 4193), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, Appl. Environ. Microbiol. 63:4504), JDF-3 DNA polymerase (Patent application WO 0132887), and *Pyrococcus* GB-D (PGB-D) DNA polymerase (Juncosa-Ginesta et al., 1994, Biotechniques, 16:820). The polymerase activity of any of the above enzymes can be determined by means well known in the art.

The term "thermostable polymerase," refers to an enzyme that is stable to heat, is heat resistant, and retains sufficient activity to effect subsequent polynucleotide extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in, e.g., U.S. Pat. Nos. 4,683,202, 4,683,195, and 4,965,188, which are incorporated herein by reference. As used herein, a thermostable polymerase is suitable for use in a temperature cycling reaction such as the polymerase chain reaction ("PCR"). Irreversible denaturation for purposes herein refers to permanent and complete loss of enzymatic activity. For a thermostable polymerase, enzymatic activity refers to the catalysis of the combination of the nucleotides in the proper manner to form polynucleotide extension products that are complementary to a template nucleic acid strand. Thermostable DNA polymerases from thermophilic bacteria include, e.g., DNA polymerases from *Thermus aquaticus*, among others.

The term "thermoactive" refers to an enzyme that maintains catalytic properties at temperatures commonly used for reverse transcription or anneal/extension steps in RT-PCR and/or PCR reactions (i.e., 45-80° C.). Thermostable enzymes are those which are not irreversibly inactivated or denatured when subjected to elevated temperatures necessary for nucleic acid denaturation. Thermoactive enzymes may or may not be thermostable. Thermoactive DNA polymerases can be DNA or RNA dependent from thermophilic species or from mesophilic species including, but not limited to, *Escherichia coli*, Moloney murine leukemia viruses, and Avian myoblastosis virus.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences which contain the target primer binding sites.

The term "non-specific amplification," as used herein, refers to the amplification of nucleic acid sequences other than the target sequence which results from primers hybridizing to sequences other than the target sequence and then serving as a substrate for primer extension. The hybridization of a primer to a non-target sequence is referred to as "non-specific hybridization" and is apt to occur especially during the lower temperature, reduced stringency, pre-amplification conditions, or in situations where there is a variant allele in the sample having a very closely related sequence to the true target as in the case of a single nucleotide polymorphism (SNP).

The term "primer dimer," as used herein, refers to a template-independent non-specific amplification product, which is believed to result from primer extensions wherein another primer serves as a template. Although primer dimers frequently appear to be a concatamer of two primers, i.e., a dimer, concatamers of more than two primers also occur. The term "primer dimer" is used herein generically to encompass a template-independent non-specific amplification product.

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a DNA polymerase (most typically a thermostable DNA polymerase), dNTPs, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components which includes the blocked primers of the invention.

The terms "non-activated" or "inactivated," as used herein, refer to a primer or other oligonucleotide that is incapable of participating in a primer extension reaction or a ligation reaction because either DNA polymerase or DNA ligase cannot interact with the oligonucleotide for their intended purposes. In some embodiments when the oligonucleotide is a primer, the non-activated state occurs because the primer is blocked at or near the 3'-end so as to prevent primer extension. When specific groups are bound at or near the 3'-end of the primer, DNA polymerase cannot bind to the primer and extension cannot occur. A non-activated primer is, however, capable of hybridizing to a substantially complementary nucleotide sequence.

The term "activated," as used herein, refers to a primer or other oligonucleotide that is capable of participating in a reaction with DNA polymerase or DNA ligase. A primer or other oligonucleotide becomes activated after it hybridizes to a substantially complementary nucleic acid sequence and is cleaved to generate a functional 3'- or 5'-end so that it can interact with a DNA polymerase or a DNA ligase. For example, when the oligonucleotide is a primer, and the primer is hybridized to a template, a 3'-blocking group can be removed from the primer by, for example, a cleaving enzyme such that DNA polymerase can bind to the 3' end of the primer and promote primer extension.

The term "cleavage domain" or "cleaving domain," as used herein, are synonymous and refer to a region located between the 5' and 3' end of a primer or other oligonucleotide that is recognized by a cleavage compound, for example a cleavage enzyme, that will cleave the primer or other oligonucleotide. For the purposes of this invention, the cleavage domain is designed such that the primer or other oligonucleotide is cleaved only when it is hybridized to a complementary nucleic acid sequence, but will not be cleaved when it is single-stranded. The cleavage domain or sequences flanking it may include a moiety that a) prevents or inhibits the extension or ligation of a primer or other oligonucleotide by a polymerase or a ligase, b) enhances discrimination to detect variant alleles, or c) suppresses undesired cleavage reactions. One or more such moieties may be included in the cleavage domain or the sequences flanking it.

The term "RNase H cleavage domain," as used herein, is a type of cleavage domain that contains one or more ribonucleic acid residue or an alternative analog which provides a substrate for an RNase H. An RNase H cleavage domain can be located anywhere within a primer or oligonucleotide, and is preferably located at or near the 3'-end or the 5'-end of the molecule.

An "RNase H1 cleavage domain" generally contains at least three consecutive RNA residues. An "RNase H2 cleavage domain" may contain one RNA residue, a sequence of contiguously linked RNA residues or RNA residues separated by DNA residues or other chemical groups. For example, an RNase H2 cleavage domain may include a 2'-fluoronucleoside residue, among others.

The terms "cleavage compound," or "cleaving agent" as used herein, refers to any compound that can recognize a cleavage domain within a primer or other oligonucleotide, and selectively cleave the oligonucleotide based on the presence of the cleavage domain. The cleavage compounds utilized in the invention selectively cleave the primer or other oligonucleotide comprising the cleavage domain only when it is hybridized to a substantially complementary nucleic acid sequence, but will not cleave the primer or other oligonucleotide when it is single stranded. The cleavage compound cleaves the primer or other oligonucleotide within or adjacent to the cleavage domain. The term "adjacent," as used herein, means that the cleavage compound cleaves the primer or other oligonucleotide at either the 5'-end or the 3' end of the cleavage domain. Cleavage reactions preferred in the invention yield a 5'-phosphate group and a 3'-OH group.

In a preferred embodiment, the cleavage compound is a "cleaving enzyme." A cleaving enzyme is a protein or a ribozyme that is capable of recognizing the cleaving domain when a primer or other nucleotide is hybridized to a substantially complementary nucleic acid sequence, but that will not cleave the complementary nucleic acid sequence (i.e., it provides a single strand break in the duplex). The cleaving enzyme will also not cleave the primer or other oligonucleotide comprising the cleavage domain when it is single stranded. Examples of cleaving enzymes are RNase H enzymes and other nicking enzymes.

The term "nicking," as used herein, refers to the cleavage of only one strand of the double-stranded portion of a fully or partially double-stranded nucleic acid. The position where the nucleic acid is nicked is referred to as the "nicking site" (NS). A "nicking agent" (NA) is an agent that nicks a partially or fully double-stranded nucleic acid. It may be an enzyme or any other chemical compound or composition. In certain embodiments, a nicking agent may recognize a particular nucleotide sequence of a fully or partially double-stranded nucleic acid and cleave only one strand of the fully or partially double-stranded nucleic acid at a specific position (i.e., the NS) relative to the location of the recognition sequence. Such nicking agents (referred to as "sequence specific nicking agents") include, but are not limited to, nicking endonucleases (e.g., Nt.BstNBI).

A "nicking endonuclease" (NE), as used herein, thus refers to an endonuclease that recognizes a nucleotide sequence of a completely or partially double-stranded nucleic acid molecule and cleaves only one strand of the nucleic acid molecule at a specific location relative to the recognition sequence. In such a case the entire sequence from the recognition site to the point of cleavage constitutes the "cleavage domain".

The term "blocking group," as used herein, refers to a chemical moiety that is bound to the primer or other oligonucleotide such that an amplification reaction does not occur. For example, primer extension and/or DNA ligation does not occur. Once the blocking group is removed from the primer or other oligonucleotide, the oligonucleotide is capable of participating in the assay for which it was designed (PCR, ligation, sequencing, etc.). Thus, the "blocking group" can be any chemical moiety that inhibits recognition by a polymerase or DNA ligase. The blocking group may be incorporated into the cleavage domain but is generally located on either the 5'- or 3'-side of the cleavage domain. The blocking group can be comprised of more than one chemical moiety. In the present invention the "blocking group" is typically removed after hybridization of the oligonucleotide to its target sequence.

The term "blocked-cleavable primer" refers to a primer that is inactive or inactivated for priming DNA synthesis from a polymerase owing to the presence of a blocking group at or near the 3'-terminus of the primer. A blocked-cleavable primer can be converted into a competent primer by removing the blocking group at or near the 3'-terminus of the primer by a cleavage compound or a cleaving agent (for example, a cleaving enzyme) resulting in an active or activated primer.

An RDDDDx blocked-cleavable primer (also known as "generation 1" or "Gen 1" blocked-cleavable primer) refers to a blocked-cleavable primer having at its 3'-terminus the sequence RDDDDx, wherein R is an RNA base, D is a DNA base and x is a C3 spacer group.

An RDxxD blocked-cleavable primer (also known as "generation 2" or "Gen 2" blocked-cleavable primer) refers to a blocked-cleavable primer having at its 3'-terminus the sequence RDxxD, wherein R is an RNA base, D is a DNA base and x is a C3 spacer group.

The term "fluorescent generation probe" refers either to a) an oligonucleotide having an attached fluorophore and quencher, and optionally a minor groove binder or to b) a DNA binding reagent such as SYBR™ Green dye.

The terms "fluorescent label" or "fluorophore" refers to compounds with a fluorescent emission maximum between about 350 and 900 nm. A wide variety of fluorophores can be used, including but not limited to: 5-FAM (also called 5-carboxyfluorescein; also called Spiro(isobenzofuran-1 (3H), 9'-(9H)xanthene)-5-carboxylic acid,3',6'-dihydroxy-3-oxo-6-carboxyfluorescein); 5-Hexachloro-Fluorescein; ([4, 7,2',4',5',7'-hexachloro-(3',6'-dipivaloylfluoresceinyl)-6-carboxylic acid]); 6-Hexachloro-Fluorescein; ([4,7,2',4',5', 7'-hexachloro-(3',6'-dipivaloylfluoresceinyl)-5-carboxylic acid]); 5-Tetrachloro-Fluorescein; ([4,7,2',7'-tetra-chloro-(3',6'-dipivaloylfluoresceinyl)-5-carboxylic acid]); 6-Tetra-chloro-Fluorescein; ([4,7,2',7'-tetrachloro-(3',6'-dipivaloylfluoresceinyl)-6-carboxylic acid]); 5-TAMRA (5-carboxytetramethylrhodamine); Xanthylium, 9-(2,4-dicarboxyphenyl)-3,6-bis(dimethylamino); 6-TAMRA (6-carboxytetramethylrhodamine); 9-(2,5-dicarboxyphenyl)-3,6-bis(dimethylamino); EDANS (5-((2-aminoethyl)amino) naphthalene-1-sulfonic acid); 1,5-IAEDANS (5-((((2-iodoacetyl)amino)ethyl)amino)naphthalene-1-sulfonic acid); Cy5 (Indodicarbocyanine-5); Cy3 (Indo-dicarbocyanine-3); and BODIPY FL (2,6-dibromo-4,4-difluoro-5,7-dimethyl-4-bora-3a,4a-diaza-s-indacene-3-proprionic acid); Quasar®-670 dye (Biosearch Technologies); Cal Fluor® Orange dye (Biosearch Technologies); Rox dyes; Max dyes (Integrated DNA Technologies), as well as suitable derivatives thereof.

As used herein, the term "quencher" refers to a molecule or part of a compound, which is capable of reducing the emission from a fluorescent donor when attached to or in proximity to the donor. Quenching may occur by any of several mechanisms including fluorescence resonance energy transfer, photo-induced electron transfer, paramagnetic enhancement of intersystem crossing, Dexter exchange coupling, and exciton coupling such as the formation of dark complexes. Fluorescence is "quenched" when the fluorescence emitted by the fluorophore is reduced as compared with the fluorescence in the absence of the quencher by at least 10%, for example, 15%, 20%, 30%, 40%, 50%, 60%, 70%, 80%, 90%, 95%, 98%, 99%, 99.9% or more. A number of commercially available quenchers are known in the art, and include but are not limited to DABCYL, Black Hole™ Quenchers (BHQ-1, BHQ-2, and BHQ-3), Iowa Black® FQ and Iowa Black® RQ. These are so-called dark quenchers. They have no intrinsic fluorescence in the wavelength range from 300 to 900 nm, virtually eliminating background problems seen with other quenchers such as TAMRA which is intrinsically fluorescent.

The term "ligation" as used herein refers to the covalent joining of two polynucleotide ends. In various embodiments, ligation involves the covalent joining of a 3' end of a first polynucleotide (the acceptor) to a 5' end of a second polynucleotide (the donor). Ligation results in a phosphodiester bond being formed between the polynucleotide ends. In various embodiments, ligation may be mediated by any enzyme, chemical, or process that results in a covalent joining of the polynucleotide ends. In certain embodiments, ligation is mediated by a ligase enzyme.

As used herein, "ligase" refers to an enzyme that is capable of covalently linking the 3'-hydroxyl group of one polynucleotide to the 5' phosphate group of a second polynucleotide. Examples of ligases include *E. coli* DNA ligase, T4 DNA ligase, etc.

The ligation reaction can be employed in DNA amplification methods such as the "ligase chain reaction" (LCR), also referred to as the "ligase amplification reaction" (LAR), see Barany, Proc. Natl. Acad. Sci., 88:189 (1991); and Wu and Wallace, Genomics 4:560 (1989) incorporated herein by reference. In LCR, four oligonucleotides, two adjacent oligonucleotides which uniquely hybridize to one strand of the target DNA, and a complementary set of adjacent oligonucleotides, that hybridize to the opposite strand are mixed and DNA ligase is added to the mixture. In the presence of the target sequence, DNA ligase will covalently link each set of hybridized molecules. Importantly, in LCR, two oligonucleotides are ligated together only when they base-pair with sequences without gaps. Repeated cycles of denaturation, hybridization and ligation amplify a short segment of DNA. A mismatch at the junction between adjacent oligonucleotides inhibits ligation. As in other oligonucleotide ligation assays this property allows LCR to be used to distinguish between variant alleles such as SNPs. LCR has also been used in combination with PCR to achieve enhanced detection of single-base changes, see Segev, PCT Public. No. WO9001069 (1990).

The term "unmodified form," in the context of the Taq DNA polymerase, is a term used herein for purposes of defining a host cell-specific, codon-optimized Taq DNA polymerase gene that expresses Taq DNA polymerase in the host cell. The term "unmodified form" refers to a functional DNA polymerase that has the amino acid sequence of the naturally occurring polymerase. The term "unmodified form" includes a functional DNA polymerase in a recombinant form.

The term "mutant", in the context of DNA polymerases disclosed, means a polypeptide, typically recombinant, that comprises one or more amino acid substitutions relative to a corresponding, naturally-occurring form or unmodified form of DNA polymerase.

"Recombinant", as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant DNA polymerase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "vector" refers to a piece of DNA, typically double-stranded, which may have inserted into it a piece of foreign DNA. The vector may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "affinity tag" refers to a short polypeptide sequence that permits detection and/or selection of the polypeptide sequence. For the purposes of this disclosure, a recombinant gene that encodes a recombinant DNA polymerase may include an affinity tag. In particular, the affinity tag is positioned typically at either the N-terminus or C-terminus of the coding sequence for a DNA polymerase through the use of recombination technology. Exemplary affinity tags include polyhistine (for example, $(His_6)$), glutathione-S-transferase (GST), HaloTag®, AviTag, Calmodulin-tag, polyglutamate tag, FLAG-tag, HA-tag, Myc-tag, S-tag, SBP-tag, Softag 3, V5 tag, Xpress tag, among others.

The term "host cell" refers to both single-cellular prokaryote and eukaryote organisms (e.g., bacteria, yeast, and actinomycetes) and single cells from higher order plants or animals when being grown in cell culture. Exemplary suitable host cells include *E. coli, S. cerevisiae* and *S. frugiperda*.

As used herein, "percentage of sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or "identity", in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% identity over a specified region), when compared and aligned for maximum correspondence over a comparison window, or designated region as measured using one of the following sequence comparison algorithms or by manual alignment and visual inspection. These definitions also refer to the complement of a test sequence. Optionally, the identity exists over a region that is at least about 50 nucleotides in length, or more typically over a region that is 100 to 500 or 1000 or more nucleotides in length.

The terms "similarity" or "percent similarity", in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarly exists over a region that is at least about 50 amino acids in length, or more typically over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (Adv. Appl. Math. 2:482, 1970), by the homology alignment algorithm of Needleman and Wunsch (J. Mol. Biol. 48:443, 1970), by the search for similarity method of Pearson and Lipman (Proc. Natl. Acad. Sci. USA 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Algorithms suitable for determining percent sequence identity and sequence similarity are the BLAST and BLAST 2.0 algorithms, which are described in Altschul et al. (Nuc. Acids Res. 25:3389-402, 1977), and Altschul et al. (J. Mol. Biol. 215:403-10, 1990), respectively. Software for performing BLAST analyses is publicly available through publicly available online and internet databases and the National Center for Biotechnology Information within the National Library of Medicine of the U.S. National Institutes of Health (http://www.ncbi.nlm.nih.gov/).

Rational Design of Taq DNA Polymerase Mutants

As outlined above, many strategies have been developed to improve discrimination of the polymerase chain reaction to selectively amplify a specific nucleic acid sequence based on the identity of a single nucleotide polymorphism, which in the past most often involved modifications introduced into the primer while using a naturally occurring DNA polymerase. The ability of DNA polymerases to discriminate between match and mismatch at the 3'-end of the primer nucleic acid is limited and varies greatly with the identity of the specific base pairs present. An alternative strategy to improve the selectivity of PCR amplification is to alter the properties of the DNA polymerase to improve discrimination between a primer that is a match versus one which has a terminal mismatch to the template nucleic acid. The present invention provides for DNA polymerase mutants having improved mismatch discrimination for base pairing at the 3'-terminus of the primer, leading to improved specificity of the ensuing amplification reaction.

The rhPCR method employs blocked-cleavable primers which must be unblocked by the action of RNase H2 before amplification can commence. The enzymatic unblocking step requires cleavage at a single internal RNA base within the primer, which is typically positioned at the SNP site. RNase H2 cleaves the RNA at the 5'-side, leaving a primer with a 3'-hydroxyl which is capable of priming PCR. Cleavage by RNase H2 occurs with high efficiency when the primer matches the template and with low efficiency when a mismatch is present due to a SNP. Therefore match templates are amplified with greater efficiency than mismatch templates. It is thought that the primary mechanism that permits amplification of mismatched templates begins with alternative cleavage of the substrate (i.e., the blocked-cleavable primer) at the 3'-side of the RNA residue, leading to inappropriate priming when a mismatch is present, retention of the RNA base in the primer, and conversion of the PCR product to primer sequence, which then faithfully replicates as a match in subsequent PCR cycles. Fidelity of the rhPCR process could be improved through improvements in the DNA polymerase which limit its ability to initiate DNA synthesis from a primer having a 3'-RNA residue. The present invention provides for DNA polymerase mutants having a reduced ability to initiate DNA synthesis from 3'-RNA containing primers, leading to improved specificity of the ensuing amplification reaction.

The present invention includes novel DNA polymerase mutants having improved discrimination for base identity at the 3'-end of the primer nucleic acid and/or DNA polymerase mutants having decreased priming efficiency from a 3'-RNA residue.

A novel design strategy was developed to rationally design DNA polymerase mutants having improved discrimination at the 3'-terminal base of the primer compared to discrimination of the native DNA polymerase, limiting the ability to initiate DNA synthesis if a mismatch is present or if an RNA residue is present. The process described herein employed the Taq DNA polymerase as the parent enzyme; the approach can be applied to other DNA polymerases, especially if crystal structure is known. The design strategy includes a first component based upon theoretical analyses of biophysical, biochemical and genetic information relating to the native DNA polymerase and, to a lesser extent, related polymerases which differ in amino acid sequence. The design strategy includes a second component based upon molecular biological and biochemical analyses of known genetically-engineered mutant polymerases to assist as a guide in predicting the effects of novel mutations in an attempt to rationally engineer new properties into the mutant polymerase, in this case to improve 3'-nucleotide discrimination.

In the first stage, the mechanism of Taq DNA polymerase enzymatic reaction based upon published mutational structure-activity-relationship (SAR) studies was analyzed and correlated with protein structure, when known, and predicted using molecular dynamic simulations when not known. The mechanism of enzyme catalysis has been described in the prior art (Patel, P. H., et al., J. Mol. Biol. 2001, 308:823-837; Li, Y. & Waksman, G., Protein Sci 2001, 10:1225-1233). Amino acid residues located at the C-terminus, from positions 424 to 832, are responsible for the primer extension catalytic activity of the protein. Taq DNA polymerase binds the primer-template duplex to form a binary complex. This allows an incoming substrate dNTP to bind in the pocket at the 3'-end of the primer to form an open ternary complex. If the dNTP is complementary to the template nucleotide, the active site changes conformation where the α-helix made from residues 659 to 671 rotates towards the site, and template base rotates towards the incoming dNTP, encouraging formation of a Watson-Crick base pair. This event "closes" the ternary complex, and brings the α-phosphate group of the dNTP close to the primer 3'-OH group. The oxygen of this hydroxyl group makes a nucleophilic attack on the phosphorus, forms a covalent bond and pyrophosphate is released. Taq DNA polymerase catalytic activity requires the presence of magnesium ions, which are assumed to facilitate deprotonation of the attacking hydroxyl group.

One criteria for rational design of Taq DNA polymerase mutants having improved 3'-nucleotide discrimination is to provide for novel polymerase enzyme variants having normal or near-normal polymerase processivity compared with the native DNA polymerase. For this reason, the first step of analysis serves to narrow the sequence space of amino acids that are available for alteration that should not compromise core enzymatic functions. For example, residues D610, D785, and E786 form the catalytic core. Their carboxylate groups are assumed to bind divalent metal ions, which in turn bind and stabilize the incoming dNTP and the terminal nucleotide of the primer. Mutations of these three essential residues are likely to render the polymerase inactive. Mutant polymerases which include alterations of residues D610, D785 and E786 were therefore excluded from consideration. Likewise, mutations that affect fidelity of complementary base recognition, such as residues that facilitate open to closed ternary complex formation at a complementary dNTP and the template base, were excluded from consideration.

Additional criteria of the first stage of analysis were to identify the polymerase amino acid residues in the vicinity of the 3' terminal nucleotide of the primer. For this purpose, the atomic three-dimensional structures of Taq DNA polymerase that are available from prior art (Eom, S. H., et al., Nature 1996, 382:278-281; Li, Y., et al., EMBO J. 1998, 17: 7514-7525; Doublie, S., et al., Structure 1999, 7:R31-R35; Li, Y., et al., Protein Sci 1998, 7:1116-1123) were selected for analyses. The structures were downloaded from the Protein Data Bank (H. M. Berman, et al., Nucleic Acids Research 2000, 28: 235-242). The structures of PDB ID 2KTQ and 3KTQ were thoroughly analyzed because they show the open and closed ternary complex of the large fragment of Taq DNA polymerase co-crystallized with primer and template nucleic acids (Li, Y., et al., EMBO J. 1998, 17: 7514-7525). This structure shows the location of the primer 3'-terminus at the active site and its interaction with key amino acid residues (FIG. 1).

For structure visualization, the hydrogen atom attached to the 2' carbon is replaced with a hydroxyl group for primers modified with a 3'-ribonucleotide. Those amino acid residues that are in close proximity to the 2' carbon of the nucleotide at the 3' terminus of the primer were selected for additional analysis. These amino acid residues are listed in the Table 2 and are most likely to interact with the primer 3'-terminal nucleotide. Mutation at these sites may affect catalytic activity of the polymerase when primer modifications, like OH, are attached to the 2' carbon atom of the ribose.

TABLE 2

Chemical groups in close vicinity to the 2' carbon of the terminal 3' primer nucleotide.

| Distance from C2' of the primer terminal residue[1] | Chemical group |
|---|---|
| ≤0.35 nm | dNTP to be added to primer |
| 0.35-0.40 nm | D785[2] |
| 0.40-0.45 nm | H784, V783 |
| 0.45-0.50 nm | R573 |
| 0.50-0.60 nm | E786[2] |

[1]The distances were measured in the PDB ID 2KTQ structure.
[2]Residues D785 and E786 are catalytic core residues.

A further aspect of this criterion relates to approaches to increase specificity while retaining catalytic activity of the polymerase. One approach to increasing specificity of Taq DNA polymerase would be to decrease the size of the binding pocket, so that a modified primer would not fit within it. Any additional chemical group will increases the volume of space occupied by the 3' nucleotide. To align atoms for effective catalysis and nucleophilic attack, the active site pocket must be flexible to accommodate additional atom(s), for example, the oxygen of the OH group of an RNA residue. The size of the active site can be decreased by substitution of neighboring amino acids with larger amino acids. Additional consideration is given to the amino acid properties and abilities of their side chains to engage in electrostatic and van der Waals interactions. Amino acid can be categorized into groups of positively charged (R, H, K), negatively charged (D, E), uncharged polar (S, T, N, Q), hydrophobic (A, V, I, L, M, F, Y, W), and special (C, G, P) side chains. Mutations within a group are conservative and are more likely to maintain existing properties while mutations across groups or within the special group amino acids are more likely to result in substantial changes of enzyme activity and/or specificity.

Another approach to increasing 3'-nucleotide discrimination of Taq DNA polymerase is to employ residue substitutions that decrease the flexibility of the binding pocket. Examples include substitution of amino acid aliphatic side chains with aromatic side chains, which lead to a higher energetic barrier to change rotamer conformations. As explained above, the residues of the catalytic core are preferably unaltered, residues spatially near the catalytic core are given the greatest attention for change. For example, three non-catalytic core residues of Table 2, H784, V783, and R573 are herein proposed to be substituted for larger or less flexible amino acids while the maintaining the general physical characteristics of their side chains. These residues exhibit key interactions with the ribose moiety of the primer through a water-mediated hydrogen-bonding network. R573 also binds to the primer base in the minor groove of primer-template duplex. Mutants ID 1 to ID 4 were designed using this strategy (Table 3). The next mutant, ID 5, Q582K, was designed to alter interactions with and the position of the important H784 residue. It is seen from the known crystal structure that Q582 is situated on the opposite side of H784 from the oligonucleotide primer. Substitution of Q582H may shift H784 towards the terminal primer nucleotide, leading to a more constrained binding pocket. The interactions of residue 582 with the next-to-terminal nucleotide may also be affected.

Residues that stack above the incoming dNTP molecule can also influence the size of the binding pocket in the polymerase active site. For example, substitutions at F667, which is located at this position, are known to change selectivity towards the incoming dNTP. For example, the F667Y substitution significantly improves incorporation of dideoxynucleoside triphosphates by Taq DNA polymerase (Tabor, S. & Richardson, C. C., Proc. Nat. Acad. Sci. USA 1995, 92:6339-6343), a useful property for DNA polymerases employed in Sanger method terminator DNA sequencing. Mutant ID 6 increases the size of the aromatic side chain of F667 from phenylalanine to tryptophan, in an attempt to push the dNTP against the primer terminal ribonucleotide and decrease ability of binding pocket to accommodate a 2' hydroxyl group, thereby biasing this mutant against primers containing a 3'-RNA residue. Mutant ID7 was designed based on similar conceptual framework. The H639 interacts with F667 amino acid and H639W mutant might also push F667 towards the incoming dNTP.

Additional mutations were considered that can effectively reduce the binding pocket size of the polymerase. Mutants IDs 8 to 16 were designed from a negative inferential analysis based on published studies of "relaxed specificity" mutant polymerases. Mutations have been reported that can modify polymerase specificity towards the ribose of the incoming dNTP. The prior art Taq DNA polymerase variants described were evolved from large random libraries either through selection or screening. Chen et al. described mutations that allow Taq DNA polymerase to incorporate a dNTP with large substituents on the ribose 3' carbon atom (Chen, F., et al., Proc. Nat. Acad. Sci. USA 2010, 107:1948-1953). This residue was found to be important because it also interacts with F667. The substitution L616A decreases specificity by giving more space to the phenylalanine residue. Mutant ID 8 (L616M) was designed to produce the opposite effect. The methionine substitution may subtly increase the steric constraints at this site compared to leucine. This restriction may make the active site less likely to accommodate extra substituents in a dNTP or in a primer nucleotide, which could reduce activity of 3'-RNA containing primers or those having a mismatch to template, which presumably occupies more space than primers having a perfect match to the template nucleic acid.

A similar conceptual framework was applied to design Taq DNA polymerase mutant ID 9. Mutations I614E, E615G were reported to relax the active site pocket, so that the polymerase could extend a primer using 2'-O-methyl ribonucleoside triphosphates (Fa, M., et al., J. Am. Chem. Soc. 2004, 126:1748-1754). The nature of these mutations is essentially the shift of glutamic acid from residue 615 to 614. A shift in the opposing direction, E615L, L616E may therefore impose constraints on the active site and produce a Taq DNA polymerase mutant that will not accept ribonucleotide residues.

Another approach to increasing 3'-nucleotide discrimination is to focus on sites of interest identified in Taq DNA polymerase studies that reported amino acid substitutions which increased base selection fidelity and decreased incorporation of mispaired base pairs (i.e., those mutation that improve replication fidelity). These changes could potentially affect selectivity of Taq DNA polymerase regarding to modifications of terminal primer nucleotide as well. One location that was reported to improve fidelity involves the F667 residue and neighboring amino acids (Suzuki, M., et al., J. Biol. Chem. 2000, 275:32728-32735). Another site of potential interest includes residues 782 to 784, adjacent to an essential aspartic acid residue (Strerath, M., et al., Chem Bio Chem 2007, 8:395-401). Mutants ID 10 to ID 13 were designed to alter amino acid character at these positions. F667 affects specificity as it interacts with the terminal base of the primer and stacks on the base of the incoming dNTP;

this residue resides in the O-helix. Residues 1665 and A661 are located on the opposite side of the helix. Mutation here to larger amino acids (A661E,I665W) may move the O-helix towards the active site, restricting the size of the active pocket and limiting ability of the polymerase to accept mispaired bases or RNA residues (Mutant ID 10: A661E, I665W,F667L).

Data derived from mutagenesis studies of different polymerases can also be used to help select positions for modification, but use of this data is more difficult in the absence of crystal structure or due to possible differences in effects between the polymerases. Polymerase I from *Escherichia coli* ("*E. coli* Pol") shows a somewhat similar structure at the active site when compared to Taq DNA polymerase and maintains identical essential catalytic residues. Both protein sequences exhibit high degree of homology (Li, Y., et al., EMBO J. 1998, 17: 7514-7525). Thus, mutations reported for *Escherichia coli* DNA polymerase were also considered, by extrapolating amino acid position to the corresponding positions in the Taq DNA polymerase. For example, the triplet amino acid substitutions, Q879P, V880L, H881Q, improved base fidelity of *E. coli* DNA polymerase (Summerer, D., et al., Angew. Chem. Int. Ed. 2005, 44:4712-4715). Substitutions in mutant ID 14 includes substitutions at Q782, V783, H784 in the Taq DNA polymerase active site, which appear to correspond to this *E. coli* residue triplet.

A number of additional substitutions in the *E. coli* DNA polymerase are known which decrease or increase the specificity of primer extension (Minnick, D. T., et al., J. Biol. Chem. 1999, 274:3067-3075). Mutants Q849A and R754A improved fidelity. These have locations equivalent to Q754 and R659 in the Taq DNA polymerase active site, respectively. Arginine 659 has a significant impact on selection of the base complementary to the template base. This appears to be general feature in the polymerase A family. For example, in *Thermotoga neapolitana* polymerase I, the equivalent residue is R722. Mutation of this residue to histidine increases fidelity of this polymerase (Yang, S. W., et al., Nucleic Acids Res. 2002, 30:4314-4320). These two residues were also selected for study (mutants ID 15 and 16 of Table 3). Mutant ID 17 represents combination of the mutations studied in Mutants ID 2 and 3. Mutant ID 18 represents a modification of triple mutant ID 14 (Q782P, V783L, H784Q) reduced to a double mutant (V783L, H784Q) by eliminating the Q782P mutation; the substitution of a less flexible P for Q residue will likely cause significant structural perturbation which would alter function, and Mut ID 18 may avoid this problem. Initial testing indicated that more than one mutant at position H784 showed improved mismatch discrimination, suggesting that this position was generally important for determining primer specificity. Therefore a comprehensive study of amino acid substitutions at this site was performed, comprising Mut IDs 19-36.

TABLE 3

Novel Taq DNA polymerase mutants selected for study.

| Mutant ID | Specific amino acid changes from sequence in Table I |
|---|---|
| 1 | V783I |
| 2 | V783F |
| 3 | H784Q |
| 4 | R573H |
| 5 | Q582K |
| 6 | F667W |

TABLE 3-continued

Novel Taq DNA polymerase mutants selected for study.

| Mutant ID | Specific amino acid changes from sequence in Table I |
|---|---|
| 7 | H639W |
| 8 | L616M |
| 9 | E615L, L616E |
| 10 | A661E, I665W, F667L |
| 11 | Q782I, H784F |
| 12 | Q782I, V783L, H784L |
| 13 | Q782S, V783F, H784N |
| 14 | Q782P, V783L, H784Q |
| 15 | Q754A |
| 16 | R659H |
| 17 | V783F, H784Q |
| 18 | V783L, H784Q |
| 19 | H784G |
| 20 | H784A |
| 21 | H784S |
| 22 | H784T |
| 23 | H784C |
| 24 | H784V |
| 25 | H784L |
| 26 | H784I |
| 27 | H784M |
| 28 | H784P |
| 29 | H784F |
| 30 | H784Y |
| 31 | H784W |
| 32 | H784D |
| 33 | H784E |
| 34 | H784N |
| 35 | H784K |
| 36 | H784R |

The second component of the design strategy includes molecular biological and biochemical analyses of genetically-engineered Taq DNA polymerase mutants to identify novel enzymes having improved 3'-nucleotide discrimination. This requires expression of native Taq DNA polymerase and the series of designed mutants in a suitable host, such as the bacterium *E. coli*. To maximize expression, the codons of the native gene sequence encoding Taq DNA polymerase were altered and optimized for expression in *E. coli* using standard codon usage tables for this organism (see: Codon usage tabulated from the international DNA sequence databases: status for the year 2000. Nakamura, Y., Gojobori, T. and Ikemura, T. (2000) *Nucleic Acids Res.* 28:292). Codon optimization does not alter the amino acid sequence of the expressed protein. A recombinant form of a codon-optimized gene encoding the unaltered Taq DNA polymerase peptide was assembled and cloned into a plasmid vector as an artificial gene made from synthetic oligonucleotides using standard methods (Example 1). The plasmid vector for this purpose can be any plasmid vector routinely available in the art. Synthetic recombinant forms of the series of identified desired Taq DNA polymerase mutants (Table 3, Mutant IDs 1-36) were prepared by site directed mutagenesis of the previously assembled codon-optimized recombinant native Taq DNA polymerase as the substrate for site directed mutagenesis (SDM), using techniques well known to those with skill in the art (Example 1). The unmodified and mutant Taq DNA polymerases were prepared from *E. coli* host cells following introduction of expression vectors that contain the corresponding recombinant forms of the genes operably linked to suitable transcriptional and translational control elements.

The enzymatic properties of the unmodified Taq DNA polymerase and mutant Taq DNA polymerases were evaluated for primer extension assays, thermostability, PCR assays, allele-specific PCR assays, ability to employ primers having a 3'-ribonucleotide, as well as their suitability for use in rhPCR assays. The mutant Taq DNA polymerases displayed one of four categories of enzymatic properties: (1) inactivated polymerase activity; (2) normal polymerase activity; (3) improved 3'-nucleotide discrimination activity, but having reduced activity (for example, reduced processivity); and (4) improved 3'-nucleotide discrimination and having normal or near normal polymerase activity (for example, processivity comparable to the native polymerase).

Mutant Taq DNA polymerases having the fourth category of enzymatic properties displayed comparable or enhanced 3'-mismatch discrimination (that is, comparable or improved performance in standard primer extension assays and allele-specific PCR assays when compared to the wild-type Taq DNA polymerase); enhanced 3'-nucleotide discrimination (that is, reduced primer extension activity from templates containing RNA-containing primers when compared to the wild-type Taq DNA polymerase) and enhanced rare allele discrimination (for example, improved specificity in rhPCR assay when compared to the wild-type Taq DNA polymerase). These mutant Taq DNA polymerases include mutations at one of the following residue position(s): (1) A661E; I665W; F667L triple substitution mutant peptide (Mutant ID 10 of Table 3); (2) V783F single substitution mutant peptide (Mutant ID 2 of Table 3); H784Q single substitution mutant peptide (Mutant ID 3 of Table 3); and V783L; H784Q double substitution mutant peptide (Mutant ID 18 of Table 3), H784A, single substitution mutant peptide (Mutant ID 20 of Table 3); H784S, single substitution mutant peptide (Mutant ID 21 of Table 3); H784T, single substitution mutant peptide (Mutant ID 22 of Table 3); H784V, single substitution mutant peptide (Mutant ID 24 of Table 3); H784I, single substitution mutant peptide (Mutant ID 26 of Table 3); H784M, single substitution mutant peptide (Mutant ID 27 of Table 3); H784F, single substitution mutant peptide (Mutant ID 29 of Table 3); and H784Y single substitution mutant peptide (Mutant ID 30 of Table 3).

Thus, the novel design algorithm provides a robust approach to predict mutant DNA polymerases having improved 3'-nucleotide discrimination, as adjudged by their activity in allele-specific PCR, rare allele detection assays and rhPCR assays that utilize templates with or without a 3'-RNA residue in the primer. Specifically, residues V783 and H784 were identified as critical residues which influence the ability of the polymerase to interrogate the status of the 3'-base of the primer oligonucleotide (e.g., whether this residue is matched or mismatched with template and/or whether this residue is DNA or RNA). The significance of these residues in polymerase function was heretofore not appreciated. In addition to the mutations directly testing in the example, the present invention also contemplates other amino acid substitutions at these two positions, or double-mutants affecting both the V783 and H784 sites.

The properties of these mutants are further described in the Examples presented herein. Importantly, however, the design strategy employed herein enables access to functional space for novel Taq DNA polymerase mutants that were previously unrecognized or predicted or otherwise not obtained using other approaches (for example, phylogenetic comparative analysis or earlier attempts using random mutagenesis).

Evaluation of Taq DNA Polymerase Mutants at Residue Positions 783 and 784

The present disclosure demonstrates that mutation at residue positions 783 and/or 784 results in active Taq DNA polymerase mutants having enhanced template discrimination activity, as compared to unmodified Taq DNA polymerase. Thus, the entirety of the sequence space that includes every conceivable single amino acid substitution at the individual positions 783 or 784 as well as every conceivable double amino acid substitution at both positions 783 and 784 fall within the scope of the present disclosure as related to Taq DNA polymerase. Accordingly, those active Taq DNA polymerase mutants selected from the mutant sets of 19 single residue 783 mutants, 19 single residue 784 mutants (Table 3 Mut IDs 19-30) and 361 double residue 783/784 mutants that also possess enhanced template discrimination activity fall within the scope of the present disclosure.

Because Taq DNA polymerase is a thermostable enzyme, one facile approach to screening the candidate collection of 399 single- and double-substitution mutants at residue positions 783 and 784 is to perform a PCR assay with a pre-treated sample encoding a candidate Taq DNA polymerase mutant enzyme. The sample can be a selected individual colony or corresponding micro-cultures (for example, 50 µL to 1.0 mL cultures) obtained from the individual colony transformed with recombinant DNA that expresses a desired recombinant Taq DNA polymerase mutant gene. The pre-treatment regimen can include the step of pre-incubating the sample at 70-95° C., followed by the step of clarifying the supernatant to remove the denatured cellular debris. For samples that express thermostable polymerase activity under standard PCR assay conditions, the corresponding recombination DNA can be further characterized to confirm the sequence of the desired recombinant Taq DNA polymerase mutant genotype and the polymerase protein purified for additional biochemical analysis. For the purposes of this disclosure, a Taq DNA polymerase mutant that expresses thermostable polymerase activity at a level of at least 0.01 of that expressed by wild-type Taq DNA polymerase under comparable PCR assay conditions can be adjudged as possessing thermostable polymerase activity.

Evaluation of Other Select Polymerase Candidate Mutants Functionally Homologous to Taq DNA Polymerase at Residue Positions 783 and 784

Comparative phylogenetic analysis tools can be used to identify the sequence space of other thermoactive polymerases having homologous sequence information relative to the unmodified Taq DNA polymerase at residue positions corresponding to V783 and H784. As explained supra, a strong prediction of the comparative phylogenetic analysis is that structural sequences shared among DNA polymerases across phylogenetically diverse species are conserved for functional reasons. If the identified V783/H784 residues of Taq DNA polymerase are invariant in sequence identity among wild-type polymerases from diverse species, that observation strongly supports the conclusion that nature selected against the specific variation of amino acid substitutions at those positions that result the observed enhanced template discrimination activity of the engineered Taq DNA polymerase mutants disclosed herein.

Example 11 provides an exemplary BLAST search using Taq DNA polymerase sequences encompassing positions V783 and H784 as a comparison window to identify candidate wild-type DNA polymerases from other species sharing extensive sequence identity with Taq DNA polymerase. As further elaborated in Example 11, the BLAST results revealed that virtually every identified DNA polymerase from diverse species has maintained Val and His at positions orthologous to V783 and H784 of Taq DNA polymerase. Thus, the BLAST results confirm a natural counter-selection against DNA polymerases having enhanced template discrimination activity and provide strong evidence that the disclosed engineered Taq DNA polymerase mutants having these properties are novel and non-obvious. Like that observed with the engineered Taq DNA polymerase mutants, each of the identified non-Taq DNA polymerases represent a sequence space from which engineered mutant enzymes can be generated having enhanced template discrimination activity, as compared to their respective unmodified counterparts.

In those cases where comparative phylogenetic analysis cannot access the sequence space of more evolutionary distant organisms, a comparative biophysical crystallographic analysis can provide clues to the relevant sequence residues having functional homology to Taq DNA polymerase resides V783 and H784. As explained supra, the Q782, V783 and H784 residue triplet of Taq DNA polymerase was selected for analysis based upon the corresponding triplet amino acid substitutions Q879P, V880L and H881Q of E. coli DNA polymerase having improved base fidelity and a similar active site architecture to that of Taq DNA polymerase. Conversely, based upon the noted enhanced template discrimination activity of V783 and H784 Taq DNA polymerase mutants relative to wild-type Taq DNA polymerase, the present disclosure contemplates that the corresponding substitutions at V880 and H881 of the E. coli DNA polymerase will possess enhanced template discrimination activity relative to wild-type E. coli DNA polymerase.

Identification and Characterization of Non-VH-Related Polymerase Mutants Having Enhanced Template Discrimination Activity.

The foregoing collection of DNA polymerases share extensively conserved sequences in the region corresponding to V783 and H784 of Taq DNA polymerase ("VH-related polymerases"). Comparative biophysical analysis is useful for identifying wild-type DNA polymerases having different amino acid sequences in the functionally homologous positions as V783 and H784 of Taq DNA polymerase ("non-VH-related DNA polymerases"). The instant disclosure contemplates engineering mutant polymerases having enhanced template discrimination activity from these non-VH-related DNA polymerases in the same manner as disclosed for the VH-related DNA polymerases. Candidate non-VH resides for directed mutagenesis and analysis by enhanced template discrimination activity assays include those resides within 0.40-0.45 nm of the C2' of the primer terminal residue, as revealed in the polymerase:template co-crystal structure.

Combination of Site-Specific Taq DNA Mutants with Deletion of the 5'-Exonuclease Domain.

The present invention discloses novel Taq DNA Polymerase mutants that show improved discrimination of mismatches positioned at the 3'-residue of the primer oligonucleotide and/or discrimination against the presence of an RNA residue at the 3'-end of the primer oligonucleotide. Improved mismatch discrimination has been described for the "KlenTaq" deletion mutant of Taq DNA Polymerase, which entirely removes the domain having 5'-exonuclease activity (Barnes, W. M., Gene 112:29-35, 1992). Combination of the novel mutants of the present invention with the KlenTaq 5'-exonuclease domain deletion led to further improvements in mismatch discrimination (Examples 18-22), however this combination led to decreases in enzymatic activity which may reduce utility of this family of double-mutants. In some circumstances, particularly when amplicon size is small and limited processivity could be tolerated, the enhanced decrimination of these mutants will have benefit.

Reaction Mixtures

In another aspect, reaction mixtures are provided comprising the polymerases with increased 3'-nucleotide discrimination activity. The reaction mixtures can further comprise reagents for use in, for example, nucleic acid amplification procedures (for example, PCR, RT-PCR, rhPCR), DNA sequencing procedures, or DNA labeling procedures. For example, in certain embodiments, the reaction mixtures comprise a buffer suitable for a primer extension reaction. The reaction mixtures can also contain a template nucleic acid (DNA and/or RNA), one or more primer or probe polynucleotides, nucleoside triphosphates (including, for example, deoxyribonucleotides, ribonucleotides, labeled nucleotides, unconventional nucleotides), salts (for example, $Mn^{2+}$, $Mg^{2+}$), and labels (for example, fluorophores). In some embodiments, the reaction mixture further comprises double stranded DNA binding dyes, such as SYBR green, or double stranded DNA intercalating dyes, such as ethidium bromide. In some embodiments, the reaction mixtures contain a 5'-sense primer hybridizable, under primer extension conditions, to a predetermined polynucleotide template, or a primer pair comprising the 5'-sense primer and a corresponding 3'-antisense primer. In certain embodiments, the reaction mixture further comprises a fluorogenic FRET hydrolysis probe for detection of amplified template nucleic acids, for example a Taqman® or Prime-Time® probe. In some embodiments, the reaction mixture contains two or more primers that are fully complementary to single nucleotide polymorphisms or multiple nucleotide polymorphisms. In some embodiments, the reaction mixtures contain alpha-phosphorothioate dNTPs, dUTP, dITP, and/or labeled dNTPs such as, for example, fluorescein- or cyanin-dye family dNTPs. In some embodiments, the reaction mixtures contain blocked-cleavable primers and RNase H2.

Kits

In another aspect, kits are provided for use in primer extension methods described herein. In some embodiments, the kit is compartmentalized for ease of use and contains at least one container providing a DNA polymerase of the invention having increased 3'-nucleotide discrimination in accordance with the present disclosure. One or more additional containers providing additional reagent(s) can also be included. Such additional containers can include any reagents or other elements recognized by the skilled artisan for use in primer extension procedures in accordance with the methods described above, including reagents for use in, for example, nucleic acid amplification procedures (for example, PCR, RT-PCR, rhPCR), DNA sequencing procedures, or DNA labeling procedures. For example, in certain embodiments, the kit further includes a container providing a 5'-sense primer hybridizable, under primer extension conditions, to a predetermined polynucleotide template, or a primer pair comprising the 5'-sense primer and a corresponding 3'-antisense primer. In some embodiments, the kit includes one or more containers containing one or more primers that are fully complementary to single nucleotide polymorphisms or multiple nucleotide polymorphisms, wherein the primers are useful for multiplex reactions, as described above. In some embodiments, the reaction mixtures contain one or more containers containing blocked-cleavable primers. In some embodiments, the reaction mixtures contain one or more containers containing RNase H2. In other, non-mutually exclusive variations, the kit includes one or more containers providing nucleoside triphosphates (conventional and/or unconventional). In specific embodiments, the kit includes alpha-phosphorothioate dNTPs, dUTP, dITP, and/or labeled dNTPs such as, for example, fluorescein- or cyanine-dye family dNTPs. In still other, non-mutually exclusive embodiments, the kit includes one or more containers providing a buffer suitable for a primer extension reaction. In some embodiments, the kit includes one or more labeled or unlabeled probes. Examples of probes include dual-labeled FRET (fluorescence resonance energy transfer) probes and molecular beacon probes. In another embodiment, the kit contains an aptamer, for example, for hot start PCR assays.

The present disclosure contemplates kits that provide novel DNA polymerases having enhanced template discrimination activity. As demonstrated in more detail in the examples, each DNA polymerase can display a unique signature of enhanced template discrimination activity. Certain DNA polymerases can display a relatively greater 3'-nucleotide discrimination, as compared to its other activities (3'-mismatch discrimination and rare allele discrimination), while other DNA polymerases can display a relatively greater 3'-mismatch discrimination, as compared to its other activities (3'-nucleotide discrimination and rare allele discrimination), and yet other DNA polymerases can display a relatively greater rare allele discrimination, as compared to its other activities (3'-nucleotide discrimination and 3'-mismatch discrimination). Accordingly, kits can include individual containers of specific DNA polymerases having an activity profile optimally tailored to a specific enhanced template discrimination activity for a specific assay platform. Alternatively, kits can include a single container that includes a plurality of DNA polymerases having an activity profile optimally tailored to accommodate enhanced template discrimination activity as may be needed for a plurality of assay platforms.

EXAMPLES

The present invention is further illustrated by reference to the following Examples. However, it should be noted that these Examples, like the embodiments described above, are illustrative and are not to be construed as restricting the enabled scope of the invention in any way.

Example 1. Cloning and Expression of a Codon Optimized DNA Polymerase from *Thermus aquaticus*

The amino acid and gene sequences for Taq DNA polymerase are known (Table 1, SEQ ID NOs. 1 and 2). Because codon usage differs among organisms, the codons of the native gene sequence encoding Taq DNA polymerase were optimized for expression in *E. coli* using standard codon usage tables (see: Codon usage tabulated from the international DNA sequence databases: status for the year 2000. Nakamura, Y., Gojobori, T. and Ikemura, T. (2000) *Nucleic Acids Res.* 28:292); synonymous codon changes were introduced to avoid repeated use of identical codons over a 20 amino acid stretch. A recombinant codon-optimized gene encoding the Taq DNA polymerase unmodified peptide was assembled from synthetic oligonucleotides using standard methods. The gene was made in three fragments, each of which was subcloned in a plasmid vector; sequences are shown in Table 4 (SEQ ID NOs. 3-5). Sequence identity was verified by Sanger DNA sequencing. The three Taq DNA polymerase subfragments were assembled together using the Gibson assembly method (Gibson, D. G. et al. Nature Methods, 343-345 (2009)) and cloned into a the plasmid expression vector pET-27b(+) using terminal Nde I and Not I restrictions sites to create a final, full-length codon optimized Taq DNA polymerase gene (designated "OptiTaq"). Sequence was verified by Sanger DNA sequencing; sequence is shown in Table 4 (SEQ ID NO. 6). The translated amino acid sequence of the new codon optimized gene is identical to native Taq DNA polymerase (Table 1, SEQ ID NO. 1).

TABLE 4

DNA sequence of Taq DNA Polymerase codon-optimized for expression in *E. coli*.

| Name | Sequence |
|---|---|
| SEQ ID NO. 3<br>Taq subfragment<br>#1 | CATATGCGTGGTATGCTGCCGTTGTTCGAGCCTAAAGGCCGCGTACTGTTAGTCGATGGTCA<br>TCACTTGGCCTATCGGACGTTCCATGCACTCAAAGGTCTGACGACCAGTCGTGGCGAACCGG<br>TCCAGGCTGTTTATGGTTTCGCTAAGTCTTTGCTCAAAGCACTGAAAGAAGACGGGGACGCG<br>GTAATTGTTGTATTTGATGCCAAAGCACCGAGCTTCCGCCACGAAGCTTATGGTGGCTACAA<br>GGCAGGACGCGCCCCTACCCCAGAAGATTTCCCCCGTCAGCTGGCATTAATTAAGGAGTTAG<br>TAGACCTTCTCGGCTTAGCGCGTCTGGAAGTTCCGGGTTATGAGGCGGACGATGTCCTTGCA<br>TCCTTGGCTAAAAAGGCCGAAAAAGAGGGCTACGAAGTCCGCATCTTGACGGCAGACAAAGA<br>TCTGTACCAGCTTCTGTCTGACCGTATTCATGTTTTGCACCCTGAAGGCTACTTAATCACTC<br>CGGCCTGGCTCTGGGAAAAGTACGGTCTGCGTCCCGATCAGTGGGCGGATTATCGGGCTTTG<br>ACGGGAGATGAGAGCGACAACCTGCCAGGAGTTAAGGGCATTGGTGAAAAAACCGCACGTAA<br>GCTGCTTGAAGAGTGGGGTTCCCTGGAAGCCTTGTTAAAAAATCTGGATCGTCTCAAGCCCG<br>CAATTCGTGAAAAGATCCTGGCTCATATGGACGATCTTAAATTAAGTTGGGACCTGGCCAAG<br>GTGCGCACCGATTTACCGCTTGAAGTGGATTTTGCAAAACGCCGTGAGCCGGACCGGGAACG<br>TTTACGCGCTTTCTTAGAGCGTCTGGAATTCGGTTCACTGCTTCATGAATTCGGTCTGT |
| SEQ ID NO. 4<br>Taq subfragment<br>#2 | TCGGTTCACTGCTTCATGAATTCGGTCTGTTAGAGTCTCCTAAAGCACTCGAAGAGGCACCG<br>TGGCCGCCCCCAGAAGGTGCTTTTGTTGGCTTCGTACTTTCCCGTAAGGAGCCTATGTGGGC<br>AGATCTTCTGGCTTTAGCGGCTGCACGCGGTGGCCGTGTTCACCGGGCCCCTGAGCCATACA<br>AAGCGTTACGTGATCTGAAGGAAGCACGTGGCTTGCTGGCAAAAGACCTTTCTGTTTTGGCC<br>CTGCGCGAGGGTCTTGGACTGCCGCCAGGCGACGATCCCATGTTATTGGCCTATCTGTTAGA<br>CCCTAGCAATACCACACCTGAAGGGGTCGCTCGTCGGTATGGCGGTGAATGGACTGAGGAAG<br>CCGGAGAGCGCGCCGCATTGTCCGAACGGCTCTTTGCAAACTTATGGGGTCGTCTGGAAGGG<br>GAGGAACGTCTGTTATGGTTGTATCGGGAAGTCGAACGTCCTCTTTCGGCCGTATTAGCGCA<br>TATGGAGGCAACAGGTGTGCGTTTAGATGTCGCGTACCTTCGGGCCTTATCACTGGAAGTTG<br>CAGAGGAAATCGCCCGTCTCGAGGCTGAAGTGTTCCGGTTGGCCGGTCACCCGTTTAACCTC |

TABLE 4-continued

DNA sequence of Taq DNA Polymerase codon-optimized for expression in E. coli.

| Name | Sequence |
| --- | --- |
| | AACTCCCGTGACCAGCTGGAACGCGTTTTATTCGATGAGCTTGGGCTTCCCGCAATTGGCAA<br>AACCGAAAAGACTGGCAAACGCAGTACGAGCGCTGCCGTCCTTGAGGCACTCCGCGAGGCTC<br>ACCCTATTGTAGAAAAGATCCTGCAATACCGTGAGTTGACGAAGCTTAAAAGCACTTATATT<br>GATCCTCTCCCGGATCTGATCCATCCTCGTACCGGCCGCTTGCACACACGTTTCAACCAGAC<br>GGCGACTGCAAC |
| SEQ ID NO. 5<br>Taq subfragment<br>#3 | CACACGTTTCAACCAGACGGCGACTGCAACCGGCCGTCTGTCTAGCTCGGATCCAAATCTCC<br>AGAACATTCCGGTCCGTACACCCTTGGGCCAACGTATCCGCCGGGCGTTTATCGCTGAGGAA<br>GGATGGTTACTGGTCGCATTGGACTACTCGCAGATTGAGCTGCGCGTCCTCGCACATCTCTC<br>TGGTGACGAAAATTTAATCCGCGTGTTTCAAGAGGGGCGTGATATTCACACAGAAACTGCCT<br>CATGGATGTTCGGTGTCCCACGTGAAGCAGTGGATCCTTTGATGCGCCGTGCAGCTAAAACA<br>ATTAATTTTGGAGTGCTGTACGGAATGAGCGCTCATCGCTTGAGTCAGGAACTGGCAATCCC<br>CTACGAGGAAGCGCAGGCATTCATCGAACGTTACTTTCAATCGTTTCCGAAAGTTCGCGCAT<br>GGATCGAGAAGACGCTCGAGGAAGGTCGTCGTCGGGGCTATGTCGAAACTCTGTTTGGTCGC<br>CGTCGGTACGTACCAGATCTTGAAGCCCGCGTCAAATCGGTACGGGAGGCTGCGGAGCGTAT<br>GGCATTTAATATGCCTGTACAGGGTACTGCAGCTGACCTCATGAAACTGGCAATGGTCAAGC<br>TTTTCCCGCGCTTGGAGGAAATGGGCGCACGTATGCTTCTGCAGGTCCATGACGAGCTGGTG<br>TTAGAAGCCCCTAAGGAGCGCGCCGAAGCTGTCGCGCGCCTCGCTAAAGAAGTGATGGAGGG<br>CGTTTACCCATTGGCCGTACCCCTCGAAGTGGAGGTCGGTATTGGAGAAGATTGGTTATCTG<br>CAAAGGAAGCGGCCGC |
| SEQ ID NO. 6<br>Complete codon-<br>optimized Taq<br>DNA polymerase<br>"OptiTaq" | <u>CATATG</u>CGTGGTATGCTGCCGTTGTTCGAGCCTAAAGGCCGCGTACTGTTAGTCGATGGTCA<br>TCACTTGGCCTATCGGACGTTCCATGCACTCAAAGGTCTGACGACCAGTCGTGGCGAACCGG<br>TCCAGGCTGTTTATGGTTTCGCTAAGTCTTTGCTCAAAGCACTGAAAGAAGACGGGGACGCG<br>GTAATTGTTGTATTTGATGCCAAAGCACCGAGCTTCCGCCACGAAGCTTATGGTGGCTACAA<br>GGCAGGACGCGCCCCTACCCAGAAGATTTCCCCCGTCAGCTGGCATTAATTAAGGAGTTAG<br>TAGACCTTCTCGGCTTAGCGCGTCTGGAAGTTCCGGGTTATGAGGCGGACGATGTCCTTGCA<br>TCCTTGGCTAAAAAGGCCGAAAAGAGGGCTACGAAGTCCGCATCTTGACGGCAGACAAAGA<br>TCTGTACCAGCTTCTGTCTGACCGTATTCATGTTTTGCACCCTGAAGGCTACTTAATCACTC<br>CGGCCTGGCTCTGGGAAAAGTACGGTCTGCGTCCCGATCAGTGGGCGGATTATCGGGCTTTG<br>ACGGGAGATGAGAGCGACAACCTGCCAGGAGTTAAGGGCATTGGTGAAAAAACCGCACGTAA<br>GCTGCTTGAAGAGTGGGGTTCCCTGGAAGCTTGTTAAAAAATCTGGATCGTCTCAAGCCCG<br>CAATTCGTGAAAAGATCCTGGCTCATATGGACGATCTTAAATTAAGTTGGGACCTGGCCAAG<br>GTGCGCACCGATTTACCGCTTGAAGTGGATTTTGCAAAACGCCGTGAGCCGGACCGGGAACG<br>TTTACGCGCTTTCTTAGAGCGTCTGGAATTCGGTTCACTGCTTCATGAATTCGGTCTGTTAG<br>AGTCTCCTAAAGCACTCGAAGAGGCACCGTGGCCGCCCCCAGAAGGTGCTTTTGTTGGCTTC<br>GTACTTTCCCGTAAGGAGCCTATGTGGGCAGATCTTCTGGCTTTAGCGGCTGCACGCGGTTG<br>CCGTGTTCACCGGGCCCCTGAGCCATACAAAGCGTTACGTGATCTGAAGGAAGCACGTGGCT<br>TGCTGGCAAAAGACCTTTCTGTTTTGGCCCTGCGCGAGGGTCTTGGACTGCCGCCAGGCGAC<br>GATCCCATGTTATTGGCCTATCTGTTAGACCCTAGCAATACCACACCTGAAGGGGTCGCTCG<br>TCGGTATGGCGGTGAATGGACTGAGGAAGCCGGAGAGCGCGCCGCATTGTCCGAACGGCTCT<br>TTGCAAACTTATGGGGTCGTCTGGAAGGGGAGGAACGTCTGTTATGGTTGTATCGGGAAGTC<br>GAACGTCCTCTTTCGGCCGTATTAGCGCATATGGAGGCAACAGGTGTGCGTTTAGATGTCGC<br>GTACCTTCGGGCCTTATCACTGGAAGTTGCAGAGGAAATCGCCCGTCTCGAGGCTGAAGTGT<br>TCCGGTTGGCCGGTCACCCGTTTAACCTCAACTCCCGTGACCAGCTGGAACGCGTTTTATTC<br>GATGAGCTTGGGCTTCCCGCAATTGGCAAAACCGAAAAGACTGGCAAACGCAGTACGAGCGC<br>TGCCGTCCTTGAGGCACTCCGCGAGGCTCACCCTATTGTAGAAAAGATCCTGCAATACCGTG<br>AGTTGACGAAGCTTAAAAGCACTTATATTGATCCTCTCCCGGATCTGATCCATCCTCGTACC<br>GGCCGCTTGCACACACGTTTCAACCAGACGGCGACTGCAACCGGCCGTCTGTCTAGCTCGGA<br>TCCAAATCTCCAGAACATTCCGGTCCGTACACCCTTGGGCCAACGTATCCGCCGGGCGTTTA<br>TCGCTGAGGAAGGATGGTTACTGGTCGCATTGGACTACTCGCAGATTGAGCTGCGCGTCCTC<br>GCACATCTCTCTGGTGACGAAAATTTAATCCGCGTGTTTCAAGAGGGGCGTGATATTCACAC<br>AGAAACTGCCTCATGGATGTTCGGTGTCCCACGTGAAGCAGTGGATCCTTTGATGCGCCGTG<br>CAGCTAAAACAATTAATTTTGGAGTGCTGTACGGAATGAGCGCTCATCGCTTGAGTCAGGAA<br>CTGGCAATCCCCTACGAGGAAGCGCAGGCATTCATCGAACGTTACTTTCAATCGTTTCCGAA<br>AGTTCGCGCATGGATCGAGAAGACGCTCGAGGAAGGTCGTCGTCGGGGCTATGTCGAAACTC<br>TGTTTGGTCGCCGTCGGTACGTACCAGATCTTGAAGCCCGCGTCAAATCGGTACGGGAGGCT<br>GCGGAGCGTATGGCATTTAATATGCCTGTACAGGGTACTGCAGCTGACCTCATGAAACTGGC<br>AATGGTCAAGCTTTTCCCGCGCTTGGAGGAAATGGGCGCACGTATGCTTCTGCAGGTCCATG<br>ACGAGCTGGTGTTAGAAGCCCCTAAGGAGCGCGCCGAAGCTGTCGCGCGCCTCGCTAAAGAA<br>GTGATGGAGGGCGTTTACCCATTGGCCGTACCCCTCGAAGTGGAGGTCGGTATTGGAGAAGA<br>TTGGTTATCTGCAAAGGAA<u>GCGGCCGC</u> |

For the final completed "OptiTaq" clone, Nde I and Not I restrictions sites are underlined. The ATG start codon is identified in bold font.

Example 2. Production of Codon Optimized Taq DNA Polymerase Mutants

Eighteen mutant versions of Taq DNA polymerase (Table 3, Mut IDs 1-18) were made by site directed mutagenesis of the cloned OptiTaq codon-optimized Taq DNA polymerase. Specific mutations were introduced into the OptiTaq sequence using the method of PCR site-directed mutagenesis (Weiner M P, et al., Gene. 151(1-2):119-23 (1994)). Each mutagenesis reaction employed 10 pmoles of two complementary oligonucleotides (Table 5) containing the desired base changes, annealed to the double-stranded Opti-Taq plasmid (20 ng), 5 U KOD DNA polymerase (Novagen-EMD Chemicals, San Diego, Calif.), 1.5 mM MgSO$_4$, in 1×KOD PCR buffer. Thermal cycling parameters were 95° C. for 3 minutes (95° C. for 20 sec-55° C. for 20 sec-70° C. for 2.5 minutes) for 16 cycles followed by a 70° C. soak for 4 minutes. After PCR site-directed mutagenesis, the amplified product was treated with 10 U of Dpn I (NEB, Ipswich, Mass.), at 37° C. for 1 hour, followed by inactivation at 80° C. for 20 minutes. $\frac{1}{110}^{th}$ of the digestion material was transformed into XL-1 Blue competent bacteria. Bacterial clones were isolated, plasmid DNA prepared, and individual mutations were confirmed by Sanger DNA sequencing. All mutants remained in the pET-27b(+) expression vector, which is suitable for expressing the recombinant proteins in *E. coli*.

TABLE 5

Oligonucleotides used for site-directed mutagenesis to produce 18 Taq DNA Polymerase mutants.

| Mutant ID | Amino acid changes | Sequence" Sense mutagenesis oligonucleotide | SEQ ID No. | Sequence" Antisense mutagenesis oligonucleotide | SEQ ID No. |
|---|---|---|---|---|---|
| 1 | V783I | aatgggcgcacgtatgcttct gcagATTcatgacgagctggt gttagaagccc | 7 | gggcttctaacaccagctcgtca tgAATctgcagaagcatacgtgc gcccatt | 8 |
| 2 | V783F | aatgggcgcacgtatgcttct gcagTTCcatgacgagctggt gttagaagccc | 9 | gggcttctaacaccagctcgtca tgGAActgcagaagcatacgtgc gcccatt | 10 |
| 3 | H784Q | gggcgcacgtatgcttctgca ggtcCAGgacgagctggtgtt agaagcccta | 11 | taggggcttctaacaccagctcg tcCTGgacctgcagaagcatacg tgcgccc | 12 |
| 4 | R573H | caaccagacggcgactgcaac cggcCATctgtctagctcgga tccaaatctcc | 13 | ggagatttggatccgagctagac agATGgccggttgcagtcgccgt ctggttg | 14 |
| 5 | Q582K | tctgtctagctcggatccaaa tctcAAAaacattccggtccg tacacccttgg | 15 | ccaagggtgtacggaccggaatg ttTTTgagatttggatccgagct agacaga | 16 |
| 6 | F667W | gcgccgtgcagctaaaacaat taatTGGggagtgctgtacgg aatgagcgctc | 17 | gagcgctcattccgtacagcact ccCCAattaattgttttagctgc acggcgc | 18 |
| 7 | H639W | cgtgtttcaagagggcgtga tattTGGacagaaactgcctc atggatgttcg | 19 | cgaacatccatgaggcagtttct gtCCAaatatcacgcccctcttg aaacacg | 20 |
| 8 | L616M | cgcattggactactcgcagat tgagATGcgcgtcctcgcaca tctctctggtg | 21 | caccagagagatgtgcgaggacg cgCATctcaatctgcgagtagtc caatgcg | 22 |
| 9 | E615L L616E | ggtcgcattggactactcgca gattCTGGAGcgcgtcctcgc acatctctctggtg | 23 | caccagagagatgtgcgaggacg cgCTCCAGaatctgcgagtagtc caatgcgacc | 24 |
| 10 | A661E I665W F667L | cgtgaagcagtggatcctttg atgcgccgtGAAgctaaaaca TGGaatTTGggagtgctgtac ggaatgagcgctcatcgc | 25 | gcgatgagcgctcattccgtaca gcactcCAAattCCAtgtttta gcTTCacggcgcatcaaaggatc cactgcttcacg | 26 |
| 11 | Q782I H784F | ggaaatgggcgcacgtatgct tctgATCgtcTTCgacgagct ggtgttagaagcccta | 27 | taggggcttctaacaccagctcg tcGAAgacGATcagaagcatacg tgcgcccatttcc | 28 |
| 12 | Q782I V783L H784L | ggaaatgggcgcacgtatgct tctgATTTTGCTGgacgagct ggtgttagaagcccta | 29 | taggggcttctaacaccagctc tcCAGCAAAATcagaagcatacg tgcgcccatttcc | 30 |
| 13 | Q782S V783F H784N | ggaaatgggcgcacgtatgct tctgTCCTTCAACgacgagct ggtgttagaagcccta | 31 | taggggcttctaacaccagctcg tcGTTGAAGGAcagaagcatacg tgcgcccatttcc | 32 |

TABLE 5-continued

Oligonucleotides used for site-directed mutagenesis to produce 18 Taq DNA Polymerase mutants.

| Mutant ID | Amino acid changes | Sequence" Sense mutagenesis oligonucleotide | SEQ ID No. | Sequence" Antisense mutagenesis oligonucleotide | SEQ ID No. |
|---|---|---|---|---|---|
| 14 | Q782P V783L H784Q | ggaaatgggcgcacgtatgct tctgCCGTTACAGgacgagct ggtgttagaagcccta | 33 | tagggcttctaacaccagctcg tcCTGTAACGGcagaagcatacg tgcgcccatttcc | 34 |
| 15 | Q754A | gcgtatggcatttaatatgcc tgtaGCGggtactgcagctga cctcatgaaac | 35 | gtttcatgaggtcagctgcagta ccCGCtacaggcatattaaatgc catacgc | 36 |
| 16 | R659H | acgtgaagcagtggatccttt gatgCACcgtgcagctaaaac aattaattttg | 37 | caaaattaattgttttagctgca cgGTGcatcaaaggatccactgc ttcacgt | 38 |
| 17 | V783F H784Q | aatgggcgcacgtatgcttct cagTTCCAGgacgagctggt gttagaagc | 39 | GcttctaacaccagctcgtcCTG GAActgcagaagcatacgtgcgc ccatt | 40 |
| 18 | V783L H784Q | aatgggcgcacgtatgcttct gcagCTGCAGgacgagctggt gttagaagccc | 41 | gggcttctaacaccagctcgtcC TGCAGctgcagaagcatacgtgc gcccatt | 42 |

DNA bases identical to codon optimized OptiTaq are shown in lower case; those specific for the mutations introduced by site-directed mutagenesis are shown in upper case.

Example 3. Expression of Recombinant Taq DNA Polymerases

The following example demonstrates the expression of recombinant Taq DNA polymerase unmodified and mutant peptides. The synthetic gene sequences from Examples 1, 2 and 12 were cloned in the pET-27b(+) expression vector (Novagen, EMD Biosciences, La Jolla, Calif.). This vector places six histidine residues (which together comprise a "His-tag") at the carboxy terminus of the expressed peptide, followed by a stop codon. A "His-tag" permits use of rapid, simple purification of recombinant proteins using $Ni^{2+}$ affinity chromatography methods which are well known to those with skill in the art. Alternatively, the synthetic genes could be expressed in native form without the His-tag and purified using size exclusion chromatography, anion-exchange chromatography, or other such methods, which are also well known to a person of ordinary skill in the art.

BL21(DE3) competent E. coli cells (Novagen) were transformed with ~1 ng of each plasmid. Briefly, plasmids were added to the cells on ice and gently stirred. After a 5 minute incubation on ice, cells were heat shocked at 42° C. for 30 seconds, then returned to ice for 2 minutes. Room temperature SOC (80 µL) was added to the transformed cells, followed by a 1 hour outgrow period at 37° C., with agitation at 250 rpm. Cells were plated (20 µL) on 37° C. pre-warmed LB/Kan plates (Luria Broth agar plates supplemented with 50 µg/mL kanamycin) and were placed at 37° C. overnight. The next morning, one colony was picked and grown (37° C., 250 rpm) in 10 mL LB/Kan broth (50 µg/mL) to log phase ($OD_{600}$ 0.3-0.9). Cells were then induced with Overnight Express™ Autoinduction System 1 (Novagen) in Terrific Broth at 37° C., 250 rpm following the protocol recommended by the manufacturer. Culture volumes were 100 mL for wild type OptiTaq and 200 mL for mutants. Growth saturation was reached after 18 hours, and the culture was pelleted at 10,000×g for 10 minutes in a Beckman Avanti™ J-25 Centrifuge. The pellet (~6 g) was lysed using 30 mL BugBuster® Protein Extraction Reagent (Novagen), 30 kU rLysozyme™ Solution (Novagen) and 1500 U DNase I (Life Technologies, Grand Island, N.Y.) to release soluble proteins and degrade nucleic acids according to the manufacturer's instructions. Following centrifugation at 15,000×g for 20 minutes to remove cell debris, the lysates were heated at 75° C. for 15 minutes to inactive DNase I and other cellular nucleases. The lysates were then spun at 15,000×g for 20 minutes to sediment denatured protein. The heat denaturation and centrifugation steps provide significant purity enrichment of the recombinant enzymes. Both "total" and "soluble" fractions of the bacterial lysates were analyzed using SDS 4-20% polyacrylamide gel electrophoresis for 1 hour at 125 V. Proteins were visualized with Coomassie Blue staining for 1 hour, followed by 3-4 rounds of destaining until protein bands were clear.

The recovered soluble protein was passed over a $Ni^{2+}$ affinity column containing His-Bind Resin (Novagen) and eluted with a buffer containing 200 mM imidazole (200 mM imidazole, 500 mM NaCl, 20 mM Tris-HCl, pH 7.9). The purified protein (~6 mL) was then concentrated at 3210×g in a Beckman Coulter 6R tabletop centrifuge swinging bucket rotor using an Amicon Ultra-15, PLGC Ultracel-PL Membrane, 10 KDa concentrator (EMD Millipore, Billerica, Mass.) to ~200 µL and stored at −20° C. until dialysis. The concentrated protein was then dialyzed against storage buffer (20 mM Tris pH7.5, 100 mM NaCl, 1 mM DTT, 0.1 mM EDTA, 50% glycerol, 0.1% Triton X-100) at 4° C. overnight, followed by 3×2 hours (at 1000 fold ratio of protein solution to dialysis buffer each time). The final purified protein was stored at −20° C. Using this protocol, 100 mL of an autoinduced culture yielded ~1.2 mg/67.6 µM/12,168 pmol of purified soluble protein for OptiTaq. Similar yields were obtained for the mutant DNA polymerases.

To determine protein concentration, samples were examined alongside known quantities of BSA (bovine serum albumin) using SDS 4-20% polyacrylamide gel electrophoresis for 1 hour. Proteins were visualized with Coomassie Blue staining for 1 hour, followed by 3-4 rounds of destaining until protein bands were clear. Band intensity was analyzed using ImageJ software (National Institutes of Health, Bethesda, Md.).

To evaluate purity and quality of the recombinant protein preparations, 500 ng of each recombinant protein (wild type OptiTaq and each mutant) were separated on a 4-20% SDS-PAGE gel, stained with Coomassie Blue, and visualized. The recombinant proteins all migrate at the appropriate position on the gel for proteins having a molecular weight of 97.1 kDa. The preparations show relatively high purity with few additional species detected. Gel images are shown in FIGS. 2A, 2B, 2C, and 2D. Similar gels were run for MUT IDs 22 (H784T), 24 (H784V), 30 (H784Y), 31 (H784W), and 35 (H784K), and single bands corresponding to the desired recombinant protein were visualized (data not shown).

The purified enzymes were tested for nuclease contamination using DNaseAlert™ and RNaseAlert® nuclease detection kits (Integrated DNA Technologies, Coralville, Iowa) following protocols recommended by the manufacturer. All enzyme preparations were determined to be free of contaminating nucleases.

Example 4. Characterization of Properties of 18 Mutant Taq DNA Polymerases in PCR The 18 mutant Taq DNA polymerase enzymes described in Example 3 were characterized for polymerase activity and the ability to discriminate a 3'-RNA residue in the primer oligonucleotide.

The unit activity of the purified wild-type protein was determined by comparing performance in qPCR of known quantities of OptiTaq and each mutant compared to a commercial non-hot-start Taq DNA polymerase, Taq-B DNA Polymerase (Enzymatics, Beverly, Mass.). Quantification cycle values (Cq, the amplification cycle number at which positive signal is first detected) and amplification curve shapes were analyzed to determine the nanogram amounts at which both enzymes performed similarly in the suboptimal range for each. Using these nanogram amounts and known unit values of Taq-B DNA polymerase, relative activity unit values could be extrapolated for all of the mutant DNA polymerase enzymes having sufficient activity to support PCR.

The following reaction conditions were employed: 1× qPCR buffer (20 mM Tris pH 8.4, 50 mM KCl, 3 mM MgCl$_2$, 0.01% Triton-X100), 800 µM dNTPs (200 µM each), 500 nM For primer (Hs HPRT F517, SEQ ID NO. 43), 500 nM Rev primer (Hs HPRT R591, SEQ ID NO. 44), 250 nM probe (Hs HPRT P554, SEQ ID NO. 45), 2×10$^3$ copies of linearized cloned plasmid template (HPRT-targ, SEQ ID NO. 46), in 10 µL final volume. The amount of DNA polymerase added to each reaction was varied as follows: for wild type (OptiTaq), reactions were set using 10, 1, 0.1, 0.01, and 0.001 U/µL (220, 22, 2.2, 0.22, or 0.022 ng of protein per 10 µL reaction). Mutant polymerases were run in similar concentrations. In addition, those mutant enzymes showing polymerase activity were more finely titrated testing 220, 22, 10.6, 4.8, 2.2, 1.1, 0.48, and 0.22 ng of protein per 10 µL reaction. Enzyme dilutions were made in enzyme dilution buffer (20 mM Tris pH7.5, 100 mM NaCl, 1 mM DTT, 0.1% Triton-X100, 1 mg/mL BSA, 10% glycerol). Reactions were run in 384 well format on a BIO-RAD CFX384™ Real-Time System (BIO-RAD, Hercules, Calif.) using cycling parameters 95° C. for 30 seconds followed by 60 cycles of [95° C. for 15 seconds followed by 60° C. for 1 minutes]. Detection was achieved using a fluorescence-quenched probe (5'-nuclease assay format, note that the mutations introduced into the present series of Taq mutants do not lie in the 5'-nuclease domain). Sequences of the primers, probe, and template (plasmid insert) are shown in Table 6.

TABLE 6

Sequence of oligonucleotides employed in Taq DNA polymerase activity assay.

| Name | Sequence | SEQ ID NO. |
| --- | --- | --- |
| Hs HPRT F517 | GACTTTGCTTTCCTTGGTCAG | SEQ ID NO. 43 |
| Hs HPRT R591 | GGCTTATATCCAACACTTCGTG | SEQ ID NO. 44 |
| Hs HPRT P554 | FAM-ATGGTCAAG(ZEN)GTCGCAAGCTTGCTGGT-IBFQ | SEQ ID NO. 45 |
| HPRT-targ | GACTTTGCTTTCCTTGGTCAGGCAGTATAATCCAAAGATGGTCAAGGTC GCAAGCTTGCTGGTGAAAAGGACCCCACGAAGTGTTGGATATAAGCC | SEQ ID NO. 46 |

Nucleic acid sequences are shown 5'-3'.
FAM = 6-carboxyfluorescein, IBFQ = Iowa Black FQ (fluorescence quencher), and ZEN = ZEN internal fluorescence quencher.

These 18 Taq DNA polymerase mutants were characterized as outlined above. Results are summarized in Table 7. Six mutants, including Mutant IDs 4, 5, 9 12, 13, and 17, did not show detectable DNA polymerase activity and were not studied further. Six mutants, Mutant IDs 6, 7, 11, 14, 15, and 16 had DNA polymerase activity; however, processivity was reduced from 4-50 fold relative to the wild type enzyme. Six mutants, Mutant IDs 1, 2, 3, 8, 10, and 18, showed DNA polymerase activity similar to wild type OptiTaq.

TABLE 7

Novel Taq DNA polymerase mutants selected for initial study.

| Mutant ID | Amino acid changes from wild-type Taq | Polymerase Activity | Relative activity* | ΔCq Delay in priming from an RNA base** |
| --- | --- | --- | --- | --- |
| 1 | V783I | Yes | 1 | 0 |
| 2 | V783F | Yes | 1 | 1 |
| 3 | H784Q | Yes | 1 | 1 |
| 4 | R573H | No | — | — |

TABLE 7-continued

Novel Taq DNA polymerase mutants selected for initial study.

| Mutant ID | Amino acid changes from wild-type Taq | Polymerase Activity | Relative activity* | ΔCq Delay in priming from an RNA base** |
|---|---|---|---|---|
| 5 | Q582K | No | — | — |
| 6 | F667W | Yes | 0.25 | 9 |
| 7 | H639W | Yes | 0.02 | 20 |
| 8 | L616M | Yes | 1 | 0 |
| 9 | E615L, L616E | No | — | — |
| 10 | A661E, I665W, F667L | Yes | 1 | 2.9 |
| 11 | Q782I, H784F | Yes | 0.20 | 2 |
| 12 | Q782I, V783L, H784L | No | — | — |
| 13 | Q782S, V783F, H784N | No | — | — |
| 14 | Q782P, V783L, H784Q | Yes | 0.02 | 2.5 |
| 15 | Q754A | Yes | 0.2 | >35 |
| 16 | R659H | Yes | 0.1 | >35 |
| 17 | V783F, H784Q | No | — | — |
| 18 | V783L, H784Q | Yes | 1 | 1 |

*Wild-type OptiTaq was set to "1" and the relative activity of each of the mutant polymerases was normalized to this amplification efficiency, with 1 as the maximum.
**ΔCq = [Cq Mutant ID X] − [Cq OptiTaq] when qPCR reactions are run using primers having a 3'-RNA residue.

The subset of these mutant Taq DNA polymerases which showed DNA polymerase activity were studied for their ability to discriminate between primers having a 3'-DNA versus a 3'-RNA residue relative to the wild type OptiTaq enzyme. Real-time PCR was performed as before, employing in the reactions the amount of each mutant DNA polymerase equal to 0.5 units of wild-type OptiTaq per 10 µL reaction. The following reaction conditions were employed: 1× qPCR buffer (20 mM Tris pH 8.4, 50 mM KCl, 3 mM $MgCl_2$, 0.01% Triton-X100), 800 µM dNTPs (200 µM each), 500 nM For primer (Hs SFRS9 F569 rU, SEQ ID NO. 47), 500 nM Rev primer (Hs SFRS9 R712 rA, SEQ ID NO. 48), 250 nM probe (Hs SFRS9 P644, SEQ ID NO. 49), $2 \times 10^3$ copies of linearized cloned plasmid template (SFRS9-targ, SEQ ID NO. 50), in 10 µL final volume. Reactions were run in 384 well format on a BIO-RAD CFX384™ Real-Time System (BIO-RAD, Hercules, Calif.) using cycling parameters 95° C. for 30 seconds followed by 60 cycles of [95° C. for 15 seconds followed by 60° C. for 1 minutes]. Detection was achieved using a fluorescence-quenched probe (5'-nuclease assay format). Sequences of the primers, probe, and template (plasmid insert) are shown in Table 8.

as outlined above. Results are summarized in Table 7. Mutant IDs 1 and 8 did not show any difference between primers having a 3'-DNA versus a 3'-RNA residue. Mutant IDs 2, 3, 6, 7, 10, 11, 14, 15, 16, and 18 showed an amplification delay using 3'-RNA primers. Thus the rational design strategy employed herein was successful and Taq DNA polymerase mutants were identified which discriminated against priming from a 3'-RNA residue. Those mutants which showed some delay with RNA priming and showed high processivity were studied for improvements in primer 3'-residue mismatch discrimination.

Example 5: Improved Mismatch Discrimination in Allele-Specific PCR Using Mutant Taq DNA Polymerases Of the 18 mutant enzymes studied in Example 4, Mutant IDs 2, 3, 10, and 18 showed the ability to discriminate against a 3'-RNA residue in the primer and retained high enzymatic activity/processivity. These four mutants were studied for the ability to discriminate against a 3'-terminal DNA mismatch compared with wild type OptiTaq DNA polymerase using an allele-specific qPCR assay. Amplification reactions were performed against a synthetic oligonucleotide template where a single base was varied (SNP) which was positioned to lie at the 3'-end of the reverse primer. Synthetic templates were employed having each of the 4 possible bases at this position. Reverse primers were employed having each of the 4 possible bases at the 3'-end. Relative amplification efficiency for all pairwise combinations was assessed using qPCR.

Quantitative allele-specific real-time PCR (AS-qPCR) was performed in 10 µL reaction volumes in 384 well format with $2 \times 10^3$ copies of a 103 bp synthetic template (SEQ ID NOs. 51-4). Final reaction conditions used were 20 mM Tris-HCL (pH 8.4 at 25° C.), 50 mM KCL, and 3 mM $MgCl_2$, 0.01% Triton X-100, 800 µM total dNTPs, and 200 nM of the universal forward primer (SEQ ID NO. 60), 200 nM of a reverse primer (separate reactions were set up for each of the allele-specific primers SEQ ID NOs. 55-58 or the control universal primer SEQ ID NO. 59) and 200 nM of the 5' nuclease detection probe (SEQ ID NO. 61). Each allele-specific primer was tested on each SNP template. Reactions utilized either 0.5 U (10.8 ng/11.1 nM/111 fmol) of the wild

TABLE 8

Sequence of oligonucleotides employed in the primer 3'-RNA discrimination assay.

| Name | Sequence | SEQ ID NO. |
|---|---|---|
| Hs SFRS9 F569 rU | TGTGCAGAAGGATGGAGu | SEQ ID NO. 47 |
| Hs SFRS9 R712 rA | CTGGTGCTTCTCTCAGGATa | SEQ ID NO. 48 |
| Hs SFRS9 P644 | HEX-TGGAATATG(ZEN)CCCTGCGTAAACTGGA-IBFQ | SEQ ID NO. 48 |
| SFRS9-targ | TGTGCAGAAGGATGGAGTGGGGATGGTCGAGTATCTCAGAAAAGAAGACATGGAATATGCCCTGCGTAAACTGGATGACACCAAATTCCGCTCTCATGAGGGTGAAACTTCCTACATCCGAGTTTATCCTGAGAGAAGCACCAG | SEQ ID NO. 50 |

Nucleic acid sequences are shown 5'-3' with DNA uppercase and RNA lowercase.
HEX = hexachlorofluorescein, IBFQ = Iowa Black FQ (fluorescence quencher), and ZEN = ZEN fluorescence quencher.

The 12 Taq DNA polymerase mutants that supported PCR were tested for the ability to use a 3'-RNA modified primer type OptiTaq DNA polymerase or 0.5 U of one of the 4 Taq DNA polymerase mutants studied (MUT ID No. 2 V783F, MUT ID NO. 3 H784Q, MUT ID NO. 10 A661E I665W F667L, or MUT ID NO. 18 V783L H784Q). Amplification was performed on a CFX384™ C1000™ Thermo Cycler system (Bio-Rad, Hercules, Calif.) using the following cycling parameters: 95° C. for 30 seconds initial denaturation followed by 60 cycles of 95° C. for 10 seconds, then 60° C. for 30 seconds. Oligonucleotide reagents used in this example are shown in Table 9.

TABLE 9

Synthetic oligonucleotides employed in Example 5.

| Name | Sequence (5'-3') | SEQ ID NO. |
|---|---|---|
| A Template | AGCTCTGCCCAAAGATTACCCTGACAGCTAAGTGGCAGTGGAA GTTGGCCTCAGAAGTAGTGGCCAGCTGTGTGTCGGGGAACAGT AAAGGCATGAAGCTCAG | SEQ ID NO. 51 |
| C Template | AGCTCTGCCCAAAGATTACCCTGACAGCTAAGTGGCAGTGGAA GTTGGCCTCAGAAGTAGTGGCCAGCTGTGTGTCGGGGCACAGT AAAGGCATGAAGCTCAG | SEQ ID NO. 52 |
| G Template | AGCTCTGCCCAAAGATTACCCTGACAGCTAAGTGGCAGTGGAA GTTGGCCTCAGAAGTAGTGGCCAGCTGTGTGTCGGGGGACAGT AAAGGCATGAAGCTCAG | SEQ ID NO. 53 |
| T Template | AGCTCTGCCCAAAGATTACCCTGACAGCTAAGTGGCAGTGGAA GTTGGCCTCAGAAGTAGTGGCCAGCTGTGTGTCGGGGTACAGT AAAGGCATGAAGCTCAG | SEQ ID NO. 54 |
| Syn Rev T | CTGAGCTTCATGCCTTTACTGTT | SEQ ID NO. 55 |
| Syn Rev C | CTGAGCTTCATGCCTTTACTGTC | SEQ ID NO. 56 |
| Syn Rev A | CTGAGCTTCATGCCTTTACTGTA | SEQ ID NO. 57 |
| Syn Rev G | CTGAGCTTCATGCCTTTACTGTG | SEQ ID NO. 58 |
| Syn Rev | CTGAGCTTCATGCCTTTACTGT | SEQ ID NO. 59 |
| Syn For | AGCTCTGCCCAAAGATTACCCTG | SEQ ID NO. 60 |
| Syn Probe | FAM-TTCTGAGGC(ZEN)CAACTTCCACTGCCACTTA-IBFQ | SEQ ID NO. 61 |

DNA bases are uppercase; FAM = 6-carboxyfluorescein; IBFQ = Iowa Black™ FQ fluorescence quencher; ZEN = internal ZEN fluorescence quencher; underlined base indicates the SNP site in the synthetic template DNA.

Figure 3A:
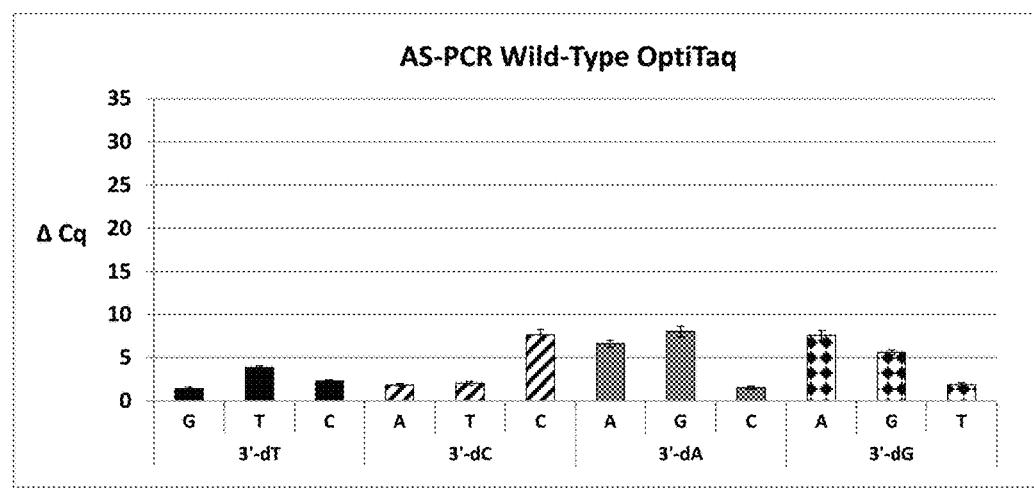
FIG. 3A shows graphical representations of the allele-specific PCR (AS-PCR) data from Tables 10 and 31 for wild type OptiTaq (sub-panel (i)), Mutant ID 2 (sub-panel (ii)) and Mutant ID 3 (sub-panel (iii)). Legend: Average ΔCq values obtained from AS-PCR reactions plus/minus standard deviation (error bars) are shown (ΔCq=Cq mismatch−Cq match) comparing mismatch discrimination of the wild-type OptiTaq with the mutant Taq DNA polymerases. All possible pairwise mismatch base combinations are included. The base identity of the SNP site in the target nucleic acid is indicated on the X-axis (A, G, C, T) along with the 3'-DNA residue of the AS-PCR reverse primer employed (dA, dG, dC, dT).
Figure 3A:
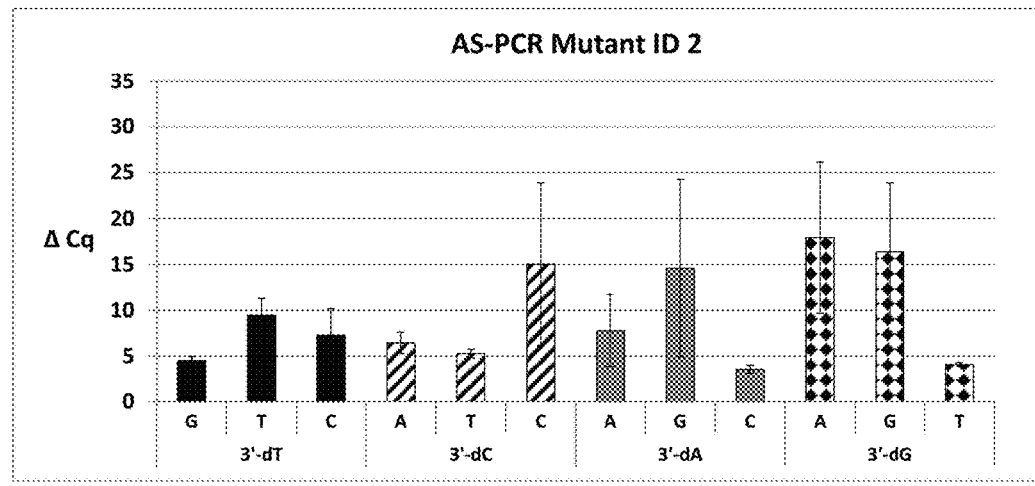
Figure 3A:
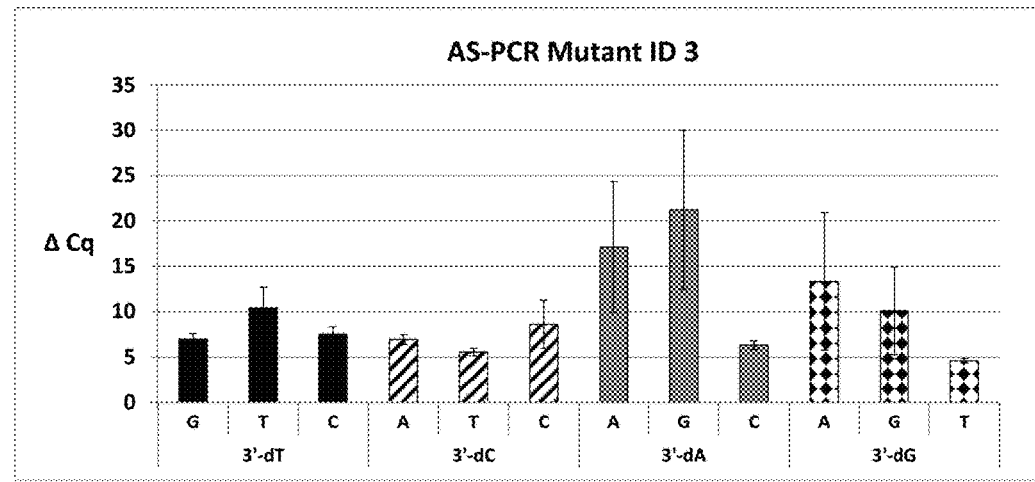
Figure 3B:
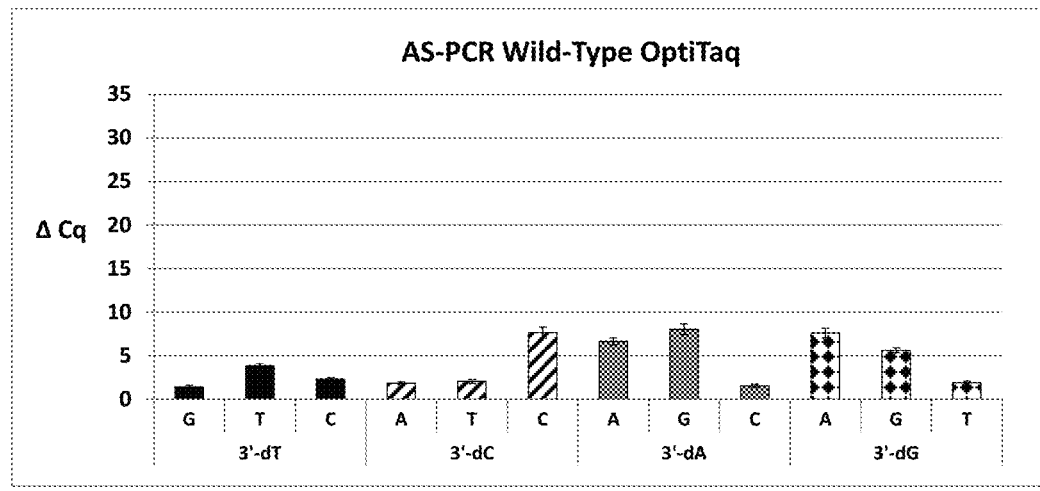
FIG. 3B shows graphical representations of the allele-specific PCR (AS-PCR) data from Tables 10 and 31 for wild type OptiTaq (sub-panel (i)), Mutant ID 10 (sub-panel (ii)) and Mutant ID 18 (sub-panel (iii)). Legend as in FIG. 3A.
Figure 3B:
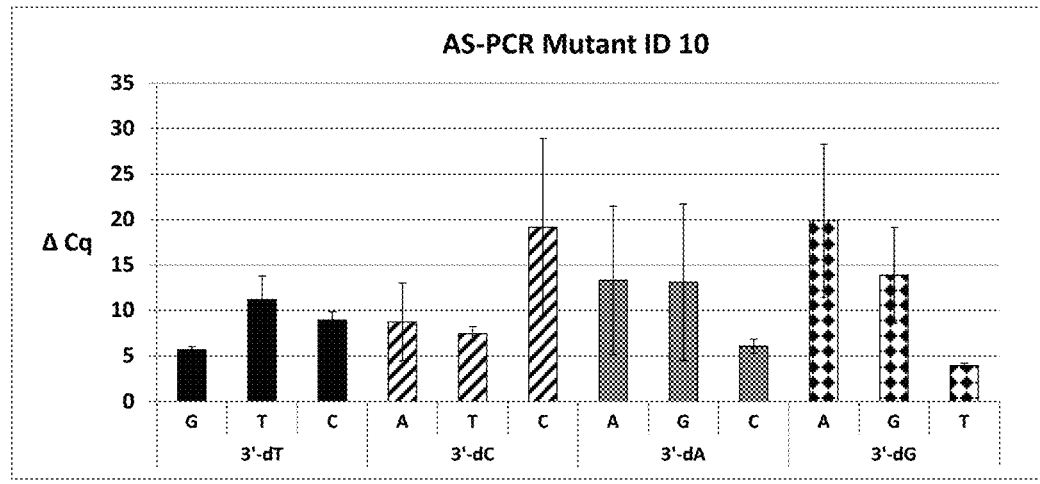
Figure 3B:
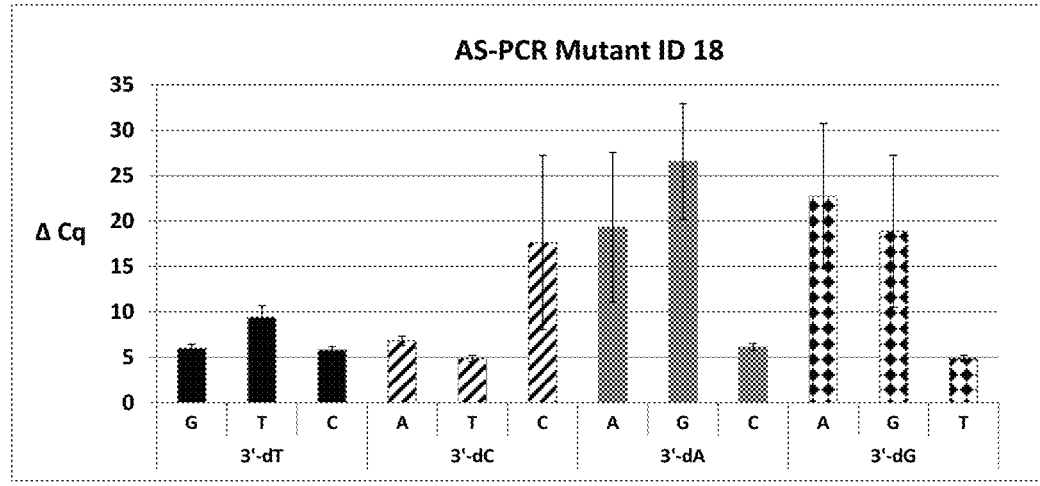
Figure 3C:
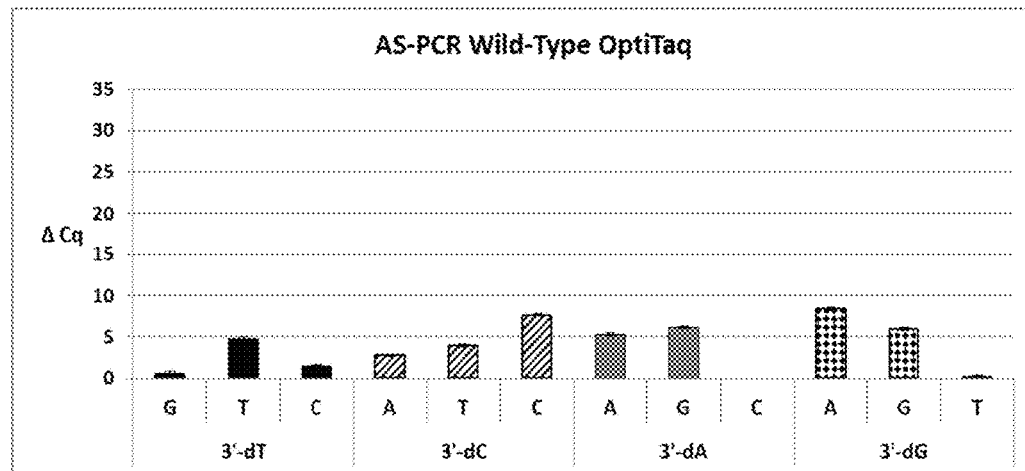
FIG. 3C shows graphical representations of the allele-specific PCR (AS-PCR) data from Tables 10 and 31 for wild type OptiTaq (sub-panel (i)), Mutant ID 3 (sub-panel (ii)) and Mutant ID 20 (sub-panel (iii)). Legend as in FIG. 3A.
Figure 3C:
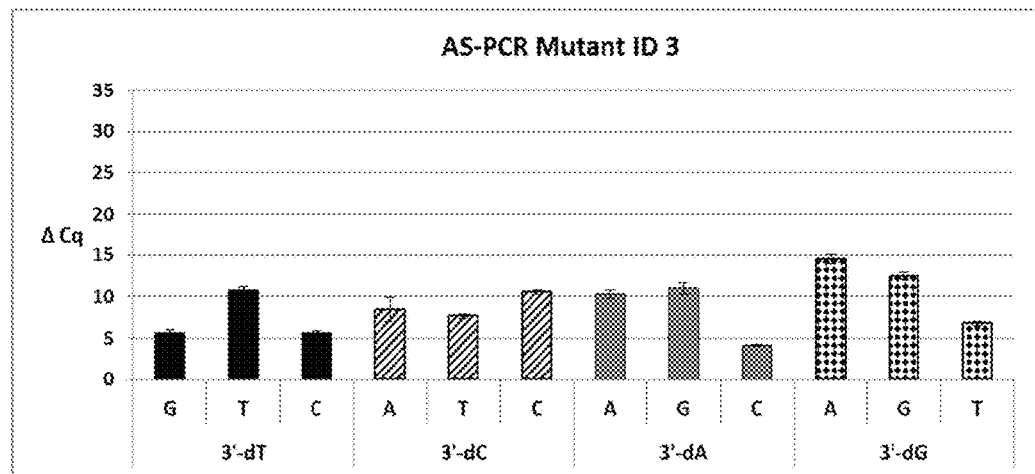
Figure 3C:
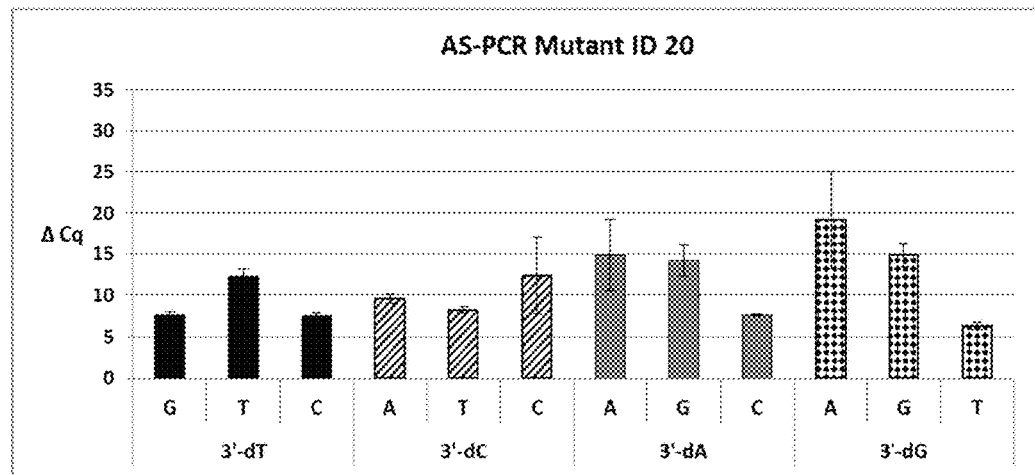
Figure 3D:
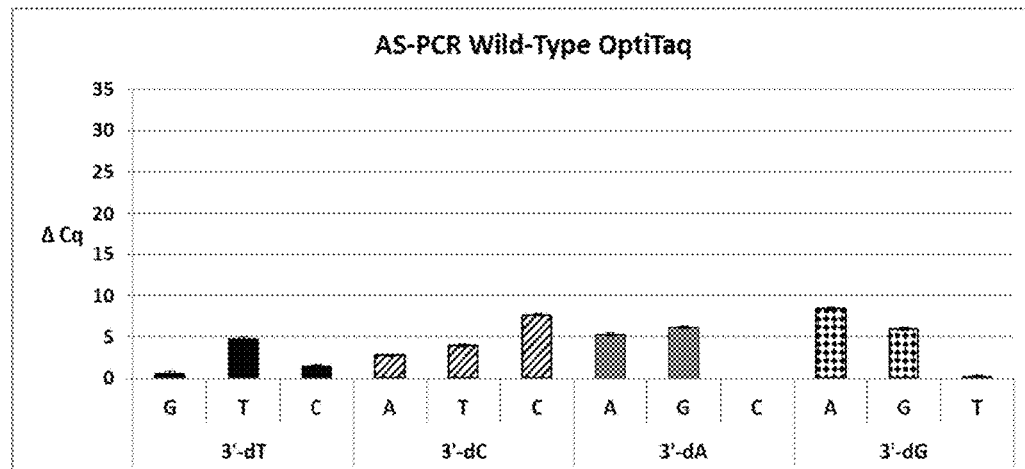
FIG. 3D shows graphical representations of the allele-specific PCR (AS-PCR) data from Tables 10 and 31 for wild type OptiTaq (sub-panel (i)), Mutant ID21 (sub-panel (ii)) and Mutant ID 22 (sub-panel (iii)). Legend as in FIG. 3A.
Figure 3D:
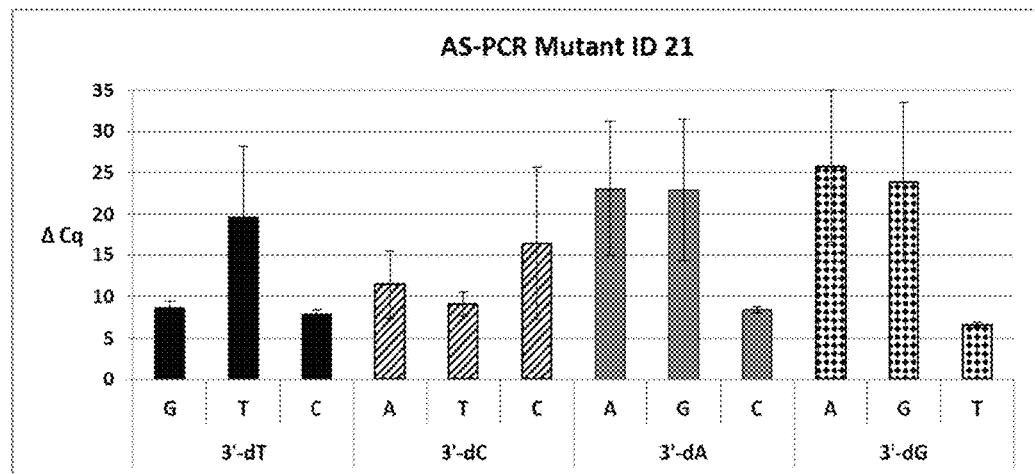
Figure 3D:
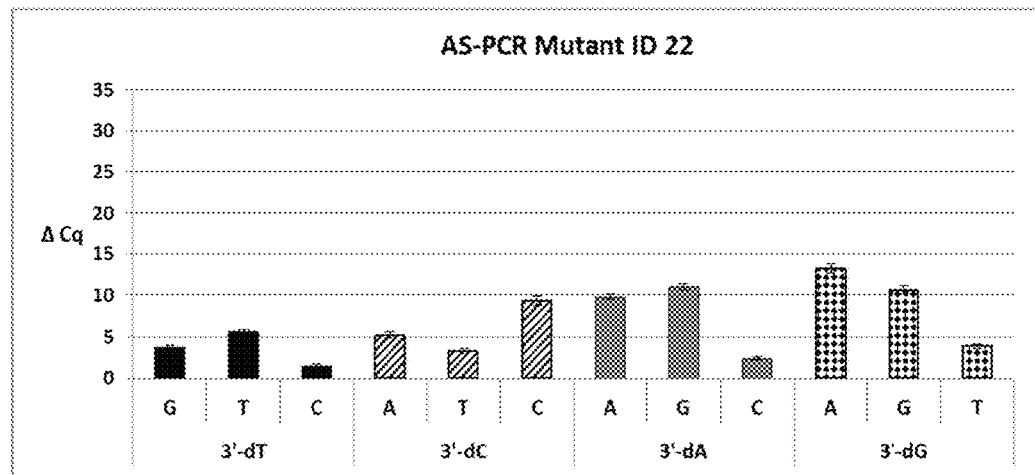
Figure 3E:
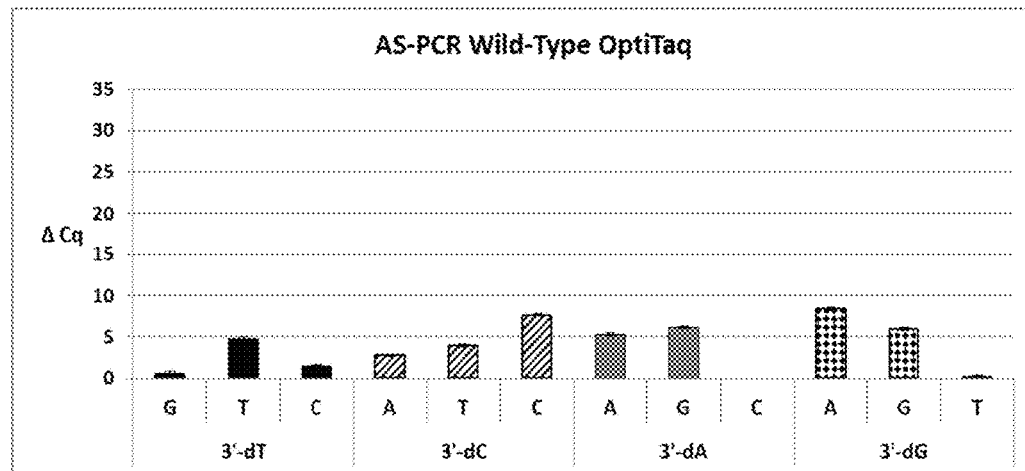
FIG. 3E. shows graphical representations of the allele-specific PCR (AS-PCR) data from Tables 10 and 31 for wild type OptiTaq (sub-panel (i)), Mutant ID 24 (sub-panel (ii)) and Mutant ID 26 (sub-panel (iii)). Legend as in FIG. 3A.
Figure 3E:
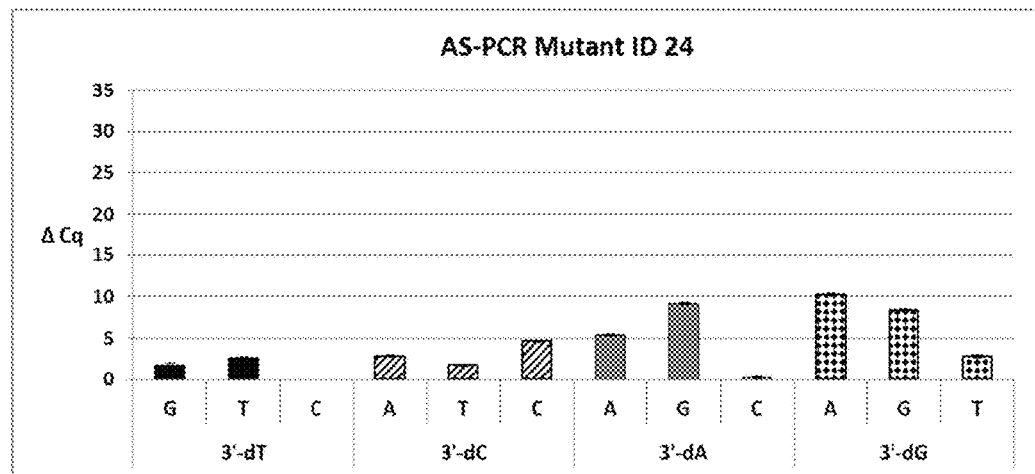
Figure 3E:
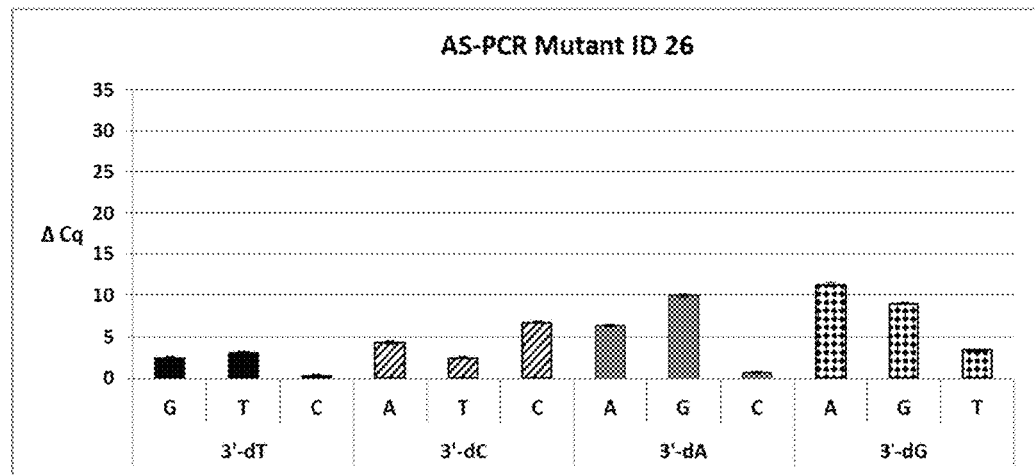
Figure 3F:
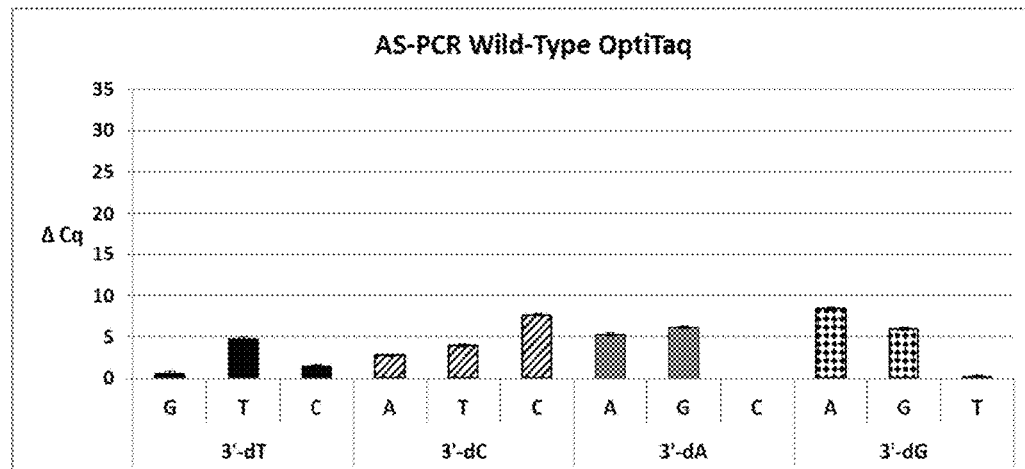
FIG. 3F shows graphical representations of the allele-specific PCR (AS-PCR) data from Tables 10 and 31 for wild type OptiTaq (sub-panel (i)), Mutant ID 27 (sub-panel (ii)) and Mutant ID 29 (sub-panel (iii)). Legend as in FIG. 3A.
Figure 3F:
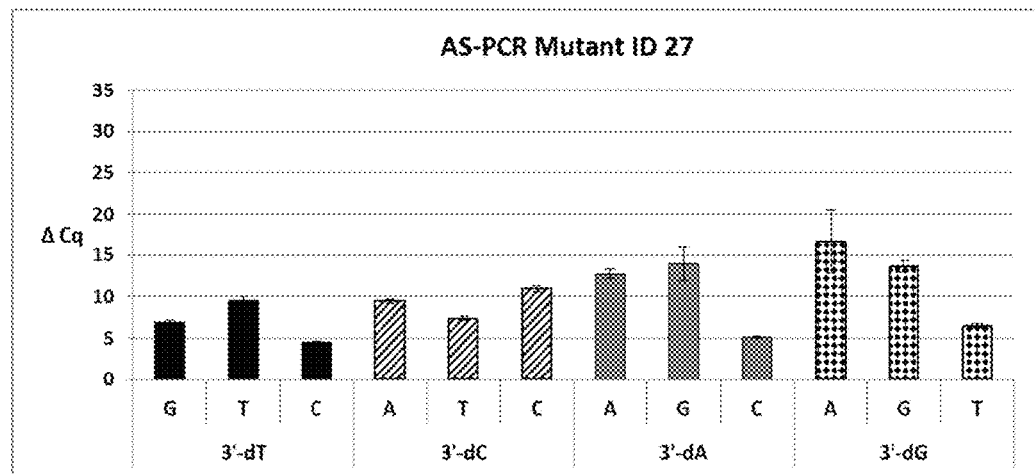
Figure 3F:
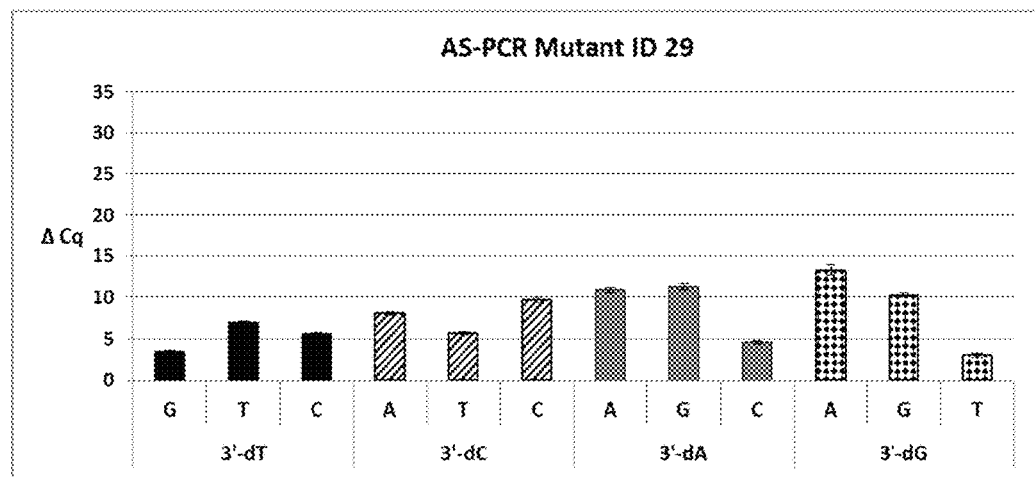
Figure 3G:
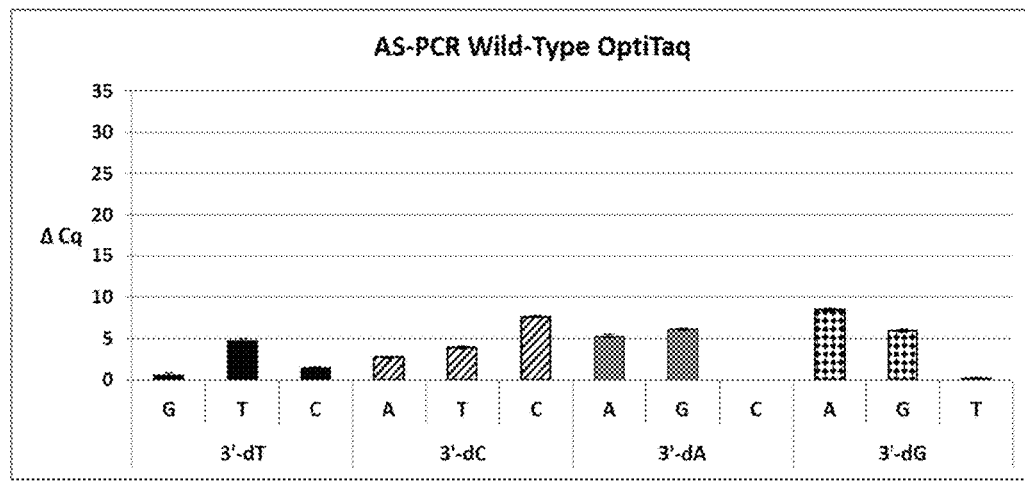
FIG. 3G shows graphical representations of the allele-specific PCR (AS-PCR) data from Tables 10 and 31 for wild type OptiTaq (sub-panel (i)) and Mutant ID 30 (sub-panel (ii)). Legend as in FIG. 3A.
Figure 3G:
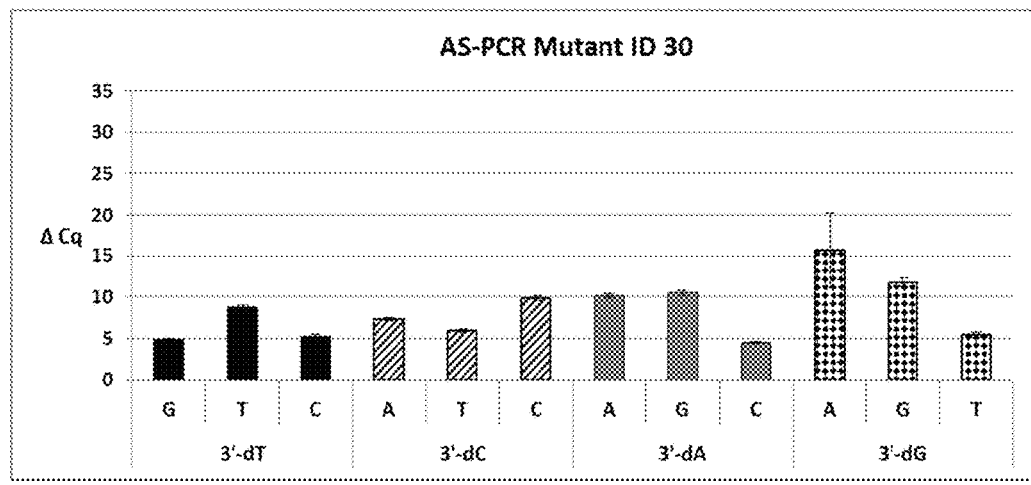

Initially all reactions were run in triplicate. Similar results were obtained for all replicates when using the wild type OptiTaq. However, results showed greater variation for the mutant polymerases. To obtain statistically meaningful results, each reaction was therefore performed 96 times for the mutant polymerases and 81 times for the wild type enzyme. ΔCq values were calculated as the Cq value obtained for each mismatched base pair minus the Cq value obtained for the matched base pair (ΔCq=Cq mismatch−Cq match). The ΔCq values for all 96 replicates were averaged and standard deviations were calculated. Results are shown in Table 10 and are graphically summarized in FIGS. 3A and 3B. Note that the reverse primer is the allele-specific primer, so the "Syn Rev T" primer (SEQ ID NO. 55) is the perfect match to the Template A (SEQ ID NO. 51), etc.

TABLE 10

ΔCq values for AS-qPCR reactions using WT OptiTaq and mutant Taq DNA polymerases.

| | Reverse Primer | | Template | | | |
|---|---|---|---|---|---|---|
| DNA Polymerase | Name | SEQ ID NO. | A SEQ ID NO. 51 | C SEQ ID NO. 52 | G SEQ ID NO. 53 | T SEQ ID NO. 54 |
| OptiTaq | Syn Rev T | 55 | — | 2.3 +/− 0.2 | 1.4 +/− 0.2 | 3.8 +/− 0.2 |
| | Syn Rev G | 58 | 7.6 +/− 0.6 | — | 5.6 +/− 0.3 | 1.9 +/− 0.2 |
| | Syn Rev C | 56 | 1.8 +/− 0.2 | 7.6 +/− 0.6 | — | 2.0 +/− 0.2 |
| | Syn Rev A | 57 | 6.6 +/− 0.4 | 1.5 +/− 0.2 | 8.0 +/− 0.6 | — |
| MUT ID 2 V783F | Syn Rev T | 55 | — | 7.3 +/− 2.9 | 4.5 +/− 0.5 | 9.5 +/− 1.8 |
| | Syn Rev G | 58 | 17.9 +/− 8.3 | — | 16.4 +/− 7.5 | 4.1 +/− 0.2 |
| | Syn Rev C | 56 | 6.5 +/− 1.2 | 15.0 +/− 8.9 | — | 5.3 +/− 0.5 |
| | Syn Rev A | 57 | 7.8 +/− 4.0 | 3.5 +/− 0.4 | 14.6 +/− 9.7 | — |
| MUT ID 3 H784Q | Syn Rev T | 55 | — | 7.5 +/− 0.8 | 7.0 +/− 0.6 | 10.4 +/− 2.3 |
| | Syn Rev G | 58 | 13.3 +/− 7.6 | — | 10.1 +/− 4.8 | 4.6 +/− 0.2 |

TABLE 10-continued

ΔCq values for AS-qPCR reactions using WT OptiTaq and mutant Taq DNA polymerases.

| DNA Polymerase | Reverse Primer Name | SEQ ID NO. | Template A SEQ ID NO. 51 | C SEQ ID NO. 52 | G SEQ ID NO. 53 | T SEQ ID NO. 54 |
|---|---|---|---|---|---|---|
| | Syn Rev C | 56 | 6.9 +/− 0.5 | 8.6 +/− 2.6 | — | 5.6 +/− 0.4 |
| | Syn Rev A | 57 | 17.1 +/− 7.2 | 6.3 +/− 0.5 | 21.2 +/− 8.7 | — |
| MUT ID 10 A661E I665W F667L | Syn Rev T | 55 | — | 9.0 +/− 0.9 | 5.7 +/− 0.3 | 11.2 +/− 2.6 |
| | Syn Rev G | 58 | 19.9 +/− 8.4 | — | 13.9 +/− 5.3 | 3.9 +/− 0.3 |
| | Syn Rev C | 56 | 8.7 +/− 4.3 | 19.2 +/− 9.7 | — | 7.4 +/− 0.8 |
| | Syn Rev A | 57 | 13.3 +/− 8.2 | 6.1 +/− 0.8 | 13.1 +/− 8.6 | — |
| MUT ID 18 V783L H784Q | Syn Rev T | 55 | — | 5.8 +/− 1.3 | 6.0 +/− 0.4 | 9.4 +/− 1.2 |
| | Syn Rev G | 58 | 22.7 +/− 8.0 | — | 18.9 +/− 8.4 | 4.9 +/− 0.3 |
| | Syn Rev C | 56 | 6.8 +/− 0.5 | 17.6 +/− 9.6 | — | 4.8 +/− 0.4 |
| | Syn Rev A | 57 | 19.3 +/− 8.2 | 6.1 +/− 0.4 | 26.6 +/− 6.4 | — |

Average ΔCq values are shown, where ΔCq = [Cq mismatch − Cq match], +/− standard deviation calculated from 96 replicates.

The wild type OptiTaq showed an average ΔCq for AS-qPCR in this synthetic amplicon system of 4.2 with a range of 1.4 to 8.0. Mutant ID 2 (V783F) showed an average ΔCq of 9.4 with a range of 3.5 to 17.9. Mutant ID 3 (H784Q) showed an average ΔCq of 9.9 with a range of 4.6 to 21.2. Mutant ID 10 (A661E, I665W, F667L) showed an average ΔCq of 10.9 with a range of 3.9 to 19.9. Mutant ID 18 (V783L, H784Q) showed an average ΔCq of 12.4 with a range of 4.9 to 26.6. Therefore in all pairwise combinations of 4 template bases and 4 3'-terminal primer bases the mutant Taq DNA polymerases of the present invention showed greater discrimination to mismatch than did the wild type OptiTaq DNA polymerase. The magnitude of improvement for each mismatch pair is defined by the ΔΔCq, which is the difference of discrimination between the mutant and wild type enzymes (ΔΔCq=ΔCq mutant−ΔCq wild type). The ΔΔCq values were calculated and are shown in Table 11.

TABLE 11

ΔΔCq values for AS-qPCR reactions for the mutant Taq DNA polymerases compared with wild type OptiTaq.

| DNA Polymerase | Reverse Primer Name | SEQ ID NO. | Template A SEQ ID NO. 51 | C SEQ ID NO. 52 | G SEQ ID NO. 53 | T SEQ ID NO. 54 |
|---|---|---|---|---|---|---|
| MUT ID NO. 2 V783F | Syn Rev T | 55 | — | 5.0 | 3.1 | 5.7 |
| | Syn Rev G | 58 | 10.3 | — | 10.8 | 2.2 |
| | Syn Rev C | 56 | 4.7 | 7.4 | — | 3.3 |
| | Syn Rev A | 57 | 1.2 | 2.0 | 6.6 | — |
| MUT ID NO. 3 H784Q | Syn Rev T | 55 | — | 5.2 | 5.6 | 6.6 |
| | Syn Rev G | 58 | 5.7 | — | 4.5 | 2.7 |
| | Syn Rev C | 56 | 5.1 | 1.0 | — | 3.6 |
| | Syn Rev A | 57 | 10.5 | 4.8 | 13.2 | — |
| MUT ID NO. 10 A661E I665W F667L | Syn Rev T | 55 | — | 6.7 | 4.3 | 7.4 |
| | Syn Rev G | 58 | 12.3 | — | 8.3 | 2.0 |
| | Syn Rev C | 56 | 6.9 | 11.6 | — | 5.4 |
| | Syn Rev A | 57 | 6.7 | 4.6 | 5.1 | — |
| MUT ID NO. 18 V783L H784Q | Syn Rev T | 55 | — | 3.5 | 4.6 | 5.6 |
| | Syn Rev G | 58 | 15.1 | — | 13.3 | 3.0 |
| | Syn Rev C | 56 | 5.0 | 10.0 | — | 2.8 |
| | Syn Rev A | 57 | 12.7 | 4.6 | 18.6 | — |

Average ΔΔCq values are shown, where ΔΔCq = [ΔCq mutant − ΔCq wild type], from data in Table 10.

Mutant ID 2 (V783F) showed an average ΔΔCq of 5.2 compared to wild type OptiTaq. Mutant ID 3 (H784Q) showed an average ΔΔCq of 5.7 compared to wild type OptiTaq. Mutant ID 10 (A661E, I665W, F667L) showed an average ΔΔCq of 6.7 compared to wild type OptiTaq. Mutant ID 18 (V783L, H784Q) showed an average ΔΔCq of 8.2 compared to wild type OptiTaq. Therefore each of the mutant Taq DNA polymerases of the present invention showed a significant improvement over wild type OptiTaq in mismatch discrimination, and, importantly, mismatch discrimination was improved for every possible mismatch base pair combination. Overall, mutant ID 18 (V783L, H784Q) showed the best SNP discrimination within the set of 4 mutant enzymes studied in this example using an AS-PCR assay.

Example 6: Discrimination Against a Primer 3'-RNA Residue by Taq DNA Polymerase Mutants All 18 Taq DNA polymerase mutants were screened for the ability to discriminate against priming from a 3'-RNA residue in Example 4. The four mutants studied in AS-PCR in Example 5 (MUT IDs 2, 3, 10, and 18) which showed good 3'-mismatch discrimination were studied in greater detail in the present example for the ability to discriminate against the presence of a 3'-terminal RNA residue in the primer, examining for possible base-specific effects. Amplification reactions were performed against a synthetic oligonucleotide template where a single base was varied (SNP) which was positioned to lie at the 3'-end of the reverse primer. Synthetic templates were employed having each of the 4 possible bases at this position. Reverse primers were employed having each of the 4 possible RNA bases at the 3'-end and results were compared to control reactions using primers having each of the 4 possible DNA bases at the 3'-end. Relative amplification efficiency was assessed using qPCR.

Quantitative real-time PCR (qPCR) was performed in 10 μL reaction volumes in 384 well format with 2×10³ copies of a 103 bp synthetic template (SEQ ID NOs. 51-54). Final reaction conditions used were 20 mM Tris-HCL (pH 8.4 at 25° C.), 50 mM KCL, and 3 mM MgCl$_2$, 0.01% Triton X-100, 800 μM total dNTPs, and 200 nM of the universal forward primer (SEQ ID NO. 60), 200 nM of a reverse primer (separate reactions were set up for each of the four 3'-RNA primers SEQ ID NOs. 62-65, each of the four 3'DNA primers SEQ ID NOs. 55-58, or the control universal primer SEQ ID NO. 59) and 200 nM of the 5' nuclease detection probe (SEQ ID NO. 61). Each primer was tested only on the complementary template (mismatch conditions were not tested). Reactions utilized either 0.5 U (10.8 ng/11.1 nM/111 fmol) of the wild type OptiTaq DNA polymerase or 0.5 U of one of the 4 Taq DNA polymerase mutants studied (MUT ID No. 2 V783F, MUT ID NO. 3 H784Q, MUT ID NO. 10 A661E I665W F667L, or MUT ID NO. 18 V783L H784Q). Amplification was performed on a CFX384™ C1000™ Thermo Cycler system (Bio-Rad, Hercules, Calif.) using the following cycling parameters: 95° C. for 30 seconds initial denaturation followed by 60 cycles of 95° C. for 10 seconds, then 60° C. for 30 seconds. Oligonucleotide reagents used in this example are shown in Table 12. A total of 96 replicates were performed for each pairwise combination.

TABLE 12

Synthetic oligonucleotides employed in Example 6.

| Name | Sequence (5'-3') | SEQ ID NO. |
|---|---|---|
| A Template | AGCTCTGCCCAAAGATTACCCTGACAGCTAAGTGGCAGTGGAA GTTGGCCTCAGAAGTAGTGGCCAGCTGTGTGTCGGGG<u>A</u>ACAGT AAAGGCATGAAGCTCAG | SEQ ID NO. 51 |
| C Template | AGCTCTGCCCAAAGATTACCCTGACAGCTAAGTGGCAGTGGAA GTTGGCCTCAGAAGTAGTGGCCAGCTGTGTGTCGGGG<u>C</u>ACAGT AAAGGCATGAAGCTCAG | SEQ ID NO. 52 |
| G Template | AGCTCTGCCCAAAGATTACCCTGACAGCTAAGTGGCAGTGGAA GTTGGCCTCAGAAGTAGTGGCCAGCTGTGTGTCGGGG<u>G</u>ACAGT AAAGGCATGAAGCTCAG | SEQ ID NO. 53 |
| T Template | AGCTCTGCCCAAAGATTACCCTGACAGCTAAGTGGCAGTGGAA GTTGGCCTCAGAAGTAGTGGCCAGCTGTGTGTCGGGG<u>T</u>ACAGT AAAGGCATGAAGCTCAG | SEQ ID NO. 54 |
| Syn Rev T | CTGAGCTTCATGCCTTTACTGTT | SEQ ID NO. 55 |
| Syn Rev C | CTGAGCTTCATGCCTTTACTGTC | SEQ ID NO. 56 |
| Syn Rev A | CTGAGCTTCATGCCTTTACTGTA | SEQ ID NO. 57 |
| Syn Rev G | CTGAGCTTCATGCCTTTACTGTG | SEQ ID NO. 58 |
| Syn Rev rU | CTGAGCTTCATGCCTTTACTGTu | SEQ ID NO. 62 |
| Syn Rev rC | CTGAGCTTCATGCCTTTACTGTc | SEQ ID NO. 63 |
| Syn Rev rA | CTGAGCTTCATGCCTTTACTGTa | SEQ ID NO. 64 |
| Syn Rev rG | CTGAGCTTCATGCCTTTACTGTg | SEQ ID NO. 65 |
| Syn Rev | CTGAGCTTCATGCCTTTACTGT | SEQ ID NO. 59 |
| Syn For | AGCTCTGCCCAAAGATTACCCTG | SEQ ID NO. 60 |
| Syn Probe | FAM-TTCTGAGGC(ZEN)CAACTTCCACTGCCACTTA-IBFQ | SEQ ID NO. 61 |

DNA bases are uppercase and RNA bases are lowercase; FAM = 6-carboxyfluorescein; IBFQ =Iowa Black™ FQ fluorescence quencher; ZEN = internal ZEN fluorescence quencher; underlined base indicates the SNP site in the synthetic template DNA.

Figure 4:
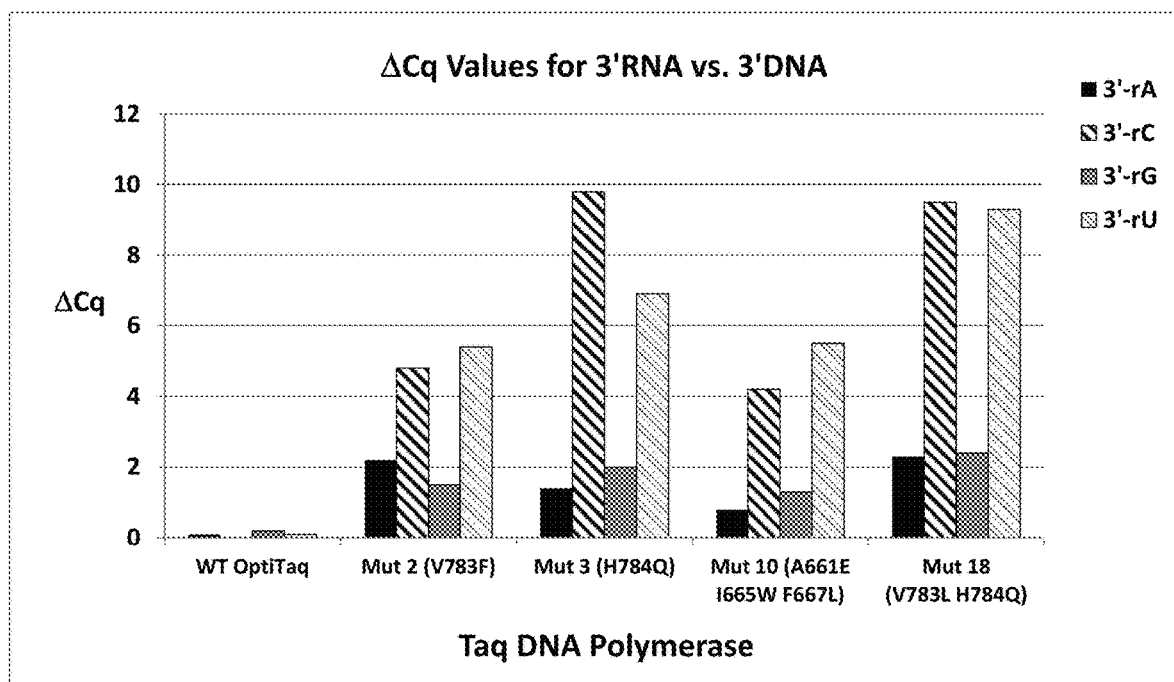
FIG. 4 shows a graphical representation of the ΔCq values (Table 13) obtained from comparing qPCR results using primers ending with a 3'-RNA residue and primers ending with a 3'-DNA residue for wild type OptiTaq with four mutant Taq DNA polymerases, where ΔCq=Cq 3'-RNA-Cq 3'-DNA; rA is compared with dA, rC is compared with dC, rG is compared with dG, and rU is compared with dT. Identity of each DNA polymerase studied is shown on the X-axis.

Average Cq values were calculated for the 96-replicate sets. ΔCq values were calculated as the difference between the average Cq values for the 3'-RNA primer reactions from the average Cq values for the 3'-DNA primer reactions (ΔCq=Cq 3'-RNA−Cq 3'-DNA). Higher ΔCq values indicate a greater degree of discrimination against priming from a 3'-RNA primer. Results are shown in Table 13 and are graphically summarized in FIG. 4.

TABLE 13

ΔCq values for qPCR reactions using WT OptiTaq and mutant Taq DNA polymerases comparing 3'-DNA vs. 3'-RNA primers.

| DNA Polymerase | Reverse Primers compared | | | |
|---|---|---|---|---|
| | Name | SEQ ID NO. | Template | ΔCq |
| OptiTaq | Syn Rev T | 55 | A | 0.1 |
| | Syn Rev rU | 62 | SEQ ID NO. 51 | |
| | Syn Rev G | 58 | C | 0.2 |
| | Syn Rev rG | 65 | SEQ ID NO. 52 | |
| | Syn Rev C | 56 | G | 0.0 |
| | Syn Rev rC | 63 | SEQ ID NO. 53 | |
| | Syn Rev A | 57 | T | 0.1 |
| | Syn Rev rA | 64 | SEQ ID NO. 54 | |
| MUT ID 2 V783F | Syn Rev T | 55 | A | 5.4 |
| | Syn Rev rU | 62 | SEQ ID NO. 51 | |
| | Syn Rev G | 58 | C | 1.5 |
| | Syn Rev rG | 65 | SEQ ID NO. 52 | |
| | Syn Rev C | 56 | G | 4.8 |
| | Syn Rev rC | 63 | SEQ ID NO. 53 | |
| | Syn Rev A | 57 | T | 2.2 |
| | Syn Rev rA | 64 | SEQ ID NO. 54 | |
| MUT ID 3 H784Q | Syn Rev T | 55 | A | 6.9 |
| | Syn Rev rU | 62 | SEQ ID NO. 51 | |
| | Syn Rev G | 58 | C | 2.0 |
| | Syn Rev rG | 65 | SEQ ID NO. 52 | |
| | Syn Rev C | 56 | G | 9.8 |
| | Syn Rev rC | 63 | SEQ ID NO. 53 | |
| | Syn Rev A | 57 | T | 1.4 |
| | Syn Rev rA | 64 | SEQ ID NO. 54 | |
| MUT ID 10 A661E I665W F667L | Syn Rev T | 55 | A | 5.5 |
| | Syn Rev rU | 62 | SEQ ID NO. 51 | |
| | Syn Rev G | 58 | C | 1.3 |
| | Syn Rev rG | 65 | SEQ ID NO. 52 | |
| | Syn Rev C | 56 | G | 4.2 |
| | Syn Rev rC | 63 | SEQ ID NO. 53 | |
| | Syn Rev A | 57 | T | 0.8 |
| | Syn Rev rA | 64 | SEQ ID NO. 54 | |
| MUT ID 18 V783L H784Q | Syn Rev T | 55 | A | 9.3 |
| | Syn Rev rU | 62 | SEQ ID NO. 51 | |
| | Syn Rev G | 58 | C | 2.4 |
| | Syn Rev rG | 65 | SEQ ID NO. 52 | |
| | Syn Rev C | 56 | G | 9.5 |
| | Syn Rev rC | 63 | SEQ ID NO. 53 | |
| | Syn Rev A | 57 | T | 2.3 |
| | Syn Rev rA | 64 | SEQ ID NO. 54 | |

Average ΔCq values are shown, where ΔCq = Cq 3'-RNA primer − Cq 3'-DNA primer.

Wild type OptiTaq did not show any significant discrimination between a 3'-DNA and a 3'-RNA primer. All four mutant Taq DNA polymerases, however, showed reduced priming efficiency when using a 3'-RNA primer. Thus the goal of creating novel polymerases which discriminate against a 3'-RNA residue in a primer was achieved using the intelligent mutagenesis design strategy described herein. Interestingly, the magnitude of discrimination was much greater for RNA pyrimidine residues (rC or rU) than for RNA purine residues (rA or rG).

Example 7: Improved Mismatch Discrimination in rhPCR Using Mutant Taq DNA Polymerases RNase H-based PCR (rhPCR) employs the enzyme RNase H2 to convert a blocked-cleavable oligonucleotide which cannot prime DNA synthesis into a form that can prime DNA synthesis and initiate PCR. The blocked-cleavable oligonucleotide, or blocked-cleavable primer, contains a single RNA residue near the 3'-end of the oligonucleotide (which comprises the cleavage site) and is modified at or near the 3'-end so that the primer cannot prime DNA synthesis and/or has lost template function and so is incompetent to support PCR even if primer extension can occur. This method can be used for genotyping (SNP discrimination) and relies on the ability of RNase H2 to distinguish between base-pair match vs. mismatch at the RNA base cleavage site when hybridized to the target nucleic acid. In rhPCR, SNP discrimination occurs at the primer unblocking step, not at the primer extension step (in AS-PCR, discrimination occurs at the primer extension step). Examples of this enzyme cleaving strategy, similar RNase H strategies, and methods of blocking primer extension or inhibiting template function and thereby disabling PCR are described in U.S. Pat. No. 7,112,406 to Behlke et al., entitled POLYNOMIAL AMPLIFICATION OF NUCLEIC ACIDS, U.S. Pat. No. 5,763,181 to Han et al., entitled CONTINOUS FLUOROMETRIC ASSAY FOR DETECTING NUCLEIC ACID CLEAVAGE, U.S. Pat. No. 7,135,291 to Sagawa et al., entitled METHOD OF DETECTING NUCLEOTIDE POLYMORPHISM; U.S. Pat. App. No. 20090068643 to Behlke and Walder, entitled DUAL FUNCTION PRIMERS FOR AMPLIFYING DNA AND METHODS OF USE; and U.S. Pat. App. No. 20100167353 to Walder et al., entitled RNASE H-BASED ASSAYS UTILIZING MODIFIED RNA MONOMERS and in Dobosy et al., RNase H-dependent PCR (rhPCR): improved specificity and single nucleotide polymorphism detection using blocked cleavable primers, BMC Biotechnology., 11:e80 (2011).

In AS-PCR the SNP is positioned at the 3'-end of the primer. In this configuration, a mispriming event (where DNA synthesis is initiated in the presence of a 3'-terminal mismatch) leads to incorporation of the base present in the primer into the nascent DNA strand and thereby into the PCR amplicon. This event converts the PCR product to the primer sequence so that the amplified DNA now matches primer and no longer matches the original input sample nucleic acid sequence. Since the amplicon sequence now matches the primer and not the input sample, amplification proceeds at high efficiency.

In rhPCR, cleavage of the blocked-cleavable primer by RNase H2 occurs at the 5'-side of the RNA residue; if the SNP is positioned at the RNA residue (e.g., the RNA base pairs with the SNP), then the first base incorporated by DNA polymerase during primer extension and PCR is the SNP site and results in daughter products which remain identical to the input nucleic acid sequence. Rarely, non-canonical RNase H2 cleavage occurs at the 3'-side of the RNA base, which leaves the RNA residue at the 3'-end of the primer positioned overlying the SNP. In this case, the rhPCR reaction proceeds like AS-PCR, where the 3'-end of the primer is positioned at the SNP site and is either a match or mismatch to the target nucleic acid. Like AS-PCR, in the case of a mismatch, the sequence of the DNA extension product and PCR amplicon converts to the sequence of the primer and thus might not faithfully replicate the sequence of the sample during amplification. Any method which reduces the frequency of this undesired mispriming event will improve mismatch discrimination in the rhPCR assay. Therefore, although base discrimination in rhPCR is primarily mediated by RNase H2 at the primer cleavage stage, use of a DNA polymerase that has an improved ability to discriminate against a 3'-terminal mismatch and/or a 3'-terminal RNA residue may improve the overall mismatch discrimination capacity of rhPCR by preventing extension when undesired 3'-cleavage events occur. The DNA polymerase mutants described herein both reduce priming efficiency when a 3'-mismatch is present (improve mismatch discrimination) and reduce priming efficiency when a 3'-terminal RNA residue is present in the primer (discriminate against a primer 3'-RNA residue) compared with wild type Taq DNA polymerase. The present example demonstrates that the novel mutant Taq DNA polymerases of the present invention improve specificity and SNP discrimination of rhPCR.

Quantitative real-time rhPCR was performed comparing performance of wild type OptiTaq DNA polymerase with mutant Taq DNA polymerases Mutant IDs 2, 3, 10, and 18. Two different blocked-cleavable primer designs were tested, including the generation 1 (Gen1) "RDDDDx" primers and the generation 2 (Gen2) "RDxxD" primers (see: US Patent Application 2012/0258455 by Behlke et al., entitled, RNASE H-BASED ASSAYS UTILIZING MODIFIED RNA MONOMERS). Amplification reactions were performed using the same synthetic oligonucleotide template employed in Example 5 where a single base was varied (the SNP site) which was positioned to lie at the RNA residue in both Gen1 and Gen2 blocked-cleavable (rhPCR) primers. Synthetic templates were employed having each of the 4 possible bases at this position. Reverse primers were employed having each of the 4 possible complementary bases at this position (the RNA base). The same forward primer was used for all reactions. Relative amplification efficiency was assessed using real-time PCR.

Quantitative rhPCR was performed in 10 μL reaction volumes in 384 well format with 2×10⁶ copies of a 103 bp synthetic template (SEQ ID NOs. 51-4). Final reaction conditions used were 20 mM Tris-HCL (pH 8.4 at 25° C.), 50 mM KCL, 3 mM MgCl$_2$, 0.01% Triton X-100, 800 μM total dNTPs, 200 nM of the universal forward primer (SEQ ID NO. 60), 200 nM of a reverse primer, and 200 nM of the 5' nuclease detection probe (SEQ ID NO. 61). Reverse primers included Gen1 RDDDDx configuration allele-specific rhPCR primers (SEQ ID NOs. 66-69), Gen2 RDxxD configuration allele-specific rhPCR primers (SEQ ID NOs. 70-73) and a control universal reverse primer (SEQ ID NO. 59). Each of the rhPCR blocked-cleavable reverse primers were tested on each of the four SNP templates. Reactions utilized either 0.5 U (10.8 ng/11.1 nM/111 fmol) of the wild type OptiTaq DNA polymerase or 0.5 U of one of the four Taq DNA polymerase mutants (MUT ID 2, V783F; MUT ID 3, H784Q; MUT ID 10, A661E I665W F667L; or MUT ID 18, V783L H784Q). P. abyssi RNase H2 was added to each reaction in 1 μL volume. Reactions using the control and Gen1 blocked-cleavable RDDDDx rhPCR primers employed 2.6 mU RNase H2 per 10 μL reaction (5 fmoles, 0.5 nM enzyme). Reactions using the Gen2 blocked-cleavable RDxxD rhPCR primers employed 25 mU RNase H2 10 μL reaction (48 fmoles, 4.8 nM enzyme) for the rC and rA primers (SEQ ID NOs. 71 and 72) and 200 mU RNase H2 per 10 μL reaction (384 fmoles, 38 nM enzyme) for the rG and rU primers (SEQ ID NOs. 70 and 73). Cycling was performed on a Roche LightCycler® 480 (Roche Applied Science, Indianapolis, Ind., USA) as follows: 95° C. for 3 minutes followed by 75 cycles of 95° C. for 10 seconds and 60° C. for 30 seconds. All reactions were performed in triplicate. Oligonucleotide reagents used in this example are shown in Table 14.

TABLE 14

Synthetic oligonucleotides employed in Example 7.

| Name | Sequence (5'-3') | SEQ ID NO. |
|---|---|---|
| A Template | AGCTCTGCCCAAAGATTACCCTGACAGCTAAGTGGCAGTGGAA GTTGGCCTCAGAAGTAGTGGCCAGCTGTGTGTCGGGG<u>A</u>ACAGT AAAGGCATGAAGCTCAG | SEQ ID NO. 51 |
| C Template | AGCTCTGCCCAAAGATTACCCTGACAGCTAAGTGGCAGTGGAA GTTGGCCTCAGAAGTAGTGGCCAGCTGTGTGTCGGGG<u>C</u>ACAGT AAAGGCATGAAGCTCAG | SEQ ID NO. 52 |
| G Template | AGCTCTGCCCAAAGATTACCCTGACAGCTAAGTGGCAGTGGAA GTTGGCCTCAGAAGTAGTGGCCAGCTGTGTGTCGGGG<u>G</u>ACAGT AAAGGCATGAAGCTCAG | SEQ ID NO. 53 |
| T Template | AGCTCTGCCCAAAGATTACCCTGACAGCTAAGTGGCAGTGGAA GTTGGCCTCAGAAGTAGTGGCCAGCTGTGTGTCGGGG<u>T</u>ACAGT AAAGGCATGAAGCTCAG | SEQ ID NO. 54 |
| Syn Rev | CTGAGCTTCATGCCTTTACTGT | SEQ ID NO. 59 |
| Syn For | AGCTCTGCCCAAAGATTACCCTG | SEQ ID NO. 60 |
| Syn Probe | FAM-TTCTGAGGC(ZEN)CAACTTCCACTGCCACTTA-IBFQ | SEQ ID NO. 61 |
| Syn Rev rU DDDDx | CTGAGCTTCATGCCTTTACTGTuCCCCx | SEQ ID NO. 66 |
| Syn Rev rC DDDDx | CTGAGCTTCATGCCTTTACTGTcCCCCx | SEQ ID NO. 67 |
| Syn Rev rA DDDDx | CTGAGCTTCATGCCTTTACTGTaCCCCx | SEQ ID NO. 68 |
| Syn Rev rG DDDDx | CTGAGCTTCATGCCTTTACTGTgCCCCx | SEQ ID NO. 69 |

TABLE 14-continued

Synthetic oligonucleotides employed in Example 7.

| Name | Sequence (5'-3') | SEQ ID NO. |
|---|---|---|
| Syn Rev rU DxxD | CTGAGCTTCATGCCTTTACTGTuCxxC | SEQ ID NO. 70 |
| Syn Rev rC DxxD | CTGAGCTTCATGCCTTTACTGTcCxxC | SEQ ID NO. 71 |
| Syn Rev rA DxxD | CTGAGCTTCATGCCTTTACTGTaCxxC | SEQ ID NO. 72 |
| Syn Rev rG DxxD | CTGAGCTTCATGCCTTTACTGTgCxxC | SEQ ID NO. 73 |

DNA bases are uppercase and RNA bases are lowercase; FAM = 6-carboxyfluorescein; IBFQ = Iowa Black ™ FQ fluorescence quencher; ZEN = internal ZEN fluorescence quencher; underlined base indicates the SNP site in the synthetic template DNA; "x" = C3 Spacer (propanediol).

MUT ID 10 (A661E, I665W, F667L) unexpectedly showed large amplification delays when the primers matched the SNP site in the target in the rhPCR reactions using this synthetic amplicon system. This polymerase, however, did not show any delays when using a human genomic DNA system for rhPCR (see Examples 8 and 9). MUT ID 10 was therefore excluded from analysis in the synthetic system experiments. Data generated using the other three mutant polymerases were analyzed and ΔCq values were calculated comparing matched versus mismatched primer/template pairs, where ΔCq=Cq mismatch− Cq match. Results are shown in Table 15 for the Gen1 RDDDDx blocked-cleavable rhPCR primers and in Table 16 for the Gen2 RDxxD blocked-cleavable rhPCR primers.

TABLE 15

ΔCq values for rhPCR reactions using WT OptiTaq and mutant Taq DNA polymerases with Gen1 RDDDDx blocked-cleavable rhPCR primers.

| | Reverse Primer | | Template | | | |
|---|---|---|---|---|---|---|
| DNA Polymerase | Name | SEQ ID NO. | A SEQ ID NO. 51 | G SEQ ID NO. 53 | T SEQ ID NO. 54 | C SEQ ID NO. 52 |
| OptiTaq | Syn Rev rU DDDDx | 66 | — | 10.5 | 3.4 | 6.6 |
| | Syn Rev rC DDDDx | 67 | 3.3 | — | 1.3 | 2.2 |
| | Syn Rev rA DDDDx | 68 | 9.5 | 10.5 | — | 3.5 |
| | Syn Rev rG DDDDx | 69 | 9.5 | 10.8 | 11.8 | — |
| MUT ID 2 V783F | Syn Rev rU DDDDx | 66 | — | 11.1 | 5.1 | 9.0 |
| | Syn Rev rC DDDDx | 67 | 4.0 | — | 1.9 | 3.6 |
| | Syn Rev rA DDDDx | 68 | 10.4 | 11.1 | — | 5.6 |
| | Syn Rev rG DDDDx | 69 | 10.2 | 10.5 | 10.7 | — |
| MUT ID 3 H784Q | Syn Rev rU DDDDx | 66 | — | 11.3 | 5.0 | 10.0 |
| | Syn Rev rC DDDDx | 67 | 7.6 | — | 4.3 | 5.9 |
| | Syn Rev rA DDDDx | 68 | 10.8 | 11.3 | — | 7.6 |
| | Syn Rev rG DDDDx | 69 | 10.9 | 10.9 | 11.0 | — |
| MUT ID 18 V783L | Syn Rev rU DDDDx | 66 | — | 12.3 | 6.7 | 11.5 |
| H784Q | Syn Rev rC DDDDx | 67 | 9.9 | — | 8.3 | 10.4 |
| | Syn Rev rA DDDDx | 68 | 11.5 | 13.2 | — | 6.8 |
| | Syn Rev rG DDDDx | 69 | 11.3 | 12.0 | 12.6 | — |

Average ΔCq values are shown, where ΔCq = [Cq mismatch − Cq match].

TABLE 16

ΔCq values for rhPCR reactions using WT OptiTaq and mutant Taq DNA polymerases with Gen2 RDxxD blocked-cleavable rhPCR primers.

| | Reverse Primer | | Template | | | |
|---|---|---|---|---|---|---|
| DNA Polymerase | Name | SEQ ID NO. | A SEQ ID NO. 51 | G SEQ ID NO. 53 | T SEQ ID NO. 54 | C SEQ ID NO. 52 |
| OptiTaq | Syn Rev rU DxxD | 70 | — | 11.6 | 15.1 | 12.8 |
| | Syn Rev rC DxxD | 71 | 6.3 | — | 6.7 | 4.6 |
| | Syn Rev rA DxxD | 72 | 13.7 | 15.6 | — | 14.3 |
| | Syn Rev rG DxxD | 73 | 13.2 | 11.4 | 10.2 | — |
| MUT ID 2 V783F | Syn Rev rU DxxD | 70 | — | 12.2 | 15.0 | 14.0 |
| | Syn Rev rC DxxD | 71 | 8.3 | — | 6.5 | 4.4 |
| | Syn Rev rA DxxD | 72 | 14.1 | 15.9 | — | 14.2 |
| | Syn Rev rG DxxD | 73 | 13.8 | 12.2 | 11.6 | — |
| MUT ID 3 H784Q | Syn Rev rU DxxD | 70 | — | 12.4 | 15.0 | 14.1 |
| | Syn Rev rC DxxD | 71 | 9.5 | — | 7.8 | 6.4 |
| | Syn Rev rA DxxD | 72 | 16.9 | 19.1 | — | 18.4 |
| | Syn Rev rG DxxD | 73 | 15.0 | 13.0 | 12.7 | — |

TABLE 16-continued

ΔCq values for rhPCR reactions using WT OptiTaq and mutant Taq DNA polymerases with Gen2 RDxxD blocked-cleavable rhPCR primers.

| DNA Polymerase | Reverse Primer Name | SEQ ID NO. | A SEQ ID NO. 51 | G SEQ ID NO. 53 | T SEQ ID NO. 54 | C SEQ ID NO. 52 |
|---|---|---|---|---|---|---|
| MUT ID 18 V783L H784Q | Syn Rev rU DxxD | 70 | — | 13.0 | 15.3 | 14.3 |
| | Syn Rev rC DxxD | 71 | 6.9 | — | 9.6 | 3.6 |
| | Syn Rev rA DxxD | 72 | 15.8 | 15.3 | — | 14.5 |
| | Syn Rev rG DxxD | 73 | 15.0 | 13.4 | 13.7 | — |

Average ΔCq values are shown, where ΔCq = [Cq mismatch − Cq match].

In almost all cases, mismatch discrimination was superior for rhPCR reactions run using the mutant Taq DNA polymerases than wild type OptiTaq. The magnitude of improvement is best seen by examining the ΔΔCq values, which is the difference of discrimination seen using wild type OptiTaq and the mutants (ΔΔCq=ΔCq mutant−ΔCq wild type). These results are shown in Table 17 for the Gen1 RDDDDx primers and in Table 18 for the Gen2 RDxxD primers. When using the Gen1 RDDDDx primers, the overall greatest benefit was seen when the mismatched base was a "C" in the target nucleic acid and least benefit was seen when the blocked-cleavable primer contained a rG paired with a mismatched T in the target. The greatest improvements were obtained using the mutant Taq DNA polymerase MUT ID 18 (V783L H784Q). The average ΔΔCq for MUT ID 2 (V783F) was 1.0. The average ΔΔCq for MUT ID 3 (H784Q) was 2.0. The average ΔΔCq for MUT ID 18 (V783L, H784Q) was 3.6. Benefits obtained using mutant Taq DNA polymerases was lower for the Gen2 RDxxD primers, which already showed high ΔCq values using wild type OptiTaq. Average ΔΔCq for the three mutant polymerases studied in the Example were 0.6, 2.1, and 1.2. Therefore greatest benefit when using the Gen2 RDxxD primers was seen with MUT ID 3 (H784Q).

TABLE 17

ΔΔCq values for rhPCR reactions using mutant Taq DNA polymerases compared with wild type OptiTaq for Gen1 RDDDDx blocked-cleavable rhPCR primers.

| DNA Polymerase | Reverse Primer Name | SEQ ID NO. | A SEQ ID NO. 51 | G SEQ ID NO. 53 | T SEQ ID NO. 54 | C SEQ ID NO. 52 |
|---|---|---|---|---|---|---|
| MUT ID 2 V783F | Syn Rev rU DDDDx | 66 | — | 0.6 | 1.7 | 2.4 |
| | Syn Rev rC DDDDx | 67 | 0.7 | — | 0.6 | 1.4 |
| | Syn Rev rA DDDDx | 68 | 0.9 | 0.6 | — | 2.1 |
| | Syn Rev rG DDDDx | 69 | 0.7 | −0.3 | 1.1 | — |
| MUT ID 3 H784Q | Syn Rev rU DDDDx | 66 | — | 0.8 | 1.6 | 3.4 |
| | Syn Rev rC DDDDx | 67 | 4.3 | — | 3.0 | 3.7 |
| | Syn Rev rA DDDDx | 68 | 1.3 | 0.8 | — | 4.1 |
| | Syn Rev rG DDDDx | 69 | 1.4 | 0.1 | −0.8 | — |
| MUT ID 18 V783L H784Q | Syn Rev rU DDDDx | 66 | — | 1.8 | 3.3 | 4.9 |
| | Syn Rev rC DDDDx | 67 | 6.6 | — | 7.0 | 8.2 |
| | Syn Rev rA DDDDx | 68 | 2.0 | 2.7 | — | 3.3 |
| | Syn Rev rG DDDDx | 69 | 1.8 | 1.2 | 0.8 | — |

ΔΔCq values are shown, where ΔΔCq = [ΔCq mutant − ΔCq wild type polymerase].

TABLE 18

ΔΔCq values for rhPCR reactions using mutant Taq DNA polymerases compared with wild type OptiTaq for Gen2 RDxxD blocked-cleavable rhPCR primers.

| DNA Polymerase | Reverse Primer Name | SEQ ID NO. | A SEQ ID NO. 51 | G SEQ ID NO. 53 | T SEQ ID NO. 54 | C SEQ ID NO. 52 |
|---|---|---|---|---|---|---|
| MUT ID 2 V783F | Syn Rev rU DxxD | 70 | — | 0.6 | −0.1 | 1.2 |
| | Syn Rev rC DxxD | 71 | 2.0 | — | −0.2 | −0.2 |
| | Syn Rev rA DxxD | 72 | 0.4 | 0.3 | — | −0.1 |
| | Syn Rev rG DxxD | 73 | 0.6 | 0.8 | 1.4 | — |
| MUT ID 3 H784Q | Syn Rev rU DxxD | 70 | — | 0.8 | −0.1 | 1.3 |
| | Syn Rev rC DxxD | 71 | 3.2 | — | 1.1 | 1.8 |
| | Syn Rev rA DxxD | 72 | 3.2 | 3.5 | — | 4.1 |
| | Syn Rev rG DxxD | 73 | 2.8 | 1.6 | 2.5 | — |

TABLE 18-continued

ΔΔCq values for rhPCR reactions using mutant Taq DNA polymerases compared with wild type OptiTaq for Gen2 RDxxD blocked-cleavable rhPCR primers.

| DNA Polymerase | Reverse Primer Name | SEQ ID NO. | Template A SEQ ID NO. 51 | Template G SEQ ID NO. 53 | Template T SEQ ID NO. 54 | Template C SEQ ID NO. 52 |
|---|---|---|---|---|---|---|
| MUT ID 18 V783L H784Q | Syn Rev rU DxxD | 70 | — | 1.4 | 0.2 | 1.5 |
| | Syn Rev rC DxxD | 71 | 0.6 | — | 2.9 | −1.0 |
| | Syn Rev rA DxxD | 72 | 2.1 | −0.3 | — | 0.2 |
| | Syn Rev rG DxxD | 73 | 1.8 | 2.0 | 3.5 | — |

ΔΔCq values are shown, where ΔΔCq = [ΔCq mutant − ΔCq wild type polymerase].

Example 8: Improved Mismatch Discrimination in rhPCR Using Mutant Taq DNA Polymerases in a Human Genomic DNA SNP Assay Example 7 demonstrated utility of the novel mutant Taq DNA polymerases of the present invention in a synthetic amplicon rhPCR SNP discrimination assay system. The present Example demonstrates utility of the novel mutant Taq DNA polymerases in a human genomic DNA rhPCR SNP discrimination assays system, examining a SNP site in the SMAD7 gene (NM_005904, C/T SNP, rs4939827). The assays employed target DNAs GM18562 (homozygous C/C) and GM18537 (homozygous T/T) from the Coriell Institute for Medical Research (Camden, N.J., USA). Two different blocked-cleavable primer designs were tested, including the generation 1 (Gen1) "RDDDDx" primers and the generation 2 (Gen2) "RDxxD" primers (see: US Patent Application 2012/0258455 by Behlke et al., entitled, RNASE H-BASED ASSAYS UTILIZING MODIFIED RNA MONOMERS).

Quantitative real-time rhPCR was performed in 10 μL reaction volumes in 384 well format with 20 ng (the equivalent of 6600 copies of target) of human genomic DNA (GM18562 or GM18537). Reactions utilized either 0.5 U (10.8 ng/11.1 nM/111 fmol) of wild type OptiTaq DNA polymerase or 0.5 U of one of the four Taq DNA polymerase mutants (MUT ID 2, V783F; MUT ID 3, H784Q; MUT ID 10, A661E 1665W F667L; or MUT ID 18, V783L H784Q). Final reaction conditions used were 20 mM Tris-HCL (pH 8.4 at 25° C.), 50 mM KCL, 3 mM MgCl₂, 0.01% Triton X-100, 800 μM total dNTPs, 200 nM of a forward primer (SEQ ID NOs. 75-79), 200 nM of the universal reverse primer (SEQ ID NO. 74), and 200 nM of the SMAD7 probe (SEQ ID NO. 80). Sequence of the 85 bp SMAD7 amplicon is shown as SEQ ID NO. 81. Forward primers included RDDDDx configuration Gen1 allele-specific rhPCR primers (SEQ ID NOs. 76 and 77), RDxxD configuration Gen2 allele-specific rhPCR primers (SEQ ID NOs. 78 and 79) and the control universal forward primer (SEQ ID NO. 75) which is not allele specific. Oligonucleotide reagents employed in this Example are shown in Table 19. Reactions included 1 μL of P.a. RNase H2 at a concentration of 2.6 mU per 10 μL reaction (5 fmoles, 0.5 nM) for the Gen1 RDDDDx primers and control primer (SEQ ID NOs. 75-77) or 200 mU per 10 μL reaction (384 fmoles, 38.4 nM) for the Gen2 RDxxD primers (SEQ ID NOs. 78 and 79). Amplification was performed on a Roche LightCycler® 480 (Roche Applied Science, Indianapolis, Ind., USA) as follows: 95° C. for 3 minutes followed by 75 cycles of 95° C. for 10 seconds and 60° C. for 30 seconds. All reactions were performed in triplicate.

TABLE 19

Synthetic oligonucleotides employed in Example 8.

| Name | Sequence (5'-3') | SEQ ID NO. |
|---|---|---|
| SMAD7 Rev | CTCACTCTAAACCCCAGCATT | 74 |
| SMAD7 For | CAGCCTCATCCAAAAGAGGAAA | 75 |
| SMAD7 For rC DDDDx | CAGCCTCATCCAAAAGAGGAAAcAGGAx | 76 |
| SMAD7 For rU DDDDx | CAGCCTCATCCAAAAGAGGAAAuAGGAx | 77 |
| SMAD7 For rC DxxD | CAGCCTCATCCAAAAGAGGAAAcAxxA | 78 |
| SMAD7 For rU DxxD | CAGCCTCATCCAAAAGAGGAAAuAxxA | 79 |
| SMAD7 probe | FAM-CCCAGAGCTCCCTCAGACTCCT-IBFQ | 80 |

TABLE 19-continued

Synthetic oligonucleotides employed in Example 8.

| Name | Sequence (5'-3') | SEQ ID NO. |
|---|---|---|
| SMAD7 target | CAGCCTCATCCAAAAGAGGAAATAGGACCCCAGAGCTCCCTCA GACTCCTCAGGAAACACAGACAATGCTGGGGTTTAGAGTGAG | 81 |

DNA bases are uppercase and RNA bases are lowercase; FAM = 6-carboxyfluorescein; IBFQ = Iowa Black ™ FQ fluorescence quencher; "x" = C3 Spacer (propanediol). Primer and probe binding sites in the SMAD7 target are underlined.

Results using the Gen1 RDDDDx rhPCR primers are shown in Table 20 and using the Gen2 RDxxD rhPCR primers are shown in Table 21. Overall, use of the mutant Taq DNA polymerases showed small but real improvements in SNP discrimination in this human genomic DNA rhPCR assay using the Gen1 RDDDDx primers. However, large improvements in discrimination were seen using the Gen2 RDxxD primers. The Gen2 RDxxD primers inherently show greater SNP discrimination and these levels were increased so that ΔCq values are in some cases were greater than 40 amplification cycles between match and mismatch; this level of discrimination would be "greater than assay" for most users, as qPCR reactions are seldom run for over 45-50 cycles and positive signal was not detected in these cases until after 70 cycles (Table 21). Therefore use of the new mutant Taq DNA polymerases improves SNP discrimination in rhPCR genotyping assays.

TABLE 20

SNP discrimination of a site in the SMAD7 gene using Gent RDDDDx primers comparing wild type OptiTaq with four mutant Tag DNA polymerases.

| DNA Polymerase | For Primer | SEQ ID NO. | mU RNase h2 per 10 µL rxn | Cq Value C/C DNA | Cq Value T/T DNA | ΔCq |
|---|---|---|---|---|---|---|
| Wild type OptiTaq | SMAD7 For | 75 | 2.6 | 24.3 | 25.3 | — |
| | SMAD7 For rC DDDDx | 76 | 2.6 | 26.1 | 38.1 | 11.9 |
| | SMAD7 For rU DDDDx | 77 | 2.6 | 36.6 | 26.8 | 9.8 |
| MUT ID 2 V783F | SMAD7 For | 75 | 2.6 | 24.7 | 25.5 | — |
| | SMAD7 For rC DDDDx | 76 | 2.6 | 26.2 | 40.3 | 14.1 |
| | SMAD7 For rU DDDDx | 77 | 2.6 | 37.8 | 27.6 | 10.1 |
| MUT ID 3 H784Q | SMAD7 For | 75 | 2.6 | 25.3 | 27.1 | — |
| | SMAD7 For rC DDDDx | 76 | 2.6 | 26.2 | 46.1 | 19.9 |
| | SMAD7 For rU DDDDx | 77 | 2.6 | 38.9 | 32.4 | 6.5 |
| MUT ID 10 A661E I665W F667L | SMAD7 For | 75 | 2.6 | 24.3 | 25.8 | — |
| | SMAD7 For rC DDDDx | 76 | 2.6 | 25.6 | 43.9 | 18.3 |
| | SMAD7 For rU DDDDx | 77 | 2.6 | 42.6 | 28.5 | 14.1 |
| MUT ID 18 V783L H784Q | SMAD7 For | 75 | 50 | 24.6 | 25.6 | — |
| | SMAD7 For rC DDDDx | 76 | 50 | 25.2 | 35.7 | 10.5 |
| | SMAD7 For rU DDDDx | 77 | 50 | 37.9 | 26.4 | 11.5 |

DNA targets included GM18562 (homozygous C/C) and GM18537 (homozygous T/T) from the Coriell Institute for Medical Research. ΔCq = [Cq mismatch − Cq match].

TABLE 21

SNP discrimination of a site in the SMAD7 gene using Gen2 RDxxD primers comparing wild type OptiTaq with four mutant Tag DNA polymerases.

| DNA Polymerase | For Primer | SEQ ID NO. | mU RNase h2 per 10 µL rxn | Cq Value C/C DNA | Cq Value T/T DNA | ΔCq |
|---|---|---|---|---|---|---|
| Wild type OptiTaq | SMAD7 For | 75 | 2.6 | 24.3 | 25.3 | — |
| | SMAD7 For rC DxxD | 78 | 200 | 25.9 | 40.4 | 14.5 |
| | SMAD7 For rU DxxD | 79 | 200 | 47.9 | 26.6 | 21.3 |
| MUT ID 2 V783F | SMAD7 For | 75 | 2.6 | 24.7 | 25.5 | — |
| | SMAD7 For rC DxxD | 78 | 200 | 26.6 | 64.4 | 37.7 |

TABLE 21-continued

SNP discrimination of a site in the SMAD7 gene using Gen2 RDxxD primers comparing wild type OptiTaq with four mutant Taq DNA polymerases.

| DNA Polymerase | For Primer | SEQ ID NO. | mU RNase h2 per 10 μL rxn | Cq Value C/C DNA | Cq Value T/T DNA | ΔCq |
|---|---|---|---|---|---|---|
|  | SMAD7 For rU DxxD | 79 | 200 | 59.7 | 28.0 | 31.6 |
| MUT ID 3 H784Q | SMAD7 For | 75 | 2.6 | 25.3 | 27.1 | — |
|  | SMAD7 For rC DxxD | 78 | 200 | 26.7 | 71.7 | 45.0 |
|  | SMAD7 For rU DxxD | 79 | 200 | 62.5 | 28.9 | 33.7 |
| MUT ID 10 A661E I665W F667L | SMAD7 For | 75 | 2.6 | 24.3 | 25.8 | — |
|  | SMAD7 For rC DxxD | 78 | 200 | 25.6 | 74.4 | 48.8 |
|  | SMAD7 For rU DxxD | 79 | 200 | 54.3 | 28.2 | 26.0 |
| MUT ID 18 V783L H784Q | SMAD7 For | 75 | 50 | 24.6 | 25.6 | — |
|  | SMAD7 For rC DxxD | 78 | 200 | 25.1 | 52.7 | 27.6 |
|  | SMAD7 For rU DxxD | 79 | 200 | 43.0 | 27.6 | 15.3 |

DNA targets included GM18562 (homozygous C/C) and GM18537 (homozygous T/T) from the Coriell Institute for Medical Research. ΔCq = [Cq mismatch − Cq match].

Figure 5A:
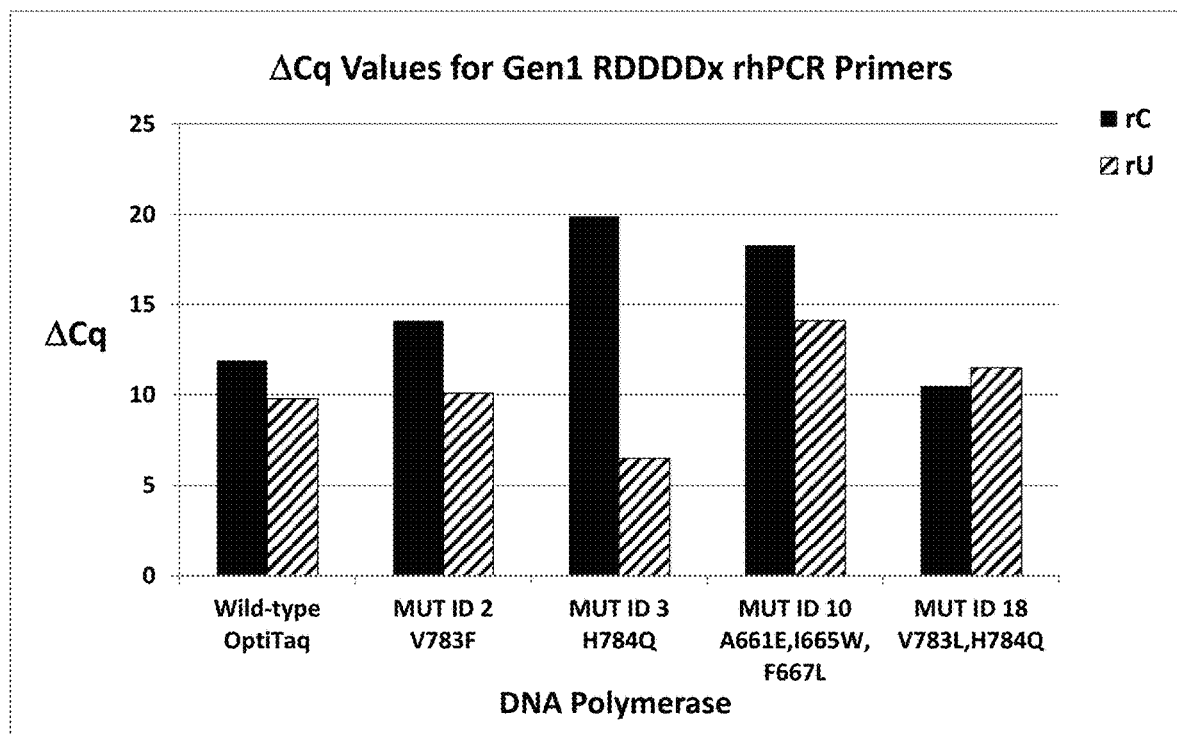
FIG. 5A shows graphical representations of the ΔCq values (Tables 20 and 34) obtained from comparing mismatch discrimination between wild type OptiTaq with Mutant ID 2, Mutant ID 3, Mutant ID 10, and Mutant ID 18 Taq DNA polymerases detecting a human genomic DNA SNP in the SMAD7 gene (NM_005904, C/T SNP, rs4939827) using Gen1 RDDDDx blocked-cleavable primers in a quantitative rhPCR assay. ΔCq=[Cq mismatch−Cq match]. Legend: Identity of each DNA polymerase studied is shown on the X-axis. The RDDDDx blocked-cleavable primer contained either a rC or rU residue as the cleavable base, specific for the "C" or "T" allele, as indicated.
Figure 6A:
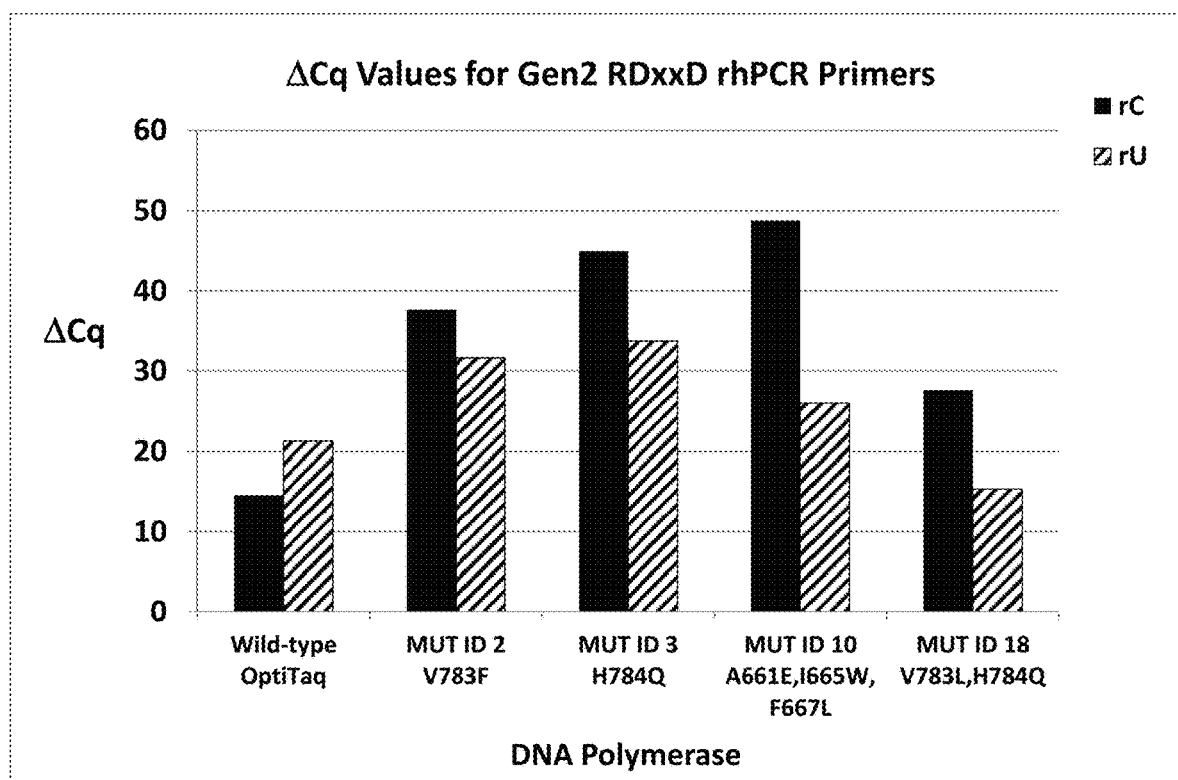
FIG. 6A shows a graphical representation of the ΔCq values (Tables 21 and 35) obtained from comparing mismatch discrimination between wild type OptiTaq with Mutant ID 2, Mutant ID 3, Mutant ID 10, and Mutant ID 18 Taq DNA polymerases detecting a human genomic DNA SNP in the SMAD7 gene (NM_005904, C/T SNP, rs4939827) using Gen2 RDxxD blocked-cleavable primers in a quantitative rhPCR assay. ΔCq=[Cq mismatch−Cq match]. Legend: Identity of each DNA polymerase studied is shown on the X-axis. The RDxxD blocked-cleavable primer contained either a rC or rU residue as the cleavable base, specific for the "C" or "T" allele, as indicated.

The ΔCq values for the SMAD7 SNP genotyping assays are graphically summarized in FIG. 5A for the Gen1 RDDDDx primers and in FIG. 6A for the Gen2 RDxxD primers. It is interesting to note that, for the rhPCR genotyping assays studied in Example 8, MUT ID 10 (A661E I665W F667L) showed the greatest improvement compare with wild type OptiTaq, especially when using the Gen2 RDxxD primers. Example 5 demonstrated utility of the mutant Taq DNA polymerases in AS-PCR, and in this case use of MUT ID 18 (V783L H784Q) showed the greatest benefit and MUT ID 3 (H784Q) showed the next greatest relative benefit. It is clear that not only do the different mutant Taq DNA polymerases of the present invention have utility in different amplification assays but that the different mutants show varying levels of benefit depending on the nature of the assay used. It is therefore useful to have a collection of mutant polymerases whose properties can be matched to different assays/applications so that maximal benefit is obtained.

Example 9: Improved Discrimination of Rare Alleles in Genomic DNA Using rhPCR with Mutant Taq DNA Polymerases Use of the Gen2 RDxxD blocked-cleavable primers in rhPCR can detect the presence of a SNP at a level of 1:1,000 to 1:10,000 in the background of wild type genomic DNA using native (wild type) Taq DNA polymerase (see: US Patent Application 2012/0258455 by Behlke et al., entitled, RNASE H-BASED ASSAYS UTILIZING MODIFIED RNA MONOMERS). The present example demonstrates that the mutant Taq DNA polymerases of the present invention improve rare allele discrimination in the rhPCR assay.

Rare allele detection experiments were designed to detect the base identity of a SNP site in the SMAD7 gene (NM_005904, C/T SNP, rs4939827) and employed target DNAs GM18562 (homozygous C/C) and GM18537 (homozygous T/T) (Coriell Institute for Medical Research, Camden, N.J., USA). Control reactions were set up using 2 ng (660 copies), 0.2 ng (66 copies), or 0.02 ng (6.6 copies) of input matched target DNA. Rare allele detection reactions were set up using 2 ng (660 copies), 0.2 ng (66 copies), or 0.02 ng (6.6 copies) of input matched target DNA of one allele plus 200 ng (66,000 copies) of the other (mismatched) allele. Background was established in reactions that contained 0 copies of matched target DNA plus 200 ng (66,000 copies) of the mismatched target DNA. Both combinations were tested: GM18562 (C/C) as the rare allele in the presence of excess GM18537 (T/T) and GM18537 (T/T) as the rare allele in the presence of excess GM18562 (C/C).

Quantitative real-time rhPCR was performed in 10 μL reaction volumes in 384 well format. Final reaction conditions used were 10 mM Tris-HCL (pH 8.4 at 25° C.), 50 mM KCL, 3.5 mM $MgCl_2$, 0.01% Triton-X100, 0.8 mM dNTPs, 200 nM of one of the SMAD7 forward primers (SEQ ID NOs. 75, 78, and 79), 200 nM of the SMAD7 reverse primer (SEQ ID NO. 74), and 200 nM of the SMAD7 probe (SEQ ID NO. 80). The 85 bp SMAD7 amplicon defined by these primers is shown as SEQ ID NO. 81. Note that the forward primers were either unmodified (control, SEQ ID NO. 75) or were specific for the SMAD7 C-allele (SEQ ID NO. 78) or the SMAD7 T-allele (SEQ ID NO. 79) using blocked-cleavable rhPCR Gen2 RDxxD design. Reactions utilized either 0.5 U of the wild type OptiTaq DNA polymerase or 0.5 U of one of the four Taq DNA polymerase mutants studied (MUT ID No. 2, V783F; MUT ID NO. 3, H784Q; MUT ID NO. 10, A661E I665W F667L; or MUT ID NO. 18, V783L H784Q). Reactions included P. abyssi RNase H2 at a concentration of 200 mU per 10 μL reaction (384 fmoles) when using the SMAD7 For rC DxxD (SEQ ID NO. 78) primer and control reactions or 500-600 mU per 10 μL reaction (960-1152 fmoles) when using the SMAD7 For rU DxxD (SEQ ID NO. 79) primer. Oligonucleotide reagents used in this Example are shown in Table 22. Cycling was performed on a Roche LightCycler® 480 (Roche Applied Science, Indianapolis, Ind., USA) as follows: 95° C. for 3 minutes followed by 65 cycles of 95° C. for 10 seconds and 60° C. for 30 seconds. All reactions were performed in triplicate.

TABLE 22

Synthetic oligonucleotides employed in Example 9.

| Name | Sequence (5'-3') | SEQ ID NO. |
|---|---|---|
| SMAD7 Rev | CTCACTCTAAACCCCAGCATT | 74 |
| SMAD7 For | CAGCCTCATCCAAAAGAGGAAA | 75 |
| SMAD7 For rC DxxD | CAGCCTCATCCAAAAGAGGAAAcAxxA | 78 |
| SMAD7 For rU DxxD | CAGCCTCATCCAAAAGAGGAAAuAxxA | 79 |
| SMAD7 probe | FAM-CCCAGAGCTCCCTCAGACTCCT-IBFQ | 80 |
| SMAD7 target | CAGCCTCATCCAAAAGAGGAAATAGGACCCCAGAGCTCCCTCAGACTCCTCAGGAAACACAGACAATGCTGGGGTTTAGAGTGAG | 81 |

DNA bases are uppercase and RNA bases are lowercase; FAM = 6-carboxyfluorescein; IBFQ = Iowa Black ™ FQ fluorescence quencher; "x" = C3 Spacer (propanediol). Primer and probe binding sites in the SMAD7 target are underlined.

Results were analyzed and are shown in Table 23. The control columns show Cq values for matched primer/target reactions with no mismatched target present and establish a quantification standard curve. The rare allele detection columns show Cq values for detection of 660, 66, 6, or 0 (background control) copies of matched primer/target in the presence of 66,000 copies of mismatched target. It is generally assumed that at least a 3 cycle difference (ΔCq=3.0 or greater) between background and positive signal is needed to call a reaction "positive" for rare allele detection; a 5 cycle difference (ΔCq=5.0 or greater) is preferred. In this system, background is the signal observed when amplification is done using no input target that is matched to the primer, so signal arises solely from amplification originating off the mismatched target.

Using wild type OptiTaq DNA polymerase, detection of the "C" allele in an excess of "T" background and detection of the "T" allele in an excess of "C" background both met the ΔCq 3.0 and ΔCq 5.0 levels of stringency to call a 1:1000 rare allele detection event (66 copies of match target in the presence of 66,000 copies of mismatch target). The 1:10,000 reactions (6 copies of match target in the presence of 66,000 copies of mismatch target) did not meet either of these criteria. Thus rhPCR had a 1:1000 rare allele detection limit using wild type OptiTaq in this genomic DNA SNP system.

In contrast, rhPCR using each of the four mutants showed a 1:10,000 rare allele detection limit for both the "C" and "T" allele targets with a ΔCq stringency cutoff of 3.0. MUT ID 3 (H784Q) showed a 1:10,000 rare allele detection limit for both the "C" and "T" targets in this genomic SNP system for the higher ΔCq stringency cutoff of 5.0. The other three mutant Taq DNA polymerases (MUT ID No. 2, V783F; MUT ID NO. 10, A661E 1665W F667L; and MUT ID NO. 18, V783L H784Q) showed a 1:10,000 rare allele detection limit for the "C" allele target with a ΔCq stringency cutoff of 5.0 and a 1:10,000 rare allele detection limit for the "T" allele target with a ΔCq stringency cutoff of 3.0. We therefore conclude that the new mutant Taq DNA polymerases of the present invention provide for improved rare allele detection reactions using blocked-cleavable primers in rhPCR compared with use of the wild type DNA polymerase.

TABLE 23

Rare allele detection using Gen2 RDxxD rhPCR primers comparing wild type OptiTaq with new mutant Taq DNA polymerases

| DNA Polymerase | For Primer | SEQ ID NO. | RNase H2 per 10 µL rxn | 200 ng mismatched template (66,000 copies of "wild type") | | | | Control (No mismatched template) | | | |
|---|---|---|---|---|---|---|---|---|---|---|---|
| | | | | 660 Match (1:100) | 66 Match (1:1,000) | 6 Match (1:10,000) | 0 Match (background) | 660 Match | 66 Match | 6 Match | 0 Match |
| Wild type OptiTaq | SMAD7 For | 75 | 200 mU | 22.1 | 21.2 | 21.2 | 21.8 | 27.9 | 31.3 | 34.4 | >65 |
| | SMAD7 For rC DxxD | 78 | 200 mU | 28.2 | 31.5 | 35.1 | 37.0 | 28.8 | 33.3 | 37.3 | >65 |
| | SMAD7 For rU DxxD | 79 | 500 mU | 31.0 | 34.7 | 37.7 | 39.7 | 31.2 | 34.6 | 41.0 | >65 |
| MUT ID 2 (V783F) | SMAD7 For | 75 | 200 mU | 22.2 | 22.2 | 22.1 | 22.2 | 28.9 | 32.7 | 35.7 | >65 |
| | SMAD7 For rC DxxD | 78 | 200 mU | 28.2 | 31.7 | 35.4 | 45.4 | 29.0 | 33.3 | 37.5 | >65 |
| | SMAD7 For rU DxxD | 79 | 500 mU | 28.6 | 32.5 | 36.7 | 41.3 | 28.2 | 34.0 | 42.0 | >65 |

TABLE 23-continued

Rare allele detection using Gen2 RDxxD rhPCR primers comparing wild type OptiTaq with new mutant Taq DNA polymerases

| DNA Polymerase | For Primer | SEQ ID NO. | RNase H2 per 10 µL rxn | 200 ng mismatched template (66,000 copies of "wild type") | | | | Control (No mismatched template) | | | |
|---|---|---|---|---|---|---|---|---|---|---|---|
| | | | | 660 Match (1:100) | 66 Match (1:1,000) | 6 Match (1:10,000) | 0 Match (background) | 660 Match | 66 Match | 6 Match | 0 Match |
| MUT ID 3 (H784Q) | SMAD7 For | 75 | 200 mU | 23.5 | 23.6 | 24.5 | 24.1 | 30.5 | 33.4 | 38.0 | >65 |
| | SMAD7 For rC DxxD | 78 | 200 mU | 29.8 | 33.8 | 37.6 | >65 | 30.5 | 35.5 | 39.6 | >65 |
| | SMAD7 For rU DxxD | 79 | 500 mU | 32.9 | 37.7 | 44.0 | 52.3 | 30.1 | 35.9 | 44.9 | >65 |
| MUT ID 10 (A661E I665W F667L) | SMAD7 For | 75 | 200 mU | 22.2 | 22.4 | 22.5 | 22.8 | 28.3 | 31.9 | 35.5 | >65 |
| | SMAD7 For rC DxxD | 78 | 200 mU | 31.8 | 34.7 | 38.5 | 59.3 | 30.0 | 33.9 | 37.8 | >65 |
| | SMAD7 For rU DxxD | 79 | 600 mU | 33.5 | 38.4 | 43.2 | 46.2 | 31.9 | 36.5 | 41.0 | >65 |
| MUT ID 18 (V783L H784Q) | SMAD7 For | 75 | 200 mU | 22.4 | 22.4 | 22.7 | 22.5 | 27.8 | 31.5 | 34.8 | >65 |
| | SMAD7 For rC DxxD | 78 | 200 mU | 28.8 | 32.9 | 37.5 | 46.5 | 29.5 | 33.4 | 37.8 | >65 |
| | SMAD7 For rU DxxD | 79 | 500 mU | 30.1 | 34.0 | 38.4 | 41.8 | 29.4 | 36.0 | 44.7 | >65 |

Cq values are shown. For the rare allele detection series (selective detection of 6-660 copes one genotype in the presence of 66,000 copies of the other genotype), those reactions having a ΔCq of 3.0 or better are highlighted in bold font and those having a ΔCq of 5.0 or better are highlighted in bold font with underline. ΔCq = [(Cq 0 copies match) − (Cq 6 copies match)], or ΔCq = [(Cq 0 copies match) − (Cq 66 copies match)], or ΔCq = [(Cq 0 copies match) − (Cq 660 copies match)].

Example 10. Sequence of Taq DNA Polymerase Mutants Showing Improved Discrimination for Mismatch or the Presence of an RNA Residue at the 3'-End of the Primer The complete amino acid and nucleotide sequences of the codon optimized mutant enzymes employed in Examples 5-9 are shown below. Although these sequences are easily derived from information provided in Tables 1, 3, 4 and 5 by one with skill in the art, the final assembled sequences are provided below for clarity. Base changes are identified in bold underlined font for the nucleic acid and amino acid substitutions.

```
SEQ ID NO. 82, nucleotide sequence of Mutant ID 2 (V783F).
CATATGCGTGGTATGCTGCCGTTGTTCGAGCCTAAAGGCCGCGTACTGTTAGTCGATGGTCATCACTTGGCCTATCG
GACGTTCCATGCACTCAAAGGTCTGACGACCAGTCGTGGCGAACCGGTCCAGGCTGTTTATGGTTTCGCTAAGTCTT
TGCTCAAAGCACTGAAAGAAGACGGGGACGCGGTAATTGTTGTATTTGATGCCAAAGCACCGAGCTTCCGCCACGAA
GCTTATGGTGGCTACAAGGCAGGACGCGCCCCTACCCCAGAAGATTTCCCCCGTCAGCTGGCATTAATTAAGGAGTT
AGTAGACCTTCTCGGCTTAGCGCGTCTGGAAGTTCCGGGTTATGAGGCGGACGATGTCCTTGCATCCTTGGCTAAAA
AGGCCGAAAAAGAGGGCTACGAAGTCCGCATCTTGACGGCAGACAAAGATCTGTACCAGCTTCTGTCTGACCGTATT
CATGTTTTGCACCCTGAAGGCTACTTAATCACTCCGGCCTGGCTCTGGGAAAAGTACGGTCTGCGTCCCGATCAGTG
GGCGGATTATCGGGCTTTGACGGGAGATGAGAGCGACAACCTGCCAGGAGTTAAGGGCATTGGTGAAAAAACCGCAC
GTAAGCTGCTTGAAGAGTGGGGTTCCCTGGAAGCCTTGTTAAAAAATCTGGATCGTCTCAAGCCCGCAATTCGTGAA
AAGATCCTGGCTCATATGGACGATCTTAAATTAAGTTGGGACCTGGCCAAGGTGCGCACCGATTTACCGCTTGAAGT
GGATTTTGCAAAACGCCGTGAGCCGGACCGGGAACGTTTACGCGCTTTCTTAGAGCGTCTGGAATTCGGTTCACTGC
TTCATGAATTCGGTCTGTTAGAGTCTCCTAAAGCACTCGAAGAGGCACCGTGGCCGCCCCAGAAGGTGCTTTTGTT
GGCTTCGTACTTTCCCGTAAGGAGCCTATGTGGGCAGATCTTCTGGCTTTAGCGGCTGCACGCGGTGGCCGTGTTCA
CCGGGCCCCTGAGCCATACAAAGCGTTACGTGATCTGAAGGAAGCACGTGGCTTGCTGGCAAAAGACCTTTCTGTTT
TGGCCCTGCGCGAGGGTCTTGGACTGCCGCCAGGCGACGATCCCATGTTATTGGCCTATCTGTTAGACCCTAGCAAT
ACCACACCTGAAGGGGTCGCTCGTCGGTATGGCGGTGAATGGACTGAGGAAGCCGGAGAGCGCGCCGCATTGTCCGA
ACGGCTCTTTGCAAACTTATGGGGTCGTCTGGAAGGGGAGGAACGTCTGTTATGGTTGTATCGGGAAGTCGAACGTC
CTCTTTCGGCCGTATTAGCGCATATGGAGGCAACAGGTGTGCGTTTAGATGTCGCGTACCTTCGGGCCTTATCACTG
GAAGTTGCAGAGGAAATCGCCCGTCTCGAGGCTGAAGTGTTCCGGTTGGCCGGTCACCCGTTTAACCTCAACTCCCG
TGACCAGCTGGAACGCGTTTTATTCGATGAGCTTGGGCTTCCCGCAATTGGCAAAACCGAAAAGACTGGCAAACGCA
GTACGAGCGCTGCCGTCCTTGAGGCACTCCGCGAGGCTCACCCTATTGTAGAAAAGATCCTGCAATACCGTGAGTTG
ACGAAGCTTAAAAGCACTTATATTGATCCTCTCCCGGATCTGATCCATCCTCGTACCGGCCGCTTGCACACAGTTT
CAACCAGACGGCGACTGCAACCGGCCGTCTGTCTAGCTCGGATCCAAATCTCCAGAACATTCCGGTCCGTACACCCT
TGGGCCAACGTATCCGCCGGGCGTTTATCGCTGAGGAAGGATGGTTACTGGTCGCATTGGACTACTCGCAGATTGAG
CTGCGCGTCCTCGCACATCTCTCTGGTGACGAAAATTTAATCCGCGTGTTTCAAGAGGGGCGTGATATTCACACAGA
AACTGCCTCATGGATGTTCGGTGTCCCACGTGAAGCAGTGGATCCTTTGATGCGCCGTGCAGCTAAAACAATTAATT
```

-continued

```
TTGGAGTGCTGTACGGAATGAGCGCTCATCGCTTGAGTCAGGAACTGGCAATCCCCTACGAGGAAGCGCAGGCATTC
ATCGAACGTTACTTTCAATCGTTTCCGAAAGTTCGCGCATGGATCGAGAAGACGCTCGAGGAAGGTCGTCGTCGGGG
CTATGTCGAAACTCTGTTTGGTCGCCGTCGGTACGTACCAGATCTTGAAGCCCGCGTCAAATCGGTACGGGAGGCTG
CGGAGCGTATGGCATTTAATATGCCTGTACAGGGTACTGCAGCTGACCTCATGAAACTGGCAATGGTCAAGCTTTTC
CCGCGCTTGGAGGAAATGGGCGCACGTATGCTTCTGCAGTTCCATGACGAGCTGGTGTTAGAAGCCCCTAAGGAGCG
CGCCGAAGCTGTCGCGCGCCTCGCTAAAGAAGTGATGGAGGGCGTTTACCCATTGGCCGTACCCCTCGAAGTGGAGG
TCGGTATTGGAGAAGATTGGTTATCTGCAAAGGAAGCGGCCGC
```

SEQ ID NO. 83, amino acid sequence of Mutant ID 2 (V783F).
```
MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQFHDELVLEAPKERAEAVARLAKEVMEGVYPLAVPLEVEVGIGEDWLSAKEAA
```

SEQ ID NO. 84, nucleotide sequence of Mutant ID 3 (H784Q).
```
CATATGCGTGGTATGCTGCCGTTGTTCGAGCCTAAAGGCCGCGTACTGTTAGTCGATGGTCATCACTTGGCCTATCG
GACGTTCCATGCACTCAAAGGTCTGACGACCAGTCGTGGCGAACCGGTCCAGGCTGTTTATGGTTTCGCTAAGTCTT
TGCTCAAAGCACTGAAAGAAGACGGGGACGCGGTAATTGTTGTATTTGATGCCAAAGCACCGAGCTTCCGCCACGAA
GCTTATGGTGGCTACAAGGCAGGACGCGCCCCTACCCCAGAAGATTTCCCCCGTCAGCTGGCATTAATTAAGGAGTT
AGTAGACCTTCTCGGCTTAGCGCGTCTGGAAGTTCCGGGTTATGAGGCGGACGATGTCCTTGCATCCTTGGCTAAAA
AGGCCGAAAAGGAGGGCTACGAAGTCCGCATCTTGACGGCAGACAAAGATCTGTACCAGCTTCTGTCTGACCGTATT
CATGTTTTGCACCCTGAAGGCTACTTAATCACTCCGGCCTGGCTCTGGGAAAAGTACGGTCTGCGTCCCGATCAGTG
GGCGGATTATCGGGCTTTGACGGGAGATGAGAGCGACAACCTGCCAGGAGTTAAGGGCATTGGTGAAAAAACCGCAC
GTAAGCTGCTTGAAGAGTGGGGTTCCCTGGAAGCCTTGTTAAAAAATCTGGATCGTCTCAAGCCCGCAATTCGTGAA
AAGATCCTGGCTCATATGGACGATCTTAAATTAAGTTGGGACCTGGCCAAGGTGCGCACCGATTTACCGCTTGAAGT
GGATTTTGCAAAACGCCGTGAGCCGGACCGGGAACGTTTACGCGCTTTCTTAGAGCGTCTGGAATTCGGTTCACTGC
TTCATGAATTCGGTCTGTTAGAGTCTCCTAAAGCACTCGAAGAGGCACCGTGGCCGCCCCCAGAAGGTGCTTTTGTT
GGCTTCGTACTTTCCCGTAAGGAGCCTATGTGGGCAGATCTTCTGGCTTTAGCGGCTGCACGCGGTGGCCGTGTTCA
CCGGGCCCCTGAGCCATACAAAGCGTTACGTGATCTGAAGGAAGCACGTGGCTTGCTGGCAAAAGACCTTTCTGTTT
TGGCCCTGCGCGAGGGTCTTGGACTGCCGCCAGGCGACGATCCCATGTTATTGGCCTATCTGTTAGACCCTAGCAAT
ACCACACCTGAAGGGGTCGCTCGTCGGTATGGCGGTGAATGGACTGAGGAAGCCGGAGAGCGCGCCGCATTGTCCGA
ACGGCTCTTTGCAAACTTATGGGGTCGTCTGGAAGGGGAGGAACGTCTGTTATGGTTGTATCGGGAAGTCGAACGTC
CTCTTTCGGCCGTATTAGCGCACATGGAGGCAACAGGTGTGCGTTTAGATGTCGCGTACCTTCGGGCCTTATCACTG
GAAGTTGCAGAGGAAATCGCCCGTCTCGAGGCTGAAGTGTTCCGGTTGGCCGGTCACCCGTTTAACCTCAACTCCCG
TGACCAGCTGGAACGCGTTTTATTCGATGAGCTTGGGCTTCCCGCAATTGGCAAAACCGAAAAGACTGGCAAACGCA
GTACGAGCGCTGCCGTCCTTGAGGCACTCCGCGAGGCTCACCCTATTGTAGAAAAGATCCTGCAATACCGTGAGTTG
ACGAAGCTTAAAAGCACTTATATTGATCCTCTCCCGGATCTGATCCATCCTCGTACCGGCCGCTTGCACACACGTTT
CAACCAGACGGCGACTGCAACCGGCCGTCTGTCTAGCTCGGATCCAAATCTCCAGAACATTCCGGTCCGTACACCCT
TGGGGCCAACGTATCCGCCGGGCGTTTATCGCTGAGGAAGGATGGTTACTGGTCGCATTGGACTACTCGCAGATTGAG
CTGCGCGTCCTCGCACATCTCTGGTGACGAAATTTAATCCGCGTGTTTCAGGAGGGGCGTGATATTCACACAGA
AACTGCCTCATGGATGTTCGGTGTCCCACGTGAAGCAGTGGATCCTTTGATGCGCCGTGCAGCTAAAACAATTAATT
TTTGGAGTGCTGTACGGAATGAGCGCTCATCGCTTGAGTCAGGAACTGGCAATCCCCTACGAGGAAGCGCAGGCATTC
ATCGAACGTTACTTTCAATCGTTTCCGAAAGTTCGCGCATGGATCGAGAAGACGCTCGAGGAAGGTCGTCGTCGGGG
CTATGTCGAAACTCTGTTTGGTCGCCGTCGGTACGTACCAGATCTTGAAGCCCGCGTCAAATCGGTACGGGAGGCTG
CGGAGCGTATGGCATTTAATATGCCTGTACAGGGTACTGCAGCTGACCTCATGAAACTGGCAATGGTCAAGCTTTTC
CCGCGCTTGGAGGAAATGGGCGCACGTATGCTTCTGCAGGTCCAGGACGAGCTGGTGTTAGAAGCCCCTAAGGAGCG
CGCCGAAGCTGTCGCGCGCCTCGCTAAAGAAGTGATGGAGGGCGTTTACCCATTGGCCGTACCCCTCGAAGTGGAGG
TCGGTATTGGAGAAGATTGGTTATCTGCAAAGGAAGCGGCCGC
```

SEQ ID NO. 85, amino acid sequence of Mutant ID 3 (H784Q).
```
MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQVQQDELVLEAPKERAEAVARLAKEVMEGVYPLAVPLEVEVGIGEDWLSAKEAA
```

SEQ ID NO. 86, nucleotide sequence of Mutant ID 10 (A661E, I665W, F667L).
```
CATATGCGTGGTATGCTGCCGTTGTTCGAGCCTAAAGGCCGCGTACTGTTAGTCGATGGTCATCACTTGGCCTATCG
GACGTTCCATGCACTCAAAGGTCTGACGACCAGTCGTGGCGAACCGGTCCAGGCTGTTTATGGTTTCGCTAAGTCTT
TGCTCAAAGCACTGAAAGAAGACGGGGACGCGGTAATTGTTGTATTTGATGCCAAAGCACCGAGCTTCCGCCACGAA
GCTTATGGTGGCTACAAGGCAGGACGCGCCCCTACCCCAGAAGATTTCCCCCGTCAGCTGGCATTAATTAAGGAGTT
AGTAGACCTTCTCGGCTTAGCGCGTCTGGAAGTTCCGGGTTATGAGGCGGACGATGTCCTTGCATCCTTGGCTAAAA
AGGCCGAAAAGGAGGGCTACGAAGTCCGCATCTTGACGGCAGACAAAGATCTGTACCAGCTTCTGTCTGACCGTATT
CATGTTTTGCACCCTGAAGGCTACTTAATCACTCCGGCCTGGCTCTGGGAAAAGTACGGTCTGCGTCCCGATCAGTG
GGCGGATTATCGGGCTTTGACGGGAGATGAGAGCGACAACCTGCCAGGAGTTAAGGGCATTGGTGAAAAAACCGCAC
GTAAGCTGCTTGAAGAGTGGGGTTCCCTGGAAGCCTTGTTAAAAAATCTGGATCGTCTCAAGCCCGCAATTCGTGAA
AAGATCCTGGCTCATATGGACGATCTTAAATTAAGTTGGGACCTGGCCAAGGTGCGCACCGATTTACCGCTTGAAGT
GGATTTTGCAAAACGCCGTGAGCCGGACCGGGAACGTTTACGCGCTTTCTTAGAGCGTCTGGAATTCGGTTCACTGC
```

-continued

```
TTCATGAATTCGGTCTGTTAGAGTCTCCTAAAGCACTCGAAGAGGCACCGTGGCCGCCCCCAGAAGGTGCTTTTGTT
GGCTTCGTACTTTCCCGTAAGGAGCCTATGTGGGCAGATCTTCTGGCTTTAGCGGCTGCACGCGGTGGCCGTGTTCA
CCGGGCCCCTGAGCCATACAAAGCGTTACGTGATCTGAAGGAAGCACGTGGCTTGCTGGCAAAAGACCTTTCTGTTT
TGGCCCTGCGCGAGGGTCTTGGACTGCCGCCAGGCGACGATCCCATGTTATTGGCCTATCTGTTAGACCCTAGCAAT
ACCACACCTGAAGGGGTCGCTCGTCGGTATGGCGGTGAATGGACTGAGGAAGCCGGAGAGCGCGCCGCATTGTCCGA
ACGGCTCTTTGCAAACTTATGGGGTCGTCTGGAAGGGGAGGAACGTCTGTTATGGTTGTATCGGGAAGTCGAACGTC
CTCTTTCGGCCGTATTAGCGCATATGGAGGCAACAGGTGTGCGTTTAGATGTCGCGTACCTTCGGGCCTTATCACTG
GAAGTTGCAGAGGAAATCGCCCGTCTCGAGGCTGAAGTGTTCCGGTTGGCCGGTCACCCGTTTAACCTCAACTCCCG
TGACCAGCTGGAACGCGTTTTATTCGATGAGCTTGGGCTTCCCGCAATTGGCAAAACCGAAAAGACTGGCAAACGCA
GTACGAGCGCTGCCGTCCTTGAGGCACTCCGCGAGGCTCACCCTATTGTAGAAAAGATCCTGCAATACCGTGAGTTG
ACGAAGCTTAAAAGCACTTATATTGATCCTCTCCCGGATCTGATCCATCCTCGTACCGGCCGCTTGCACACACGTTT
CAACCAGACGGCGACTGCAACCGGCCGTCGTCTAGCTCGGATCCAAATCTCCAGAACATTCCGGTCCGTACACCCT
TGGGCCAACGTATCCGCCGGGCGTTATCGCTGAGGAAGGATGGTTACTGGTCGCATTGGACTACTCGCAGATTGAG
CTGCGCGTCCTCGCACATCTCTCTGGTGACGAAAATTTAATCCGCGTGTTTCAAGAGGGGCGTGATATTCACACAGA
AACTGCCTCATGGATGTTCGGTGTCCCACGTGAAGCAGTGGATCCTTTGATGCGCCGTGAAGCTAAAACATGGAATT
TGGGAGTGCTGTACGGAATGAGCGCTCATCGCTTGAGTCAGGAACTGGCAATCCCTACGAGGAAGCGCAGGCATTC
ATCGAACGTTACTTTCAATCGTTTCCGAAAGTTCGCGCATGGATCGAGAAGACGCTCGAGGAAGGTCGTCGTCGGGG
CTATGTCGAAACTCTGTTTGGTCGCCGTCGGTACGTACCAGATCTTGAAGCCCGCTCAAATCGGTACGGGAGGCTG
CGGAGCGTATGGCATTTAATATGCCTGTACAGGGTACTGCAGCTGACCTCATGAAACTGGCAATGGTCAAGCTTTTC
CCGCGCTTGGAGGAAATGGGCGCACGTATGCTTCTGCAGGTCCATGACGAGCTGGTGTTAGAAGCCCTAAGGAGCG
CGCCGAAGCTGTCGCGCGCCTCGCTAAAGAAGTGATGGAGGGCGTTTACCCATTGGCCGTACCCCTCGAAGTGGAGG
TCGGTATTGGAGAAGATTGGTTATCTGCAAAGGAAGCGGCCGC
```

SEQ ID NO. 87, amino acid sequence of Mutant ID 10 (A661E, I665W, F667L).
MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVERLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRREAKTWNLGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQVHDELVLEAPKERAEAVARLAKEVMEGVYPLAVPLEVEVGIGEDWLSAKEAA SEQ ID NO. 88, nucleotide sequence of Mutant ID 18 (V783L, H784Q).
```
CATATGCGTGGTATGCTGCCGTTGTTCGAGCCTAAAGGCCGCGTACTGTTAGTCGATGGTCATCACTTGGCCTATCG
GACGTTCCATGCACTCAAAGGTCTGACGACCAGTCGTGGCGAACCGGTCCAGGCTGTTTATGGTTTCGCTAAGTCTT
TGCTCAAAGCACTGAAAGAAGACGGGGACGCGGTAATTGTTGTATTTGATGCCAAAGCACCGAGCTTCCGCCACGAA
GCTTATGGTGGCTACAAGGCAGGACGCGCCCCTACCCCAGAAGATTTCCCCCGTCAGCTGGCATTAATTAAGGAGTT
AGTAGACCTTCTCGGCTTAGCGCGTCTGGAAGTTCCGGGTTATGAGGCGGACGATGTCCTTGCATCCTTGGCTAAAA
AGGCCGAAAAGGAGGGCTACGAAGTCCGCATCTTGACGGCAGAAAGATCTGTACCAGCTTCTGCTGACCGTATT
CATGTTTTGCACCCTGAAGGCTACTTAATCACTCCGGCCTGGCTCTGGGAAAAGTACGGTCTGCGTCCCGATCAGTG
GGCGGATTATCGGGCTTTGACGGGAGATGAGAGCGACAACCTGCCAGGAGTTAAGGGCATTGGTGAAAAAACCGCAC
GTAAGCTGCTTGAAGAGTGGGGTTCCCTGGAAGCCTTGTTAAAAAATCTGGATCGTCTCAAGCCCGCAATTCGTGAA
AAGATCCTGGCTCATATGGACGATCTTAAATTAAGTTGGGACCTGGCCAAGGTGCGCACCGATTTACCGCTTGAAGT
GGATTTTGCAAAACGCCGTGAGCCGGACCGGGAACGTTTACGCGCTTTCTTAGAGCGTCTGGAATTCGGTTCACTGC
TTCATGAATTCGGTCTGTTAGAGTCTCCTAAAGCACTCGAAGAGGCACCGTGGCCGCCCCCAGAAGGTGCTTTTGTT
GGCTTCGTACTTTCCCGTAAGGAGCCTATGTGGGCAGATCTTCTGGCTTTAGCGGCTGCACGCGGTGGCCGTGTTCA
CCGGGCCCCTGAGCCATACAAAGCGTTACGTGATCTGAAGGAAGCACGTGGCTTGCTGGCAAAAGACCTTTCTGTTT
TGGCCCTGCGCGAGGGTCTTGGACTGCCGCCAGGCGACGATCCCATGTTATTGGCCTATCTGTTAGACCCTAGCAAT
ACCACACCTGAAGGGGTCGCTCGTCGGTATGGCGGTGAATGGACTGAGGAAGCCGGAGAGCGCGCCGCATTGTCCGA
ACGGCTCTTTGCAAACTTATGGGGTCGTCTGGAAGGGGAGGAACGTCTGTTATGGTTGTATCGGGAAGTCGAACGTC
CTCTTTCGGCCGTATTAGCGCATATGGAGGCAACAGGTGTGCGTTTAGATGTCGCGTACCTTCGGGCCTTATCACTG
GAAGTTGCAGAGGAAATCGCCCGTCTCGAGGCTGAAGTGTTCCGGTTGGCCGGTCACCCGTTTAACCTCAACTCCCG
TGACCAGCTGGAACGCGTTTTATTCGATGAGCTTGGGCTTCCCGCAATTGGCAAAACCGAAAAGACTGGCAAACGCA
GTACGAGCGCTGCCGTCCTTGAGGCACTCCGCGAGGCTCACCCTATTGTAGAAAAGATCCTGCAATACCGTGAGTTG
ACGAAGCTTAAAAGCACTTATATTGATCCTCTCCCGGATCTGATCCATCCTCGTACCGGCCGCTTGCACACACGTTT
CAACCAGACGGCGACTGCAACCGGCCGTCGTCTAGCTCGGATCCAAATCTCCAGAACATTCCGGTCCGTACACCCT
TGGGCCAACGTATCCGCCGGGCGTTATCGCTGAGGAAGGATGGTTACTGGTCGCATTGGACTACTCGCAGATTGAG
CTGCGCGTCCTCGCACATCTCTCTGGTGACGAAAATTTAATCCGCGTGTTTCAAGAGGGGCGTGATATTCACACAGA
AACTGCCTCATGGATGTTCGGTGTCCCACGTGAAGCAGTGGATCCTTTGATGCGCCGTGCAGCTAAAACAATTAATT
TTGGAGTGCTGTACGGAATGAGCGCTCATCGCTTGAGTCAGGAACTGGCAATCCCTACGAGGAAGCGCAGGCATTC
ATCGAACGTTACTTTCAATCGTTTCCGAAAGTTCGCGCATGGATCGAGAAGACGCTCGAGGAAGGTCGTCGTCGGGG
CTATGTCGAAACTCTGTTTGGTCGCCGTCGGTACGTACCAGATCTTGAAGCCCGCTCAAATCGGTACGGGAGGCTG
CGGAGCGTATGGCATTTAATATGCCTGTACAGGGTACTGCAGCTGACCTCATGAAACTGGCAATGGTCAAGCTTTTC
CCGCGCTTGGAGGAAATGGGCGCACGTATGCTTCTGCAGCTGCAGGACGAGCTGGTGTTAGAAGCCCTAAGGAGCG
CGCCGAAGCTGTCGCGCGCCTCGCTAAAGAAGTGATGGAGGGCGTTTACCCATTGGCCGTACCCCTCGAAGTGGAGG
TCGGTATTGGAGAAGATTGGTTATCTGCAAAGGAAGCGGCCGT
```

SEQ ID NO. 89, amino acid sequence of Mutant ID 18 (V783L, H784Q).
MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEETARLEAEVERLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI -continued

```
ERYFQSFPKVRAWIEKTLEEGRRRGYVETLFGRRRYVPDLEARVKSVREAAERMAFNMPVQGTAADLMKLAMVKLFP
RLEEMGARMLLQLQDELVLEAPKERAEAVARLAKEVMEGVYPLAVPLEVEVGIGEDWLSAKEAA
```

Example 11. BLAST Search for Additional Wild-Type VH-Related DNA Polymerases

A BLAST search using Taq DNA polymerase sequences G755 through P812 (SEQ ID NO. 90) as a comparison window was performed using available on-line databases through the National Center for Biotechnology Information of the National Library of Medicine of the National Institutes of Health (http://www.ncbi.nlm.nih.gov). The BLAST search revealed numerous wild-type DNA polymerase from other species sharing extensive sequence identity with Taq DNA polymerase, including identity at positions V783 and H784 of Taq DNA polymerase ("VH-related DNA polymerases"). An exemplary listing of these thermostable polymerases is illustrated in Table 24 and similar listing of putatively thermosensitive polymerases is illustrated in Table 25. In all the identified wild-type polymerase genes except one (*Facklamia hominis*), the amino acids corresponding to V783 and H784 of Taq DNA polymerase are preserved. In the exceptional case, however, namely, *Facklamia hominis*, an Ile naturally occurs at the residue position of the Taq DNA polymerase corresponding to V783. However, the Taq DNA polymerase mutant corresponding to Mutant ID 1 that includes this particular substitution behaves like the wild-type Taq DNA polymerase. Thus, the DNA polymerase of *Facklamia hominis* apparently deviates from the strong selection of Val at this position is postulated to maintain wild-type activity if either a Val or Ile residue is present. These BLAST results confirm a natural counter-selection against DNA polymerases having enhanced template discrimination activity and provide strong evidence that the disclosed engineered Taq DNA polymerase mutants having these properties are novel and non-obvious.

These identified DNA polymerases share extensive sequence homology with Taq DNA polymerase in the region that includes residues V783 and V784 of Taq DNA polymerase. Like that observed with the engineered Taq DNA polymerase mutants, each of the identified non-Taq DNA polymerases represent a sequence space from which engineered mutant enzymes can be generated having enhanced template discrimination activity, as compared to their respective unmodified counterparts. The magnitude of the enhanced template discrimination activity obtained for identical amino acid substitutions for non-Taq DNA polymerases may not be identical when compared to the respective unmodified non-Taq DNA polymerases or even when compared to the magnitude of enhanced template discrimination activity observed for the corresponding Taq DNA polymerase mutant. Nevertheless, a strong prediction of this disclosure is that at least some amino acid substitutions in non-Taq DNA polymerases having homology to residues V783 and/or H784 of Taq DNA polymerase will display enhanced template discrimination activity relative to their respective unmodified counterparts.

TABLE 24

Non-Taq thermostable DNA polymerases having homology to Taq sequences in region of V783 and H784

| Accession No. | Species | Alignment (Query: Taq; Sbjct: Species) | | SEQ | Identity* |
|---|---|---|---|---|---|
| ref\|WP_018111631.1\| SEQ ID NO. 91 | Thermus igniterrae | Query<br>Sbjct | 1 GTAADLMKLAMVKLFPRLEEMGARMLLQVHDELVLEAPKERAEAVARLAKEVMEGVYP<br>    GTAADLMKLAMV+LFPRL+E+GARMLLQVHDELVLEAPK+RAE VA LAKEVMEGV+P<br>752 GTAADLMKLAMVRLFPRLQELGARMLLQVHDELVLEAPKDRAEBRVAALAKEVMEGVWP | 58<br><br>809 | 88% |
| ref\|WP_022798807.1\| SEQ ID NO. 92 | Thermus islandicus | Query<br>Sbjct | 1 GTAADLMKLAMVKLFPRLEEMGARMLLQVHDELVLEAPKERAEAVARLAKEVMEGVYP<br>    GTAADLMKLAMVKLFPRL E GARMLLQVHDEL+LEAPK+RAE VA LAKEVMEGVYP<br>752 GTAADLMKLAMVKLFPRLREAGARMLLQVHDELLLEAPKDRAEEVAALAKEVMEGVYP | 58<br><br>809 | 90% |
| ref\|YP_005654546.1\| SEQ ID NO. 93 | Thermus sp. CCB_US3_UF1 | Query<br>Sbjct | 1 GTAADLMKLAMVKLFPRLEEMGARMLLQVHDELVLEAPKERAEAVARLAKEVMEGVYP<br>    GTAADLMKLAMV+LFP L +GARMLLQVHDEL+LEAPKERAE VARLA+EVMEGV+P<br>756 GTAADLMKLAMVRLFPLLPGVGARMLLQVHDELLLEAPKERAEEVARLAREVMEGVWP | 58<br><br>813 | 84% |
| ref\|WP_018461567.1\| SEQ ID NO. 94 | Thermus oshimai | Query<br>Sbjct | 1 GTAADLMKLAMVKLFPRLEEMGARMLLQVHDELVLEAPKERAEAVARLAKEVMEGVYP<br>    GTAADLMKLAMVKLFPRL +G R+LLQVHDELVLEAPK RAE A+LAKE MEGVYP<br>753 GTAADLMKLAMVKLFPRLRPLGVRILLQVHDELVLEAPKARAEEAAQLAKETMEGVYP | 58<br><br>810 | 83% |
| ref\|WP_008632471.1\| SEQ ID NO. 95 | Thermus sp. RL | Query<br>Sbjct | 1 GTAADLMKLAMVKLFPRLEEMGARMLLQVHDELVLEAPKERAEAVARLAKEVMEGVYP<br>    GTAADLMKLAMVKLFPRL EMGARMLLQVHDEL+LEAP+ RAE VA LAKE ME YP<br>754 GTAADLMKLAMVKLFPRLREMGARMLLQVHDELLLEAPQARAEEVAALAKEAMEKAYP | 58<br><br>811 | 84% |
| ref\|YP_005640602.1\| SEQ ID NO. 96 | Thermus thermophilus SG0.5JP17-16 | Query<br>Sbjct | 1 GTAADLMKLAMVKLFPRLEEMGARMLLQVHDELVLEAPKERAEAVARLAKEVMEGVYP<br>    GTAADLMKLAMVKLFPRL EMGARMLLQVHDEL+LEAP+ RAE VA LAKE ME YP<br>754 GTAADLMKLAMVKLFPRLREMGARMLLQVHDELLLEAPQARAEEVAALAKEAMEKAYP | 58<br><br>811 | 84% |
| ref\|WP_019550117.1\| SEQ ID NO. 97 | Thermus scotoductus | Query<br>Sbjct | 1 GTAADLMKLAMVKLFPRLEEMGARMLLQVHDELVLEAPKERAEAVARLAKEVMEGVYP<br>    GTAADLMKLAMVKLFPRL+E+GARMLLQVHDELVLEAPKE+AE VA+ AK ME V+P<br>753 GTAADLMKLAMVKLFPRLQELGARMLLQVHDELVLEAPKEQAEEVAQEAKRTMEEVWP | 58<br><br>810 | 83% |

TABLE 24-continued

Non-Taq thermostable DNA polymerases having homology to Taq sequences in region of V783 and H784

| Accession No. | Species | | Alignment (Query: Taq; Sbjct: Species) | | SEQ Identity* |
|---|---|---|---|---|---|
| gb\|AAB81398.1\| SEQ ID NO. 98 | Thermus caldophilus | Query<br>Sbjct | 1 GTAADLMKLAMVKLFPRLEEMGARMLLQVHDELVLEAPKERAEAVARLAKEVMEGVYP<br>  GTAADLMKLAMVKLFPRL EMGARMLL QVHDEL+LEAP+ AE VA LAKE ME YP<br>757 GTAADLMKLAMVKLFPRLREMGARMLLQVHDELLLEAPQAGAEEVAALAKEAMEKAYP | 58<br><br>814 | 83% |
| ref\|YP 004367987.1\| SEQ ID NO. 99 | Marinithermus hydrothermalis DSM 14884 | Query<br>Sbjct | 1 GTAADLMKLAMVKLFPRLEEMGARMLLQVHDELVLEAPKERAEAVARLAKEVMEGVY<br>  GTAADLMKLAMVKL P +  +GAR++LQVHDELVLEAP+ERAEAVAR+ +EVMEG +<br>758 GTAADLMKLAMVKLAPEIRSLGARLILQVHDELVLEAPQERAEAVARVVREVMEGAW | 57<br><br>814 | 75% |
| gb\|AAR11876.1\| SEQ ID NO. 100 | Thermus filiformis | Query<br>Sbjct | 1 GTAADLMKLAMVKLFPRLEEMGARMLLQVHDELVLEAPKERAEAVARLAKEVMEGVYP<br>  GTAADLMK+AMVKLFPRL+ +GA +LLQVHDELVLE  L KEVME  YP<br>755 GTAADLMKIAMVKLFPRLKPLGAHLLLQVHDELVLEVPEDRAFEAKALVKEVMENTYP | 58<br><br>812 | 72% |
| ref\|WP 018465880.1\| SEQ ID NO. 101 | Meiothermus timidus | Query<br>Sbjct | 1 GTAADLMKLAMVKLFPRLEEMGARMLLQVHDELVLEAPKERAEAVARLAKEVMEGVY<br>  GTAADLMKLAMVKL P+LE + A ++LQVHDELV+EAP+ERAE VA LA+E M +<br>774 GTAADLMKLAMVKLGPKLEPLDAHLVLQVHDELVIEAPRERAEEVAELARETMRTAW | 57<br><br>830 | 68% |
| ref\|WP 013637959.1\| SEQ ID NO. 102 | Desulfurobacterium thermolithotrophum | Query<br>Sbjct | 1 GTAADLMKLAMVKLFPRLEEMGARMLLQVHDELVLEAPKERAEAVARLAKEVMEGV<br>  GTAAD+MKLAMVKL+ +LE++GA M+LQVHDE+V+EA +E+ E + ++ KE ME V<br>765 GTAADIMKLAMVKLYKKLEKLGAYMVLQVHDEIVIEALEKTEEIMKIVKETMENV | 56<br><br>820 | 61% |
| ref\|YP 005442159.1\| SEQ ID NO. 103 | Caldilinea aerophila | Query<br>Sbjct | 1 GTAADLMKLAMVKLFPRLEEMG--ARMLLQVHDELVLEAPKERAEAVARLAKEVMEGVY<br>  GTAAD+MK+AM++L+ RL+ G  R+L+QVHDELVLEAP E  L +E M  Y<br>875 GTAADIMKIAMIRLYERLQNDGYRTRLLIQVHDELVLEAPPEELESATHLVRETMANAY | 57<br><br>933 | 54% |

*Sequence identity refers to the percent identity of the query sequence with wild type Taq DNA polymerase.

TABLE 25

Non-Taq putatively thermosensitive DNA polymerasess having homology to
Taq sequence in the region of V783 and H784

| Accession No. | Species | Alignment (Query: Taq; Sbjct: Species) | | | SEQ Identity* |
|---|---|---|---|---|---|
| ref\|WP 015519435.1\| SEQ ID NO: 104 | Eubacterium siraeum | Query<br>Sbjct | 1 GTAADLMKLAMVKLFPRLEEMG--ARMLLQVHDELVLEAPKERAEAVARLAKEVMEG<br>    GTAAD++K+AM+K++ RLEE G AR++LQVHDEL++EA ++ AE VA L KE ME<br>751 GTAADIIKIAMIKVYNRLEESGLDARLILQVHDELIVEAKEDCAEKVALLLKEEMEN | 55<br><br>807 | 60% |
| ref\|WP 022236670.1\| SEQ ID NO: 105 | Clostridium leptum | Query<br>Sbjct | 1 GTAADLMKLAMVKLFPRL--EEMGARMLLQVHDELVLEAPKERAEAVARLAKEVMEG<br>    GTAAD++K+AMV++ RL E M AR++LQVHDEL++EAP++ AE AR+ E MEG<br>320 GTAADIIKIAMVRVDRRLKRENMRARLILQVHDELIVEAPEDEAEQAARILTEEMEG | 55<br><br>376 | 58% |
| ref\|WP 002333048.1\| SEQ ID NO: 106 | Enterococcus | Query<br>Sbjct | 1 GTAADLMKLAMVKLFPRLEEMG--ARMLLQVHDELVLEAPKERAEAVARLAKEVME<br>    G+AAD++K+AM++L RL+E G A MLLQVHDELV E PK+ E++ +L KEVME<br>803 GSAADILKIAMIELDKRLKETGLQATMLLQVHDELVFEVPKKELESLDKLVKEVME | 54<br><br>858 | 59% |
| ref\|WP 016648372.1\| SEQ ID NO: 107 | Facklamia hominis | Query<br>Sbjct | 1 GTAADLMKLAMVKLFPRLEEMG--ARMLLQVHDELVLEAPKERAEAVARLAKEVMEG<br>    GTAAD++KLAMV+L RLEE G +R+LLQ+HDEL+LE PKE + +L EVME<br>803 GTAADIIKLAMVRLQARLEEAGLSSRLLLQIHDELILEGPKEEMPQLQKLVVEVMES | 55<br><br>859 | 60% |
| ef\|WP 000412792\| SEQ ID NO: 108 | Bacillus anthracis | Query<br>Sbjct | 1 GTAADLMKLAMVKLFPRLEEMG--ARMLLQVHDELVLEAPKERAEAVARLAKEVME<br>    GTAAD++K AM+ + RLEE G AR+LLQVHDEL+ EAPKE E + +L EVME<br>799 GTAADIIKKAMIIMADRLEEEGLQARLLLQVHDELIFEAPKEEVEKLEKLVPEVME | 54<br><br>854 | 61% |
| ref\|NP 981011.1\| SEQ ID NO: 109 | Bacillus cereus ATCC 10987 | Query<br>Sbjct | 1 GTAADLMKLAMVKLFPRLEEMG--ARMLLQVHDELVLEAPKERAEAVARLAKEVME<br>    GTAAD++K AM+ + RLEE G AR+LLQVHDEL+ EAPKE E + +L EVME<br>799 GTAADIIKKAMIIMADRLEEEGLQARLLLQVHDELIFEAPKEEIEKLEKLVPEVME | 54<br><br>854 | 61% |

*Sequence identity refers to the percent identity of the query sequence with wild type Taq DNA polymerase.

Example 12. Production of Additional Codon Optimized Taq DNA Polymerase Mutants at Position H784

After determining the properties of the first eighteen mutant versions of the Taq polymerase (Table 3, Mut IDs 1-18), an additional eighteen mutant versions of Taq DNA polymerase (Table 3, Mut IDs 19-30) were made by site directed mutagenesis of the cloned OptiTaq codon-optimized WT Taq DNA polymerase. The full set represents all possible amino acid variations at position 784 in Taq polymerase. Specific mutations were introduced into the OptiTaq sequence using the method of PCR site-directed mutagenesis (Weiner M P, et al., Gene. 151(1-2):119-23 (1994)). Each mutagenesis reaction employed 10 pmoles of two complementary oligonucleotides (Table 26) containing the desired base changes, annealed to the double-stranded Opti-Taq plasmid (20 ng), 5 U KOD DNA polymerase (Novagen-EMD Chemicals, San Diego, Calif.), 1.5 mM MgSO$_4$, in 1×KOD PCR buffer. Thermal cycling parameters were 95° C. for 3 minutes (95° C. for 20 sec-55° C. for 20 sec-70° C. for 2.5 minutes) for 16 cycles followed by a 70° C. soak for 4 minutes. After PCR site-directed mutagenesis, the amplified product was treated with 10 U of Dpn I (NEB, Ipswich, Mass.), at 37° C. for 1 hour, followed by inactivation at 80° C. for 20 minutes. $\frac{1}{110}^{th}$ of the digestion material was transformed into XL-1 Blue competent bacteria. Bacterial clones were isolated, plasmid DNA prepared, and individual mutations were confirmed by Sanger DNA sequencing. All mutants remained in the pET-27b(+) expression vector, which is suitable for expressing the recombinant proteins in E. coli. Expression and purification of the recombinant mutants of the Taq polymerase were performed as described in Example 3.

TABLE 26

Oligonucleotides used for site-directed mutagenesis to produce 18 Taq DNA Polymerase mutants at position 784.

| Mutant ID | Amino acid changes | Sequence" Sense mutagenesis oligonucleotide | SEQ ID No. | Sequence" Antisense mutagenesis oligonucleotide | SEQ ID No. |
|---|---|---|---|---|---|
| 19 | H784G | gggcgcacgtatgcttctgca ggtcGGTgacgagctggtgtt agaagcccta | 110 | taggggcttctaacaccagctcg tcACCgacctgcagaagcatacg tgcgccc | 111 |
| 20 | H784A | gggcgcacgtatgcttctgca ggtcGCGgacgagctggtgtt agaagcccta | 112 | taggggcttctaacaccagctcg tcCGCgacctgcagaagcatacg tgcgccc | 113 |

TABLE 26-continued

Oligonucleotides used for site-directed mutagenesis to produce 18 Taq DNA Polymerase mutants at position 784.

| Mutant ID | Amino acid changes | Sequence" Sense mutagenesis oligonucleotide | SEQ ID No. | Sequence" Antisense mutagenesis oligonucleotide | SEQ ID No. |
|---|---|---|---|---|---|
| 21 | H784S | gggcgcacgtatgcttctgca ggtcAGCgacgagctggtgtt agaagcccta | 114 | taggggcttctaacaccagctcg tcGCTgacctgcagaagcatacg tgcgccc | 115 |
| 22 | H784T | gggcgcacgtatgcttctgca ggtcACGgacgagctggtgtt agaagcccta | 116 | taggggcttctaacaccagctcg tcCGTgacctgcagaagcatacg tgcgccc | 117 |
| 23 | H784C | gggcgcacgtatgcttctgca ggtcTGCgacgagctggtgtt agaagcccta | 118 | taggggcttctaacaccagctcg tcGCAgacctgcagaagcatacg tgcgccc | 119 |
| 24 | H784V | gggcgcacgtatgcttctgca ggtcGTAgacgagctggtgtt agaagcccta | 120 | taggggcttctaacaccagctcg tcTACgacctgcagaagcatacg tgcgccc | 121 |
| 25 | H784L | gggcgcacgtatgcttctgca ggtcTTGgacgagctggtgtt agaagcccta | 122 | taggggcttctaacaccagctcg tcCAAgacctgcagaagcatacg tgcgccc | 123 |
| 26 | H784I | gggcgcacgtatgcttctgca ggtcATTgacgagctggtgtt agaagcccta | 124 | taggggcttctaacaccagctcg tcAATgacctgcagaagcatacg tgcgccc | 125 |
| 27 | H784M | gggcgcacgtatgcttctgca ggtcATGgacgagctggtgtt agaagcccta | 126 | taggggcttctaacaccagctcg tcCATgacctgcagaagcatacg tgcgccc | 127 |
| 28 | H784P | gggcgcacgtatgcttctgca ggtcCCAgacgagctggtgtt agaagcccta | 128 | taggggcttctaacaccagctcg tcTGGgacctgcagaagcatacg tgcgccc | 129 |
| 29 | H784F | gggcgcacgtatgcttctgca ggtcTTTgacgagctggtgtt agaagcccta | 130 | taggggcttctaacaccagctcg tcAAAgacctgcagaagcatacg tgcgccc | 131 |
| 30 | H784Y | gggcgcacgtatgcttctgca ggtcTATgacgagctggtgtt agaagcccta | 132 | taggggcttctaacaccagctcg tcATAgacctgcagaagcatacg tgcgccc | 133 |
| 31 | H784W | gggcgcacgtatgcttctgca ggtcTGGgacgagctggtgtt agaagcccta | 134 | taggggcttctaacaccagctcg tcCCAgacctgcagaagcatacg tgcgccc | 135 |
| 32 | H784D | gggcgcacgtatgcttctgca ggtcGATgacgagctggtgtt agaagcccta | 136 | taggggcttctaacaccagctcg tcATCgacctgcagaagcatacg tgcgccc | 137 |
| 33 | H784E | gggcgcacgtatgcttctg caggtcGAAgacgagctgg tgttagaagcccta | 138 | taggggcttctaacaccagctcg tcTTCgacctgcagaagcatacg tgcgccc | 139 |
| 34 | H784N | gggcgcacgtatgcttctgca ggtcAACgacgagctggtgtt agaagcccta | 140 | taggggcttctaacaccagctcg tcGTTgacctgcagaagcatacg tgcgccc | 141 |
| 35 | H784K | gggcgcacgtatgcttctgca ggtcAAAgacgagctggtgtt agaagcccta | 142 | taggggcttctaacaccagctcg tcTTTgacctgcagaagcatacg tgcgccc | 143 |
| 36 | H784R | gggcgcacgtatgcttctgca ggtcCGGgacgagctggtgtt agaagcccta | 144 | taggggcttctaacaccagctcg tcCCGgacctgcagaagcatacg tgcgccc | 145 |

DNA bases identical to codon optimized OptiTaq are shown in lower case; those specific for the mutations introduced by site-directed mutagenesis are shown in upper case.

Example 13. Characterization of Properties of 18 Mutant Taq DNA Polymerases Altered at Position H784 in PCR The 18 mutant Taq DNA polymerase enzymes described in Example 12 were characterized for polymerase activity and ability to discriminate a 3'-RNA residue in the primer oligonucleotide.

The unit activity of the purified wild-type protein was determined by comparing performance in qPCR of known quantities of OptiTaq and each mutant compared to a commercial native non-hot-start Taq DNA polymerase, Taq-B DNA Polymerase (Enzymatics, Beverly, Mass.). Quantification cycle values (Cq, the amplification cycle number at which positive signal is first detected) and amplification curve shapes were analyzed to determine the nanogram amounts at which both enzymes performed similarly in the suboptimal range for each. Using these nanogram amounts and known unit values of Taq-B DNA polymerase, relative activity unit values could be extrapolated for all of the mutant DNA polymerase enzymes having sufficient activity to support PCR.

The following reaction conditions were employed: 1× qPCR buffer (20 mM Tris pH 8.4, 50 mM KCl, 3 mM $MgCl_2$, 0.01% Triton-X100), 800 µM dNTPs (200 µM each), 500 nM For primer (Hs HPRT F517, SEQ ID NO. 43), 500 nM Rev primer (Hs HPRT R591, SEQ ID NO. 44), 250 nM probe (Hs HPRT P554, SEQ ID NO. 45), $2 \times 10^3$ copies of linearized cloned plasmid template (HPRT-targ, SEQ ID NO. 46), in 10 µL final volume. The amount of DNA polymerase added to each reaction was varied as follows: for wild type (OptiTaq), reactions were set using 10, 1, 0.1, 0.01, and 0.001 U/µL (220, 22, 2.2, 0.22, or 0.022 ng of protein per 10 µL reaction). Mutant polymerases were run in similar concentrations. In addition, those mutant enzymes showing polymerase activity were more finely titrated testing 220, 22, 10.6, 4.8, 2.2, 1.1, 0.48, and 0.22 ng of protein per 10 µL reaction. Enzyme dilutions were made in enzyme dilution buffer (20 mM Tris pH7.5, 100 mM NaCl, 1 mM DTT, 0.1% Triton-X100, 1 mg/mL BSA, 10% glycerol). Reactions were run in 384 well format on a BIO-RAD CFX384™ Real-Time System (BIO-RAD, Hercules, Calif.) using cycling parameters 95° C. for 30 seconds followed by 60 cycles of [95° C. for 15 seconds followed by 60° C. for 1 minutes]. Detection was achieved using a fluorescence-quenched probe (5'-nuclease assay format, note that the mutations introduced into the present series of Taq mutants do not lie in the 5'-nuclease domain). Sequences of the primers, probe, and template (plasmid insert) are shown in Table 27.

TABLE 27

Sequence of oligonucleotides employed in Taq DNA polymerase activity assay.

| Name | Sequence | SEQ ID NO. |
|---|---|---|
| Hs HPRT F517 | GACTTTGCTTTCCTTGGTCAG | SEQ ID NO. 43 |
| Hs HPRT R591 | GGCTTATATCCAACACTTCGTG | SEQ ID NO. 44 |
| Hs HPRT P554 | FAM-ATGGTCAAG(ZEN)GTCGCAAGCT TGCTGGT-IBFQ | SEQ ID NO. 45 |

TABLE 27-continued

Sequence of oligonucleotides employed in Taq DNA polymerase activity assay.

| Name | Sequence | SEQ ID NO. |
|---|---|---|
| HPRT-targ | GACTTTGCTTTCCTTGGTCAGGCAGTAT AATCCAAAGATGGTCAAGGTCGCAAGCT TGCTGGTGAAAAGGACCCCACGAAGTGT TGGATATAAGCC | SEQ ID NO. 46 |

Nucleic acid sequences are shown 5'-3'.
FAM = 6-carboxyfluorescein,
IBFQ = Iowa Black FQ (fluorescence quencher), and
ZEN = ZEN internal fluorescence quencher.

These 18 Taq DNA polymerase mutants were characterized as outlined above. Results are summarized in Table 28. Ten mutants, including Mutant IDs 19, 23, 25, 28, and 31 to 36, did not show detectable DNA polymerase activity and were not studied further. Four mutants, Mutant IDs 20, 21, 27 and 29 had DNA polymerase activity; however, processivity was reduced from 4-6 fold relative to the wild type enzyme. Three mutants, Mutant IDs 24, 26, and 30, showed DNA polymerase activity similar to wild type OptiTaq.

TABLE 28

Activity of novel Taq DNA polymerase mutants.

| Mutant ID | Amino acid changes from wild-type Taq | Polymerase Activity | Relative activity* | ΔCq Delay in priming from an RNA base** |
|---|---|---|---|---|
| 19 | H784G | No | — | — |
| 20 | H784A | Yes | 0.2 | 1 |
| 21 | H784S | Yes | 0.16 | 2 |
| 22 | H784T | Yes | 1 | 0 |
| 23 | H784C | No | — | — |
| 24 | H784V | Yes | 0.45 | >35 |
| 25 | H784L | No | — | — |
| 26 | H784I | Yes | 0.5 | 6 |
| 27 | H784M | Yes | 0.22 | >35 |
| 28 | H784P | No | — | — |
| 29 | H784F | Yes | 0.22 | 3 |
| 30 | H784Y | Yes | 0.45 | 5 |
| 31 | H784W | No | — | — |
| 32 | H784D | No | — | — |
| 33 | H784E | No | — | — |
| 34 | H784N | No | — | — |
| 35 | H784K | No | — | — |
| 36 | H784R | No | — | — |

*Wild-type OptiTaq was set to "1" and the relative activity of each of the mutant polymerases was normalized to this amplification efficiency, with 1 as the maximum.
**ΔCq = [Cq Mutant ID X] − [Cq OptiTaq] when qPCR reactions are run using primers having a 3'-RNA residue.

The subset of these mutant Taq DNA polymerases which showed suitable levels of DNA polymerase activity were studied for their ability to discriminate between primers have a 3'-DNA versus a 3'-RNA residue relative to the wild type OptiTaq enzyme. Real-time PCR was performed as before, employing in the reactions the amount of each mutant DNA polymerase equal to 0.5 units of wild-type OptiTaq per 10 µL reaction. The following reaction conditions were employed: 1× qPCR buffer (20 mM Tris pH 8.4, 50 mM KCl, 3 mM $MgCl_2$, 0.01% Triton-X100), 800 µM dNTPs (200 µM each), 500 nM For primer (Hs SFRS9 F569 rU, SEQ ID NO. 47), 500 nM Rev primer (Hs SFRS9 R712 rA, SEQ ID NO. 48), 250 nM probe (Hs SFRS9 P644, SEQ ID NO. 49), $2 \times 10^3$ copies of linearized cloned plasmid template (SFRS9-targ, SEQ ID NO. 50), in 10 µL final volume. Reactions were run in 384 well format on a BIO-RAD CFX384™ Real-Time System (BIO-RAD, Hercules, Calif.) using cycling parameters 95° C. for 30 seconds followed by 60 cycles of [95° C. for 15 seconds followed by 60° C. for 1 minutes]. Detection was achieved using a fluorescence-quenched probe (5'-nuclease assay format). Sequences of the primers, probe, and template (plasmid insert) are shown in Table 29.

TABLE 29

Sequence of oligonucleotides employed in the primer 3'-RNA discrimination assay.

| Name | Sequence | SEQ ID NO. |
|---|---|---|
| Hs SFRS9 F569 rU | TGTGCAGAAGGATGGAGu | SEQ ID NO. 47 |
| Hs SFRS9 R712 rA | CTGGTGCTTCTCTCAGGATa | SEQ ID NO. 48 |
| Hs SFRS9 P644 | HEX-TGGAATATG(ZEN)CCCTGCGT AAACTGGA-IBFQ | SEQ ID NO. 48 |
| SFRS9-targ | TGTGCAGAAGGATGGAGTGGGGATGG TCGAGTATCTCAGAAAAGAAGACATG GAATATGCCCTGCGTAAACTGGATGA CACCAAATTCCGCTCTCATGAGGGTG AAACTTCCTACATCCGAGTTTATCCT GAGAGAAGCACCAG | SEQ ID NO. 50 |

Nucleic acid sequences are shown 5'-3' with DNA uppercase and RNA lowercase.
HEX = hexachlorofluorescein,
IBFQ = Iowa Black FQ (fluorescence quencher), and
ZEN = ZEN fluorescence quencher.

The eight Taq DNA polymerase mutants that supported PCR were tested for the ability to use a 3'-RNA modified primer as outlined above. Results are summarized in Table 28. Mutant IDs 20 and 22 did not show any significant difference between primers having a 3'-DNA versus a 3'-RNA residue. Mutant IDs 21, 24, 26, 27, 29, and 30 showed an amplification delay using 3'-RNA primers. Thus, additional Taq DNA polymerase mutants were identified which discriminate against priming from a 3'-RNA residue. Those mutants which showed some delay with RNA priming and showed high processivity were further studied for improvements in primer 3'-residue mismatch discrimination.

Example 14: Improved Mismatch Discrimination in Allele-Specific PCR Using Mutant Taq DNA Polymerases Altered at Position H784

Of the 18 mutant enzymes studied in Example 12 and 13, Mutant IDs 21, 24, 26, 27, 29, and 30 showed the ability to discriminate against a 3'-RNA residue in the primer and retained high enzymatic activity/processivity. These six mutants and additionally Mutant IDs 20 and 22 were studied for the ability to discriminate against a 3'-terminal DNA mismatch compared with wild type OptiTaq DNA polymerase using an allele-specific qPCR assay. Amplification reactions were performed against a synthetic oligonucleotide template where a single base was varied (SNP) which was positioned to lie at the 3'-end of the reverse primer. Synthetic templates were employed having each of the 4 possible bases at this position. Reverse primers were employed having each of the 4 possible bases at the 3'-end. Relative amplification efficiencies of all pairwise primer/template combinations were assessed using qPCR.

Quantitative allele-specific real-time PCR (AS-qPCR) was performed in 10 μL reaction volumes in 384 well format with $2 \times 10^5$ copies of a 103 bp synthetic template (SEQ ID NOs. 51-4). Final reaction conditions used were 20 mM Tris-HCL (pH 8.4 at 25° C.), 50 mM KCL, and 3 mM $MgCl_2$, 0.01% Triton X-100, 800 μM total dNTPs, and 200 nM of the universal forward primer (SEQ ID NO. 60), 200 nM of a reverse primer (separate reactions were set up for each of the allele-specific primers SEQ ID NOs. 55-58 or the control universal primer SEQ ID NO. 59) and 200 nM of the 5' nuclease detection probe (SEQ ID NO. 61). Each allele-specific primer was tested on each SNP template. Reactions utilized either 0.5 U (10.8 ng/11.1 nM/111 fmol) of the wild type OptiTaq DNA polymerase or 0.5 U of one of the nine Taq DNA polymerase mutants studied (Mutant ID 3 (H784Q) (10.8 ng/11.1 nM/111 fmol); Mutant ID 20 H784A (54 ng/55.5 nM/555 fmol); Mutant ID22 H784T (10.8 ng/11.1 nM/111 fmol); Mutant ID 24 H784V (24 ng/24.7 nM/246.7 fmol); Mutant ID 26 H784I (21.6 ng/22.2 nM/222 fmol); Mutant ID 27 H784M (10.8 ng/11.1 nM/111 fmol); Mutant ID 29 H784F (49.1 ng/49.4 nM/494.5 fmol); Mutant ID 30 H784Y) (24 ng/24.7 nM/246.7 fmol). Amplification was performed on a CFX384™ C1000™ Thermo Cycler system (Bio-Rad, Hercules, Calif.) using the following cycling parameters: 95° C. for 30 seconds initial denaturation followed by 60 cycles of 95° C. for 10 seconds, then 60° C. for 30 seconds. Oligonucleotide reagents used in this example are shown in Table 30.

TABLE 30

Synthetic oligonucleotides employed in Example 13.

| Name | Sequence (5'-3') | SEQ ID NO. |
|---|---|---|
| A Template | AGCTCTGCCCAAAGATTACCCTGACAGCTAAGTGGCAGTGGAA GTTGGCCTCAGAAGTAGTGGCCAGCTGTGTGTCGGGG<u>A</u>ACAGT AAAGGCATGAAGCTCAG | SEQ ID NO. 51 |
| C Template | AGCTCTGCCCAAAGATTACCCTGACAGCTAAGTGGCAGTGGAA GTTGGCCTCAGAAGTAGTGGCCAGCTGTGTGTCGGGG<u>C</u>ACAGT AAAGGCATGAAGCTCAG | SEQ ID NO. 52 |
| G Template | AGCTCTGCCCAAAGATTACCCTGACAGCTAAGTGGCAGTGGAA GTTGGCCTCAGAAGTAGTGGCCAGCTGTGTGTCGGGG<u>G</u>ACAGT AAAGGCATGAAGCTCAG | SEQ ID NO. 53 |
| T Template | AGCTCTGCCCAAAGATTACCCTGACAGCTAAGTGGCAGTGGAA GTTGGCCTCAGAAGTAGTGGCCAGCTGTGTGTCGGGG<u>T</u>ACAGT AAAGGCATGAAGCTCAG | SEQ ID NO. 54 |

TABLE 30-continued

Synthetic oligonucleotides employed in Example 13.

| Name | Sequence (5'-3') | SEQ ID NO. |
|---|---|---|
| Syn Rev T | CTGAGCTTCATGCCTTTACTGTT | SEQ ID NO. 55 |
| Syn Rev C | CTGAGCTTCATGCCTTTACTGTC | SEQ ID NO. 56 |
| Syn Rev A | CTGAGCTTCATGCCTTTACTGTA | SEQ ID NO. 57 |
| Syn Rev G | CTGAGCTTCATGCCTTTACTGTG | SEQ ID NO. 58 |
| Syn Rev | CTGAGCTTCATGCCTTTACTGT | SEQ ID NO. 59 |
| Syn For | AGCTCTGCCCAAAGATTACCCTG | SEQ ID NO. 60 |
| Syn Probe | FAM-TTCTGAGGC(ZEN)CAACTTCCACTGCCACTTA-IBFQ | SEQ ID NO. 61 |

DNA bases are uppercase;
FAM = 6-carboxyfluorescein;
IBFQ = Iowa Black ™ FQ fluorescence quencher;
ZEN = internal ZEN fluorescence quencher;
underlined base indicates the SNP site in the synthetic template DNA.

Initially all reactions were run in triplicate. Similar results were obtained for all replicates when using the wild type OptiTaq. However, results showed greater variation for the mutant polymerases. To obtain statistically meaningful results, each reaction was therefore performed 24 times for the mutant polymerases and 21 times for the wild type enzyme. ΔCq values were calculated as the Cq value obtained for each mismatched base pair minus the Cq value obtained for the matched base pair (ΔCq=Cq mismatch–Cq match). The ΔCq values for all 24 replicates were averaged and standard deviations were calculated. Results are shown in Table 31 and are graphically summarized in FIGS. 3C, 3D, 3E, 3F, and 3G. Note that the reverse primer is the allele-specific primer, so the "Syn Rev T" primer (SEQ ID NO. 55) is the perfect match to the Template A (SEQ ID NO. 51), etc.

TABLE 31

ΔCq values for AS-qPCR reactions using WT OptiTaq and H784 mutant Taq DNA polymerases.

| DNA Polymerase | Reverse Primer Name | SEQ ID NO. | Template A SEQ ID NO. 51 | Template C SEQ ID NO. 52 | Template G SEQ ID NO. 53 | Template T SEQ ID NO. 54 |
|---|---|---|---|---|---|---|
| OptiTaq | Syn Rev T | 55 | — | 1.4 +/− 0.1 | 0.6 +/− 0.2 | 4.8 +/− 0.2 |
|  | Syn Rev G | 58 | 8.5 +/− 0.2 | — | 5.9 +/− 0.2 | 3.5 +/− 0.2 |
|  | Syn Rev C | 56 | 2.8 +/− 0.2 | 7.7 +/− 0.1 | — | 3.9 +/− 0.1 |
|  | Syn Rev A | 57 | 5.3 +/− 0.2 | −0.8 +/− 0.1 | 6.1 +/− 0.1 | — |
| MUT ID 3 H784Q | Syn Rev T | 55 | — | 5.7 +/− 0.2 | 5.7 +/− 0.3 | 10.8 +/− 0.4 |
|  | Syn Rev G | 58 | 14.5 +/− 0.6 | — | 12.5 +/− 0.5 | 6.8 +/− 0.2 |
|  | Syn Rev C | 56 | 8.5 +/− 1.5 | 10.6 +/− 0.2 | — | 7.7 +/− 0.3 |
|  | Syn Rev A | 57 | 10.3 +/− 0.5 | 4.1 +/− 0.1 | 11.0 +/− 0.7 | — |
| MUT ID 20 H784A | Syn Rev T | 55 | — | 7.6 +/− 0.3 | 7.7 +/− 0.4 | 12.3 +/− 0.8 |
|  | Syn Rev G | 58 | 19.1 +/− 6.0 | — | 14.8 +/− 1.4 | 6.3 +/− 0.5 |
|  | Syn Rev C | 56 | 9.6 +/− 0.5 | 12.4 +/− 4.7 | — | 8.2 +/− 0.4 |
|  | Syn Rev A | 57 | 14.9 +/− 4.4 | 7.6 +/− 0.2 | 14.2 +/− 1.9 | — |
| MUT ID 21 H784S | Syn Rev T | 55 | — | 7.9 +/− 0.5 | 19.6 +/− 8.5 | 8.6 +/− 0.8 |
|  | Syn Rev G | 58 | 25.8 +/− 9.2 | — | 23.9 +/− 9.6 | 6.6 +/− 0.3 |
|  | Syn Rev C | 56 | 11.4 +/− 4.0 | 16.4 +/− 9.2 | — | 9.1 +/− 1.5 |
|  | Syn Rev A | 57 | 23.1 +/− 8.2 | 8.4 +/− 0.4 | 22.9 +/− 8.6 | — |
| MUT ID 22 H784T | Syn Rev T | 55 | — | 1.5 +/− 0.3 | 3.7 +/− 0.3 | 5.6 +/− 0.3 |
|  | Syn Rev G | 58 | 13.3 +/− 0.6 | — | 10.7 +/− 0.5 | 3.9 +/− 0.2 |
|  | Syn Rev C | 56 | 5.2 +/− 0.3 | 9.3 +/− 0.5 | — | 3.3 +/− 0.3 |
|  | Syn Rev A | 57 | 9.8 +/− 0.3 | 2.4 +/− 0.2 | 11.0 +/− 0.4 | — |
| MUT ID 24 H784V | Syn Rev T | 55 | — | −0.3 +/− 0.2 | 1.8 +/− 0.2 | 2.6 +/− 0.2 |
|  | Syn Rev G | 58 | 10.2 +/− 0.2 | — | 8.4 +/− 0.1 | 2.8 +/− 0.2 |
|  | Syn Rev C | 56 | 2.8 +/− 0.1 | 4.6 +/− 0.1 | — | 1.8 +/− 0.1 |
|  | Syn Rev A | 57 | 5.4 +/− 0.1 | 0.2 +/− 0.1 | 9.2 +/− 0.2 | — |
| MUT ID 26 H784I | Syn Rev T | 55 | — | 0.3 +/− 0.2 | 3.1 +/− 0.1 | 2.4 +/− 0.2 |
|  | Syn Rev G | 58 | 11.3 +/− 0.2 | — | 9.0 +/− 0.2 | 3.4 +/− 0.2 |
|  | Syn Rev C | 56 | 4.3 +/− 0.2 | 6.7 +/− 0.1 | — | 2.5 +/− 0.2 |
|  | Syn Rev A | 57 | 6.3 +/− 0.1 | 0.7 +/− 0.1 | 10.0 +/− 0.2 | — |

TABLE 31-continued

ΔCq values for AS-qPCR reactions using WT OptiTaq and H784 mutant Taq DNA polymerases.

|  |  |  | Template | | | |
|---|---|---|---|---|---|---|
|  |  |  | A | C | G | T |
| DNA Polymerase | Reverse Primer Name | SEQ ID NO. | SEQ ID NO. 51 | SEQ ID NO. 52 | SEQ ID NO. 53 | SEQ ID NO. 54 |
| MUT ID 27 H784M | Syn Rev T | 55 | — | 4.5 +/− 0.2 | 6.9 +/− 0.2 | 9.6 +/− 0.5 |
|  | Syn Rev G | 58 | 16.7 +/− 3.9 | — | 13.7 +/− 0.7 | 6.5 +/− 0.3 |
|  | Syn Rev C | 56 | 9.5 +/− 0.3 | 11.0 +/− 0.4 | — | 7.4 +/− 0.3 |
|  | Syn Rev A | 57 | 12.7 +/− 0.1 | 5.1 +/− 0.1 | 14.0 +/− 2.0 | — |
| MUT ID 29 H784F | Syn Rev T | 55 | — | 5.6 +/− 0.2 | 3.5 +/− 0.1 | 7.0 +/− 0.2 |
|  | Syn Rev G | 58 | 13.3 +/− 0.6 | — | 10.3 +/− 0.3 | 3.0 +/− 0.2 |
|  | Syn Rev C | 56 | 8.1 +/− 0.2 | 9.7 +/− 0.3 | — | 5.7 +/− 0.2 |
|  | Syn Rev A | 57 | 10.9 +/− 0.3 | 4.6 +/− 0.2 | 11.3 +/− 0.4 | — |
| MUT ID 30 H784Y | Syn Rev T | 55 | — | 5.3 +/− 0.2 | 4.9 +/− 0.2 | 8.8 +/− 0.2 |
|  | Syn Rev G | 58 | 15.7 +/− 4.6 | — | 11.8 +/− 0.5 | 5.5 +/− 0.3 |
|  | Syn Rev C | 56 | 7.3 +/− 0.2 | 9.9 +/− 0.3 | — | 6.0 +/− 0.2 |
|  | Syn Rev A | 57 | 10.2 +/− 0.2 | 4.5 +/− 0.2 | 10.5 +/− 0.3 | — |

Average ΔCq values are shown, where ΔCq = [Cq mismatch − Cq match], +/− standard deviation calculated from 96 replicates.

The wild type OptiTaq showed an average ΔCq for AS-qPCR in this synthetic amplicon system of 4.1 with a range of −0.8 to 8.5. Mutant ID 3 (H784Q) showed an average ΔCq of 9.9 with a range of 4.6 to 21.2. Mutant ID 20 (H784A) showed an average ΔCq of 11.2 with a range of 6.3 to 14.9. Mutant ID 21 (H784S) showed an average ΔCq of 15.3 with a range of 6.6 to 25.8. Mutant ID 22 (H784T) showed an average ΔCq of 6.6 with a range of 1.5 to 13.3. Mutant ID 24 (H784V) showed an average ΔCq of 4.1 with a range of −0.3 to 10.2. Mutant ID 26 (H784I) showed an average ΔCq of 5.0 with a range of 0.3 to 11.3. Mutant ID 27 (H784M) showed an average ΔCq of 9.8 with a range of 4.5 to 16.7. Mutant ID 29 (H784F) showed an average ΔCq of 7.8 with a range of 3.5 to 13.3. Mutant ID 30 (H784Y) showed an average ΔCq of 8.3 with a range of 5.3 to 15.7. Therefore, in nearly all pairwise combinations of 4 template bases and 4 3'-terminal primer bases, the mutant Taq DNA polymerases of the present invention showed greater discrimination to mismatch than did the wild type OptiTaq DNA polymerase. The magnitude of improvement for each mismatch pair is defined by the ΔΔCq, which is the difference of discrimination between the mutant and wild type enzymes (ΔΔCq=ΔCq mutant−ΔCq wild type). The ΔΔCq values were calculated and are shown in Table 32.

TABLE 32

ΔΔCq values for AS-qPCR reactions for the H784 mutant Taq DNA polymerases compared with wild type OptiTaq.

|  |  |  | Template | | | |
|---|---|---|---|---|---|---|
|  |  |  | A | C | G | T |
| DNA Polymerase | Reverse Primer Name | SEQ ID NO. | SEQ ID NO. 51 | SEQ ID NO. 52 | SEQ ID NO. 53 | SEQ ID NO. 54 |
| MUT ID NO. 3 H784Q | Syn Rev T | 55 | — | 4.3 | 5.1 | 6.0 |
|  | Syn Rev G | 58 | 6.0 | — | 6.6 | 3.3 |
|  | Syn Rev C | 56 | 5.7 | 2.9 | — | 3.8 |
|  | Syn Rev A | 57 | 5.0 | 4.9 | 4.9 | — |
| MUT ID 20 H784A | Syn Rev T | 55 | — | 6.2 | 7.1 | 7.5 |
|  | Syn Rev G | 58 | 10.6 | — | 8.9 | 2.8 |
|  | Syn Rev C | 56 | 6.8 | 4.7 | — | 4.3 |
|  | Syn Rev A | 57 | 9.6 | 8.4 | 8.1 | — |
| MUT ID 21 H784S | Syn Rev T | 55 | — | 6.5 | 19.0 | 3.8 |
|  | Syn Rev G | 58 | 17.3 | — | 18.0 | 3.1 |
|  | Syn Rev C | 56 | 8.6 | 8.7 | — | 5.2 |
|  | Syn Rev A | 57 | 17.8 | 9.2 | 16.8 | — |
| MUT ID 22 H784T | Syn Rev T | 55 | — | 0.1 | 3.1 | 0.8 |
|  | Syn Rev G | 58 | 4.8 | — | 4.8 | 0.4 |
|  | Syn Rev C | 56 | 2.4 | 1.6 | — | 0.6 |
|  | Syn Rev A | 57 | 4.5 | 3.2 | 4.9 | — |
| MUT ID 24 H784V | Syn Rev T | 55 | — | −1.7 | 1.2 | −2.2 |
|  | Syn Rev G | 58 | 1.7 | — | 2.5 | −0.7 |
|  | Syn Rev C | 56 | 0.0 | −3.1 | — | −2.1 |
|  | Syn Rev A | 57 | 0.1 | 1.0 | 3.1 | — |
| MUT ID 26 H784I | Syn Rev T | 55 | — | −1.1 | 2.5 | −2.4 |
|  | Syn Rev G | 58 | 2.8 | — | 3.1 | −0.1 |
|  | Syn Rev C | 56 | 1.5 | −1.0 | — | −1.4 |
|  | Syn Rev A | 57 | 1.0 | 1.5 | 3.9 | — |
| MUT ID 27 H784M | Syn Rev T | 55 | — | 3.1 | 6.3 | 4.8 |
|  | Syn Rev G | 58 | 8.2 | — | 7.8 | 3.0 |
|  | Syn Rev C | 56 | 6.7 | 3.3 | — | 3.5 |
|  | Syn Rev A | 57 | 7.4 | 5.9 | 7.9 | — |
| MUT ID 29 H784F | Syn Rev T | 55 | — | 4.2 | 2.9 | 2.2 |
|  | Syn Rev G | 58 | 4.8 | — | 4.4 | −0.5 |
|  | Syn Rev C | 56 | 5.3 | 2.0 | — | 1.8 |
|  | Syn Rev A | 57 | 5.6 | 5.4 | 5.2 | — |
| MUT ID 30 H784Y | Syn Rev T | 55 | — | 3.9 | 4.3 | 4.0 |
|  | Syn Rev G | 58 | 7.2 | — | 5.9 | 2.0 |
|  | Syn Rev C | 56 | 4.5 | 2.2 | — | 2.1 |
|  | Syn Rev A | 57 | 4.9 | 5.3 | 4.4 | — |

Average ΔΔCq values are shown, where ΔΔCq = [ΔCq mutant − ΔCq wild type], from data in Table 17.

Mutant ID 3 (H784Q) showed an average ΔΔCq of 4.9 compared to wild type OptiTaq. Mutant ID 20 (H784A) showed an average ΔΔCq of 7.1 compared to wild type OptiTaq. Mutant ID 21 (H784S) showed an average ΔΔCq of 11.2 compared to wild type OptiTaq. Mutant ID 22 (H784T) showed an average ΔΔCq of 2.5 compared to wild type OptiTaq. Mutant ID 24 (H784V) showed an average ΔΔCq of −0.2 compared to wild type OptiTaq. Mutant ID 26 (H784I) showed an average ΔΔCq of 1.0 compared to wild type OptiTaq. Mutant ID 27 (H784M) showed an average ΔΔCq of 5.7 compared to wild type OptiTaq. Mutant ID 29

(H784F) showed an average ΔΔCq of 3.6 compared to wild type OptiTaq. Mutant ID 30 (H784Y) showed an average ΔΔCq of 4.2 compared to wild type OptiTaq. Therefore, with the exception of Mutant ID 24 (H784V), each of the mutant Taq DNA polymerases of the present invention showed a significant improvement over wild type OptiTaq in mismatch discrimination. Overall, mutant ID 21 (H784S) showed the best SNP discrimination within the set of 9 mutant enzymes studied in this example using this AS-PCR assay.

Example 15: Improved Mismatch Discrimination in rhPCR Using Mutant Taq DNA Polymerases in a Human Genomic DNA SNP Assay Example 14 demonstrated utility of the novel mutant Taq DNA polymerases of the present invention in a synthetic amplicon rhPCR SNP discrimination assay system. The present Example demonstrates utility of the novel mutant Taq DNA polymerases in a human genomic DNA rhPCR SNP discrimination assays system, examining a SNP site in the SMAD7 gene (NM_005904, C/T SNP, rs4939827). The assays employed target DNAs GM18562 (homozygous C/C) and GM18537 (homozygous T/T) from the Coriell Institute for Medical Research (Camden, N.J., USA). Two different blocked-cleavable primer designs were tested, including the generation 1 (Gen1) "RDDDDx" primers and the generation 2 (Gen2) "RDxxD" primers (see: US Patent Application 2012/0258455 by Behlke et al., entitled, RNASE H-BASED ASSAYS UTILIZING MODIFIED RNA MONOMERS).

Quantitative real-time rhPCR was performed in 10 μL reaction volumes in 384 well format with 20 ng (the equivalent of 6600 copies of target) of human genomic DNA (GM18562 or GM18537). Reactions utilized either 0.5 U (10.8 ng/11.1 nM/111 fmol) of wild type OptiTaq DNA polymerase or 0.5 U of one of the nine Taq DNA polymerase mutants (MUT ID 3, H784Q; MUT ID 20, H784A; MUT ID 21, H784S; MUT ID 22, H784T; MUT ID 24, H784V; MUT ID 26, H784I; MUT ID 27 H784M MUT ID 29, H784F; MUT ID 30, H784Y). Final reaction conditions used were 20 mM Tris-HCL (pH 8.4 at 25° C.), 50 mM KCL, 3 mM MgCl$_2$, 0.01% Triton X-100, 800 μM total dNTPs, 200 nM of a forward primer (SEQ ID NOs. 75-79), 200 nM of the universal reverse primer (SEQ ID NO. 74), and 200 nM of the SMAD7 probe (SEQ ID NO. 80). Sequence of the 85 bp SMAD7 amplicon is shown as SEQ ID NO. 81. Forward primers included RDDDDx configuration Gen1 allele-specific rhPCR primers (SEQ ID NOs. 76 and 77), RDxxD configuration Gen2 allele-specific rhPCR primers (SEQ ID NOs. 78 and 79) and the control universal forward primer (SEQ ID NO. 75) which is not allele specific. Oligonucleotide reagents employed in this Example are shown in Table 33. Reactions included 1 μL of P.a. RNase H2 at a concentration of 2.6 mU per 10 μL reaction (5 fmoles, 0.5 nM) with the exception of MUT ID 21 (H784S) for which 200 mU per 10 μL (384 fmoles, 38.4 nM) was used for the Gen1 RDDDDx primers and control primer (SEQ ID NOs. 75-77) or 200 mU per 10 μL reaction (384 fmoles, 38.4 nM) for the Gen2 RDxxD primers (SEQ ID NOs. 78 and 79). Amplification was performed on a Roche LightCycler® 480 (Roche Applied Science, Indianapolis, Ind., USA) as follows: 95° C. for 3 minutes followed by 95 cycles of 95° C. for 10 seconds and 60° C. for 30 seconds. All reactions were performed in triplicate.

TABLE 33

Synthetic oligonucleotides employed in Example 14.

| Name | Sequence (5'-3') | SEQ ID NO. |
|---|---|---|
| SMAD7 Rev | CTCACTCTAAACCCCAGCATT | 74 |
| SMAD7 For | CAGCCTCATCCAAAAGAGGAAA | 75 |
| SMAD7 For rC DDDDx | CAGCCTCATCCAAAAGAGGAAAcAGGAx | 76 |
| SMAD7 For rU DDDDx | CAGCCTCATCCAAAAGAGGAAAuAGGAx | 77 |
| SMAD7 For rC DxxD | CAGCCTCATCCAAAAGAGGAAAcAxxA | 78 |
| SMAD7 For rU DxxD | CAGCCTCATCCAAAAGAGGAAAuAxxA | 79 |
| SMAD7 probe | FAM-CCCAGAGCTCCCTCAGACTCCT-IBFQ | 80 |
| SMAD7 target | CAGCCTCATCCAAAAGAGGAAATAGGACCCC AGAGCTCCCTCAGACTCCTCAGGAAACACAG ACAATGCTGGGGTTTAGAGTGAG | 81 |

DNA bases are uppercase and RNA bases are lowercase;
FAM = 6-carboxyfluorescein;
IBFQ = Iowa Black ™ FQ fluorescence quencher;
"x" = C3 Spacer (propanediol).
Primer and probe binding sites in the SMAD7 target are underlined.

Results using the Gen1 RDDDDx rhPCR primers are shown in Table 34 using the Gen2 RDxxD rhPCR primers are shown in Table 35. Use of the mutant Taq DNA polymerases showed significant improvements in SNP discrimination in this human genomic DNA rhPCR assay using the Gen1 RDDDDx primers, although amplification efficiency was often reduced, as shown by the increases in the match Cqs. Large improvements in discrimination were seen using the Gen2 RDxxD primers, although amplification efficiency was often lost here as well. The Gen2 RDxxD primers inherently show greater SNP discrimination and these levels were increased so that ΔCq values are in some cases were greater than 40 amplification cycles between match and mismatch; this level of discrimination would be "greater than assay" for most users, as qPCR reactions are seldom run for over 45-50 cycles and positive signal was not detected in these cases until after 70 cycles (Table 35). Therefore use of the new mutant Taq DNA polymerases improves SNP discrimination in rhPCR genotyping assays.

TABLE 34

SNP discrimination of a site in the SMAD7 gene using Gen1 RDDDDx primers comparing wild type OptiTaq with four mutant Tag DNA polymerases.

| DNA Polymerase | For Primer | SEQ ID NO. | mU RNase h2 per 10 μL rxn | Cq Value C/C DNA | Cq Value T/T DNA | ΔCq |
|---|---|---|---|---|---|---|
| Wild type OptiTaq | SMAD7 For | 75 | 2.6 | 24.1 | 24.9 | — |
| OptiTaq | SMAD7 For | 76 | 2.6 | 24.3 | 36.3 | 11.9 |

TABLE 34-continued

SNP discrimination of a site in the SMAD7 gene using Gen1 RDDDDx primers comparing wild type OptiTaq with four mutant Taq DNA polymerases.

| DNA Polymerase | For Primer | SEQ ID NO. | mU RNase h2 per 10 μL rxn | Cq Value C/C DNA | Cq Value T/T DNA | ΔCq |
|---|---|---|---|---|---|---|
| | rC DDDDx SMAD7 For rU DDDDx | 77 | 2.6 | 35.1 | 27.5 | 7.6 |
| MUT ID 3 H784Q | SMAD7 For | 75 | 2.6 | 26.0 | 28.1 | — |
| | SMAD7 For rC DDDDx | 76 | 2.6 | 29.4 | 49.1 | 19.7 |
| | SMAD7 For rU DDDDx | 77 | 2.6 | 48.1 | 37.6 | 10.4 |
| MUT ID 20 H784A | SMAD7 For | 75 | 2.6 | 31.4 | 33.9 | — |
| | SMAD7 For rCDDDDx | 76 | 2.6 | 37.4 | 75.9 | 38.4 |
| | SMAD7 For rU DDDDx | 77 | 2.6 | 65.4 | 46.2 | 19.3 |
| MUT ID 21 H784S | SMAD7 For | 75 | 200 | 29.7 | 30.4 | — |
| | SMAD7 For rC DDDDx | 76 | 200 | 32.0 | 46.1 | 14.1 |
| | SMAD7 For rU DDDDx | 77 | 200 | 47.1 | 32.8 | 14.3 |
| MUT ID 22 H784T | SMAD7 For | 75 | 2.6 | 24.2 | 24.9 | — |
| | SMAD7 For rC DDDDx | 76 | 2.6 | 25.8 | 39.0 | 13.3 |
| | SMAD7 For rU DDDDx | 77 | 2.6 | 37.6 | 28.8 | 8.8 |
| MUT ID 24 H784V | SMAD7 For | 75 | 2.6 | 24.4 | 24.1 | |
| | SMAD7 For rC DDDDx | 76 | 2.6 | 24.7 | 34.5 | 9.8 |
| | SMAD7 For rU DDDDx | 77 | 2.6 | 36.0 | 25.6 | 10.4 |
| MUT ID 26 H784I | SMAD7 For | 75 | 2.6 | 24.4 | 24.9 | |
| | SMAD7 For rC DDDDx | 76 | 2.6 | 28.5 | 40.5 | 12.0 |
| | SMAD7 For rU DDDDx | 77 | 2.6 | 42.5 | 30.6 | 11.8 |
| MUT ID 27 H784M | SMAD7 For | 75 | 2.6 | 30.9 | 30.5 | |
| | SMAD7 For rC DDDDx | 76 | 2.6 | 36.1 | 58.8 | 22.7 |
| | SMAD7 For rU DDDDx | 77 | 2.6 | 51.7 | 37.7 | 14.0 |
| MUT ID 29 H784F | SMAD7 For | 75 | 2.6 | 25.8 | 26.5 | |
| | SMAD7 For rC DDDDx | 76 | 2.6 | 30.9 | 50.9 | 19.9 |
| | SMAD7 For rU DDDDx | 77 | 2.6 | 46.9 | 36.2 | 10.7 |
| MUT ID 29 H784Y | SMAD7 For | 75 | 2.6 | 27.3 | 26.7 | |
| | SMAD7 For rC DDDDx | 76 | 2.6 | 31.4 | 46.6 | 15.3 |
| | SMAD7 For rU DDDDx | 77 | 2.6 | 50.2 | 37.1 | 13.1 |

DNA targets included GM18562 (homozygous C/C) and GM18537 (homozygous T/T) from the Coriell Institute for Medical Research. ΔCq = [Cq mismatch − Cq match].

TABLE 35

SNP discrimination of a site in the SMAD7 gene using Gen2 RDxxD primers comparing wild type OptiTaq with four mutant Taq DNA polymerases.

| DNA Polymerase | For Primer | SEQ ID NO. | mU RNase h2 per 10 μL rxn | Cq Value C/C DNA | Cq Value T/T DNA | ΔCq |
|---|---|---|---|---|---|---|
| Wild type OptiTaq | SMAD7 For | 75 | 200 | 24.7 | 25.1 | — |
| | SMAD7 For rC DxxD | 78 | 200 | 24.9 | 39.6 | 14.7 |
| | SMAD7 For rU DxxD | 79 | 200 | 43.4 | 26.0 | 17.4 |
| MUT ID 3 H784Q | SMAD7 For | 75 | 200 | 26.5 | 27.5 | — |
| | SMAD7 For rC DxxD | 78 | 200 | 27.2 | 56.0 | 28.8 |
| | SMAD7 For rU DxxD | 79 | 200 | 73.4 | 37.1 | 36.3 |
| MUT ID 20 H784A | SMAD7 For | 75 | 200 | 26.0 | 26.7 | — |
| | SMAD7 For rC DxxD | 78 | 200 | 26.1 | 58.7 | 32.6 |

TABLE 35-continued

SNP discrimination of a site in the SMAD7 gene using Gen2 RDxxD primers comparing wild type OptiTaq with four mutant Taq DNA polymerases.

| DNA Polymerase | For Primer | SEQ ID NO. | mU RNase h2 per 10 μL rxn | Cq Value C/C DNA | Cq Value T/T DNA | ΔCq |
|---|---|---|---|---|---|---|
|  | SMAD7 For rU DxxD | 79 | 200 | 64.1 | 33.2 | 31.2 |
| MUT ID 21 H784S | SMAD7 For | 75 | 200 | 27.0 | 27.3 | — |
|  | SMAD7 For rC DxxD | 78 | 200 | 29.9 | 69.1 | 39.3 |
|  | SMAD7 For rU DxxD | 79 | 200 | >95 | 62.6 | >32.4 |
| MUT ID 22 H784T | SMAD7 For | 75 | 200 | 24.8 | 25.2 | — |
|  | SMAD7 For rC DxxD | 78 | 200 | 24.8 | 45.2 | 20.4 |
|  | SMAD7 For rU DxxD | 79 | 200 | 57.5 | 26.8 | 30.8 |
| MUT ID 24 H784V | SMAD7 For | 75 | 200 | 25.3 | 24.8 |  |
|  | SMAD7 For rC DxxD | 78 | 200 | 25.3 | 39.9 | 14.6 |
|  | SMAD7 For rU DxxD | 79 | 200 | 39.3 | 24.8 | 39.3 |
| MUT ID 26 H784I | SMAD7 For | 75 | 200 | 24.6 | 24.8 |  |
|  | SMAD7 For rC DxxD | 78 | 200 | 24.8 | 44.0 | 19.2 |
|  | SMAD7 For rU DxxD | 79 | 200 | 46.2 | 26.9 | 46.2 |
| MUT ID 27 H784M | SMAD7 For | 75 | 200 | 30.0 | 29.7 |  |
|  | SMAD7 For rC DxxD | 78 | 200 | 31.9 | 80.1 | 48.2 |
|  | SMAD7 For rU DxxD | 79 | 200 | 83.1 | 40.6 | 83.1 |
| MUT ID 29 H784F | SMAD7 For | 75 | 200 | 27.3 | 26.1 |  |
|  | SMAD7 For rC DxxD | 78 | 200 | 27.8 | 51.3 | 23.6 |
|  | SMAD7 For rU DxxD | 79 | 200 | 56.3 | 29.1 | 56.3 |
| MUT ID 30 H784Y | SMAD7 For | 75 | 200 | 29.0 | 28.7 |  |
|  | SMAD7 For rC DxxD | 78 | 200 | 29.2 | 71.8 | 42.5 |
|  | SMAD7 For rU DxxD | 79 | 200 | 73.5 | 30.4 | 73.5 |

DNA targets included GM18562 (homozygous C/C) and GM18537 (homozygous T/T) from the Coriell Institute for Medical Research. ΔCq = [Cq mismatch − Cq match].

Figure 5B:
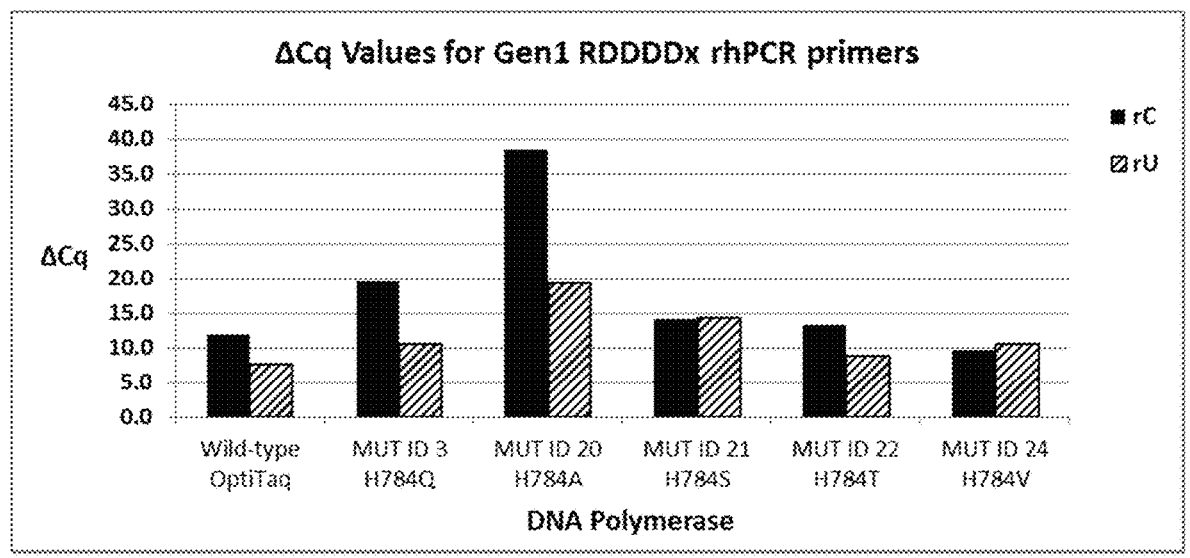
FIG. 5B shows graphical representations of the ΔCq values (Tables 20 and 34) obtained from comparing mismatch discrimination between wild type OptiTaq with Mutant ID 3, Mutant ID 20, Mutant ID 21, Mutant ID 22, and Mutant ID 24 Taq DNA polymerases detecting a human genomic DNA SNP in the SMAD7 gene (NM_005904, C/T SNP, rs4939827) using Gen1 RDDDDx blocked-cleavable primers in a quantitative rhPCR assay. ΔCq=[Cq mismatch−Cq match]. Legend as in FIG. 5A.
Figure 5C:
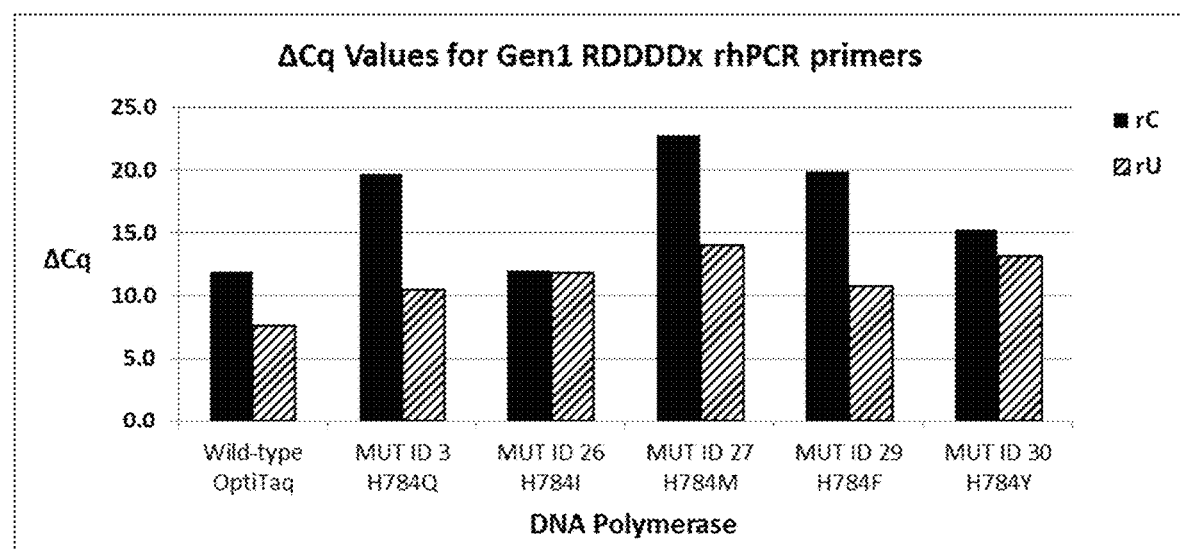
FIG. 5C shows graphical representations of the ΔCq values (Tables 20 and 34) obtained from comparing mismatch discrimination between wild type OptiTaq with Mutant ID 3, Mutant ID 26, Mutant ID 27, Mutant ID 29, and Mutant ID 30 Taq DNA polymerases detecting a human genomic DNA SNP in the SMAD7 gene (NM_005904, C/T SNP, rs4939827) using Gen1 RDDDDx blocked-cleavable primers in a quantitative rhPCR assay. ΔCq=[Cq mismatch−Cq match]. Legend as in FIG. 5A.
Figure 6B:
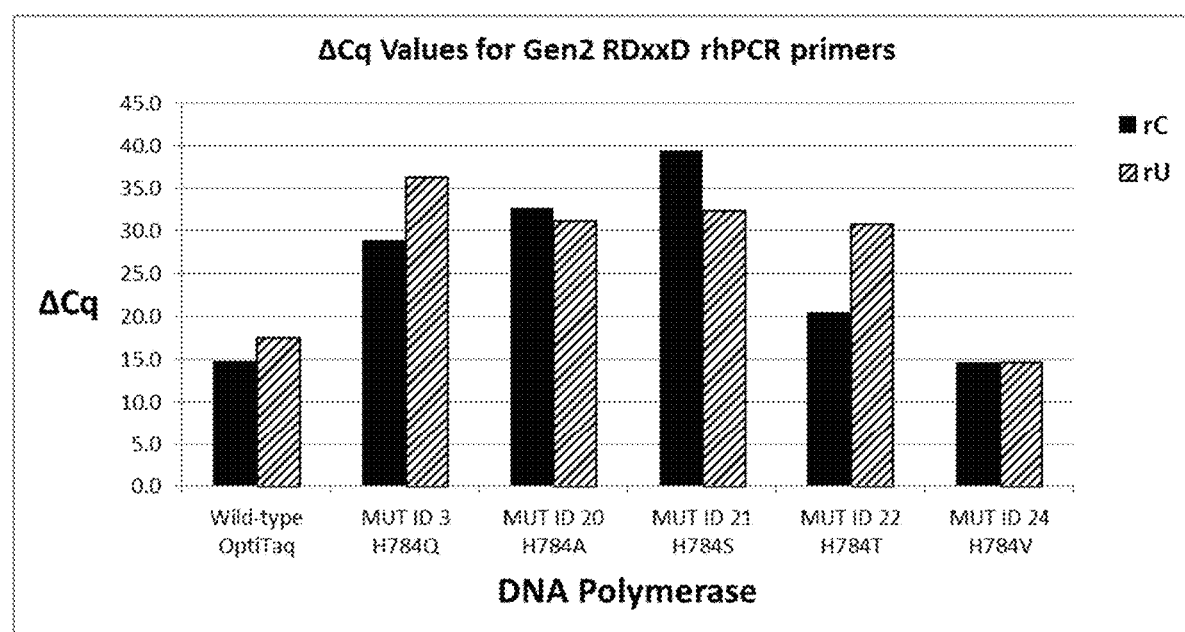
FIG. 6B shows a graphical representation of the ΔCq values (Tables 21 and 35) obtained from comparing mismatch discrimination between wild type OptiTaq with Mutant ID 3, Mutant ID 20, Mutant ID 21, Mutant ID 22, and Mutant ID 24 Taq DNA polymerases detecting a human genomic DNA SNP in the SMAD7 gene (NM_005904, C/T SNP, rs4939827) using Gen2 RDxxD blocked-cleavable primers in a quantitative rhPCR assay. ΔCq=[Cq mismatch–Cq match]. Legend as in FIG. 6A.
Figure 6C:
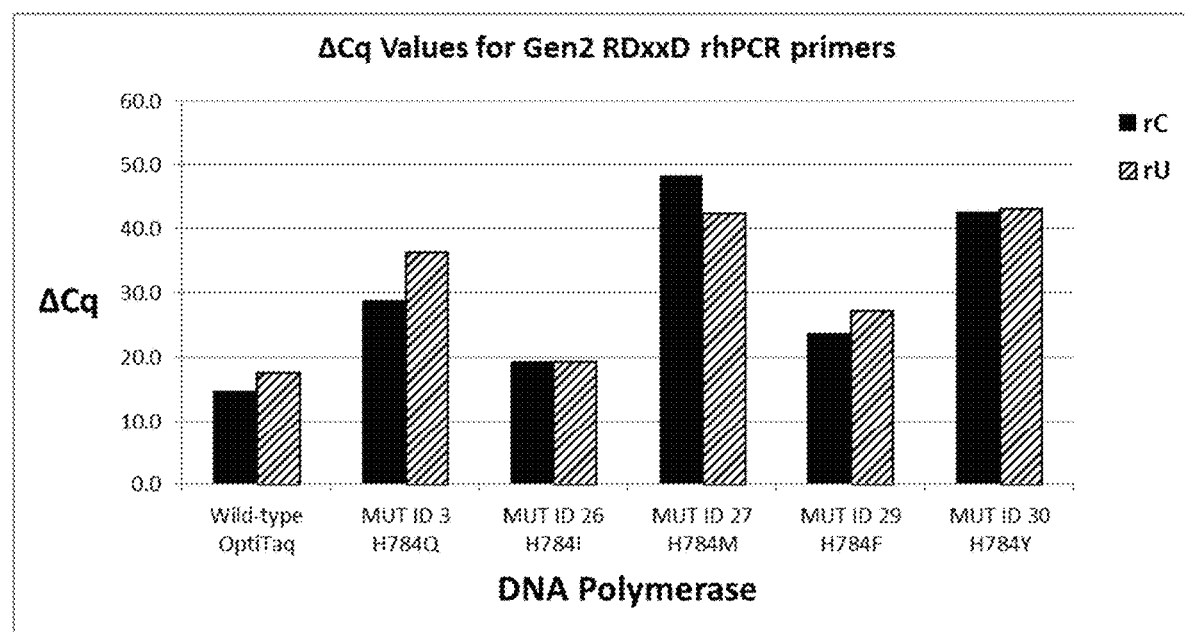
FIG. 6C shows a graphical representation of the ΔCq values (Tables 21 and 35) obtained from comparing mismatch discrimination between wild type OptiTaq with Mutant ID 3, Mutant ID 26, Mutant ID 27, Mutant ID 29, and Mutant ID 30 Taq DNA polymerases detecting a human genomic DNA SNP in the SMAD7 gene (NM_005904, C/T SNP, rs4939827) using Gen2 RDxxD blocked-cleavable primers in a quantitative rhPCR assay. ΔCq=[Cq mismatch–Cq match]. Legend as in FIG. 6A.

The ΔCq values for the SMAD7 SNP genotyping assays are graphically summarized in FIGS. 5B and 5C for the Gen1 RDDDDx primers and in FIGS. 6B and 6C for the Gen2 RDxxD primers. It is clear that not only do the different mutant Taq DNA polymerases of the present invention have utility in different amplification assays but that the different mutants show varying levels of benefit depending on the nature of the assay used. It is therefore useful to have a collection of mutant polymerases whose properties can be matched to different assays/applications so that maximal benefit is obtained.

Example 16: Improved Discrimination of Rare Alleles in Genomic DNA Using rhPCR with Mutant Taq DNA Polymerases Use of the Gen2 RDxxD blocked-cleavable primers in rhPCR can detect the presence of a SNP at a level of 1:1,000 to 1:10,000 in the background of wild type genomic DNA using native (wild type) Taq DNA polymerase (see: US Patent Application 2012/0258455 by Behlke et al., entitled, RNASE H-BASED ASSAYS UTILIZING MODIFIED RNA MONOMERS). The present example demonstrates that the mutant Taq DNA polymerases of the present invention improve rare allele discrimination in the rhPCR assay.

Rare allele detection experiments were designed to detect the base identity of a SNP site in the SMAD7 gene (NM_005904, C/T SNP, rs4939827) and employed target DNAs GM18562 (homozygous C/C) and GM18537 (homozygous T/T) (Coriell Institute for Medical Research, Camden, N.J., USA). Control reactions were set up using 2 ng (660 copies), 0.2 ng (66 copies), or 0.02 ng (6.6 copies) of input matched target DNA. Rare allele detection reactions were set up using 2 ng (660 copies), 0.2 ng (66 copies), or 0.02 ng (6.6 copies) of input matched target DNA of one allele plus 200 ng (66,000 copies) of the other (mismatched) allele. Background was established in reactions that contained 0 copies of matched target DNA plus 200 ng (66,000 copies) of the mismatched target DNA. Both combinations were tested: GM18562 (C/C) as the rare allele in the presence of excess GM18537 (T/T) and GM18537 (T/T) as the rare allele in the presence of excess GM18562 (C/C).

Quantitative real-time rhPCR was performed in 10 μL reaction volumes in 384 well format. Final reaction conditions used were 10 mM Tris-HCL (pH 8.4 at 25° C.), 50 mM KCL, 3.5 mM MgCl$_2$, 0.01% Triton-X100, 0.8 mM dNTPs, 200 nM of one of the SMAD7 forward primers (SEQ ID NOs. 75, 78, and 79), 200 nM of the SMAD7 reverse primer (SEQ ID NO. 74), and 200 nM of the SMAD7 probe (SEQ ID NO. 80). The 85 bp SMAD7 amplicon defined by these primers is shown as SEQ ID NO. 81. Note that the forward primers were either unmodified (control, SEQ ID NO. 75) or were specific for the SMAD7 C-allele (SEQ ID NO. 78) or the SMAD7 T-allele (SEQ ID NO. 79) using blocked-cleavable rhPCR Gen2 RDxxD design. Reactions utilized either 0.5 U of the wild type OptiTaq DNA polymerase or 0.5 U of one of three example Taq DNA polymerase mutants studied (MUT ID 20(H784A); MUT ID 27(H784M); MUT ID 30(H784Y)). Reactions included *P. abyssi* RNase H2 at a concentration of 200 mU per 10 µL reaction (384 fmoles) when using the SMAD7 For rC DxxD (SEQ ID NO. 78) primer and control reactions or 500-600 mU per 10 µL reaction (960-1152 fmoles) when using the SMAD7 For rU DxxD (SEQ ID NO. 79) primer. Oligonucleotide reagents used in this Example are shown in Table 36. Cycling was performed on a Roche LightCycler® 480 (Roche Applied Science, Indianapolis, Ind., USA) as follows: 95° C. for 3 minutes followed by 65 cycles of 95° C. for 10 seconds and 60° C. for 30 seconds. All reactions were performed in triplicate.

TABLE 36

Synthetic oligonucleotides employed in Example 16.

| Name | Sequence (5'-3') | SEQ ID NO. |
|---|---|---|
| SMAD7 Rev | CTCACTCTAAACCCCAGCATT | 74 |
| SMAD7 For | CAGCCTCATCCAAAAGAGGAAA | 75 |
| SMAD7 For rC DxxD | CAGCCTCATCCAAAAGAGGAAAcAxxA | 78 |
| SMAD7 For rU DxxD | CAGCCTCATCCAAAAGAGGAAAuAxxA | 79 |
| SMAD7 probe | FAM-CCCAGAGCTCCCTCAGACTCCT-IBFQ | 80 |
| SMAD7 target | <u>CAGCCTCATCCAAAAGAGGAAA</u>TAGGAC<u>CCC AGAGCTCCCTCAGACTCCT</u>CAGGAAACACAG ACAATGCTGGGGTTTAGAGTGAG | 81 |

DNA bases are uppercase and RNA bases are lowercase;
FAM = 6-carboxyfluorescein;
IBFQ = Iowa Black ™ FQ fluorescence quencher;
"x" = C3 Spacer (propanediol).
Primer and probe binding sites in the SMAD7 target are underlined.

Results were analyzed and are shown in Table 37. The control columns show Cq values for matched primer/target reactions with no mismatched target present and establish a quantification standard curve. MUT ID NO. 3, H784Q is included in data analysis for comparison. The rare allele detection columns show Cq values for detection of 660, 66, 6, or 0 (background control) copies of matched primer/target in the presence of 66,000 copies of mismatched target. It is generally assumed that at least a 3 cycle difference ($\Delta Cq=3.0$ or greater) between background and positive signal is needed to call a reaction "positive" for rare allele detection; a 5 cycle difference ($\Delta Cq=5.0$ or greater) is preferred. In this system, background is the signal observed when amplification is done using no input target that is matched to the primer, so signal arises solely from amplification originating off the mismatched target.

Using wild type OptiTaq DNA polymerase, detection of the "C" allele in an excess of "T" background and detection of the "T" allele in an excess of "C" background both met the $\Delta Cq$ 3.0 and $\Delta Cq$ 5.0 levels of stringency to call a 1:1000 rare allele detection event (66 copies of match target in the presence of 66,000 copies of mismatch target). The 1:10,000 reactions (6 copies of match target in the presence of 66,000 copies of mismatch target) did not meet either of these criteria. Thus rhPCR had a 1:1000 rare allele detection limit using wild type OptiTaq in this genomic DNA SNP system.

In contrast, rhPCR using each of the four mutants showed a 1:10,000 rare allele detection limit for both the "C" and "T" allele targets with a $\Delta Cq$ stringency cutoff of 3.0. MUT ID 3 (H784Q) showed a 1:10,000 rare allele detection limit for both the "C" and "T" targets in this genomic SNP system for the higher $\Delta Cq$ stringency cutoff of 5.0. The other three mutant Taq DNA polymerases (MUT ID 20(H784A); MUT ID 27(H784M); MUT ID 30(H784Y)) showed a 1:10,000 rare allele detection limit for the "C" allele target with a $\Delta Cq$ stringency cutoff of 5.0 and a 1:10,000 rare allele detection limit for the "T" allele target with a $\Delta Cq$ stringency cutoff of 3.0. We therefore conclude that the new mutant Taq DNA polymerases of the present invention provide for improved rare allele detection reactions using blocked-cleavable primers in rhPCR compared with use of the wild type DNA polymerase.

TABLE 37

Rare allele detection using Gen2 RDxxD rhPCR primers comparing wild type OptiTaq with new mutant Taq DNA polymerases

| DNA Polymerase | For Primer | SEQ ID NO. | RNase H2 per 10 µL rxn | 200 ng mismatched template (66,000 copies of "wild type") | | | | Control (No mismatched template) | | | |
|---|---|---|---|---|---|---|---|---|---|---|---|
| | | | | 660 Match (1:100) | 66 Match (1:1,000) | 6 Match (1:10,000) | 0 Match (background) | 660 Match | 66 Match | 6 Match | 0 Match |
| Wild type OptiTaq | SMAD7 For | 75 | 200 mU | 22.1 | 21.2 | 21.2 | 21.8 | 27.9 | 31.3 | 34.4 | >65 |
| | SMAD7 For rC DxxD | 78 | 200 mU | 28.2 | 31.5 | 35.1 | 37.0 | 28.8 | 33.3 | 37.3 | >65 |
| | SMAD7 For rU DxxD | 79 | 500 mU | 31.0 | 34.7 | 37.7 | 39.7 | 31.2 | 34.6 | 41.0 | >65 |
| MUT ID 3 (H784Q) | SMAD7 For | 75 | 200 mU | 23.5 | 23.6 | 24.5 | 24.1 | 30.5 | 33.4 | 38.0 | >65 |
| | SMAD7 For rC DxxD | 78 | 200 mU | 29.8 | 33.8 | 37.6 | >65 | 30.5 | 35.5 | 39.6 | >65 |
| | SMAD7 For rU DxxD | 79 | 500 mU | 32.9 | 37.7 | 44.0 | 52.3 | 30.1 | 35.9 | 44.9 | >65 |

TABLE 37-continued

Rare allele detection using Gen2 RDxxD rhPCR primers comparing wild type OptiTaq with new mutant Taq DNA polymerases

| DNA Polymerase | For Primer | SEQ ID NO. | RNase H2 per 10 μL rxn | 200 ng mismatched template (66,000 copies of "wild type") | | | | Control (No mismatched template) | | | |
|---|---|---|---|---|---|---|---|---|---|---|---|
| | | | | 660 Match (1:100) | 66 Match (1:1,000) | 6 Match (1:10,000) | 0 Match (background) | 660 Match | 66 Match | 6 Match | 0 Match |
| MUT ID 20 (H784A) | SMAD7 For | 75 | 200 mU | 23.5 | 24.1 | 24.7 | 24.9 | 31.6 | 36.1 | 40.2 | >65 |
| | SMAD7 For rC DxxD | 78 | 200 mU | 31.3 | 36.7 | 43.2 | 55.3 | 33.5 | 39.5 | 44.7 | >65 |
| | SMAD7 For rU DxxD | 79 | 500 mU | 35.7 | 40.0 | 43.8 | 54.7 | 33.3 | 38.8 | 41.5 | >65 |
| MUT ID 27 (H784M) | SMAD7 For | 75 | 200 mU | 24.2 | 24.8 | 25.4 | 26.4 | 31.6 | 36.2 | 40.2 | >65 |
| | SMAD7 For rC DxxD | 78 | 200 mU | 33.7 | 38.5 | 42.0 | 54.4 | 33.6 | 37.8 | 41.7 | >65 |
| | SMAD7 For rU DxxD | 79 | 600 mU | 39.7 | 43.2 | 45.8 | 50.0 | 31.9 | 36.5 | 41.0 | >65 |
| MUT ID 30 (H784Y) | SMAD7 For | 75 | 200 mU | 24.8 | 24.9 | 24.8 | 26.3 | 38.6 | 38.9 | 46.9 | >65 |
| | SMAD7 For rC DxxD | 78 | 200 mU | 28.8 | 32.9 | 37.5 | 46.5 | 29.5 | 33.4 | 37.8 | >65 |
| | SMAD7 For rU DxxD | 79 | 500 mU | 39.9 | 45.8 | 54.6 | 57.0 | 37.7 | 44.6 | 53.1 | >65 |

Cq values are shown. For the rare allele detection series (selective detection of 6-660 copes one genotype in the presence of 66,000 copies of the other genotype), those reactions having a ΔCq of 3.0 or better are highlighted in bold font and those having a ΔCq of 5.0 or better are highlighted in bold font with underline. ΔCq = [(Cq 0 copies match) − (Cq 6 copies match)], or ΔCq = [(Cq 0 copies match) − (Cq 66 copies match)], or ΔCq = [(Cq 0 copies match) − (Cq 660 copies match)].

Example 17. Sequence of Taq DNA Polymerase Mutants Showing Improved Discrimination for Mismatch or the Presence of an RNA Residue at the 3'-End of the Primer The complete amino acid and nucleotide sequences of the codon optimized mutant enzymes employed in Examples 11-15 are shown below. Although these sequences are easily derived from information provided in Tables 1, 3, 4 and 26 by one with skill in the art, the final assembled sequences are provided below for clarity. Base changes are identified in bold underlined font for the nucleic acid and amino acid substitutions.

```
SEQ ID NO. 146, nucleotide sequence of Mutant ID 20 (H784A).
CATATGCGTGGTATGCTGCCGTTGTTCGAGCCTAAAGGCCGCGTACTGTTAGTCGATGGTCATCACTTGGCCTATCG
GACGTTCCATGCACTCAAAGGTCTGACGACCAGTCGTGGCGAACCGGTCCAGGCTGTTTATGGTTTCGCTAAGTCTT
TGCTCAAAGCACTGAAAGAAGACGGGGACGCGGTAATTGTTGTATTTGATGCCAAAGCACCGAGCTTCCGCCACGAA
GCTTATGGTGGCTACAAGGCAGGACGCGCCCCTACCCCAGAAGATTTCCCCCGTCAGCTGGCATTAATTAAGGAGTT
AGTAGACCTTCTCGGCTTAGCGCGTCTGGAAGTTCCGGGTTATGAGGCGGACGATGTCCTTGCATCCTTGGCTAAAA
AGGCCGAAAAAGAGGGCTACGAAGTCCGCATCTTGACGGCAGACAAAGATCTGTACCAGCTTCGTCTGACCGTATT
CATGTTTTGCACCCTGAAGGCTACTTAATCACTCCGGCCTGGCTCTGGGAAAAGTACGGTCTGCGTCCCGATCAGTG
GGCGGATTATCGGGCTTTGACGGGAGATGAGAGCGACAACCTGCCAGGAGTTAAGGGCATTGGTGAAAAAACCGCAC
GTAAGCTGCTTGAAGAGTGGGGTTCCCTGGAAGCCTTGTTAAAAAATCTGGATCGTCTCAAGCCCGCAATTCGTGAA
AAGATCCTGGCTCATATGGACATCTTAAATTAAGTTGGGACCTGGCCAAGGTGCGCACCGATTTACCGCTTGAAGT
GGATTTTGCAAAACGCCGTGAGCCGGACCGGGAACGTTTACGCGCTTTCTTAGAGCGTCTGGAATTCGGTTCACTGC
TTCATGAATTCGGTCTGTTAGAGTCTCCTAAAGCACTCGAAGAGGCACCGTGGCCGCCCCAGAAGGTGCTTTTGTT
GGCTTCGTACTTTCCCGTAAGGAGCCTATGTGGGCAGATCTTCTGGCTTTAGCGGCTGCACGCGGTGGCCGTGTTCA
CCGGGCCCCTGAGCCATACAAAGCGTTACGTGATCTGAAGGAAGCACGTGGCTTGCTGGCAAAAGACCTTTCTGTTT
TGGCCCTGCGCGAGGGTCTTGGACTGCCGCCAGGCGACGATCCCATGTTATTGGCCTATCTGTTAGACCCTAGCAAT
ACCACACCTGAAGGGTCGCTCGTCGGTATGGCGGTGAATGACTGAGGAAGCCGGAGAGCGCGCCATTGTCCGA
ACGGCTCTTTGCAAACTTATGGGGTCGTCTGGAAGGGGAGGAACGTCTGTTATGGTTGTATCGGGAAGTCGAACGTC
CTCTTTCGGCCGTATTAGCGCATATGGAGGCAACAGGTGTGCGTTTAGATGTCGCGTACCTTCGGGCCTTATCACTG
GAAGTTGCAGAGGAAATCGCCCGTCTCGAGGCTGAAGTGTTCCGGTTGGCCGGTCACCCGTTTAACCTCAACTCCCG
TGACCAGCTGGAACGCGTTTTATTCGATGAGCTTGGGCTTCCCGCAATTGGCAAAACCGAAAAGACTGGCAAACGCA
GTACGAGCGCTGCCGTCCTTGAGGCACTCCGCGAGGCTCACCCTATTGTAGAAAAGATCCTGCAATACCGTGAGTTG
ACGAAGCTTAAAAGCACTTATATTGATCCTCTCCCGGATCTGATCCATCCTCGTACCGGCCGCTTGCACACACGTTT
CAACCAGACGGCGACTGCAACCGGCCGTCTGTCTAGCTCGGATCCAAATCTCCAGAACATTCCGGTCCGTACACCCT
TGGGCCAACGTATCCGCCGGGCGTTTATCGCTGAGGAAGGATGGTTACTGGTCGCATTGGACTACTCGCAGATTGAG
CTGCGCGTCCTCGCACATCTCTCTGGTGACGAAAATTTAATCCGCGTGTTTCAAGAGGGGCGTGATATTCACACAGA
AACTGCCTCATGGATGTTCGGTGTCCCACGTGAAGCAGTGGATCCTTTGATGCGCCGTGCAGCTAAAACAATTAATT
TTGGAGTGCTGTACGGAATGAGCGCTCATCGCTTGAGTCAGGAACTGGCAATCCCCTACGAGGAAGCGCAGGCATTC
```

-continued

ATCGAACGTTACTTTCAATCGTTTCCGAAAGTTCGCGCATGGATCGAGAAGACGCTCGAGGAAGGTCGTCGTCGGGG
CTATGTCGAAACTCTGTTTGGTCGCCGTCGGTACGTACCAGATCTTGAAGCCCGCGTCAAATCGGTACGGGAGGCTG
CGGAGCGTATGGCATTTAATATGCCTGTACAGGGTACTGCAGCTGACCTCATGAAACTGGCAATGGTCAAGCTTTTC
CCGCGCTTGGAGGAAATGGGCGCACGTATGCTTCTGCAGGTCGCGGACGAGCTGGTGTTAGAAGCCCCTAAGGAGCG
CGCCGAAGCTGTCGCGCGCCTCGCTAAAGAAGTGATGGAGGGCGTTTACCCATTGGCCGTACCCCTCGAAGTGGAGG
TCGGTATTGGAGAAGATTGGTTATCTGCAAAGGAAGCGGCCGC

SEQ ID NO. 147, amino acid sequence of Mutant ID 20 (H784A).
MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQVADELVLEAPKERAEAVARLAKEVMEGVYPLAVPLEVEVGIGEDWLSAKEAA SEQ ID NO. 148, nucleotide sequence of Mutant ID 21 (H784S).
CATATGCGTGGTATGCTGCCGTTGTTCGAGCCTAAAGGCCGCGTACTGTTAGTCGATGGTCATCACTTGGCCTATCG
GACGTTCCATGCACTCAAAGGTCTGACGACCAGTCGTGGCGAACCGGTCCAGGCTGTTTATGGTTTCGCTAAGTCTT
TGCTCAAAGCACTGAAAGAAGACGGGGACGCGGTAATTGTTGTATTTGATGCCAAAGCACCGAGCTTCCGCCACGAA
GCTTATGGTGGCTACAAGGCAGGACGCGCCCCTACCCCAGAAGATTTCCCCCGTCAGCTGGCATTAATTAAGGAGTT
AGTAGACCTTCTCGGCTTAGCGCGTCTGGAAGTTCCGGGTTATGAGGCGGACGATGTCCTTGCATCCTTGGCTAAAA
AGGCCGAAAAGAGGGCTACGAAGTCCGCATCTTGACGGCAGACAAAGATCTGTACCAGCTTCTGTCTGACCGTATT
CATGTTTTGCACCCTGAAGGCTACTTAATCACTCCGGCCTGGCTCTGGGAAAAGTACGGTCTGCGTCCCGATCAGTG
GGCGGATTATCGGGCTTTGACGGGAGATGAGAGCGACAACCTGCCAGGAGTTAAGGGCATTGGTGAAAAAACCGCAC
GTAAGCTGCTTGAAGAGTGGGGTTCCCTGGAAGCTTGTTAAAAAATCTGGATCGTCTCAAGCCCGCAATTCGTGAA
AAGATCCTGGCTCATATGGACGATCTTAAATTAAGTTGGGACCTGGCCAAGGTGCGCACCGATTTACCGCTTGAAGT
GGATTTTGCAAAACGCCGTGAGCCGGACCGGGAACGTTTACGCGCTTTCTTAGAGCGTCTGGAATTCGGTTCACTGC
TTCATGAATTCGGTCTGTTAGAGTCTCCTAAAGCACTCGAAGAGGCACCGTGGCCGCCCCCAGAAGGTGCTTTTGTT
GGCTTCGTACTTTCCCGTAAGGAGCCTATGTGGGCAGATCTTCTGGCTTTAGCGGCTGCACGCGGTGGCCGTGTTCA
CCGGGCCCCTGAGCCATACAAAGCGTTACGTGATCTGAAGGAAGCACGTGGCTTGCTGGCAAAAGACCTTTCTGTTT
TGGCCCTGCGCGAGGGTCTTGGACTGCCGCCAGGCGACGATCCCATGTTATTGGCCTATCTGTTAGACCCTAGCAAT
ACCACACCTGAAGGGGTCGCTCGTCGGTATGGCGGTGAATGGACTGAGGAAGCCGGAGAGCGCGCCGCATTGTCCGA
ACGGCTCTTTGCAAACTTATGGGGTCGTCTGGAAGGGGAGGAACGTCTGTTATGGTTGTATCGGGAAGTCGAACGTC
CTCTTTCGGCCGTATTAGCGCATATGGAGGCAACAGGTGTGCGTCTGGATGTCGCGTACCTTCGGGCCTTATCACTG
GAAGTTGCAGAGGAAATCGCCCGTCTCGAGGCTGAAGTGTTCCGGTTGGCCGGTCACCGTTTAACCTCAACTCCCG
TGACCAGCTGGAACGCGTTTTATTCGATGAGCTTGGGCTTCCCGCAATTGGCAAAACCGAAAAGACTGGCAAACGCA
GTACGAGCGCTGCCGTCCTTGAGGCACTCCGCGAGGCTCACCCTATTGTAGAAAAGATCCTGCAATACCGTGAGTTG
ACGAAGCTTAAAAGCACTTATATTGATCCTCTCCCGGATCTGATCCATCCTCGTACCGGCCGCTTGCACACACGTTT
CAACCAGACGGCGACTGCAACCGGCCGTCTGTCTAGCTCGGATCCAAATCTCCAGAACATTCCGGTCCGTACACCCT
TGGGCCAACGTATCCGCCGGGCGTTTATCGCTGAGGAAGGATGGTTACTGGTCGCATTGACTACTCGCAGATTGAG
CTGCGCGTCCTCGCACATCTCTCTGGTGACGAAAATTTAATCCGCGTGTTTCAAGAGGGGCGTGATATTCACACAGA
AACTGCCTCATGGATGTTCGGTGTCCCACGTGAAGCAGTGGATCCTTTGATGCGCCGTGCAGCTAAAACAATTAATT
TTGGAGTGCTGTACGGAATGAGCGCTCATCGCTTGAGTCAGGAACTGGCAATCCCCTACGAGGAAGCGCAGGCATTC
ATCGAACGTTACTTTCAATCGTTTCCGAAAGTTCGCGCATGGATCGAGAAGACGCTCGAGGAAGGTCGTCGTCGGGG
CTATGTCGAAACTCTGTTTGGTCGCCGTCGGTACGTACCAGATCTTGAAGCCCGCGTCAAATCGGTACGGGAGGCTG
CGGAGCGTATGGCATTTAATATGCCTGTACAGGGTACTGCAGCTGACCTCATGAAACTGGCAATGGTCAAGCTTTTC
CCGCGCTTGGAGGAAATGGGCGCACGTATGCTTCTGCAGGTCAGCGACGAGCTGGTGTTAGAAGCCCCTAAGGAGCG
CGCCGAAGCTGTCGCGCGCCTCGCTAAAGAAGTGATGGAGGGCGTTTACCCATTGGCCGTACCCCTCGAAGTGGAGG
TCGGTATTGGAGAAGATTGGTTATCTGCAAAGGAAGCGGCCGC SEQ ID NO. 149, amino acid sequence of Mutant ID 21 (H784S).
MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQVSDELVLEAPKERAEAVARLAKEVMEGVYPLAVPLEVEVGIGEDWLSAKEAA SEQ ID NO. 150, nucleotide sequence of Mutant ID 22 (H784T).
CATATGCGTGGTATGCTGCCGTTGTTCGAGCCTAAAGGCCGCGTACTGTTAGTCGATGGTCATCACTTGGCCTATCG
GACGTTCCATGCACTCAAAGGTCTGACGACCAGTCGTGGCGAACCGGTCCAGGCTGTTTATGGTTTCGCTAAGTCTT
TGCTCAAAGCACTGAAAGAAGACGGGGACGCGGTAATTGTTGTATTTGATGCCAAAGCACCGAGCTTCCGCCACGAA
GCTTATGGTGGCTACAAGGCAGGACGCGCCCCTACCCCAGAAGATTTCCCCCGTCAGCTGGCATTAATTAAGGAGTT
AGTAGACCTTCTCGGCTTAGCGCGTCTGGAAGTTCCGGGTTATGAGGCGGACGATGTCCTTGCATCCTTGGCTAAAA
AGGCCGAAAAGAGGGCTACGAAGTCCGCATCTTGACGGCAGACAAAGATCTGTACCAGCTTCTGTCTGACCGTATT
CATGTTTTGCACCCTGAAGGCTACTTAATCACTCCGGCCTGGCTCTGGGAAAAGTACGGTCTGCGTCCCGATCAGTG
GGCGGATTATCGGGCTTTGACGGGAGATGAGAGCGACAACCTGCCAGGAGTTAAGGGCATTGGTGAAAAAACCGCAC
GTAAGCTGCTTGAAGAGTGGGGTTCCCTGGAAGCTTGTTAAAAAATCTGGATCGTCTCAAGCCCGCAATTCGTGAA
AAGATCCTGGCTCATATGGACGATCTTAAATTAAGTTGGGACCTGGCCAAGGTGCGCACCGATTTACCGCTTGAAGT
GGATTTTGCAAAACGCCGTGAGCCGGACCGGGAACGTTTACGCGCTTTCTTAGAGCGTCTGGAATTCGGTTCACTGC
TTCATGAATTCGGTCTGTTAGAGTCTCCTAAAGCACTCGAAGAGGCACCGTGGCCGCCCCCAGAAGGTGCTTTTGTT -continued

```
GGCTTCGTACTTTCCCGTAAGGAGCCTATGTGGGCAGATCTTCTGGCTTTAGCGGCTGCACGCGGTGGCCGTGTTCA
CCCGGGCCCCTGAGCCATACAAAGCGTTACGTGATCTGAAGGAAGCACGTGGCTTGCTGGCAAAAGACCTTTCTGTTT
TGGCCCTGCGCGAGGGTCTTGGACTGCCGCCAGGCGACGATCCCATGTTATTGGCCTATCTGTTAGACCCTAGCAAT
ACCACACCTGAAGGGGTCGCTCGTCGGTATGGCGGTAATGGACTGAGGAAGCCGGAGAGCGCGCCGCATTGTCCGA
ACGGCTCTTTGCAAACTTATGGGGTCGTCTGGAAGGGGAGGAACGTCTGTTATGGTTGTATCGGGAAGTCGAACGTC
CTCTTTCGGCCGTATTAGCGCATATGGAGGCAACAGGTGTGCGTTTAGATGTCGCGTACCTTCGGGCCTTATCACTG
GAAGTTGCAGAGGAAATCGCCCGTCTCGAGGCTGAAGTGTTCCGGTTGGCCGGTCACCCGTTTAACCTCAACTCCCG
TGACCAGCTGGAACGCGTTTTATTCGATGAGCTTGGGCTTCCCGCAATTGGCAAAACCGAAAAGACTGGCAAACGCA
GTACGAGCGCTGCCGTCCTTGAGGCACTCCGCGAGGCTCACCCTATTGTAGAAAAGATCCTGCAATACCGTGAGTTG
ACGAAGCTTAAAAGCACTTATATTGATCCTCTCCCGGATCTGATCCATCCTCGTACCGGCCGCTTGCACACACGTTT
CAACCAGACGGCGACTGCAACCGGCCGTCTGTCTAGCTCGGATCCAAATCTCCAGAACATTCCGGTCCGTACACCCT
TGGGCCAACGTATCCGCCGGGCGTTTATCGCTGAGGAAGGATGGTTACTGGTCGCATTGACTACTCGCAGATTGAG
CTGCGCGTCCTCGCACATCTCTCTGGTGACGAAAATTTAATCCGCGTGTTTCAAGAGGGGCGTGATATTCACACAGA
AACTGCCTCATGGATGTTCGGTGTCCCACGTGAAGCAGTGGATCCTTTGATGCGCCGTGCAGCTAAAACAATTAATT
TTGGAGTGCTGTACGGAATGAGCGCTCATCGCTTGAGTCAGGAACTGGCAATCCCCTACGAGGAAGCGCAGGCATTC
ATCGAACGTTACTTTCAATCGTTTCCGAAAGTTCGCGCATGGATCGAGAAGACGCTCGAGGAAGGTCGTCGTCGGGG
CTATGTCGAAACTCTGTTTGGTCGCCGTCGGTACGTACCAGATCTTGAAGCCCGCGTCAAATCGGTACGGGAGGCTG
CGGAGCGTATGGCATTTAATATGCCTGTACAGGGTACTGCAGCTGACCTCATGAAACTGGCAATGGTCAAGCTTTTC
CCGCGCTTGGAGGAAATGGGCGCACGTATGCTTCTGCAGGTCACGGACGAGCTGGTGTTAGAAGCCCCTAAGGAGCG
CGCCGAAGCTGTCGCGCGCCTCGCTAAAGAAGTGATGGAGGGCGTTTACCCATTGGCCGTACCCCTCGAAGTGGAGG
TCGGTATTGGAGAAGATTGGTTATCTGCAAAGGAAGCGGCCGC
```

SEQ ID NO. 151, amino acid sequence of Mutant ID 22 (H784T).
MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQVTDELVLEAPKERAEAVARLAKEVMEGVYPLAVPLEVEVGIGEDWLSAKEAA SEQ ID NO. 152, nucleotide sequence of Mutant ID 24 (H784V).
```
CATATGCGTGGTATGCTGCCGTTGTTCGAGCCTAAAGGCCGCGTACTGTTAGTCGATGGTCATCACTTGGCCTATCG
GACGTTCCATGCACTCAAAGGTCTGACGACCAGTCGTGGCGAACCGGTCCAGGCTGTTTATGGTTTCGCTAAGTCTT
TGCTCAAAGCACTGAAAGAAGACGGGGACGCGGTAATTGTTGTATTTGATGCCAAAGCACCGAGCTTCCGCCACGAA
GCTTATGGTGGCTACAAGGCAGGACGCGCCCCTACCCCAGAAGATTTCCCCCGTCAGCTGGCATTAATTAAGGAGTT
AGTAGACCTTCTCGGCTTAGCGCGTCTGGAAGTTCCGGGTTATGAGGCGGACGATGTCCTTGCATCCTTGGCTAAAA
AGGCCGAAAAGAGGGCTACGAAGTCCGCATCTTGACGGCAGACAAAGATCTGTACCAGCTTCTGTCTGACCGTATT
CATGTTTTGCACCCTGAAGGCTACTTAATCACTCCGGCCTGGCTCTGGGAAAAATACGGTCTGCGTCCCGATCAGTG
GGCGGATTATCGGGCTTTGACGGGAGATGAGAGCGACAACCTGCCAGGAGTTAAGGGCATTGGTGAAAAAACCGCAC
GTAAGCTGCTTGAAGAGTGGGGTTCCCTGGAAGCCTTGTTAAAAAATCTGGATCGTCTCAAGCCCGCAATTCGTGAA
AAGATCCTGGCTCATATGGACGATCTTAAATTAAGTTGGGACCTGGCCAAGGTGCGCACCGATTTACCGCTTGAAGT
GGATTTTGCAAAACGCCGTGAGCCGGACCGGGAACGTTTACGGCCTTTCTTAGAGCGTCTGGAATTCGGTTCACTGC
TTCATGAATTCGGTCTGTTAGAGTCTCCTAAAGCACTCGAAGAGGCACCGTGGCCGCCCCCAGAAGGTGCTTTTGTT
GGCTTCGTACTTTCCCGTAAGGAGCCTATGTGGGCAGATCTTCTGGCTTTAGCGGCTGCACGCGGTGGCCGTGTTCA
CCCGGGCCCCTGAGCCATACAAAGCGTTACGTGATCTGAAGGAAGCACGTGGCTTGCTGGCAAAAGACCTTTCTGTTT
TGGCCCTGCGCGAGGGTCTTGGACTGCCGCCAGGCGACGATCCCATGTTATTGGCCTATCTGTTAGACCCTAGCAAT
ACCACACCTGAAGGGGTCGCTCGTCGGTATGGCGGTAATGGACTGAGGAAGCCGGAGAGCGCGCCGCATTGTCCGA
ACGGCTCTTTGCAAACTTATGGGGTCGTCTGGAAGGGGAGGAACGTCTGTTATGGTTGTATCGGGAAGTCGAACGTC
CTCTTTCGGCCGTATTAGCGCATATGGAGGCAACAGGTGTGCGTTTAGATGTCGCGTACCTTCGGGCCTTATCACTG
GAAGTTGCAGAGGAAATCGCCCGTCTCGAGGCTGAAGTGTTCCGGTTGGCCGGTCACCCGTTTAACCTCAACTCCCG
TGACCAGCTGGAACGCGTTTTATTCGATGAGCTTGGGCTTCCCGCAATTGGCAAAACCGAAAAGACTGGCAAACGCA
GTACGAGCGCTGCCGTCCTTGAGGCACTCCGCGAGGCTCACCCTATTGTAGAAAAGATCCTGCAATACCGTGAGTTG
ACGAAGCTTAAAAGCACTTATATTGATCCTCTCCCGGATCTGATCCATCCTCGTACCGGCCGCTTGCACACACGTTT
CAACCAGACGGCGACTGCAACCGGCCGTCTGTCTAGCTCGGATCCAAATCTCCAGAACATTCCGGTCCGTACACCCT
TGGGCCAACGTATCCGCCGGGCGTTTATCGCTGAGGAAGGATGGTTACTGGTCGCATTGACTACTCGCAGATTGAG
CTGCGCGTCCTCGCACATCTCTCTGGTGACGAAAATTTAATCCGCGTGTTTCAAGAGGGGCGTGATATTCACACAGA
AACTGCCTCATGGATGTTCGGTGTCCCACGTGAAGCAGTGGATCCTTTGATGCGCCGTGCAGCTAAAACAATTAATT
TTGGAGTGCTGTACGGAATGAGCGCTCATCGCTTGAGTCAGGAACTGGCAATCCCCTACGAGGAAGCGCAGGCATTC
ATCGAACGTTACTTTCAATCGTTTCCGAAAGTTCGCGCATGGATCGAGAAGACGCTCGAGGAAGGTCGTCGTCGGGG
CTATGTCGAAACTCTGTTTGGTCGCCGTCGGTACGTACCAGATCTTGAAGCCCGCGTCAAATCGGTACGGGAGGCTG
CGGAGCGTATGGCATTTAATATGCCTGTACAGGGTACTGCAGCTGACCTCATGAAACTGGCAATGGTCAAGCTTTTC
CCGCGCTTGGAGGAAATGGGCGCACGTATGCTTCTGCAGGTCGTAGACGAGCTGGTGTTAGAAGCCCCTAAGGAGCG
CGCCGAAGCTGTCGCGCGCCTCGCTAAAGAAGTGATGGAGGGCGTTTACCCATTGGCCGTACCCCTCGAAGTGGAGG
TCGGTATTGGAGAAGATTGGTTATCTGCAAAGGAAGCGGCCGC
```

SEQ ID NO. 153, amino acid sequence of Mutant ID 24 (H784V).
MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI -continued ERYFQSFPKVRAWIEKTLEEGRRRGYVETLFGRRRYVPDLEARVKSVREAAERMAFNMPVQGTAADLMKLAMVKLFP
RLEEMGARMLLQVVDELVLEAPKERAEAVARLAKEVMEGVYPLAVPLEVEVGIGEDWLSAKEAA SEQ ID NO. 154, nucleotide sequence of Mutant ID 26 (H784I).
CATATGCGTGGTATGCTGCCGTTGTTCGAGCCTAAAGGCCGCGTACTGTTAGTCGATGGTCATCACTTGGCCTATCG
GACGTTCCATGCACTCAAAGGTCTGACGACCAGTCGTGGCGAACCGGTCCAGGCTGTTTATGGTTTCGCTAAGTCTT
TGCTCAAAGCACTGAAAGAAGACGGGGACGCGGTAATTGTTGTATTTGATGCCAAAGCACCGAGCTTCCGCCACGAA
GCTTATGGTGGCTACAAGGCAGGACGCGCCCCTACCCCAGAAGATTTCCCCCGTCAGCTGGCATTAATTAAGGAGTT
AGTAGACCTTCTCGGCTTAGCGCGTCTGGAAGTTCCGGGTTATGAGGCGGACGATGTCCTTGCATCCTTGGCTAAAA
AGGCCGAAAAGAGGGCTACGAAGTCCGCATCTTGACGGCAGACAAAGATCTGTACCAGCTTCTGTCTGACCGTATT
CATGTTTTGCACCCTGAAGGCTACTTAATCACTCCGGCCTGGCTCTGGGAAAAGTACGGTCTGCGTCCCGATCAGTG
GGCGGATTATCGGGCTTTGACGGGAGATGAGAGCGACAACCTGCCAGGAGTTAAGGGCATTGGTGAAAAAACCGCAC
GTAAGCTGCTTGAAGAGTGGGGTTCCCTGGAAGCTTGTTAAAAAATCTGGATCGTCTCAAGCCCGCAATTCGTGAA
AAGATCCTGGCTCATATGGACGATCTTAAATTAAGTTGGGACCTGGCCAAGGTGCGCACCGATTTACCGCTTGAAGT
GGATTTTGCAAAACGCCGTGAGCCGGACCGGGAACGTTTACGCGCTTTCTTAGAGCGTCTGGAATTCGGTTCACTGC
TTCATGAATTCGGTCTGTTAGAGTCTCCTAAAGCACTCGAAGAGGCACCGTGGCCGCCCCCAGAAGGTGCTTTTGTT
GGCTTCGTACTTTCCCGTAAGGAGCCTATGTGGGCAGATCTTCTGGCTTTAGCGGCTGCACGCGGTGGCCGTGTTCA
CCGGGCCCCTGAGCCATACAAAGCGTTACGTGATCTGAAGGAAGCACGTGGCTTGCTGGCAAAAGACCTTTCTGTTT
TGGCCCTGCGCGAGGGTCTTGGACTGCCGCCAGGCGACGATCCCATGTTATTGGCCTATCTGTTAGACCCTAGCAAT
ACCACACCTGAAGGGGTCGCTCGTCGGTATGGCGGTGAATGGACTGAGGAAGCCGGAGAGCGCGCCGCATTGTCCGA
ACGGCTCTTTGCAAACTTATGGGGTCGTCTGGAAGGGGAGGAACGTCTGTTATGGTTGTATCGGGAAGTCGAACGTC
CTCTTTCGGCCGTATTAGCGCATATGGAGGCAACAGGTGTGCGTTTAGATGTCGCGTACCTTCGGGCCTTATCACTG
GAAGTTGCAGAGGAAATCGCCCGTCTCGAGGCTGAAGTGTTCCGGTTGGCCGGTCACCCGTTTAACCTCAACTCCCG
TGACCAGCTGGAACGCGTTTTATTCGATGAGCTTGGGCTTCCCGCAATTGGCAAAACCGAAAAGACTGGCAAACGCA
GTACGAGCGCTGCCGTCCTTGAGGCACTCCGCGAGGCTCACCCTATTGTAGAAAAGATCCTGCAATACCGTGAGTTG
ACGAAGCTTAAAAGCACTTATATTGATCCTCTCCCGGATCTGATCCATCCTCGTACCGGCCGCTTGCACACACGTTT
CAACCAGACGGCGACTGCAACCGGCCGTCTGTCTAGCTCGGATCCAAATCTCCAGAACATTCCGGTCCGTACACCCT
TGGGCCAACGTATCCGCCGGGCGTTTATCGCTGAGGAAGGATGGTTACTGGTCGCATTGACTACTCGCAGATTGAG
CTGCGCGTCCTCGCACATCTCTCTGGTGACGAAAATTTAATCCGCGTGTTTCAAGAGGGGCGTGATATTCACACAGA
AACTGCCTCATGGATGTTCGGTGTCCCACGTGAAGCAGTGGATCCTTTGATGCGCCGTGCAGCTAAAACAATTAATT
TTGGAGTGCTGTACGGAATGAGCGCTCATCGCTTGAGTCAGGAACTGGCAATCCCCTACGAGGAAGCGCAGGCATTC
ATCGAACGTTACTTTCAATCGTTTCCGAAAGTTCGCGCATGGATCGAGAAGACGCTCGAGGAAGGTCGTCGTCGGGG
CTATGTCGAAACTCTGTTTGGTCGCCGTCGGTACGTACCAGATCTTGAAGCCCGCGTCAAATCGGTACGGGAGGCTG
CGGAGCGTATGGCATTTAATATGCCTGTACAGGGTACTGCAGCTGACCTCATGAAACTGGCAATGGTCAAGCTTTTC
CCGCGCTTGGAGGAAATGGGCGCACGTATGCTTCTGCAGGTCATTGACGAGCTGGTGTTAGAAGCCCCTAAGGAGCG
CGCCGAAGCTGTCGCGCGCCTCGCTAAAGAAGTGATGGAGGGCGTTTACCCATTGGCCGTACCCCTCGAAGTGGAGG
TCGGTATTGGAGAAGATTGGTTATCTGCAAAGGAAGCGGCCGC SEQ ID NO. 155, amino acid sequence of Mutant ID 26 (H784I).
MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQVIDELVLEAPKERAEAVARLAKEVMEGVYPLAVPLEVEVGIGEDWLSAKEAA SEQ ID NO. 156, nucleotide sequence of Mutant ID 27 (H784M).
CATATGCGTGGTATGCTGCCGTTGTTCGAGCCTAAAGGCCGCGTACTGTTAGTCGATGGTCATCACTTGGCCTATCG
GACGTTCCATGCACTCAAAGGTCTGACGACCAGTCGTGGCGAACCGGTCCAGGCTGTTTATGGTTTCGCTAAGTCTT
TGCTCAAAGCACTGAAAGAAGACGGGGACGCGGTAATTGTTGTATTTGATGCCAAAGCACCGAGCTTCCGCCACGAA
GCTTATGGTGGCTACAAGGCAGGACGCGCCCCTACCCCAGAAGATTTCCCCCGTCAGCTGGCATTAATTAAGGAGTT
AGTAGACCTTCTCGGCTTAGCGCGTCTGGAAGTTCCGGGTTATGAGGCGGACGATGTCCTTGCATCCTTGGCTAAAA
AGGCCGAAAAGAGGGCTACGAAGTCCGCATCTTGACGGCAGACAAAGATCTGTACCAGCTTCTGTCTGACCGTATT
CATGTTTTGCACCCTGAAGGCTACTTAATCACTCCGGCCTGGCTCTGGGAAAAGTACGGTCTGCGTCCCGATCAGTG
GGCGGATTATCGGGCTTTGACGGGAGATGAGAGCGACAACCTGCCAGGAGTTAAGGGCATTGGTGAAAAAACCGCAC
GTAAGCTGCTTGAAGAGTGGGGTTCCCTGGAAGCTTGTTAAAAAATCTGGATCGTCTCAAGCCCGCAATTCGTGAA
AAGATCCTGGCTCATATGGACGATCTTAAATTAAGTTGGGACCTGGCCAAGGTGCGCACCGATTTACCGCTTGAAGT
GGATTTTGCAAAACGCCGTGAGCCGGACCGGGAACGTTTACGCGCTTTCTTAGAGCGTCTGGAATTCGGTTCACTGC
TTCATGAATTCGGTCTGTTAGAGTCTCCTAAAGCACTCGAAGAGGCACCGTGGCCGCCCCCAGAAGGTGCTTTTGTT
GGCTTCGTACTTTCCCGTAAGGAGCCTATGTGGGCAGATCTTCTGGCTTTAGCGGCTGCACGCGGTGGCCGTGTTCA
CCGGGCCCCTGAGCCATACAAAGCGTTACGTGATCTGAAGGAAGCACGTGGCTTGCTGGCAAAAGACCTTTCTGTTT
TGGCCCTGCGCGAGGGTCTTGGACTGCCGCCAGGCGACGATCCCATGTTATTGGCCTATCTGTTAGACCCTAGCAAT
ACCACACCTGAAGGGGTCGCTCGTCGGTATGGCGGTGAATGGACTGAGGAAGCCGGAGAGCGCGCCGCATTGTCCGA
ACGGCTCTTTGCAAACTTATGGGGTCGTCTGGAAGGGGAGGAACGTCTGTTATGGTTGTATCGGGAAGTCGAACGTC
CTCTTTCGGCCGTATTAGCGCATATGGAGGCAACAGGTGTGCGTTTAGATGTCGCGTACCTTCGGGCCTTATCACTG
GAAGTTGCAGAGGAAATCGCCCGTCTCGAGGCTGAAGTGTTCCGGTTGGCCGGTCACCCGTTTAACCTCAACTCCCG
TGACCAGCTGGAACGCGTTTTATTCGATGAGCTTGGGCTTCCCGCAATTGGCAAAACCGAAAAGACTGGCAAACGCA
GTACGAGCGCTGCCGTCCTTGAGGCACTCCGCGAGGCTCACCCTATTGTAGAAAAGATCCTGCAATACCGTGAGTTG
ACGAAGCTTAAAAGCACTTATATTGATCCTCTCCCGGATCTGATCCATCCTCGTACCGGCCGCTTGCACACACGTTT
CAACCAGACGGCGACTGCAACCGGCCGTCTGTCTAGCTCGGATCCAAATCTCCAGAACATTCCGGTCCGTACACCCT
TGGGCCAACGTATCCGCCGGGCGTTTATCGCTGAGGAAGGATGGTTACTGGTCGCATTGACTACTCGCAGATTGAG
CTGCGCGTCCTCGCACATCTCTCTGGTGACGAAAATTTAATCCGCGTGTTTCAAGAGGGGCGTGATATTCACACAGA
AACTGCCTCATGGATGTTCGGTGTCCCACGTGAAGCAGTGGATCCTTTGATGCGCCGTGCAGCTAAAACAATTAATT
TTGGAGTGCTGTACGGAATGAGCGCTCATCGCTTGAGTCAGGAACTGGCAATCCCCTACGAGGAAGCGCAGGCATTC
ATCGAACGTTACTTTCAATCGTTTCCGAAAGTTCGCGCATGGATCGAGAAGACGCTCGAGGAAGGTCGTCGTCGGGG
CTATGTCGAAACTCTGTTTGGTCGCCGTCGGTACGTACCAGATCTTGAAGCCCGCGTCAAATCGGTACGGGAGGCTG -continued
CGGAGCGTATGGCATTTAATATGCCTGTACAGGGTACTGCAGCTGACCTCATGAAACTGGCAATGGTCAAGCTTTTC
CCGCGCTTGGAGGAAATGGGCGCACGTATGCTTCTGCAGGTCATGGACGAGCTGGTGTTAGAAGCCCCTAAGGAGCG
CGCCGAAGCTGTCGCGCGCCTCGCTAAAGAAGTGATGGAGGGCGTTTACCCATTGGCCGTACCCCTCGAAGTGGAGG
TCGGTATTGGAGAAGATTGGTTATCTGCAAAGGAAGCGGCCGC SEQ ID NO. 157, amino acid sequence of Mutant ID 27 (H784M).
MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQVMDELVLEAPKERAEAVARLAKEVMEGVYPLAVPLEVEVGIGEDWLSAKEAA SEQ ID NO. 158, nucleotide sequence of Mutant ID 29 (H784F).
CATATGCGTGGTATGCTGCCGTTGTTCGAGCCTAAAGGCCGCGTACTGTTAGTCGATGGTCATCACTTGGCCTATCG
GACGTTCCATGCACTCAAAGGTCTGACGACCAGTCGTGGCGAACCGGTCCAGGCTGTTTATGGTTTCGCTAAGTCTT
TGCTCAAAGCACTGAAAGAAGACGGGGACGCGGTAATTGTTGTATTTGATGCCAAAGCACCGAGCTTCCGCCACGAA
GCTTATGGTGGCTACAAGGCAGGACGCGCCCCTACCCCAGAAGATTTCCCCCGTCAGCTGGCATTAATTAAGGAGTT
AGTAGACCTTCTCGGCTTAGCGCGTCTGGAAGTTCCGGGTTATGAGGCGGACGATGTCCTTGCATCCTTGGCTAAAA
AGGCCGAAAAGAGGGCTACGAAGTCCGCATCTTGACGGCAGACAAAGATCTGTACCAGCTTCTGTCTGACCGTATT
CATGTTTTGCACCCTGAAGGCTACTTAATCACTCCGGCCTGGCTCTGGGAAAAGTACGGTCTGCGTCCCGATCAGTG
GGCGGATTATCGGGCTTTGACGGGAGATGAGAGCGACAACCTGCCAGGAGTTAAGGGCATTGGTGAAAAAACCGCAC
GTAAGCTGCTTGAAGAGTGGGGTTCCCTGGAAGCCTTGTTAAAAAATCTGGATCGTCTCAAGCCCGCAATTCGTGAA
AAGATCCTGGCTCATATGGACGATCTTAAATTAAGTTGGGACCTGGCCAAGGTGCGCACCGATTTACCGCTTGAAGT
GGATTTTGCAAAACGCCGTGAGCCGGACCGGGAACGTTTACGCGCTTTCTTAGAGCGTCTGGAATTCGGTTCACTGC
TTCATGAATTCGGTCTGTTAGAGTCTCCTAAAGCACTCGAAGAGGCACCGTGGCCGCCCCAGAAGGTGCTTTTGTT
GGCTTCGTACTTTCCCGTAAGGAGCCTATGTGGGCAGATCTTCTGGCTTTAGCGGCTGCACGCGGTGGCCGTGTTCA
CCGGGCCCCTGAGCCATACAAAGCGTTACGTGATCTGAAGGAAGCACGTGGCTTGCTGGCAAAAGACCTTTCTGTTT
TGGCCCTGCGCGAGGGTCTTGGACTGCCGCCAGGCGACGATCCCATGTTATTGGCCTATCTGTTAGACCCTAGCAAT
ACCACACCTGAAGGGGTCGCTCGTCGGTATGGCGGTGAATGGACTGAGGAAGCCGGAGAGCGCGCCGCCATTGTCCGA
ACGGCTCTTTGCAAACTTATGGGGTCGTCTGGAAGGGGAGGAACGTCTGTTATGGTTGTATCGGGAAGTCGAACGTC
CTCTCTTTCGGCCGTATTAGCGCATATGGAGGCAACAGGTGTGCGTTTAGATGTCGCGTACCTTCGGGCCTTATCACTG
GAAGTTGCAGAGGAAATCGCCCGTCTCGAGGCTGAAGTGTTCCGGTTGGCCGGTCACCCGTTTAACCTCAACTCCCG
TGACCAGCTGGAACGCGTTTTATTCGATGAGCTTGGGCTTCCCGCAATTGGCAAAACCGAAAAGACTGGCAAACGCA
GTACGAGCGCTGCCGTCCTTGAGGCACTCCGCGAGGCTCACCCTATTGTAGAAAAGATCCTGCAATACCGTGAGTTG
ACGAAGCTTAAAAGCACTTATATTGATCCTCTCCCGGATCTGATCCATCCTGTACCGGCCGCTTGCACACACGTTT
CAACCAGACGGCGACTGCAACCGGCCGTCTGTCTAGCTCGGATCCAAATCTCCAGAACATTCCGGTCCGTACACCCT
TGGGCCAACGTATCCGCCGGGCGTTTATCGCTGAGGAAGGATGGTTACTGGTCGCATTGGACTACTCGCAGATTGAG
CTGCGCGTCCTCGCACATCTCTCTGGTGACGAAAATTTAATCCGCGTGTTTCAAGAGGGCGTGATATTCACACAGA
AACTGCCTCATGGATGTTCGGTGTCCCACGTGAAGCAGTGGATCCTTTGATGCGCCGTGCAGCTAAAACAATTAATT
TTTGGAGTGCTGTACGGAATGAGCGCTCATCGCTTGAGTCAGGAACTGGCAATCCCCTACGAGGAAGCGCAGGCATTC
ATCGAACGTTACTTTCAATCGTTTCCGAAAGTTCGCGCATGATCGAGAAGACGCTCGAGGAAGGTCGTCGTCGGGAG
CTATGTCGAAACTCTGTTTGGTCGCCGTCGGTACGTACCAGATCTTGAAGCCCGCGTCAAATCGGTACGGGAGGCTG
CGGAGCGTATGGCATTTAATATGCCTGTACAGGGTACTGCAGCTGACCTCATGAAACTGGCAATGGTCAAGCTTTTC
CCGCGCTTGGAGGAAATGGGCGCACGTATGCTTCTGCAGGTCTTTGACGAGCTGGTGTTAGAAGCCCCTAAGGAGCG
CGCCGAAGCTGTCGCGCGCCTCGCTAAAGAAGTGATGGAGGGCGTTTACCCATTGGCCGTACCCCTCGAAGTGGAGG
TCGGTATTGGAGAAGATTGGTTATCTGCAAAGGAAGCGGCCGC SEQ ID NO. 159, amino acid sequence of Mutant ID 29 (H784F).
MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQVFDELVLEAPKERAEAVARLAKEVMEGVYPLAVPLEVEVGIGEDWLSAKEAA SEQ ID NO. 160, nucleotide sequence of Mutant ID 30 (H784Y).
CATATGCGTGGTATGCTGCCGTTGTTCGAGCCTAAAGGCCGCGTACTGTTAGTCGATGGTCATCACTTGGCCTATCG
GACGTTCCATGCACTCAAAGGTCTGACGACCAGTCGTGGCGAACCGGTCCAGGCTGTTTATGGTTTCGCTAAGTCTT
TGCTCAAAGCACTGAAAGAAGACGGGGACGCGGTAATTGTTGTATTTGATGCCAAAGCACCGAGCTTCCGCCACGAA
GCTTATGGTGGCTACAAGGCAGGACGCGCCCCTACCCCAGAAGATTTCCCCCGTCAGCTGGCATTAATTAAGGAGTT
AGTAGACCTTCTCGGCTTAGCGCGTCTGGAAGTTCCGGGTTATGAGGCGGACGATGTCCTTGCATCCTTGGCTAAAA
AGGCCGAAAAGAGGGCTACGAAGTCCGCATCTTGACGGCAGACAAAGATCTGTACCAGCTTCTGTCTGACCGTATT
CATGTTTTGCACCCTGAAGGCTACTTAATCACTCCGGCCTGGCTCTGGGAAAAGTACGGTCTGCGTCCCGATCAGTG
GGCGGATTATCGGGCTTTGACGGGAGATGAGAGCGACAACCTGCCAGGAGTTAAGGGCATTGGTGAAAAAACCGCAC
GTAAGCTGCTTGAAGAGTGGGGTTCCCTGGAAGCCTTGTTAAAAAATCTGGATCGTCTCAAGCCCGCAATTCGTGAA
AAGATCCTGGCTCATATGGACGATCTTAAATTAAGTTGGGACCTGGCCAAGGTGCGCACCGATTTACCGCTTGAAGT
GGATTTTGCAAAACGCCGTGAGCCGGACCGGGAACGTTTACGCGCTTTCTTAGAGCGTCTGGAATTCGGTTCACTGC
TTCATGAATTCGGTCTGTTAGAGTCTCCTAAAGCACTCGAAGAGGCACCGTGGCCGCCCCAGAAGGTGCTTTTGTT
GGCTTCGTACTTTCCCGTAAGGAGCCTATGTGGGCAGATCTTCTGGCTTTAGCGGCTGCACGCGGTGGCCGTGTTCA
CCGGGCCCCTGAGCCATACAAAGCGTTACGTGATCTGAAGGAAGCACGTGGCTTGCTGGCAAAAGACCTTTCTGTTT -continued

```
TGGCCCTGCGCGAGGGTCTTGGACTGCCGCCAGGCGACGATCCCATGTTATTGGCCTATCTGTTAGACCCTAGCAAT
ACCACACCTGAAGGGGTCGCTCGTCGGTATGGCGGTGAATGGACTGAGGAAGCCGGAGAGCGCGCCGCATTGTCCGA
ACGGCTCTTTGCAAACTTATGGGGTCGTCTGGAAGGGGAGGAACGTCTGTTATGGTTGTATCGGGAAGTCGAACGTC
CTCTTTCGGCCGTATTAGCGCATATGGAGGCAACAGGTGTGCGTTTAGATGTCGCGTACCTTCGGGCCTTATCACTG
GAAGTTGCAGAGGAAATCGCCCGTCTCGAGGCTGAAGTGTTCCGGTTGGCCGGTCACCCGTTTAACCTCAACTCCCG
TGACCAGCTGGAACGCGTTTTATTCGATGAGCTTGGGCTTCCCGCAATTGGCAAAACCGAAAAGACTGGCAAACGCA
GTACGAGCGCTGCCGTCCTTGAGGCACTCCGCGAGGCTCACCCTATTGTAGAAAAGATCCTGCAATACCGTGAGTTG
ACGAAGCTTAAAAGCACTTATATTGATCCTCTCCCGGATCTGATCCATCCTCGTACCGGCCGCTTGCACACACGTTT
CAACCAGACGGCGACTGCAACCGGCCGTCTGTCTAGCTCGGATCCAAATCTCCAGAACATTCCGGTCCGTACACCCT
TGGGCCAACGTATCCGCCGGGCGTTTATCGCTGAGGAAGGATGGTTACTGGTCGCATTGGACTACTCGCAGATTGAG
CTGCGCGTCCTCGCACATCTCTCTGGTGACGAAAATTTAATCCGCGTGTTTCAAGAGGGGCGTGATATTCACACAGA
AACTGCCTCATGGATGTTCGGTGTCCCACGTGAAGCAGTGGATCCTTTGATGCGCCGTGCAGCTAAAACAATTAATT
TTGGAGTGCTGTACGGAATGAGCGCTCATCGCTTGAGTCAGGAACTGGCAATCCCCTACGAGGAAGCGCAGGCATTC
ATCGAACGTTACTTTCAATCGTTTCCGAAAGTTCGCGCATGGATCGAGAAGACGCTCGAGGAAGGTCGTCGTCGGGG
CTATGTCGAAACTCTGTTTGGTCGCCGTCGGTACGTACCAGATCTTGAAGCCCGCGTCAAATCGGTACGGGAGGCTG
CGGAGCGTATGGCATTTAATATGCCTGTACAGGGTACTGCAGCTGACCTCATGAAACTGGCAATGGTCAAGCTTTTC
CCGCGCTTGGAGGAAATGGGCGCACGTATGCTTCTGCAGGTCTATGACGAGCTGGTGTTAGAAGCCCCTAAGGAGCG
CGCCGAAGCTGTCGCGCGCCTCGCTAAAGAAGTGATGGAGGGCGTTTACCCATTGGCCGTACCCCTCGAAGTGGAGG
TCGGTATTGGAGAAGATTGGTTATCTGCAAAGGAAGCGGCCGC
```

SEQ ID NO. 161, amino acid sequence of Mutant ID 30 (H784Y).
MRGMLPLFEPKGRVLLVDGHHLAYRTFHALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAKKAEKEGYEVRILTADKDLYQLLSDRIH
VLHPEGYLITPAWLWEKYGLRPDQWADYRALTGDESDNLPGVKGIGEKTARKLLEEWGSLEALLKNLDRLKPAIREK
ILAHMDDLKLSWDLAKVRTDLPLEVDFAKRREPDRERLRAFLERLEFGSLLHEFGLLESPKALEEAPWPPPEGAFVG
FVLSRKEPMWADLLALAAARGGRVHRAPEPYKALRDLKEARGLLAKDLSVLALREGLGLPPGDDPMLLAYLLDPSNT
TPEGVARRYGGEWTEEAGERAALSERLFANLWGRLEGEERLLWLYREVERPLSAVLAHMEATGVRLDVAYLRALSLE
VAEEIARLEAEVFRLAGHPFNLNSRDQLERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRTPLGQRIRRAFIAEEGWLLVALDYSQIEL
RVLAHLSGDENLIRVFQEGRDIHTETASWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREAAERMAFNMPVQGTAADLMKLAMVKLFP
RLEEMGARMLLQVYDELVLEAPKERAEAVARLAKEVMEGVYPLAVPLEVEVGIGEDWLSAKEAA

Example 18. Production of Codon Optimized Taq DNA Polymerase Mutants Modified to Eliminate 5' Exonuclease Activity Additional Taq DNA Polymerase mutants were made that eliminated the 5' exonuclease activity of several of the mutants from Table 3. Taq DNA Polyermase missing the 5'-exonuclease activity was previously named "KlenTaq" (Barnes, W. M., Gene 112:29-35, 1992). Deletion of the N-terminal 5' exonuclease domain of Taq polymerase improves the mismatch discrimination properties of the enzyme (Barnes, W. M., Gene 112:29-35, 1992). The present study characterized whether specificity improvements seen in the Taq DNA Polymerase mutants of the present invention were combined with mutations which eliminated 5'-exonuclease activity. The examples shown here are meant to be exemplary, and in no way limit the range of the claims. Specific mutations were introduced into the OptiTaq sequence using the method of PCR site-directed mutagenesis (Weiner M P, et al., Gene. 151(1-2):119-23 (1994)). Each mutagenesis reaction employed 10 pmoles of two oligonucleotides (Table 38) to amplify around the plasmid containing the DNA polymerase, excluding the 5' exonuclease domain. These primers were manufactured to contain a 5' phosphate, which allowed for re-ligation after amplification. Briefly, these primers were annealed to the double-stranded plasmid containing previously characterized mutant DNA polymerases (MUT IDs 2, 3, 10, 18, 21, and 30) (20 ng each), 5 U KOD DNA polymerase (Novagen-EMD Chemicals, San Diego, Calif.), 1.5 mM $MgSO_4$, in 1×KOD PCR buffer. Thermal cycling parameters were 95° C. for 3 minutes (95° C. for 20 sec-55° C. for 20 sec-70° C. for 2 minutes) for 25 cycles followed by a 70° C. soak for 4 minutes. After PCR site-directed mutagenesis, the amplified product was treated with 10 U of Dpn I (NEB, Ipswich, Mass.), at 37° C. for 1 hour, followed by inactivation at 80° C. for 20 minutes. $\frac{1}{6}^{th}$ of the digestion material was ligated together with T4 DNA ligase (NEB, Ipswich, Mass.) at 16° C. for 20 minutes, followed by inactivation at 65° C. for 10 minutes. $\frac{1}{15}$th of the ligated material was transformed into XL-1 Blue competent bacteria. Bacterial clones were isolated, plasmid DNA prepared, and deletion of the 5' exonuclease domains were confirmed by Sanger DNA sequencing. All mutants remained in the pET-27b(+) expression vector, which is suitable for expressing the recombinant proteins in E. coli. Expression and purification of the recombinant mutants of the Taq polymerase were performed as described in Example 3.

TABLE 38

Oligonucleotides used for site-directed mutagenesis to produce 18 Taq DNA Polymerase mutants.

| Mutant ID | Mutant name | Sequence" Sense mutagenesis oligonucleotide | SEQ ID No. | Sequence" Antisense mutagenesis oligonucleotide | SEQ ID No. |
|---|---|---|---|---|---|
| 37 | OptiTaq KlenTaq | Phos-ggttcactgcttcatgaattcggtc | 162 | Phos-catatgtattctccttcttaaagttaaacaaa | 163 |
| 38 | A661E, I665W, F667L KlenTaq | Phos-ggttcactgcttcatgaattcggtc | 162 | Phos-catatgtattctccttcttaaagttaaacaaa | 163 |

TABLE 38-continued

Oligonucleotides used for site-directed mutagenesis to produce 18 Taq DNA Polymerase mutants.

| Mutant ID | Mutant name | Sequence" Sense mutagenesis oligonucleotide | SEQ ID No. | Sequence" Antisense mutagenesis oligonucleotide | SEQ ID No. |
|---|---|---|---|---|---|
| 39 | V783F KlenTaq | Phos-ggttcactgcttcatgaattcggtc | 162 | Phos-catatgtattctccttcttaaagttaaacaaa | 163 |
| 40 | H784Q KlenTaq | Phos-ggttcactgcttcatgaattcggtc | 162 | Phos-catatgtattctccttcttaaagttaaacaaa | 163 |
| 41 | V783L H784Q KlenTaq | Phos-ggttcactgcttcatgaattcggtc | 162 | Phos-catatgtattctccttcttaaagttaaacaaa | 163 |
| 42 | H784S KlenTaq | Phos-ggttcactgcttcatgaattcggtc | 162 | Phos-catatgtattctccttcttaaagttaaacaaa | 163 |
| 43 | H784Y KlenTaq | Phos-ggttcactgcttcatgaattcggtc | 162 | Phos-catatgtattctccttcttaaagttaaacaaa | 163 |

DNA bases identical to codon optimized OptiTaq are shown in lower case; those specific for the mutations introduced by site-directed mutagenesis are shown in upper case.

Example 19. Characterization of Properties of 7 5'-Exonuclease-Deficient Mutant Taq DNA Polymerases in PCR The 7 mutant Taq DNA polymerase enzymes described in Example 18 were characterized for polymerase activity.

The unit activity of the purified wild-type protein was determined by comparing performance in qPCR of known quantities of OptiTaq and each mutant compared to a commercial non-hot-start Taq DNA polymerase, Taq-B DNA Polymerase (Enzymatics, Beverly, Mass.). Quantification cycle values (Cq, the amplification cycle number at which positive signal is first detected) and amplification curve shapes were analyzed to determine the nanogram amounts at which both enzymes performed similarly in the suboptimal range for each. Using these nanogram amounts and known unit values of Taq-B DNA polymerase, relative activity unit values could be extrapolated for all of the mutant DNA polymerase enzymes having sufficient activity to support PCR. Testing was also done to determine the MgCl$_2$ concentrations at which the polymerases would show optimal activity.

The following reaction conditions were employed: 1× qPCR buffer (20 mM Tris pH 8.4, 50 mM KCl, 0.01% Triton-X100), 800 μM dNTPs (200 μM each), 500 nM For primer (Hs HPRT F517, SEQ ID NO. 43), 500 nM Rev primer (Hs HPRT R591, SEQ ID NO. 44), 250 nM RNase H2 cleavable probe (Hs HPRT RN2 Probe, SEQ ID NO. 164), 20 mU *Pyrococcus abyssi* RNase H2, 2×10$^3$ copies of linearized cloned plasmid template (HPRT-targ, SEQ ID NO. 46), in 10 μL final volume. MgC$_2$ was tested at 3, 4, or 5 mM in each case. The amount of DNA polymerase added to each reaction was varied as follows: for wild type (OptiTaq), reactions were set using 10, 1, 0.1, 0.01, and 0.001 U/μL (220, 22, 2.2, 0.22, or 0.022 ng of protein per 10 μL reaction). Mutant polymerases were run in similar concentrations. In addition, those mutant enzymes showing polymerase activity were more finely titrated testing 220, 22, 10.6, 4.8, 2.2, 1.1, 0.48, and 0.22 ng of protein per 10 μL reaction. Polymerase dilutions were made in enzyme dilution buffer (20 mM Tris pH7.5, 100 mM NaCl, 1 mM DTT, 0.1% Triton-X100, 1 mg/mL BSA, 10% glycerol). Reactions were run in 384 well format on a BIO-RAD CFX384™ Real-Time System (BIO-RAD, Hercules, Calif.) using cycling parameters 95° C. for 30 seconds followed by 60 cycles of [95° C. for 15 seconds followed by 60° C. for 1 minutes]. Detection was achieved using a fluorescence-quenched probe (cleaved by the action of the P.a. RNase H2 enzyme). Sequences of the primers, probe, and template (plasmid insert) are shown in Table 39.

TABLE 39

Sequence of oligonucleotides employed in Taq DNA polymerase activity assay.

| Name | Sequence | SEQ ID NO. |
|---|---|---|
| Hs HPRT F517 | GACTTTGCTTTCCTTGGTCAG | SEQ ID NO. 43 |
| Hs HPRT R591 | GGCTTATATCCAACACTTCGTG | SEQ ID NO. 44 |
| Hs HPRT RN2 Probe | FAM-ATGGTCAAGGTCGCAAGcTTGCT GGT-IBFQ | SEQ ID NO. 164 |
| HPRT-targ | GACTTTGCTTTCCTTGGTCAGGCAGTA TAATCCAAAGATGGTCAAGGTCGCAAG CTTGCTGGTGAAAAGGACCCCACGAAG TGTTGGATATAAGCC | SEQ ID NO. 46 |

DNA bases are uppercase and RNA bases are lowercase; Nucleic acid sequences are shown 5'-3'.
FAM = 6-carboxyfluorescein,
IBFQ = Iowa Black FQ (fluorescence quencher), and
ZEN = ZEN internal fluorescence quencher.

These 7 Taq DNA polymerase 5'-exonuclease-deficient mutants were characterized as outlined above. Results are summarized in Table 40. All seven mutants had DNA polymerase activity; however, processivity in Mutant IDs 38, 39, 40, 41, 42, and 43 was reduced from 10-50 fold relative to the wild type enzyme. One mutant, Mutant ID 37

(OptiTaq KlenTaq), showed DNA polymerase activity nearly identical to wild type OptiTaq. Therefore the combination of complete deletion of the 5'-exonuclease domain of Taq DNA Polymerase coupled with point mutations that improve polymerase specificity all significantly compromised enzyme activity and processivity.

TABLE 40

Novel Taq DNA polymerase mutants selected for initial study.

| Mutant ID | Amino acid changes from wild-type Taq | Polymerase Activity | Relative activity* | Optimal MgCl$_2$ concentration (mM) |
|---|---|---|---|---|
| 37 | OptiTaq KlenTaq | Yes | 1 | 3 |
| 38 | A661E, I665W, F667L KlenTaq | Yes | 0.1 | 5 |
| 39 | V783F KlenTaq | Yes | 0.05 | 4 |
| 40 | H784Q KlenTaq | Yes | 0.03 | 4 |
| 41 | V783L H784Q KlenTaq | Yes | 0.02 | 5 |
| 42 | H784S KlenTaq | Yes | 0.02 | 5 |
| 43 | H784Y KlenTaq | Yes | 0.05 | 5 |

*Wild-type OptiTaq was set to "1" and the relative activity of each of the mutant polymerases was normalized to this amplification efficiency, with 1 as the maximum.

Example 20: Improved Mismatch Discrimination in Allele-Specific PCR Using Mutant Taq DNA Polymerases Also Having Deletion of the 5'-Exonuclease Domain Of the 7 mutant enzymes studied in Example 18 and 19, Mutant IDs 37, 38, 39, 40, 41, 42, and 43 retained sufficient enzymatic activity/processivity to characterize. These seven mutants were studied for the ability to discriminate against a 3'-terminal DNA mismatch compared with wild type OptiTaq DNA polymerase using an allele-specific qPCR assay. Amplification reactions were performed against a synthetic oligonucleotide template where a single base was varied (SNP) which was positioned to lie at the 3'-end of the reverse primer. Synthetic templates were employed having each of the 4 possible bases at this position. Reverse primers were employed having each of the 4 possible bases at the 3'-end. Relative amplification efficiency was assessed using qPCR.

Quantitative allele-specific real-time PCR (AS-qPCR) was performed in 10 µL reaction volumes in 384 well format with 2×10$^5$ copies of a 103 bp synthetic template (SEQ ID NOs. 51-4). Final reaction conditions used were 20 mM Tris-HCL (pH 8.4 at 25° C.), 50 mM KCL, the amount of MgCl$_2$ which was determined to be optimal for each polymerase in Example 19, 0.01% Triton X-100, 800 µM total dNTPs, and 200 nM of the universal forward primer (SEQ ID NO. 60), 200 nM of a reverse primer (separate reactions were set up for each of the allele-specific primers SEQ ID NOs. 55-58 or the control universal primer SEQ ID NO. 59) and 200 nM of the RNase H2 cleavable probe (SEQ ID NO. 165). 20 mU *Pyrococcus abyssi* RNase H2 was also include in each reaction. Each allele-specific primer was tested on each SNP template. Reactions utilized either 0.5 U (10.8 ng/11.1 nM/111 fmol) of the OptiTaq KlenTaq DNA polymerase (Mutant ID 37) or 0.5 U of one of the six Taq DNA polymerase mutants studied (Mutant ID 38 (108 ng/111 nM/1110 fmol); Mutant ID 39 (216 ng/222 nM/2220 fmol); Mutant ID 40 (360 ng/370 nM/3700 fmol); Mutant ID 41 (1060 ng/555 nM/5550 fmol); Mutant ID 42 (1060 ng/555 nM/5550 fmol); Mutant ID 43 (216 ng/222 nM/2220 fmol)). Amplification was performed on a CFX384™ C1000™ Thermo Cycler system (Bio-Rad, Hercules, Calif.) using the following cycling parameters: 95° C. for 30 seconds initial denaturation followed by 60 cycles of 95° C. for 10 seconds, then 60° C. for 30 seconds. Oligonucleotide reagents used in this example are shown in Table 41.

TABLE 41

Synthetic oligonucleotides employed in Example 20.

| Name | Sequence (5'-3') | SEQ ID NO. |
|---|---|---|
| A Template | AGCTCTGCCCAAAGATTACCCTGACAGCTAAGTGGCAGTGGAA GTTGGCCTCAGAAGTAGTGGCCAGCTGTGTGTCGGGG<u>A</u>ACAGT AAAGGCATGAAGCTCAG | SEQ ID NO. 51 |
| C Template | AGCTCTGCCCAAAGATTACCCTGACAGCTAAGTGGCAGTGGAA GTTGGCCTCAGAAGTAGTGGCCAGCTGTGTGTCGGGG<u>C</u>ACAGT AAAGGCATGAAGCTCAG | SEQ ID NO. 52 |
| G Template | AGCTCTGCCCAAAGATTACCCTGACAGCTAAGTGGCAGTGGAA GTTGGCCTCAGAAGTAGTGGCCAGCTGTGTGTCGGGG<u>G</u>ACAGT AAAGGCATGAAGCTCAG | SEQ ID NO. 53 |
| T Template | AGCTCTGCCCAAAGATTACCCTGACAGCTAAGTGGCAGTGGAA GTTGGCCTCAGAAGTAGTGGCCAGCTGTGTGTCGGGG<u>T</u>ACAGT AAAGGCATGAAGCTCAG | SEQ ID NO. 54 |
| Syn Rev T | CTGAGCTTCATGCCTTTACTGTT | SEQ ID NO. 55 |
| Syn Rev C | CTGAGCTTCATGCCTTTACTGTC | SEQ ID NO. 56 |
| Syn Rev A | CTGAGCTTCATGCCTTTACTGTA | SEQ ID NO. 57 |
| Syn Rev G | CTGAGCTTCATGCCTTTACTGTG | SEQ ID NO. 58 |
| Syn Rev | CTGAGCTTCATGCCTTTACTGT | SEQ ID NO. 59 |

TABLE 41-continued

Synthetic oligonucleotides employed in Example 20.

| Name | Sequence (5'-3') | SEQ ID NO. |
|---|---|---|
| Syn For | AGCTCTGCCCAAAGATTACCCTG | SEQ ID NO. 60 |
| RN2 Probe | FAM-TTCTGAGGCCAACuCCACTGCCACTTA-IBFQ | SEQ ID NO. 165 |

DNA bases are uppercase and RNA bases are lowercase;
FAM = 6-carboxyfluorescein;
IBFQ = Iowa Black ™ FQ fluorescence quencher;
ZEN = internal ZEN fluorescence quencher;
underlined base indicates the SNP site in the synthetic template DNA.

Figure 7A:
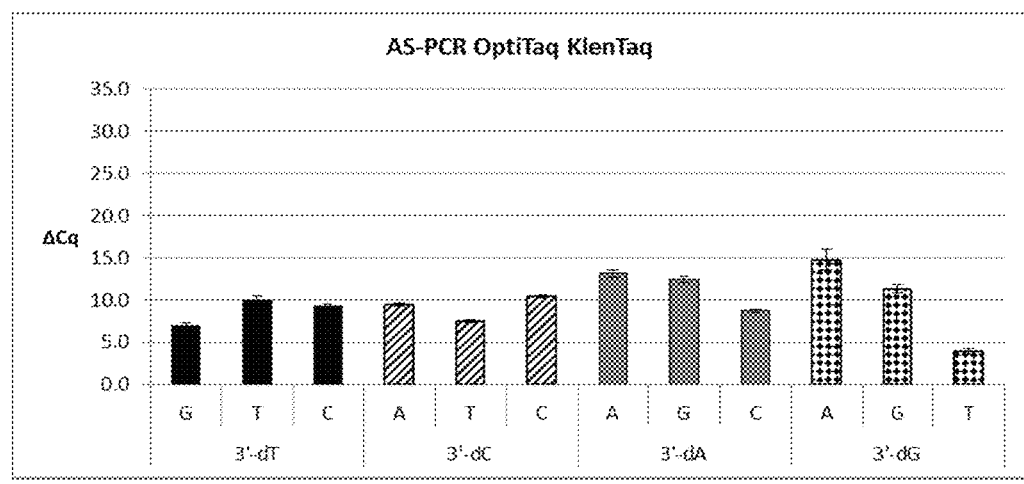
FIG. 7A shows graphical representations of the allele-specific PCR (AS-PCR) data from Tables 10 and 31 for OptiTaq KlenTaq (Mutant ID 37) (sub-panel (i)), Mutant ID 38 (sub-panel (ii)) and Mutant ID 39 (sub-panel (iii)). Legend: Average ΔCq values obtained from AS-PCR reactions plus/minus standard deviation (error bars) are shown (ΔCq=Cq mismatch–Cq match) comparing mismatch discrimination of the wild-type OptiTaq with four mutant Taq DNA polymerases. All possible pairwise mismatch base combinations are included. The base identity of the SNP site in the target nucleic acid is indicated on the X-axis (A, G, C, T) along with the 3'-DNA residue of the AS-PCR reverse primer employed (dA, dG, dC, dT).
Figure 7A:
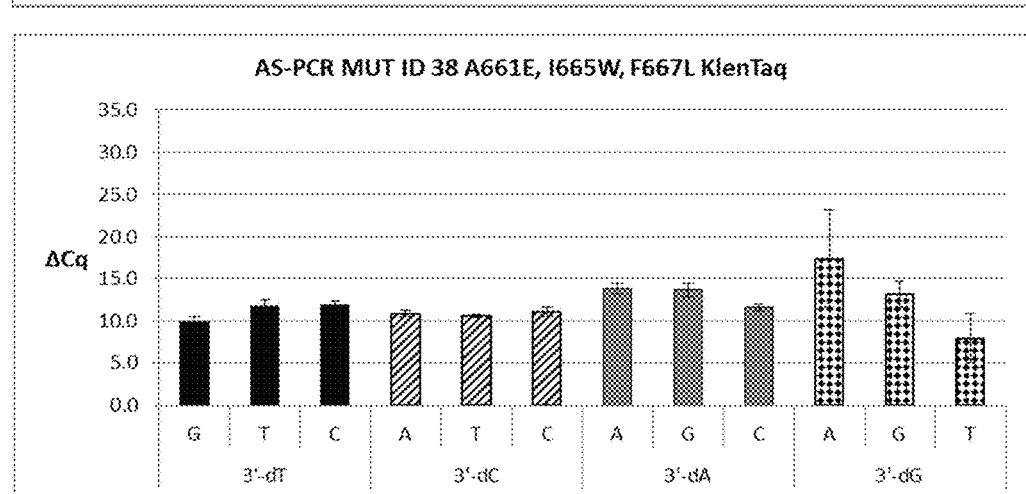
Figure 7A:
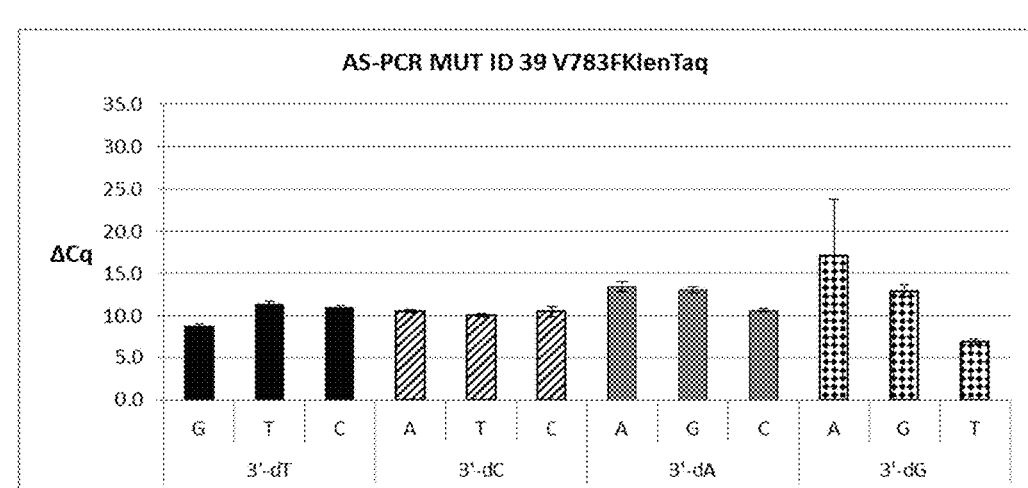
Figure 7B:
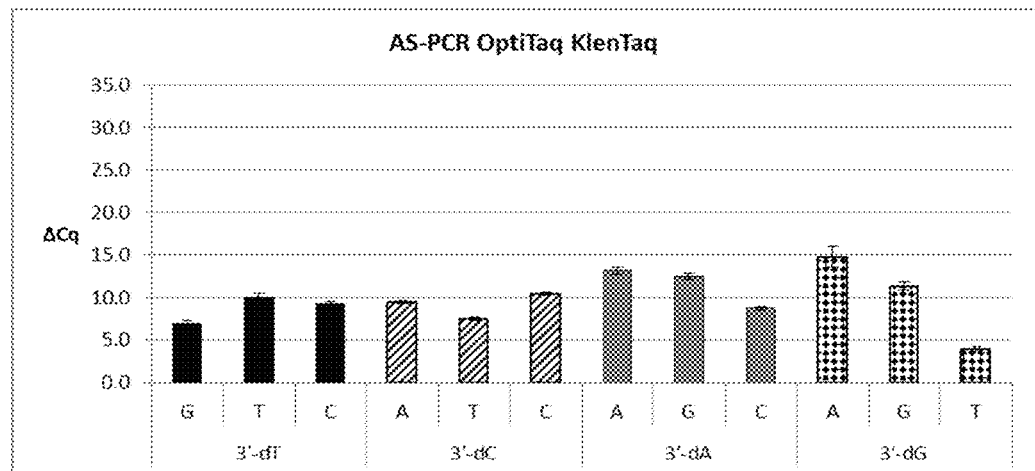
FIG. 7B. shows graphical representations of the allele-specific PCR (AS-PCR) data from Tables 10 and 31 for OptiTaq KlenTaq (Mutant ID 37) (sub-panel (i)), Mutant ID 40 (sub-panel (ii)) and Mutant ID 41 (sub-panel (iii)). Legend as in FIG. 7A.
Figure 7B:
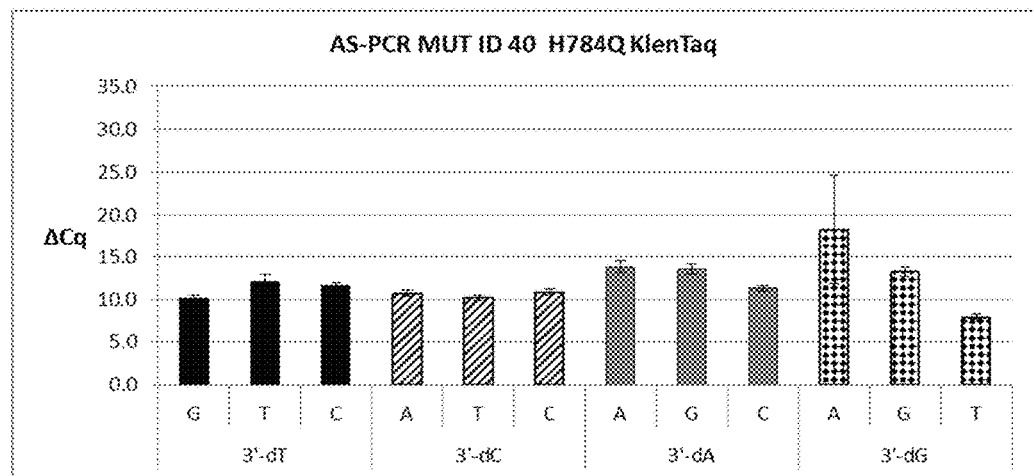
Figure 7B:
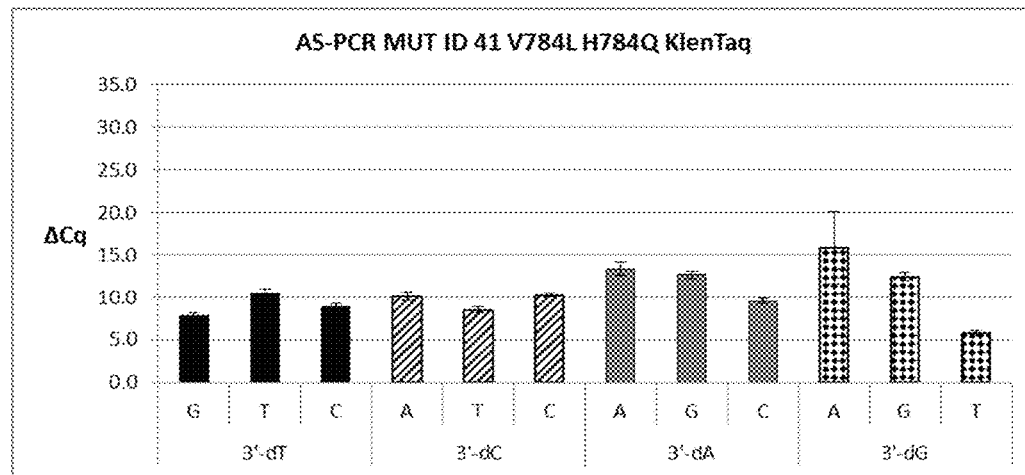
Figure 7C:
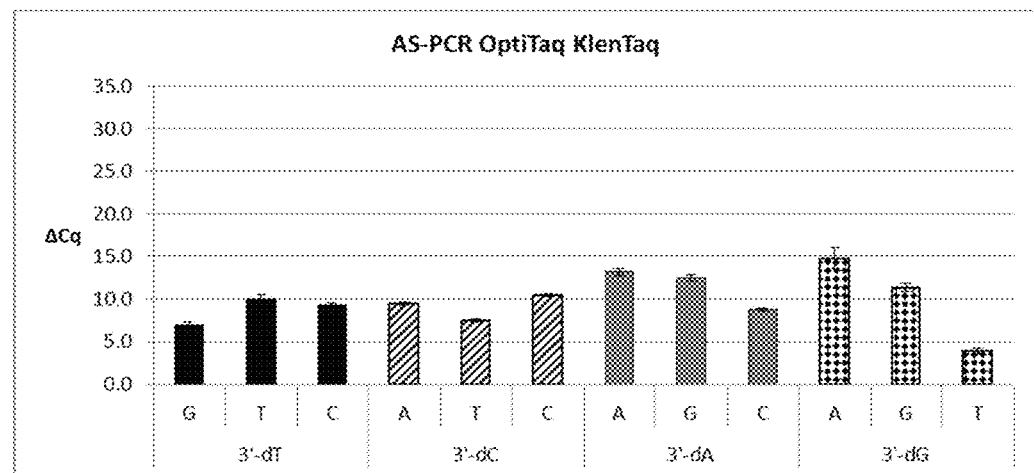
FIG. 7C. shows graphical representations of the allele-specific PCR (AS-PCR) data from Tables 10 and 31 for OptiTaq KlenTaq (Mutant ID 37) (sub-panel (i)), Mutant ID 42 (sub-panel (ii)) and Mutant ID 43 (sub-panel (iii)). Legend as in FIG. 7A.
Figure 7C:
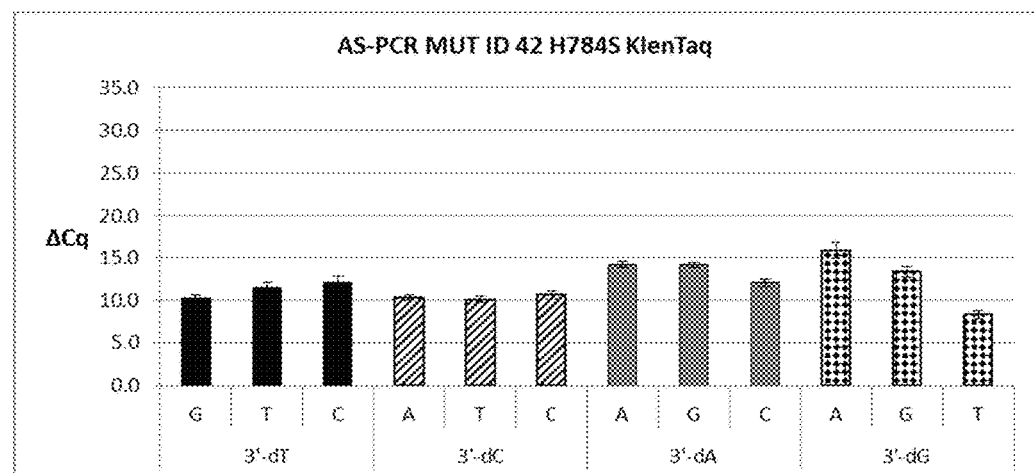
Figure 7C:
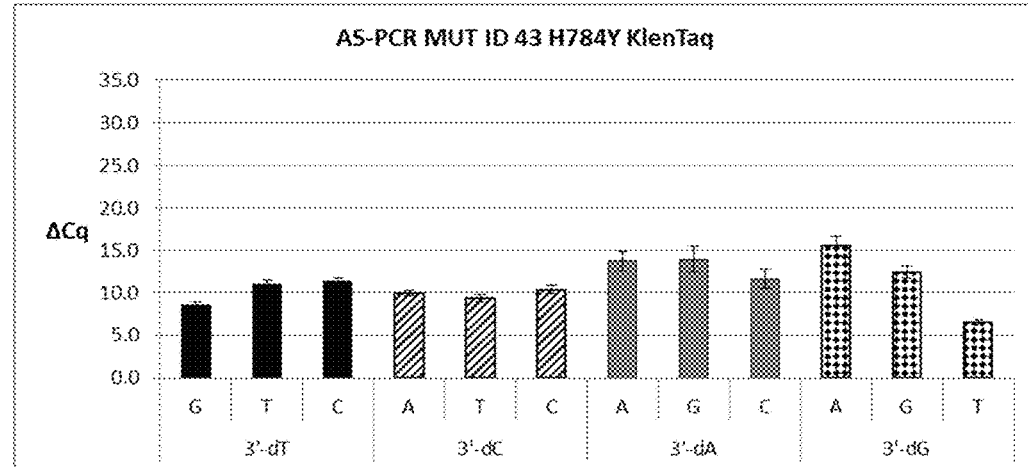

Initially all reactions were run in triplicate. Similar results were obtained for all replicates when using the wild type OptiTaq. However, results showed greater variation for the mutant polymerases. To obtain statistically meaningful results, each reaction was therefore performed 24 times for the mutant polymerases and 21 times for the wild type enzyme. ΔCq values were calculated as the Cq value obtained for each mismatched base pair minus the Cq value obtained for the matched base pair (ΔCq=Cq mismatch−Cq match). The ΔCq values for all 24 replicates were averaged and standard deviations were calculated. Results are shown in Table 42 and are graphically summarized in FIGS. 7A, 7B, and 7C. Note that the reverse primer is the allele-specific primer, so the "Syn Rev T" primer (SEQ ID NO. 55) is the perfect match to the Template A (SEQ ID NO. 51), etc.

TABLE 42

ΔCq values for AS-qPCR reactions using KlenTaq mutant Taq DNA polymerases.

| | | | Template | | | |
|---|---|---|---|---|---|---|
| | Reverse Primer | | A | C | G | T |
| DNA Polymerase | Name | SEQ ID NO. | SEQ ID NO. 51 | SEQ ID NO. 52 | SEQ ID NO. 53 | SEQ ID NO. 54 |
| Mutant ID 37 OptiTaq KlenTaq | Syn Rev T | 55 | — | 9.2 +/− 0.3 | 6.9 +/− 0.4 | 10.0 +/− 0.4 |
| | Syn Rev G | 58 | 14.7 +/− 1.2 | — | 11.3 +/− 0.5 | 3.9 +/− 0.3 |
| | Syn Rev C | 56 | 9.4 +/− 0.2 | 10.4 +/− 0.2 | — | 7.5 +/− 0.2 |
| | Syn Rev A | 57 | 13.3 +/− 0.4 | 8.7 +/− 0.2 | 12.4 +/− 0.4 | — |
| Mutant ID 38 A661E, I665W, F667L KlenTaq | Syn Rev T | 55 | — | 11.8 +/− 0.5 | 9.9 +/− 0.6 | 11.7 +/− 0.7 |
| | Syn Rev G | 58 | 17.4 +/− 5.8 | — | 13.1 +/− 1.5 | 7.9 +/− 2.9 |
| | Syn Rev C | 56 | 10.8 +/− 0.4 | 11.0 +/− 0.5 | — | 10.5 +/− 0.2 |
| | Syn Rev A | 57 | 13.8 +/− 0.6 | 11.5 +/− 0.4 | 13.6 +/− 0.8 | — |
| Mutant ID 39 V783F KlenTaq | Syn Rev T | 55 | — | 10.9 +/− 0.3 | 8.7 +/− 0.3 | 11.3 +/− 0.4 |
| | Syn Rev G | 58 | 17.1 +/− 6.7 | — | 12.9 +/− 0.7 | 6.9 +/− 0.3 |
| | Syn Rev C | 56 | 10.5 +/− 0.2 | 10.5 +/− 0.6 | — | 10.0 +/− 0.2 |
| | Syn Rev A | 57 | 13.4 +/− 0.6 | 10.6 +/− 0.2 | 13.0 +/− 0.4 | — |
| Mutant ID 40 H784Q KlenTaq | Syn Rev T | 55 | — | 11.5 +/− 0.4 | 10.1 +/− 0.3 | 12.0 +/− 0.9 |
| | Syn Rev G | 58 | 18.2 +/− 6.4 | — | 13.2 +/− 0.5 | 7.9 +/− 0.3 |
| | Syn Rev C | 56 | 10.7 +/− 0.4 | 10.5 +/− 0.6 | — | 10.2 +/− 0.3 |
| | Syn Rev A | 57 | 13.8 +/− 0.7 | 11.3 +/− 0.3 | 13.5 +/− 0.6 | — |
| Mutant ID 41 V783L H784Q KlenTaq | Syn Rev T | 55 | — | 8.9 +/− 0.3 | 7.8 +/− 0.3 | 10.5 +/− 0.4 |
| | Syn Rev G | 58 | 15.8 +/− 4.3 | — | 12.4 +/− 0.5 | 5.8 +/− 0.3 |
| | Syn Rev C | 56 | 10.1 +/− 0.5 | 10.2 +/− 0.2 | — | 8.5 +/− 0.4 |
| | Syn Rev A | 57 | 13.3 +/− 0.8 | 9.5 +/− 0.3 | 12.6 +/− 0.4 | — |
| Mutant ID 42 H784S KlenTaq | Syn Rev T | 55 | — | 12.1 +/− 0.7 | 10.2 +/− 0.4 | 11.4 +/− 0.6 |
| | Syn Rev G | 58 | 15.8 +/− 1.0 | — | 13.3 +/− 0.6 | 8.3 +/− 0.5 |
| | Syn Rev C | 56 | 10.3 +/− 0.3 | 10.6 +/− 0.5 | — | 10.1 +/− 0.4 |
| | Syn Rev A | 57 | 14.1 +/− 0.4 | 12.0 +/− 0.4 | 14.1 +/− 0.3 | — |
| Mutant ID 43 H784Y KlenTaq | Syn Rev T | 55 | — | 11.3 +/− 0.4 | 8.5 +/− 0.4 | 11.0 +/− 0.4 |
| | Syn Rev G | 58 | 15.5 +/− 1.2 | — | 12.4 +/− 0.7 | 6.5 +/− 0.3 |
| | Syn Rev C | 56 | 9.9 +/− 0.3 | 10.3 +/− 0.5 | — | 9.3 +/− 0.4 |
| | Syn Rev A | 57 | 13.7 +/− 1.2 | 11.6 +/− 1.2 | 13.9 +/− 1.5 | — |

Average ΔCq values are shown, where ΔCq = [Cq mismatch − Cq match], +/− standard deviation calculated from 24 replicates.

The OptiTaq KlenTaq Mutant ID 37 showed an average ΔCq for AS-qPCR in this synthetic amplicon system of 9.8 with a range of 3.9 to 14.7. Mutant ID 38 (A661E, I665W, F667L KlenTaq) showed an average ΔCq of 11.9 with a range of 7.9 to 17.4. Mutant ID 39 (V783F KlenTaq) showed an average ΔCq of 11.3 with a range of 6.9 to 17.1. Mutant ID 40 (H784Q KlenTaq) showed an average ΔCq of 11.9 with a range of 7.9 to 18.2. Mutant ID 41 (V783L H784Q KlenTaq) showed an average ΔCq of 10.5 with a range of 5.8 to 15.8. Mutant ID 42 (H784S KlenTaq) showed an average ΔCq of 11.9 with a range of 8.3 to 15.8. Mutant ID 43 (H784Y KlenTaq) showed an average ΔCq of 11.2 with a range of 6.5 to 15.5. Therefore, in all pairwise combinations of 4 template bases and 4 3'-terminal primer bases the mutant Taq DNA polymerases of the present invention showed greater discrimination to mismatch than did the OptiTaq or OptiTaq KlenTaq DNA polymerases. The magnitude of improvement for each mismatch pair is defined by the ΔΔCq, which is the difference of discrimination between the mutant and wild type KlenTaq enzymes (ΔΔCq=ΔCq mutant KlenTaq−ΔCq OptiTaq KlenTaq). The ΔΔCq values were calculated and are shown in Table 43.

TABLE 43

ΔΔCq values for AS-qPCR reactions for the mutant KlenTaq DNA polymerases compared with OptiTaq KlenTaq.

| DNA Polymerase | Reverse Primer Name | SEQ ID NO. | Template A SEQ ID NO. 51 | Template C SEQ ID NO. 52 | Template G SEQ ID NO. 53 | Template T SEQ ID NO. 54 |
| --- | --- | --- | --- | --- | --- | --- |
| Mutant ID 38 A661E, I665W, F667L KlenTaq | Syn Rev T | 55 | — | 2.6 | 3 | 1.7 |
| | Syn Rev G | 58 | 2.7 | — | 1.8 | 4 |
| | Syn Rev C | 56 | 1.4 | 0.6 | — | 3 |
| | Syn Rev A | 57 | 0.7 | 2.8 | 1.2 | — |
| Mutant ID 39 V783F KlenTaq | Syn Rev T | 55 | — | 1.7 | 1.8 | 1.3 |
| | Syn Rev G | 58 | 2.4 | — | 1.6 | 3 |
| | Syn Rev C | 56 | 1.1 | 0.1 | — | 2.5 |
| | Syn Rev A | 57 | 0.3 | 1.9 | 0.6 | — |
| Mutant ID 40 H784Q KlenTaq | Syn Rev T | 55 | — | 2.3 | 3.2 | 2 |
| | Syn Rev G | 58 | 3.5 | — | 1.9 | 4 |
| | Syn Rev C | 56 | 1.3 | 0.4 | — | 2.7 |
| | Syn Rev A | 57 | 0.7 | 2.6 | 1.1 | — |
| Mutant ID 41 V783L H784Q KlenTaq | Syn Rev T | 55 | — | −0.3 | 0.9 | 0.5 |
| | Syn Rev G | 58 | 1.1 | — | 1.1 | 1.9 |
| | Syn Rev C | 56 | 0.7 | −0.2 | — | 1 |
| | Syn Rev A | 57 | 0.2 | 0.8 | 0.2 | — |
| Mutant ID 42 H784S KlenTaq | Syn Rev T | 55 | — | 2.9 | 3.3 | 1.4 |
| | Syn Rev G | 58 | 1.1 | — | 2 | 4.4 |
| | Syn Rev C | 56 | 0.9 | 0.2 | — | 2.6 |
| | Syn Rev A | 57 | 1 | 3.3 | 1.7 | — |
| Mutant ID 43H784Y KlenTaq | Syn Rev T | 55 | — | 2.1 | 1.6 | 1 |
| | Syn Rev G | 58 | 0.8 | — | 1.1 | 2.6 |
| | Syn Rev C | 56 | 0.5 | −0.1 | — | 1.8 |
| | Syn Rev A | 57 | 0.6 | 2.9 | 1.5 | — |

Average ΔΔCq values are shown, where ΔΔCq = [ΔCq mutant KlenTaq − ΔCq OptiTaq KlenTaq], from data in Table 42.

Mutant ID 38 (A661E, I665W, F667L KlenTaq) showed an average ΔΔCq of 1.7 compared to OptiTaq KlenTaq. Mutant ID 39 (V783F KlenTaq) showed an average ΔΔCq of 2.0 compared to OptiTaq KlenTaq. Mutant ID 40 (H784Q KlenTaq) showed an average ΔΔCq of 2.1 compared to OptiTaq KlenTaq. Mutant ID 41 (V783L H784Q KlenTaq) showed an average ΔΔCq of 0.7 compared to OptiTaq KlenTaq. Mutant ID 42 (H784S KlenTaq) showed an average ΔΔCq of 2.1 compared to OptiTaq KlenTaq. Mutant ID 43 (H784Y KlenTaq) showed an average ΔΔCq of 2.0 compared to OptiTaq KlenTaq. Therefore, each of the mutant Taq DNA polymerases of the present invention showed a significant improvement in mismatch discrimination over OptiTaq KlenTaq which had complete deletion of the 5'-exonuclease domain but contained no other secondary mutations. Overall, mutant IDs 40 and 42 (H784Q KlenTaq and H784S KlenTaq) showed the best SNP discrimination within the set of mutant enzymes studied in this example using an AS-PCR assay.

Example 21: Improved Mismatch Discrimination in rhPCR Using Mutant KlenTaq DNA Polymerases in a Human Genomic DNA SNP Assay Example 20 demonstrated utility of the novel mutant Taq DNA polymerases of the present invention in a synthetic amplicon rhPCR SNP discrimination assay system. The present Example demonstrates utility of the novel mutant Taq DNA polymerases in a human genomic DNA rhPCR SNP discrimination assays system, examining a SNP site in the SMAD7 gene (NM_005904, C/T SNP, rs4939827). The assays employed target DNAs GM18562 (homozygous C/C) and GM18537 (homozygous T/T) from the Coriell Institute for Medical Research (Camden, N.J., USA). One blocked-cleavable primer design was tested, the generation 1 (Gen1) "RDDDDx" primers (see: US Patent Application 2012/0258455 by Behlke et al., entitled, RNASE H-BASED ASSAYS UTILIZING MODIFIED RNA MONOMERS).

Quantitative real-time rhPCR was performed in 10 µL reaction volumes in 384 well format with 20 ng (the equivalent of 6600 copies of target) of human genomic DNA (GM18562 or GM18537). Reactions utilized either 0.5 U (10.8 ng/11.1 nM/111 fmol) of OptiTaq KlenTaq DNA polymerase or 0.5 U of one of the three Taq DNA polymerase mutants (Mutant ID 40 (360 ng/370 nM/3700 fmol); Mutant ID 41 (1060 ng/555 nM/5550 fmol); Mutant ID 43 (216 ng/222 nM/2220 fmol)). Final reaction conditions used were 20 mM Tris-HCL (pH 8.4 at 25° C.), 50 mM KCL, 3 mM MgCl$_2$, 0.01% Triton X-100, 800 µM total dNTPs, 200 nM of a forward primer (SEQ ID NOs. 75-79), 200 nM of the universal reverse primer (SEQ ID NO. 74), and 200 nM of the RNase H2 cleavable SMAD7 probe (SEQ ID NO. 166). Sequence of the 85 bp SMAD7 amplicon is shown as SEQ ID NO. 81. Forward primers included RDDDDx configuration Gen1 allele-specific rhPCR primers (SEQ ID NOs. 76 and 77), and the control universal forward primer (SEQ ID NO. 75) which is not allele specific. Oligonucleotide reagents employed in this Example are shown in Table 44. Reactions included 1 µL of P.a. RNase H2 at a concentration of 2.6 mU per 10 µL reaction (5 fmoles, 0.5 nM). Amplification was performed on a Roche LightCycler® 480 (Roche Applied Science, Indianapolis, Ind., USA) as follows: 95° C. for 3 minutes followed by 95 cycles of 95° C. for 10 seconds and 60° C. for 30 seconds. All reactions were performed in triplicate.

TABLE 44

Synthetic oligonucleotides employed in Example 21.

| Name | Sequence (5'-3') | SEQ ID NO. |
|---|---|---|
| SMAD7 Rev | CTCACTCTAAACCCCAGCATT | 74 |
| SMAD7 For | CAGCCTCATCCAAAAGAGGAAA | 75 |
| SMAD7 For rC DDDDx | CAGCCTCATCCAAAAGAGGAAAcAGGAx | 76 |
| SMAD7 For rU DDDDx | CAGCCTCATCCAAAAGAGGAAAuAGGAx | 77 |
| SMAD7 RN2 probe | FAM-CCCAGAGCTCcCTCAGACTCCT-IBFQ | 166 |
| SMAD7 target | <u>CAGCCTCATCCAAAAGAGGAAA</u>TAGGAC<u>CCCAGAGCTCCCTCA</u><br><u>GACTCCT</u>CAGGAAACACAGACAATGCTGGGGTTTAGAGTGAG | 81 |

DNA bases are uppercase and RNA bases are lowercase;
FAM = 6-carboxyfluorescein;
IBFQ = Iowa Black ™ FQ fluorescence quencher;
"x" = C3 Spacer (propanediol).
Primer and probe binding sites in the SMAD7 target are underlined.

Results using the Gen1 RDDDDx rhPCR primers are shown in Table 45. Use of the mutant Taq DNA polymerases showed significant improvements in SNP discrimination in this human genomic DNA rhPCR assay using the Gen1 RDDDDx primers, although amplification efficiency was often reduced, as shown by the increases in the match Cqs. Therefore use of the new mutant KlenTaq DNA polymerases improves SNP discrimination in rhPCR genotyping assays.

TABLE 45

SNP discrimination of a site in the SMAD7 gene using Gen1 RDDDDx primers comparing wild type OptiTaq with four mutant Taq DNA polymerases.

| DNA Polymerase | For Primer | SEQ ID NO. | mU RNase h2 per 10 μL rxn | Cq Value C/C DNA | Cq Value T/T DNA | ΔCq |
|---|---|---|---|---|---|---|
| MUT ID 37 OptiTaq KlenTaq | SMAD7 For | 75 | 2.6 | 24.4 | 23.5 | |
| | SMAD7 For rC DDDx | 76 | 2.6 | 31.1 | 38.4 | 7.3 |
| | SMAD7 For rU DDDx | 77 | 2.6 | 46.1 | 33.0 | 13.1 |
| MUT ID 40 H784Q KlenTaq | SMAD7 For | 75 | 2.6 | 24.6 | 24.5 | |
| | SMAD7 For rC DDDx | 76 | 2.6 | 28.1 | 38.8 | 10.7 |
| | SMAD7 For rU DDDx | 77 | 2.6 | 42.1 | 28.8 | 13.3 |
| MUT ID 41 V783L H784Q KlenTaq | SMAD7 For | 75 | 2.6 | 24.5 | 24.3 | |
| | SMAD7 For rC DDDx | 76 | 2.6 | 26.2 | 37.6 | 11.4 |
| | SMAD7 For rU DDDx | 77 | 2.6 | 41.2 | 27.8 | 13.4 |
| MUT ID 43 H784Y KlenTaq | SMAD7 For | 75 | 2.6 | 24.7 | 24.8 | |
| | SMAD7 For rC DDDx | 76 | 2.6 | 33.8 | 45.1 | 11.2 |
| | SMAD7 For rU DDDx | 77 | 2.6 | 50.4 | 35.2 | 15.2 |

DNA targets included GM18562 (homozygous C/C) and GM18537 (homozygous T/T) from the Coriell Institute for Medical Research. ΔCq = [Cq mismatch − Cq match].

Example 22. Sequence of Taq DNA Polymerase Mutants Showing Improved Discrimination for Mismatch or the Presence of an RNA Residue at the 3'-End of the Primer The complete amino acid and nucleotide sequences of the codon optimized mutant enzymes employed in Examples 18-21 are shown below. Although these sequences are easily derived from information provided in Tables 1, 3, 4 26 and 38 by one with skill in the art, the final assembled sequences are provided below for clarity. Base changes are identified in bold underlined font for the nucleic acid and amino acid substitutions.

```
SEQ ID NO. 167, nucleotide sequence of Mutant ID 37 (OptiTaq KlenTaq).
CATATGGGTTCACTGCTTCATGAATTCGGTCTGTTAGAGTCTCCTAAAGCACTCGAAGAGGCACCGTGGCCGCCCCC
AGAAGGTGCTTTTGTTGGCTTCGTACTTTCCCGTAAGGAGCCTATGTGGGCAGATCTTCTGGCTTTAGCGGCTGCAC
GCGGTGGCCGTGTTCACCGGGCCCCTGAGCCATACAAAGCGTTACGTGATCTGAAGGAAGCACGTGGCTTGCTGGCA
AAAGACCTTTCTGTTTTGGCCCTGCGCGAGGGTCTTGGACTGCCGCCAGGCGACGATCCCATGTTATTGGCCTATCT
GTTAGACCCTAGCAATACCACACCTGAAGGGGTCGCTCGTCGGTATGGCGGTGAATGGACTGAGGAAGCCGGAGAGC
GCGCCGCATTGTCCGAACGGCTCTTTGCAAACTTATGGGGTCGTCTGGAAGGGGAGGAACGTCTGTTATGGTTGTAT
CGGGAAGTCGAACGTCCTCTTTCGGCCGTATTAGCGCATATGGAGGCAACAGGTGTGCGTTTAGATGTCGCGTACCT
TCGGGCCTTATCACTGGAAGTTGCAGAGGAAATCGCCCGTCTCGAGGCTGAAGTGTTCCGGTTGGCCGGTCACCCGT
TTAACCTCAACTCCCGTGACCAGCTGGAACGCGTTTTATTCGATGAGCTTGGGCTTCCCGCAATTGGCAAAACCGAA
AAGACTGGCAAACGCAGTACGAGCGCTGCCGTCCTTGAGGCACTCCGCGAGGCTCACCCTATTGTAGAAAAGATCCT
GCAATACCGTGAGTTGACGAAGCTTAAAAGCACTTATATTGATCCTCTCCCGGATCTGATCCATCCTCGTACCGGCC
GCTTGCACACACGTTTCAACCAGACGGCGACTGCAACCGGCCGTCTGTCTAGCTCGGATCCAAATCTCCAGAACATT
CCGGTCCGTACACCCTTGGGCCAACGTATCCGCCGGGCGTTTATCGCTGAGGAAGGATGGTTACTGGTCGCATTGGA
CTACTCGCAGATTGAGCTGCGCGTCCTCGCACATCTCTCTGGTGACGAAAATTTAATCCGCGTGTTTCAAGAGGGGC
GTGATATTCACACAGAAACTGCCTCATGGATGTTCGGTGTCCCACGTGAAGCAGTGGATCCTTTGATGCGCCGTGCA
GCTAAAACAATTAATTTTGGAGTGCTGTACGGAATGAGCGCTCATCGCTTGAGTCAGGAACTGGCAATCCCCTACGA
GGAAGCGCAGGCATTCATCGAACGTTACTTTCAATCGTTTCCGAAAGTTCGCGCATGGATCGAGAAGACGCTCGAGG
AAGGTCGTCGTCGGGGCTATGTCGAAACTCTGTTTGGTCGCCGTCGGTACGTACCAGATCTTGAAGCCCGCGTCAAA
TCGGTACGGGAGGCTGCGGAGCGTATGGCATTTAATATGCCTGTACAGGGTACTGCAGCTGACCTCATGAAACTGGC
AATGGTCAAGCTTTTCCCGCGCTTGGAGGAAATGGGCGCACGTATGCTTCTGCAGGTCCATGACGAGCTGGTGTTAG
AAGCCCCTAAGGAGCGCGCCGAAGCTGTCGCGCGCCTCGCTAAAGAAGTGATGGAGGGCGTTTACCCATTGGCCGTA
CCCCTCGAAGTGGAGGTCGGTATTGGAGAAGATTGGTTATCTGCAAAGGAAGCGGCCGC SEQ ID NO. 168, amino acid sequence of Mutant ID 37 (OptiTaq KlenTaq).
MGSLLHEFGLLESPKALEEAPWPPPEGAFVGFVLSRKEPMWADLLALAAARGGRVHRAPEPYKALRDLKEARGLLAK
DLSVLALREGLGLPPGDDPMLLAYLLDPSNTTPEGVARRYGGEWTEEAGERAALSERLFANLWGRLEGEERLLWLYR
EVERPLSAVLAHMEATGVRLDVAYLRALSLEVAEEIARLEAEVFRLAGHPFNLNSRDQLERVLFDELGLPAIGKTEK
TGKRSTSAAVLEALREAHPIVEKILQYRELTKLKSTYIDPLPDLIHPRTGRLHTRFNQTATATGRLSSSDPNLQNIP
VRTPLGQRIRRAFIAEEGWLLVALDYSQIELRVLAHLSGDENLIRVFQEGRDIHTETASWMFGVPREAVDPLMRRAA
KTINFGVLYGMSAHRLSQELAIPYEEAQAFIERYFQSFPKVRAWIEKTLEEGRRRGYVETLFGRRRYVPDLEARVKS
VREAAERMAFNMPVQGTAADLMKLAMVKLFPRLEEMGARMLLQVHDELVLEAPKERAEAVARLAKEVMEGVYPLAVP
LEVEVGIGEDWLSAKEAA SEQ ID NO. 169, nucleotide sequence of Mutant ID 38 (A661E, I665W, F667L
KlenTaq).
CATATGGGTTCACTGCTTCATGAATTCGGTCTGTTAGAGTCTCCTAAAGCACTCGAAGAGGCACCGTGGCCGCCCCC
AGAAGGTGCTTTTGTTGGCTTCGTACTTTCCCGTAAGGAGCCTATGTGGGCAGATCTTCTGGCTTTAGCGGCTGCAC
GCGGTGGCCGTGTTCACCGGGCCCCTGAGCCATACAAAGCGTTACGTGATCTGAAGGAAGCACGTGGCTTGCTGGCA
AAAGACCTTTCTGTTTTGGCCCTGCGCGAGGGTCTTGGACTGCCGCCAGGCGACGATCCCATGTTATTGGCCTATCT
GTTAGACCCTAGCAATACCACACCTGAAGGGGTCGCTCGTCGGTATGGCGGTGAATGGACTGAGGAAGCCGGAGAGC
GCGCCGCATTGTCCGAACGGCTCTTTGCAAACTTATGGGGTCGTCTGGAAGGGGAGGAACGTCTGTTATGGTTGTAT
CGGGAAGTCGAACGTCCTCTTTCGGCCGTATTAGCGCATATGGAGGCAACAGGTGTGCGTTTAGATGTCGCGTACCT
TCGGGCCTTATCACTGGAAGTTGCAGAGGAAATCGCCCGTCTCGAGGCTGAAGTGTTCCGGTTGGCCGGTCACCCGT
TTAACCTCAACTCCCGTGACCAGCTGGAACGCGTTTTATTCGATGAGCTTGGGCTTCCCGCAATTGGCAAAACCGAA
AAGACTGGCAAACGCAGTACGAGCGCTGCCGTCCTTGAGGCACTCCGCGAGGCTCACCCTATTGTAGAAAAGATCCT
GCAATACCGTGAGTTGACGAAGCTTAAAAGCACTTATATTGATCCTCTCCCGGATCTGATCCATCCTCGTACCGGCC
GCTTGCACACACGTTTCAACCAGACGGCGACTGCAACCGGCCGTCTGTCTAGCTCGGATCCAAATCTCCAGAACATT
CCGGTCCGTACACCCTTGGGCCAACGTATCCGCCGGGCGTTTATCGCTGAGGAAGGATGGTTACTGGTCGCATTGGA
CTACTCGCAGATTGAGCTGCGCGTCCTCGCACATCTCTCTGGTGACGAAAATTTAATCCGCGTGTTTCAAGAGGGGC
GTGATATTCACACAGAAACTGCCTCATGGATGTTCGGTGTCCCACGTGAAGCAGTGGATCCTTTGATGCGCCGTGAA
GCTAAAACATGGAATTTGGGAGTGCTGTACGGAATGAGCGCTCATCGCTTGAGTCAGGAACTGGCAATCCCCTACGA
GGAAGCGCAGGCATTCATCGAACGTTACTTTCAATCGTTTCCGAAAGTTCGCGCATGGATCGAGAAGACGCTCGAGG
AAGGTCGTCGTCGGGGCTATGTCGAAACTCTGTTTGGTCGCCGTCGGTACGTACCAGATCTTGAAGCCCGCGTCAAA
TCGGTACGGGAGGCTGCGGAGCGTATGGCATTTAATATGCCTGTACAGGGTACTGCAGCTGACCTCATGAAACTGGC
AATGGTCAAGCTTTTCCCGCGCTTGGAGGAAATGGGCGCACGTATGCTTCTGCAGGTCCATGACGAGCTGGTGTTAG
AAGCCCCTAAGGAGCGCGCCGAAGCTGTCGCGCGCCTCGCTAAAGAAGTGATGGAGGGCGTTTACCCATTGGCCGTA
CCCCTCGAAGTGGAGGTCGGTATTGGAGAAGATTGGTTATCTGCAAAGGAAGCGGCCGC SEQ ID NO. 170, amino acid sequence of Mutant ID 38 (A661E, I665W, F667L
KlenTaq).
MGSLLHEFGLLESPKALEEAPWPPPEGAFVGFVLSRKEPMWADLLALAAARGGRVHRAPEPYKALRDLKEARGLLAK
DLSVLALREGLGLPPGDDPMLLAYLLDPSNTTPEGVARRYGGEWTEEAGERAALSERLFANLWGRLEGEERLLWLYR
EVERPLSAVLAHMEATGVRLDVAYLRALSLEVAEEIARLEAEVFRLAGHPFNLNSRDQLERVLFDELGLPAIGKTEK
TGKRSTSAAVLEALREAHPIVEKILQYRELTKLKSTYIDPLPDLIHPRTGRLHTRFNQTATATGRLSSSDPNLQNIP
VRTPLGQRIRRAFIAEEGWLLVALDYSQIELRVLAHLSGDENLIRVFQEGRDIHTETASWMFGVPREAVDPLMRREA
KTWNLGVLYGMSAHRLSQELAIPYEEAQAFIERYFQSFPKVRAWIEKTLEEGRRRGYVETLFGRRRYVPDLEARVKS
VREAAERMAFNMPVQGTAADLMKLAMVKLFPRLEEMGARMLLQVHDELVLEAPKERAEAVARLAKEVMEGVYPLAVP
LEVEVGIGEDWLSAKEAA
```

SEQ ID NO. 171, nucleotide sequence of Mutant ID 39 (V783F KlenTaq).
CATATGGGTTCACTGCTTCATGAATTCGGTCTGTTAGAGTCTCCTAAAGCACTCGAAGAGGCACCGTGGCCGCCCCC
AGAAGGTGCTTTTGTTGGCTTCGTACTTTCCCGTAAGGAGCCTATGTGGGCAGATCTTCTGGCTTTAGCGGCTGCAC
GCGGTGGCCGTGTTCACCGGGCCCTGAGCCATACAAAGCGTTACGTGATCTGAAGGAAGCACGTGGCTTGCTGGCA
AAAGACCTTTCTGTTTTGGCCCTGCGCGAGGGTCTTGGACTGCCGCCAGGCGACGATCCCATGTTATTGGCCTATCT
GTTAGACCCTAGCAATACCACACCTGAAGGGGTCGCTCGTCGGTATGGCGGTGAATGGACTGAGGAAGCCGGAGAGC
GCGCCGCATTGTCCGAACGGCTCTTTGCAAACTTATGGGGTCGTCTGGAAGGGGAGGAACGTCTGTTATGGTTGTAT
CGGGAAGTCGAACGTCCTCTTTCGGCCGTATTAGCGCATATGGAGGCAACAGGTGTGCGTTTAGATGTCGCGTACCT
TCGGGCCTTATCACTGGAAGTTGCAGAGGAAATCGCCCGTCTCGAGGCTGAAGTGTTCCGGTTGGCCGGTCACCCGT
TTAACCTCAACTCCCGTGACCAGCTGGAACGCGTTTTATTCGATGAGCTTGGGCTTCCCGCAATTGGCAAAACCGAA
AAGACTGGCAAACGCAGTACGAGCGCTGCCGTCCTTGAGGCACTCCGCGAGGCTCACCCTATTGTAGAAAAGATCCT
GCAATACCGTGAGTTGACGAAGCTTAAAAGCACTTATATTGATCCTCTCCCGGATCTGATCCATCCTCGTACCGGCC
GCTTGCACACACGTTTCAACCAGACGGCGACTGCAACCGGCCGTCTGTCTAGCTCGGATCCAAATCTCCAGAACATT
CCGGTCCGTACACCCTTGGGCAACGTATCCGCCGGGCGTTTATCGCTGAGGAAGGATGGTTACTGGTCGCATTGGA
CTACTCGCAGATTGAGCTGCGCGTCCTCGCACATCTCTCTGGTGACGAAAATTTAATCCGCGTGTTTCAAGAGGGGC
GTGATATTCACACAGAAACTGCCTCATGGATGTTCGGTGTCCCACGTGAAGCAGTGGATCCTTTGATGCGCCGTGCA
GCTAAAACAATTAATTTTGGAGTGCTGTACGGAATGAGCGCTCATCGCTTGAGTCAGGAACTGGCAATCCCCTACGA
GGAAGCGCAGGCATTCATCGAACGTTACTTTCAATCGTTTCCGAAAGTTCGCGCATGGATCGAGAAGACGCTCGAGG
AAGGTCGTCGTCGGGGCTATGTCGAAACTCTGTTTGGTCGCCGTCGGTACGTACCAGATCTTGAAGCCCGCGTCAAA
TCGGTACGGGAGGCTGCGGAGCGTATGGCATTTAATATGCCTGTACAGGGTACTGCAGCTGACCTCATGAAACTGGC
AATGGTCAAGCTTTTCCCGCGCTTGGAGGAAATGGGCGCACGTATGCTTCTGCAGTTCCATGACGAGCTGGTGTTAG
AAGCCCCTAAGGAGCGCGCCGAAGCTGTCGCGCGCCTCGCTAAAGAAGTGATGGAGGGCGTTTACCCATTGGCCGTA
CCCCTCGAAGTGGAGGTCGGTATTGGAGAAGATTGGTTATCTGCAAAGGAAGCGGCCGC SEQ ID NO. 172, amino acid sequence of Mutant ID 39 (V783F KlenTaq).
MGSLLHEFGLLESPKALEEAPWPPPEGAFVGFVLSRKEPMWADLLALAAARGGRVHRAPEPYKALRDL
KEARGLLAKDLSVLALREGLGLPPGDDPMLLAYLLDPSNTTPEGVARRYGGEWTEEAGERAALSERLFANLWGRLEG
EERRLLWLYREVERPLSAVLAHMEATGVRLDVAYLRALSLEVAEEIARLEAEVFRLAGHPFNLNSRDQLERVLFDELG
LPAIGKTEKTGKRSTSAAVLEALREAHPIVEKILQYRELTKLKSTYIDPLPDLIHPRTGRLHTRFNQTATATGRLSS
SDPNLQNIPVRTPLGQRIRRAFIAEEGWLLVALDYSQIELRVLAHLSGDENLIRVFQEGRDIHTETASWMFGVPREA
VDPLMRRAAKTINFGVLYGMSAHRLSQELAIPYEEAQAFIERYFQSFPKVRAWIEKTLEEGRRRGYVETLFGRRRYV
PDLEARVKSVREAAERMAFNMPVQGTAADLMKLAMVKLFPRLEEMGARMLLQLHDELVLEAPKERAEEVARLAKEVM
EGVYPLAVPLEVEVGIGEDWLSAKEAA SEQ ID NO. 173, nucleotide sequence of Mutant ID 40 (H784Q KlenTaq).
CATATGGGTTCACTGCTTCATGAATTCGGTCTGTTAGAGTCTCCTAAAGCACTCGAAGAGGCACCGTGGCCGCCCCC
AGAAGGTGCTTTTGTTGGCTTCGTACTTTCCCGTAAGGAGCCTATGTGGGCAGATCTTCTGGCTTTAGCGGCTGCAC
GCGGTGGCCGTGTTCACCGGGCCCTGAGCCATACAAAGCGTTACGTGATCTGAAGGAAGCACGTGGCTTGCTGGCA
AAAGACCTTTCTGTTTTGGCCCTGCGCGAGGGTCTTGGACTGCCGCCAGGCGACGATCCCATGTTATTGGCCTATCT
GTTAGACCCTAGCAATACCACACCTGAAGGGGTCGCTCGTCGGTATGGCGGTGAATGGACTGAGGAAGCCGGAGAGC
GCGCCGCATTGTCCGAACGGCTCTTTGCAAACTTATGGGGTCGTCTGGAAGGGGAGGAACGTCTGTTATGGTTGTAT
CGGGAAGTCGAACGTCCTCTTTCGGCCGTATTAGCGCATATGGAGGCAACAGGTGTGCGTTTAGATGTCGCGTACCT
TCGGGCCTTATCACTGGAAGTTGCAGAGGAAATCGCCCGTCTCGAGGCTGAAGTGTTCCGGTTGGCCGGTCACCCGT
TTAACCTCAACTCCCGTGACCAGCTGGAACGCGTTTTATTCGATGAGCTTGGGCTTCCCGCAATTGGCAAAACCGAA
AAGACTGGCAAACGCAGTACGAGCGCTGCCGTCCTTGAGGCACTCCGCGAGGCTCACCCTATTGTAGAAAAGATCCT
GCAATACCGTGAGTTGACGAAGCTTAAAAGCACTTATATTGATCCTCTCCCGGATCTGATCCATCCTCGTACCGGCC
GCTTGCACACACGTTTCAACCAGACGGCGACTGCAACCGGCCGTCTGTCTAGCTCGGATCCAAATCTCCAGAACATT
CCGGTCCGTACACCCTTGGGCAACGTATCCGCCGGGCGTTTATCGCTGAGGAAGGATGGTTACTGGTCGCATTGGA
CTACTCGCAGATTGAGCTGCGCGTCCTCGCACATCTCTCTGGTGACGAAAATTTAATCCGCGTGTTTCAAGAGGGGC
GTGATATTCACACAGAAACTGCCTCATGGATGTTCGGTGTCCCACGTGAAGCAGTGGATCCTTTGATGCGCCGTGCA
GCTAAAACAATTAATTTTGGAGTGCTGTACGGAATGAGCGCTCATCGCTTGAGTCAGGAACTGGCAATCCCCTACGA
GGAAGCGCAGGCATTCATCGAACGTTACTTTCAATCGTTTCCGAAAGTTCGCGCATGGATCGAGAAGACGCTCGAGG
AAGGTCGTCGTCGGGGCTATGTCGAAACTCTGTTTGGTCGCCGTCGGTACGTACCAGATCTTGAAGCCCGCGTCAAA
TCGGTACGGGAGGCTGCGGAGCGTATGGCATTTAATATGCCTGTACAGGGTACTGCAGCTGACCTCATGAAACTGGC
AATGGTCAAGCTTTTCCCGCGCTTGGAGGAAATGGGCGCACGTATGCTTCTGCAGGTCCAGGACGAGCTGGTGTTAG
AAGCCCCTAAGGAGCGCGCCGAAGCTGTCGCGCGCCTCGCTAAAGAAGTGATGGAGGGCGTTTACCCATTGGCCGTA
CCCCTCGAAGTGGAGGTCGGTATTGGAGAAGATTGGTTATCTGCAAAGGAAGCGGCCGC SEQ ID NO. 174, amino acid sequence of Mutant ID 40 (H784Q KlenTaq).
MGSLLHEFGLLESPKALEEAPWPPPEGAFVGFVLSRKEPMWADLLALAAARGGRVHRAPEPYKALRDLKEARGLLAK
DLSVLALREGLGLPPGDDPMLLAYLLDPSNTTPEGVARRYGGEWTEEAGERAALSERLFANLWGRLEGEERLLWLYR
EVERPLSAVLAHMEATGVRLDVAYLRALSLEVAEETARLEAEVERLAGHPFNLNSRDQLERVLFDELGLPAIGKTEK
TGKRSTSAAVLEALREAHPIVEKILQYRELTKLKSTYIDPLPDLIHPRTGRLHTRFNQTATATGRLSSSDPNLQNIP
VRTPLGQRIRRAFIAEEGWLLVALDYSQIELRVLAHLSGDENLIRVFQEGRDIHTETASWMFGVPREAVDPLMRRAA
KTINFGVLYGMSAHRLSQELAIPYEEAQAFIERYFQSFPKVRAWIEKTLEEGRRRGYVETLFGRRRYVPDLEARVKS
VREAAERMAFNMPVQGTAADLMKLAMVKLFPRLEEMGARMLLQVQDELVLEAPKERAEEVARLAKEVMEGVYPLAVP
LEVEVGIGEDWLSAKEAA SEQ ID NO. 175, nucleotide sequence of Mutant ID 41 (V783L H784Q KlenTaq).
CATATGGGTTCACTGCTTCATGAATTCGGTCTGTTAGAGTCTCCTAAAGCACTCGAAGAGGCACCGTGGCCGCCCCC
AGAAGGTGCTTTTGTTGGCTTCGTACTTTCCCGTAAGGAGCCTATGTGGGCAGATCTTCTGGCTTTAGCGGCTGCAC
GCGGTGGCCGTGTTCACCGGGCCCTGAGCCATACAAAGCGTTACGTGATCTGAAGGAAGCACGTGGCTTGCTGGCA
AAAGACCTTTCTGTTTTGGCCCTGCGCGAGGGTCTTGGACTGCCGCCAGGCGACGATCCCATGTTATTGGCCTATCT
GTTAGACCCTAGCAATACCACACCTGAAGGGGTCGCTCGTCGGTATGGCGGTGAATGGACTGAGGAAGCCGGAGAGC
GCGCCGCATTGTCCGAACGGCTCTTTGCAAACTTATGGGGTCGTCTGGAAGGGGAGGAACGTCTGTTATGGTTGTAT
CGGGAAGTCGAACGTCCTCTTTCGGCCGTATTAGCGCATATGGAGGCAACAGGTGTGCGTTTAGATGTCGCGTACCT
TCGGGCCTTATCACTGGAAGTTGCAGAGGAAATCGCCCGTCTCGAGGCTGAAGTGTTCCGGTTGGCCGGTCACCCGT
TTAACCTCAACTCCCGTGACCAGCTGGAACGCGTTTTATTCGATGAGCTTGGGCTTCCCGCAATTGGCAAAACCGAA
AAGACTGGCAAACGCAGTACGAGCGCTGCCGTCCTTGAGGCACTCCGCGAGGCTCACCCTATTGTAGAAAAGATCCT
GCAATACCGTGAGTTGACGAAGCTTAAAAGCACTTATATTGATCCTCTCCCGGATCTGATCCATCCTCGTACCGGCC -continued
GCTTGCACACACGTTTCAACCAGACGGCGACTGCAACCGGCCGTCTGTCTAGCTCGGATCCAAATCTCCAGAACATT
CCGGTCCGTACACCCTTGGGCAACGTATCCGCCGGGCGTTTATCGCTGAGGAAGGATGGTTACTGGTCGCATTGGA
CTACTCGCAGATTGAGCTGCGCGTCCTCGCACATCTCTCTGGTGACGAAAATTTAATCCGCGTGTTTCAAGAGGGGC
GTGATATTCACACAGAAACTGCCTCATGGATGTTCGGTGTCCCACGTGAAGCAGTGGATCCTTTGATGCGCCGTGCA
GCTAAAACAATTAATTTTGGAGTGCTGTACGGAATGAGCGCTCATCGCTTGAGTCAGGAACTGGCAATCCCCTACGA
GGAAGCGCAGGCATTCATCGAACGTTACTTTCAATCGTTTCCGAAAGTTCGCGCATGGATCGAGAAGACGCTCGAGG
AAGGTCGTCGTCGGGGCTATGTCGAAACTCTGTTTGGTCGCCGTCGGTACGTACCAGATCTTGAAGCCCGCGTCAAA
TCGGTACGGGAGGCTGCGGAGCGTATGGCATTTAATATGCCTGTACAGGGTACTGCAGCTGACCTCATGAAACTGGC
AATGGTCAAGCTTTTCCCGCGCTTGGAGGAAATGGGCGCACGTATGCTTCTGCAGCTGCAGGACGAGCTGGTGTTAG
AAGCCCCTAAGGAGCGCGCCGAAGCTGTCGCGCGCCTCGCTAAAGAAGTGATGGAGGGCGTTTACCCATTGGCCGTA
CCCCTCGAAGTGGAGGTCGGTATTGGAGAAGATTGGTTATCTGCAAAGGAAGCGGCCGC SEQ ID NO. 176, amino acid sequence of Mutant ID 41 (V783L H784Q KlenTaq).
MGSLLHEFGLLESPKALEEAPWPPPEGAFVGFVLSRKEPMWADLLALAAARGGRVHRAPEPYKALRDLKEARGLLAK
DLSVLALREGLGLPPGDDPMLLAYLLDPSNTTPEGVARRYGGEWTEEAGERAALSERLFANLWGRLEGEERLLWLYR
EVERPLSAVLAHMEATGVRLDVAYLRALSLEVAEEIARLEAEVFRLAGHPFNLNSRDQLERVLEDELGLPAIGKTEK
TGKRSTSAAVLEALREAHPIVEKILQYRELTKLKSTYIDPLPDLIHPRTGRLHTRFNQTATATGRLSSSDPNLQNIP
VRTPLGQRIRRAFIAEEGWLLVALDYSQIELRVLAHLSGDENLIRVFQEGRDIHTETASWMFGVPREAVDPLMRRAA
KTINFGVLYGMSAHRLSQELAIPYEEAQAFIERYFQSFPKVRAWIEKTLEEGRRRGYVETLFGRRRYVPDLEARVKS
VREAAERMAFNMPVQGTAADLMKLAMVKLFPRLEEMGARMLLQLHDELVLEAPKERAEAVARLAKEVMEGVYPLAVP
LEVEVGIGEDWLSAKEAA SEQ ID NO. 177, nucleotide sequence of Mutant ID 42 (H784S KlenTaq).
CATATGGGTTCACTGCTTCATGAATTCGGTCTGTTAGAGTCTCCTAAAGCACTCGAAGAGGCACCGTGGCCGCCCCC
AGAAGGTGCTTTTGTTGGCTTCGTACTTTCCCGTAAGGAGCCTATGTGGGCAGATCTTCTGGCTTTAGCGGCTGCAC
GCGGTGGCCGTGTTCACCGGGCCCTGAGCCATACAAAGCGTTACGTGATCTGAAGGAAGCACGTGGCTTGCTGGCA
AAAGACCTTTCTGTTTTGGCCCTGCGCGAGGGTCTTGGACTGCCGCCAGGCGACGATCCCATGTTATTGGCCTATCT
GTTAGACCCTAGCAATACCACACCTGAAGGGGTCGCTCGTCGGTATGGCGGTGAATGGACTGAGGAAGCCGGAGAGC
GCGCCGCATTGTCCGAACGGCTCTTTGCAAACTTATGGGGTCGTCTGGAAGGGGAGGAACGTCTGTTATGGTTGTAT
CGGGAAGTCGAACGTCCTCTTTCGGCCGTATTAGCGCATATGGAGGCAACAGGTGTGCGTTTAGATGTCGCGTACCT
TCGGGCCTTATCACTGGAAGTTGCAGAGGAAATCGCCCGTCTCGAGGCTGAAGTGTTCCGGTTGGCCGGTCACCCGT
TTAACCTCAACTCCCGTGACCAGCTGGAACGCGTTTATTCGATGAGCTTGGGCTTCCCGCAATTGGCAAAACCGAA
AAGACTGGCAAACGCAGTACGAGCGCTGCCGTCCTTGAGGCACTCCGCGAGGCTCACCCTATTGTAGAAAAGATCCT
GCAATACCGTGAGTTGACGAAGCTTAAAAGCACTTATATTGATCCTCTCCCGGATCTGATCCATCCTCGTACCGGCC
GCTTGCACACACGTTTCAACCAGACGGCGACTGCAACCGGCCGTCTGTCTAGCTCGGATCCAAATCTCCAGAACATT
CCGGTCCGTACACCCTTGGGCAACGTATCCGCCGGGCGTTTATCGCTGAGGAAGGATGGTTACTGGTCGCATTGGA
CTACTCGCAGATTGAGCTGCGCGTCCTCGCACATCTCTCTGGTGACGAAAATTTAATCCGCGTGTTTCAAGAGGGGC
GTGATATTCACACAGAAACTGCCTCATGGATGTTCGGTGTCCCACGTGAAGCAGTGGATCCTTTGATGCGCCGTGCA
GCTAAAACAATTAATTTTGGAGTGCTGTACGGAATGAGCGCTCATCGCTTGAGTCAGGAACTGGCAATCCCCTACGA
GGAAGCGCAGGCATTCATCGAACGTTACTTTCAATCGTTTCCGAAAGTTCGCGCATGGATCGAGAAGACGCTCGAGG
AAGGTCGTCGTCGGGGCTATGTCGAAACTCTGTTTGGTCGCCGTCGGTACGTACCAGATCTTGAAGCCCGCGTCAAA
TCGGTACGGGAGGCTGCGGAGCGTATGGCATTTAATATGCCTGTACAGGGTACTGCAGCTGACCTCATGAAACTGGC
AATGGTCAAGCTTTTCCCGCGCTTGGAGGAAATGGGCGCACGTATGCTTCTGCAGGTCAGCGACGAGCTGGTGTTAG
AAGCCCCTAAGGAGCGCGCCGAAGCTGTCGCGCGCCTCGCTAAAGAAGTGATGGAGGGCGTTTACCCATTGGCCGTA
CCCCTCGAAGTGGAGGTCGGTATTGGAGAAGATTGGTTATCTGCAAAGGAAGCGGCCGC SEQ ID NO. 178, amino acid sequence of Mutant ID 42 (H784S KlenTaq).
MGSLLHEFGLLESPKALEEAPWPPPEGAFVGFVLSRKEPMWADLLALAAARGGRVHRAPEPYKALRDLKEARGLLAK
DLSVLALREGLGLPPGDDPMLLAYLLDPSNTTPEGVARRYGGEWTEEAGERAALSERLFANLWGRLEGEERLLWLYR
EVERPLSAVLAHMEATGVRLDVAYLRALSLEVAEETARLEAEVFRLAGHPFNLNSRDQLERVLFDELGLPAIGKTEK
TGKRSTSAAVLEALREAHPIVEKILQYRELTKLKSTYIDPLPDLIHPRTGRLHTRFNQTATATGRLSSSDPNLQNIP
VRTPLGQRIRRAFIAEEGWLLVALDYSQIELRVLAHLSGDENLIRVFQEGRDIHTETASWMFGVPREAVDPLMRRAA
KTINFGVLYGMSAHRLSQELAIPYEEAQAFIERYFQSFPKVRAWIEKTLEEGRRRGYVETLFGRRRYVPDLEARVKS
VREAAERMAFNMPVQGTAADLMKLAMVKLFPRLEEMGARMLLQSDELVLEAPKERAEAVARLAKEVMEGVYPLAVP
LEVEVGIGEDWLSAKEAA SEQ ID NO. 179, nucleotide sequence of Mutant ID 43 (H784Y KlenTaq).
CATATGGGTTCACTGCTTCATGAATTCGGTCTGTTAGAGTCTCCTAAAGCACTCGAAGAGGCACCGTGGCCGCCCCC
AGAAGGTGCTTTTGTTGGCTTCGTACTTTCCCGTAAGGAGCCTATGTGGGCAGATCTTCTGGCTTTAGCGGCTGCAC
GCGGTGGCCGTGTTCACCGGGCCCTGAGCCATACAAAGCGTTACGTGATCTGAAGGAAGCACGTGGCTTGCTGGCA
AAAGACCTTTCTGTTTTGGCCCTGCGCGAGGGTCTTGGACTGCCGCCAGGCGACGATCCCATGTTATTGGCCTATCT
GTTAGACCCTAGCAATACCACACCTGAAGGGGTCGCTCGTCGGTATGGCGGTGAATGGACTGAGGAAGCCGGAGAGC
GCGCCGCATTGTCCGAACGGCTCTTTGCAAACTTATGGGGTCGTCTGGAAGGGGAGGAACGTCTGTTATGGTTGTAT
CGGGAAGTCGAACGTCCTCTTTCGGCCGTATTAGCGCATATGGAGGCAACAGGTGTGCGTTTAGATGTCGCGTACCT
TCGGGCCTTATCACTGGAAGTTGCAGAGGAAATCGCCCGTCTCGAGGCTGAAGTGTTCCGGTTGGCCGGTCACCCGT
TTAACCTCAACTCCCGTGACCAGCTGGAACGCGTTTATTCGATGAGCTTGGGCTTCCCGCAATTGGCAAAACCGAA
AAGACTGGCAAACGCAGTACGAGCGCTGCCGTCCTTGAGGCACTCCGCGAGGCTCACCCTATTGTAGAAAAGATCCT
GCAATACCGTGAGTTGACGAAGCTTAAAAGCACTTATATTGATCCTCTCCCGGATCTGATCCATCCTCGTACCGGCC
GCTTGCACACACGTTTCAACCAGACGGCGACTGCAACCGGCCGTCTGTCTAGCTCGGATCCAAATCTCCAGAACATT
CCGGTCCGTACACCCTTGGGCAACGTATCCGCCGGGCGTTTATCGCTGAGGAAGGATGGTTACTGGTCGCATTGGA
CTACTCGCAGATTGAGCTGCGCGTCCTCGCACATCTCTCTGGTGACGAAAATTTAATCCGCGTGTTTCAAGAGGGGC
GTGATATTCACACAGAAACTGCCTCATGGATGTTCGGTGTCCCACGTGAAGCAGTGGATCCTTTGATGCGCCGTGCA
GCTAAAACAATTAATTTTGGAGTGCTGTACGGAATGAGCGCTCATCGCTTGAGTCAGGAACTGGCAATCCCCTACGA
GGAAGCGCAGGCATTCATCGAACGTTACTTTCAATCGTTTCCGAAAGTTCGCGCATGGATCGAGAAGACGCTCGAGG
AAGGTCGTCGTCGGGGCTATGTCGAAACTCTGTTTGGTCGCCGTCGGTACGTACCAGATCTTGAAGCCCGCGTCAAA
TCGGTACGGGAGGCTGCGGAGCGTATGGCATTTAATATGCCTGTACAGGGTACTGCAGCTGACCTCATGAAACTGGC
AATGGTCAAGCTTTTCCCGCGCTTGGAGGAAATGGGCGCACGTATGCTTCTGCAGGTCTATGACGAGCTGGTGTTAG
AAGCCCCTAAGGAGCGCGCCGAAGCTGTCGCGCGCCTCGCTAAAGAAGTGATGGAGGGCGTTTACCCATTGGCCGTA
CCCCTCGAAGTGGAGGTCGGTATTGGAGAAGATTGGTTATCTGCAAAGGAAGCGGCCGC -continued SEQ ID NO. 180, amino acid sequence of Mutant ID 43 (H784Y KlenTaq).
MGSLLHEFGLLESPKALEEAPWPPPEGAFVGFVLSRKEPMWADLLALAAARGGRVHRAPEPYKALRDLKEARGLLAK
DLSVLALREGLGLPPGDDPMLLAYLLDPSNTTPEGVARRYGGEWTEEAGERAALSERLFANLWGRLEGEERLLWLYR
EVERPLSAVLAHMEATGVRLDVAYLRALSLEVAEETARLEAEVERLAGHPFNLNSRDQLERVLFDELGLPAIGKTEK
TGKRSTSAAVLEALREAHPIVEKILQYRELTKLKSTYIDPLPDLIHPRTGRLHTRFNQTATATGRLSSSDPNLQNIP
VRTPLGQRIRRAFIAEEGWLLVALDYSQIELRVLAHLSGDENLIRVFQEGRDIHTETASWMFGVPREAVDPLMRRAA
KTINFGVLYGMSAHRLSQELAIPYEEAQAFIERYFQSFPKVRAWIEKTLEEGRRRGYVETLFGRRRYVPDLEARVKS
VREAAERMAFNMPVQGTAADLMKLAMVKLFPRLEEMGARMLLQVYDELVLEAPKERAEAVARLAKEVMEGVYPLAVP
LEVEVGIGEDWLSAKEAA

INCORPORATION BY REFERENCE

All publications, patents, patent applications, Accession No. data mentioned herein are hereby incorporated by reference in their entirety as if each individual publication, patent, patent application or Accession No. data was specifically and individually indicated to be incorporated by reference. In the case of Accession No. data citations and references, the corresponding DNA polymerase amino acid and nucleotide sequences are incorporated herein by reference as if such sequences are disclosed by way of a SEQ ID NO. In case of conflict, the present application, including any definitions herein, will control.

The terminology used herein is for the purpose of describing particular embodiments only, and is not intended to be limiting. With respect to the use of substantially, any plural and/or singular terms herein, those having skill in the art can translate from the plural as is appropriate to the context and/or application. The various singular/plural permutations may be expressly set forth herein for the sake of clarity.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiments or examples disclosed, but that the present invention will include all embodiments falling within the scope of the appended claims.

What is claimed is:

1. A method for conducting primer extension on a polynucleotide template, comprising:
   contacting the polynucleotide template with a reaction mixture comprising:
   a DNA polymerase selected from the group consisting of SEQ ID NOS.: 85 and 174;
   nucleoside triphosphates;
   an RNase H2 enzyme; and
   a blocked-cleavable rhPCR primer consisting of a RDxxD blocked-cleavable rhPCR primer, wherein the RDxxD blocked-cleavable rhPCR primer consists of an oligonucleotide complementary to the polynucleotide template and having at its 3'-terminus the sequence RDxxD, wherein R is an RNA base, D is a DNA base and x is a C3 spacer group; and
   performing primer extension under suitable conditions, thereby producing an extended primer.

2. The method of claim 1, wherein the primer extension method comprises a method for conducting polymerase chain reaction (PCR).

3. The method of claim 2, wherein the method for conducting PCR comprises allele-specific PCR.

4. The method of claim 2, wherein the method for conducting PCR comprises detecting a rare allele at a level of discrimination of >1:10,000.

5. A method for performing rhPCR, comprising performing primer extension according to the method of claim 1.

* * * * *